(12) United States Patent
Enan

(10) Patent No.: US 8,734,869 B2
(45) Date of Patent: May 27, 2014

(54) SYNERGISTIC PEST-CONTROL COMPOSITIONS

(75) Inventor: Essam Enan, Davis, CA (US)

(73) Assignee: TyraTech, Inc., Melbourne, FL (US)

(*) Notice: Subject to any disclaimer, the term of this patent is extended or adjusted under 35 U.S.C. 154(b) by 445 days.

(21) Appl. No.: 12/532,604

(22) PCT Filed: Mar. 21, 2008

(86) PCT No.: PCT/US2008/003722
§ 371 (c)(1),
(2), (4) Date: May 3, 2010

(87) PCT Pub. No.: WO2009/038599
PCT Pub. Date: Mar. 26, 2009

(65) Prior Publication Data
US 2010/0303940 A1    Dec. 2, 2010

Related U.S. Application Data

(60) Provisional application No. 60/896,427, filed on Mar. 22, 2007, provisional application No. 60/896,436, filed on Mar. 22, 2007, provisional application No. 60/896,430, filed on Mar. 22, 2007, provisional application No. 60/987,013, filed on Nov. 9, 2007, provisional application No. 60/990,912, filed on Nov. 28, 2007, provisional application No. 61/023,425, filed on Jan. 24, 2008.

(51) Int. Cl.
*A01N 65/00* (2009.01)
*A61K 36/00* (2006.01)
*A01N 43/30* (2006.01)
*A61K 31/36* (2006.01)

(52) U.S. Cl.
USPC .................. 424/778; 424/725; 514/464

(58) Field of Classification Search
None
See application file for complete search history.

(56) References Cited

U.S. PATENT DOCUMENTS

| | | | |
|---|---|---|---|
| 4,278,658 A | 7/1981 | Hooper et al. | |
| 4,551,480 A | 11/1985 | Stiefel et al. | |
| 5,942,214 A | 8/1999 | Lucas et al. | |
| 6,177,465 B1* | 1/2001 | Tanaka | 514/535 |
| 6,238,682 B1 | 5/2001 | Klofta et al. | |
| 6,849,614 B1* | 2/2005 | Bessette et al. | 514/72 |
| 7,541,155 B2 | 6/2009 | Enan | |
| 7,622,269 B2 | 11/2009 | Enan | |
| 2003/0194454 A1* | 10/2003 | Bessette et al. | 424/745 |
| 2006/0083763 A1 | 4/2006 | Neale et al. | |
| 2006/0263403 A1 | 11/2006 | Enan | |
| 2008/0075796 A1 | 3/2008 | Enan | |

OTHER PUBLICATIONS

Colby, S.R., "Calculating Synergistic and Antagonistic Responses of Herbicide Combinations," Weeds 15(1), p. 20-22, 1967.
James, et al. "Field-testing of methyl salicylate for recruitment and retention of beneficial insects in grapes and hops," Journal of Chemical Ecology 30(8), p. 1613-1628, 2004.
Lynn, D.E., "Development and characterization of insect cell lines," Cytotechnology 20, p. 3-11, 1996.
Lynn, D.E., "Methods for maintaining insect cell cultures," J. Insect Science 2.9, p. 1-6, 2002.
Shulaev, et al., "Airborne signalling by methyl salicylate in plant pathogen resistance." Nature 385, p. 718-721, 1997.
U.S. Appl. No. 60/718,570, "Compositions Having Insect Control Activity and Methods for Use Thereof," Sep. 19, 2005.
U.S. Appl. No. 60/747,592, "Water-Based Formulation of Insect-Control Compositions and Methods for Production and Use Thereof," May 18, 2006.
U.S. Appl. No. 60/799,434, "Formulation of Insect-Control Compositions Having Residual Activity and Methods for Production and Use Thereof," May 10, 2006.
U.S. Appl. No. 60/805,963, "Compositions for Treating Parasitic Injections and Methods of Screening for Same," Jun. 27, 2006.
U.S. Appl. No. 60/807,600, "Compositions and Methods for Controlling Insects," Jul. 17, 2006.
PCT International Search Report in corresponding International application No. PCT/US08/03722, mailed Sep. 19, 2008.

\* cited by examiner

*Primary Examiner* — Chris R Tate
*Assistant Examiner* — Russell Fiebig
(74) *Attorney, Agent, or Firm* — Davis Wright Tremaine LLP

(57) ABSTRACT

Pest control compositions, blends, and formulations are disclosed. The blends contain, in a synergistic combinations, at least two ingredients such as Lilac Flower Oil, D-Limonene, Thyme Oil, Lime Oil, Black Seed Oil, Wintergreen Oil, Linalool, Tetrahydrolinalool, Vanillin, Isopropyl myristate, Piperonal (aldehyde), Geraniol, Geraniol 60, Triethyl Citrate, and Methyl Salicylate.

9 Claims, 29 Drawing Sheets

Armor lead blend = Blend 54

Armor lead blend = Blend 54

SYNERGISTIC PEST-CONTROL COMPOSITIONS

RELATED APPLICATIONS

This application claims the benefit of U.S. Provisional Application Nos. 60/896,427, filed Mar. 22, 2007; 60/896,436, filed Mar. 22, 2007; 60/896,430, filed Mar. 22, 2007; 60/987,013, filed Nov. 9, 2007; 60/990,912, filed Nov. 28, 2007; and 61/023,425, filed Jan. 24, 2008.

FIELD OF THE INVENTION

The present invention relates to compositions and methods related to controlling insects, including compositions having a synergistic blend of ingredients.

BACKGROUND

Various chemicals and mixtures have been studied for pesticidal activity for many years with a goal of obtaining a product which is selective for invertebrates such as insects and has little or no toxicity to vertebrates such as mammals, fish, fowl and other species and does not otherwise persist in and damage the environment.

Most of the previously known and commercialized products having sufficient pesticidal activity to be useful also have toxic or deleterious effects on mammals, fish, fowl or other species which are not the target of the product. For example, organophosphorus compounds and carbamates inhibit the activity of acetylcholinesterase in insects as well as in all classes of animals. Chlordimeform and related formamidines are known to act on octopamine receptors of insects but have been removed from the market because of cardiotoxic potential in vertebrates and carcinogenicity in animals and a varied effect on different insects. Other compounds, which can be less toxic to mammals and other non-target species, are sometimes difficult to identify.

SUMMARY OF THE INVENTION

Embodiments of the present invention include pest control blends, including, in a synergistic combination, at least two ingredients such as, for example, Lilac Flower Oil, D-Limonene, Thyme Oil, Lime Oil, Black Seed Oil, Wintergreen Oil, Linalool, Tetrahydrolinalool, Vanillin, Isopropyl myristate, Piperonal (aldehyde), Geraniol, Geraniol 60, Triethyl Citrate, Methyl Salicylate, and the like.

The pest control blends of the invention can have a coefficient of synergy of at least 1.5 for each active ingredient, as measured by a test on a target organism, wherein the test can be selected from: knockdown time, killing time, repellency, and residual effectiveness. Likewise, the coefficient of synergy can be at least 5, or at least 10, or at least 25, for at least one active ingredient.

In some embodiments, exposure to the blend disrupts cellular calcium levels within the target organism, and/or exposure to the blend disrupts cyclic AMP levels within cells of the target organism. In some embodiments, exposure to the blend can result in binding of a receptor of the olfactory cascade of the target organism. In some embodiments, one or more components of the blend can act as an agonist or antagonist on the receptor of the target organism. Some blends include at least three active ingredients, or at least four active ingredients.

Embodiments of the invention also provide pest control formulations, including any of the blends of the invention. The pest control formulation can include at least one ingredient such as, for example, Hercolyn D, Mineral Oil, Soy Bean Oil, Piperonyl Alcohol, Ethyl Linalool, Hedione, Dipropylene glycol, Citral, gamma-terpinene, Sodium Lauryl Sulfate, Thymol, Alpha-Pinene, alpha-Terpineol, Terpinolene, Para-Cymene, Trans-Anethole, Linalyl Acetate, Beta Pinene, Camphor Dextro, Terpinene-4-ol, Span 80, Tween 80, Potassium Sorbate, Sodium Benzoate, Isopar M, BHA, BHT, dl-alpha-tocopherol lineaolate, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, Polyglycerol-4-oleate, Tocopherol Gamma Tenox, Xanthan Gum, A45 Propellent, Lecithin, a propellent, water, a surfactant, a cationic agent, Sodium Benzoate, Xanthan, Ksorbate, a carrier, a stabilizer, and the like.

In other embodiments, pest control formulations include any of the blends of the invention in combination with one or more synthetic pesticides such as a pyrethroid, a chloronicotinyl insecticide, or a neonicotinoid.

In other embodiments, the invention provides methods of making a synergistic pest control formulation having desirable environmental properties. The methods can include the steps of: selecting an ingredient from a group of candidate ingredients known or believed to be generally safe for use in contact with vertebrates; screening the ingredient for binding to a G protein-coupled receptor of an invertebrate, wherein the binding results in measurable disruption of cellular calcium or cyclic AMP; combining the screened ingredient with at least one other screened ingredient, wherein the ingredients, in combination, are synergistic in an effect against a target organism. The receptor can be a receptor of the insect olfactory cascade, including, for example, a tyramine receptor, an octopamine receptor, olfactory receptor Or83b, olfactory receptor 43a, and the like.

Embodiments of the invention also provide pest control formulations, such as a pest-control composition comprising a synergistic combination of at least 2 ingredients from an ingredient family, wherein the ingredient family is an Ingredient Family listed in Table 2. Some embodiments provide a pest-control composition comprising a synergistic combination of at least 3 ingredients from an ingredient family, wherein the ingredient family is an Ingredient Family listed in Table 2 having at least 3 ingredients.

Some embodiments provide a pest-control composition comprising a synergistic combination of at least 4 ingredients from an ingredient family, wherein the ingredient family is an Ingredient Family listed in Table 2 having at least 4 ingredients.

Some embodiments provide a pest-control composition of any of claims 1-3, wherein the ingredients are present within a range specified in Range 1 of Table 2.

Some embodiments provide a pest-control composition of any of claims 1-3, wherein the ingredients are present within a range specified in Range 2 of Table 2.

Some embodiments provide a pest-control composition of any of claims 1-3, wherein the ingredients are present within a range specified in Range 3 of Table 2.

Some embodiments provide a pest-control composition of any of claims 1-3, wherein the ingredients are present within a range specified in Range 4 of Table 2.

Some embodiments provide a pest-control composition of any of claims 1-3, wherein the ingredients are present in Exemplified amounts specified in Table 2.

Some embodiments provide a pest-control composition of any of the preceding claims, wherein at least one of the ingredients is the Exemplified Form specified in Table 2.

Some embodiments provide a pest-control composition of any of the preceding claims, wherein at least two ingredients interact with a receptor selected from a tyramine receptor, an olfactory receptor Or43a, and an olfactory receptor Or83b.

Some embodiments provide a pest-control composition, wherein interaction with the receptor results in a disruption of an intracellular level of at least one of cAMP and calcium.

Some embodiments provide a pest-control composition, wherein the disruption is sustained for at least 60 seconds.

Some embodiments provide a pest-control composition, wherein the disruption in a target pest results in repellency, knockdown, or killing of the target pest.

Some embodiments provide a pest-control composition of any of the preceding claims, wherein a target pest is an insect, an arthropod, a worm, a parasitic organism, a fungus, a bacterium, or a plant.

Some embodiments provide a pest-control composition of any of the preceding claims, having a coefficient of synergy of at least 1.5.

Some embodiments provide a pest-control composition of any of the preceding claims, having a synergistic effect according to the Colby test for synergy.

Some embodiments provide a pest-control composition of any of the preceding claims, wherein the composition has a synergistic pest-control activity that exceeds additive effects of the ingredients.

Some embodiments provide a composition of any of the preceding claims, wherein the composition has a synergistic pest-control activity that comprises pest control associated with the composition at a reference concentration that is in excess of pest control associated with any single ingredient at the reference concentration.

Some embodiments provide a composition of any of the preceding claims, wherein the composition has a synergistic pest-control activity that comprises pest control associated with the composition at a reference concentration that is in excess of the additive total of pest controls associated with each ingredient, at the concentrations at which the active ingredients are present at the reference concentration of the composition.

Some embodiments provide a composition of any of the preceding claims, wherein the composition has a synergistic pest-control activity that comprises pest control associated with the composition at a first concentration that is the equivalent of pest control associated with any single ingredient at a second concentration, and the first concentration is lower than the second concentration.

Some embodiments provide a composition of any of the preceding claims, wherein the synergistic pest control comprises a residual pest control period associated with the composition that is longer than the residual pest control period associated with any single selected ingredient.

Some embodiments provide a composition of any of the preceding claims, wherein the at least two ingredients activate a same GPCR.

Some embodiments provide a composition of any of the preceding claims, wherein the at least two ingredients activate different GPCRs.

Embodiments of the invention can provide a method of controlling a pest, including providing a pest control composition; and contacting the pest with the composition, wherein the contacting results in synergistic control of a target pest.

Embodiments of the invention can provide a method of invertebrate control, including providing a composition comprising at least two active ingredients, wherein the at least two active ingredients are ligands of a G-protein coupled receptor in a target invertebrate; and contacting the invertebrate with the composition, wherein the contacting results in synergistic invertebrate control.

In some methods of embodiments of the invention, the control comprises repulsion of substantially all of the target pest or invertebrate, and in some the control comprises knockdown of substantially all of the target pest or invertebrate, and in others the control comprises killing of substantially all of the target pest or invertebrate.

Some embodiments provide a synergistic composition for controlling a target pest comprising at least one of the group consisting of Thyme Oil White, Methyl Salicylate, and Isopropyl myristate.

Some embodiments provide a synergistic composition for controlling a target pest comprising at least two of the group consisting of Thyme Oil White, Methyl Salicylate, and Isopropyl myristate.

Some embodiments provide a synergistic composition for controlling a target pest comprising Thyme Oil White, Methyl Salicylate, and Isopropyl myristate.

Some embodiments provide a synergistic composition for controlling a target pest comprising between 10 and 30% Thyme Oil White, between 30 and 60% Methyl Salicylate, and between 20 and 48% Isopropyl myristate.

Some embodiments provide a synergistic composition for controlling a target pest comprising between 18 and 23% Thyme Oil White, between 40 and 50% Methyl Salicylate, and between 30 and 38% Isopropyl myristate.

Some embodiments provide a synergistic composition for controlling a target pest comprising 20.6% Thyme Oil White, 45.1% Methyl Salicylate, and 34.3% Isopropyl myristate.

Some embodiments provide a synergistic composition for controlling a target pest comprising at least one of the group consisting of Isopropyl myristate, Wintergreen Oil, and Thyme Oil White containing 1% Thyme Oil Red.

Some embodiments provide a synergistic composition for controlling a target pest comprising at least two of the group consisting of % Isopropyl myristate, Wintergreen Oil, and Thyme Oil White containing 1% Thyme Oil Red.

Some embodiments provide a synergistic composition for controlling a target pest comprising Isopropyl myristate, Wintergreen Oil, and Thyme Oil White containing 1% Thyme Oil Red.

Some embodiments provide a synergistic composition for controlling a target pest comprising between 25 and 48% Isopropyl myristate, 30 and 60% Wintergreen Oil, and between 10 and 30% Thyme Oil White containing 1% Thyme Oil Red.

Some embodiments provide a synergistic composition for controlling a target pest comprising between 30 and 38% Isopropyl myristate, 40 and 50% Wintergreen Oil, and between 18 and 23% Thyme Oil White containing 1% Thyme Oil Red.

Some embodiments provide a synergistic composition for controlling a target pest comprising 34.3% Isopropyl myristate, 45.1% Wintergreen Oil, and 20.6% Thyme Oil White containing 1% Thyme Oil Red.

Some embodiments provide a synergistic composition for controlling a target pest comprising at least one of the group consisting of Wintergreen Oil, Isopropyl myristate, and Thyme Oil Red.

Some embodiments provide a synergistic composition for controlling a target pest comprising at least two of the group consisting of Wintergreen Oil, Isopropyl myristate, and Thyme Oil Red.

Some embodiments of the invention provide a synergistic composition for controlling a target pest comprising Wintergreen Oil, Isopropyl myristate, and Thyme Oil Red.

Some embodiments of the invention provide a synergistic composition for controlling a target pest comprising between 30 and 60% Wintergreen Oil, between 20 and 48% Isopropyl myristate, and between 10 and 30% Thyme Oil Red.

Some embodiments of the invention provide a synergistic composition for controlling a target pest comprising between 40 and 50% Wintergreen Oil, between 30 and 38% Isopropyl myristate, and between 18 and 23% Thyme Oil Red.

Some embodiments of the invention provide a synergistic composition for controlling a target pest comprising 45.10% Wintergreen Oil, 34.3% Isopropyl myristate, and 20.6% Thyme Oil Red.

Some embodiments of the invention provide a synergistic composition for controlling a target pest comprising at least one of the group consisting of Isopropyl myristate, Wintergreen Oil (Technical grade), and Thyme Oil White containing 1% Thyme Oil Red.

Some embodiments of the invention provide a synergistic composition for controlling a target pest comprising at least two of the group consisting of Isopropyl myristate, Wintergreen Oil (Technical grade), and Thyme Oil White containing 1% Thyme Oil Red Some embodiments of the invention provide a synergistic composition for controlling a target pest comprising Isopropyl myristate, Wintergreen Oil (Technical grade), and Thyme Oil White containing 1% Thyme Oil Red.

Some embodiments of the invention provide a synergistic composition for controlling a target pest comprising between 20 and 48% Isopropyl myristate, between 30 and 60% Wintergreen Oil (Technical grade), and between 10 and 30% Thyme Oil White containing 1% Thyme Oil Red.

Some embodiments of the invention provide a synergistic composition for controlling a target pest comprising between 30 and 38% Isopropyl myristate, between 40 and 50% Wintergreen Oil (Technical grade), and between 18 and 23% Thyme Oil White containing 1% Thyme Oil Red.

Some embodiments of the invention provide a synergistic composition for controlling a target pest comprising 34.3% Isopropyl myristate, 45.10% Wintergreen Oil (Technical grade), and 20.6% Thyme Oil White containing 1% Thyme Oil Red.

Some embodiments of the invention provide a synergistic composition for controlling a target pest comprising at least two of the group consisting of Thyme Oil White, Wintergreen Oil, Isopropyl myristate, and Vanillin.

Some embodiments of the invention provide a synergistic composition for controlling a target pest comprising at least three of the group consisting of Thyme Oil White, Wintergreen Oil, Isopropyl myristate, and Vanillin.

Some embodiments of the invention provide a synergistic composition for controlling a target pest comprising Thyme Oil White, Wintergreen Oil, Isopropyl myristate, and Vanillin.

Some embodiments of the invention provide a synergistic composition for controlling a target pest comprising between 10 and 30% Thyme Oil White, between 30 and 60% Wintergreen Oil, between 20 and 48% Isopropyl myristate, and between 0.01 and 0.3% Vanillin.

Some embodiments of the invention provide a synergistic composition for controlling a target pest comprising between 18 and 23% Thyme Oil White, between 40 and 50% Wintergreen Oil, between 30 and 38% Isopropyl myristate, and between 0.05 and 0.15% Vanillin.

Some embodiments of the invention provide a synergistic composition for controlling a target pest comprising 20.6% Thyme Oil White, 45.1% Wintergreen Oil, 34.2% Isopropyl myristate, and 0.1% Vanillin.

Some embodiments of the invention provide a synergistic composition for controlling a target pest comprising at least two of the group consisting of Thyme Oil Red, Wintergreen Oil, Isopropyl myristate, and Vanillin 60.

Some embodiments of the invention provide a synergistic composition for controlling a target pest comprising at least three of the group consisting of Thyme Oil Red, Wintergreen Oil, Isopropyl myristate, and Vanillin.

Some embodiments of the invention provide a synergistic composition for controlling a target pest comprising Thyme Oil Red, Wintergreen Oil, Isopropyl myristate, and Vanillin.

Some embodiments of the invention provide a synergistic composition for controlling a target pest comprising 10 and 30% Thyme Oil Red, between 30 and 60% Wintergreen Oil, between 20 and 48% Isopropyl myristate, and between 0.01 and 0.3% Vanillin.

Some embodiments of the invention provide a synergistic composition for controlling a target pest comprising 18 and 23% Thyme Oil Red, 40 and 50% Wintergreen Oil, and between 30 and 38% Isopropyl myristate, and between 0.05 and 0.15% Vanillin.

Some embodiments of the invention provide a synergistic composition for controlling a target pest comprising 20.6% Thyme Oil Red, 45.1% Wintergreen Oil, 34.2% Isopropyl myristate, and 0.1% Vanillin.

Some embodiments of the invention provide a synergistic composition for controlling a target pest comprising at least one of the group consisting of Thyme Oil White, Isopropyl myristate, and Geraniol Fine, FCC.

Some embodiments of the invention provide a synergistic composition for controlling a target pest comprising at least two of the group consisting of Thyme Oil White, Isopropyl myristate, and Geraniol Fine, FCC.

Some embodiments of the invention provide a synergistic composition for controlling a target pest comprising Thyme Oil White, Isopropyl myristate, and Geraniol Fine, FCC.

Some embodiments of the invention provide a synergistic composition for controlling a target pest comprising between 30 and 55% Thyme Oil White, between 28 and 50% Isopropyl myristate, and between 15 and 26% Geraniol Fine, FCC.

Some embodiments of the invention provide a synergistic composition for controlling a target pest comprising between 36 and 46% Thyme Oil White, between 34 and 42% Isopropyl myristate, and between 18 and 22% Geraniol Fine, FCC.

Some embodiments of the invention provide a synergistic composition for controlling a target pest comprising 41.86% Thyme Oil White, 38.34% Isopropyl myristate, and 19.80% Geraniol Fine, FCC.

Some embodiments of the invention provide a synergistic composition for controlling a target pest comprising at least one of the group consisting of Thyme Oil White, Isopropyl myristate, and Geraniol Fine, FCC.

Some embodiments of the invention provide a synergistic composition for controlling a target pest comprising at least two of the group consisting of Thyme Oil White, Isopropyl myristate, and Geraniol Fine, FCC.

Some embodiments of the invention provide a synergistic composition for controlling a target pest comprising Thyme Oil White, Isopropyl myristate, and Geraniol Fine, FCC.

Some embodiments of the invention provide a synergistic composition for controlling a target pest comprising between 12 and 30% Thyme Oil White, between 45 and 75% Isopropyl myristate, and between 12 and 30% Geraniol Fine, FCC.

Some embodiments of the invention provide a synergistic composition for controlling a target pest comprising 18 and 24% Thyme Oil White, between 53 and 65% Isopropyl myristate, and between 18 and 23% Geraniol Fine, FCC.

Some embodiments of the invention provide a synergistic composition for controlling a target pest comprising 21.30% Thyme Oil White, 58.54% Isopropyl myristate, and 20.16% Geraniol Fine, FCC.

Some embodiments of the invention provide a synergistic composition for controlling a target pest comprising at least one of the group consisting of Thyme Oil White, Isopropyl myristate, and Geraniol Fine, FCC.78. A synergistic composition for controlling a target pest comprising at least two of the group consisting of Thyme Oil White, Isopropyl myristate, and Geraniol Fine, FCC.

Some embodiments of the invention provide a synergistic composition for controlling a target pest comprising Thyme Oil White, Isopropyl myristate, and Geraniol Fine, FCC.

Some embodiments of the invention provide a synergistic composition for controlling a target pest comprising between 22 and 40% Thyme Oil White, between 28 and 50% Isopropyl myristate, and between 20 and 40% Geraniol Fine, FCC.

Some embodiments of the invention provide a synergistic composition for controlling a target pest comprising between 28 and 35% Thyme Oil White, between 34 and 43% Isopropyl myristate, and between 26 and 33% Geraniol Fine, FCC.

Some embodiments of the invention provide a synergistic composition for controlling a target pest comprising 31.57% Thyme Oil White, 38.56% Isopropyl myristate, 29.87% Geraniol Fine, FCC.

Some embodiments of the invention provide a synergistic composition for controlling a target pest comprising at least one of the group consisting of Thyme Oil White, Isopropyl myristate, and Geraniol Fine, FCC.

Some embodiments of the invention provide a synergistic composition for controlling a target pest comprising at least two of the group consisting of Thyme Oil White, Isopropyl myristate, and Geraniol Fine, FCC.

Some embodiments of the invention provide a synergistic composition for controlling a target pest comprising Thyme Oil White, Isopropyl myristate, and Geraniol Fine, FCC.

Some embodiments of the invention provide a synergistic composition for controlling a target pest comprising 36.85% Thyme Oil White, 48.21% Isopropyl myristate, 14.94% Geraniol Fine, FCC.

Some embodiments of the invention provide a synergistic composition for controlling a target pest comprising 36.85% Thyme Oil White, 48.21% Isopropyl myristate, 14.94% Geraniol Fine, FCC.

Some embodiments of the invention provide a synergistic composition for controlling a target pest comprising 36.85% Thyme Oil White, 48.21% Isopropyl myristate, 14.94% Geraniol Fine, FCC.

Some embodiments of the invention provide a synergistic composition for controlling a target pest comprising at least one of the group consisting of Thyme Oil White containing 1% Thyme Oil Red, Isopropyl myristate, and Geraniol Fine, FCC.

Some embodiments of the invention provide a synergistic composition for controlling a target pest comprising at least two of the group consisting of Thyme Oil White containing 1% Thyme Oil Red, Isopropyl myristate, and Geraniol Fine, FCC.

Some embodiments of the invention provide a synergistic composition for controlling a target pest comprising Thyme Oil White containing 1% Thyme Oil Red, Isopropyl myristate, and Geraniol Fine, FCC.

Some embodiments of the invention provide a synergistic composition for controlling a target pest comprising between 25 and 50% Thyme Oil White containing 1% Thyme Oil Red, between 35 and 65% Isopropyl myristate, and between 8 and 25% Geraniol Fine, FCC.

Some embodiments of the invention provide a synergistic composition for controlling a target pest comprising between 33 and 40% Thyme Oil White containing 1% Thyme Oil Red, between 44 and 55% Isopropyl myristate, and between 13 and 17% Geraniol Fine, FCC.

Some embodiments of the invention provide a synergistic composition for controlling a target pest comprising 36.85% Thyme Oil White containing 1% Thyme Oil Red, 48.21% Isopropyl myristate, 14.94% Geraniol Fine, FCC.

Some embodiments of the invention provide a synergistic composition for controlling a target pest comprising at least two or three of the group consisting of Potassium Sorbate, Polyglycerol-4-oleate, Xanthan Gum, Lecithin, Water, and Blend 41.

Some embodiments of the invention provide a synergistic composition for controlling a target pest comprising at least four of the group consisting of Potassium Sorbate, Polyglycerol-4-oleate, Xanthan Gum, Lecithin, Water, and Blend 41.

Some embodiments of the invention provide a synergistic composition for controlling a target pest comprising Potassium Sorbate, Polyglycerol-4-oleate, Xanthan Gum, Lecithin, Water, and Blend 41.

Some embodiments of the invention provide a synergistic composition for controlling a target pest comprising between 0.01 and 0.25% Potassium Sorbate, between 0.05 and 0.5% Polyglycerol-4-oleate, between 0.1 and 0.6% Xanthan Gum, between 0.01 and 0.1% Lecithin, between 60 and 98% Water, and between 5 and 25% Blend 41.

Some embodiments of the invention provide a synergistic composition for controlling a target pest comprising between 0.05 and 0.16% Potassium Sorbate, between 0.1 and 0.2% Polyglycerol-4-oleate, between 0.2 and 0.36% Xanthan Gum, between 0.03 and 0.04% Lecithin, between 76 and 94% Water, and between 13 and 17% Blend 41.

Some embodiments of the invention provide a synergistic composition for controlling a target pest comprising 0.11% Potassium Sorbate, 0.15% Polyglycerol-4-oleate, 0.28% Xanthan Gum, 0.034% Lecithin, 84.4% Water, and 15.01% Blend 41.

Some embodiments of the invention provide a synergistic composition for controlling a target pest comprising at least three to five of the group consisting of Thyme Oil White, Wintergreen Oil, Isopropyl myristate, Potassium Sorbate, Polyglycerol-4-oleate, Xanthan Gum, Lecithin, and Water.

Some embodiments of the invention provide a synergistic composition for controlling a target pest comprising at least six or seven of the group consisting of Thyme Oil White, Wintergreen Oil, Isopropyl myristate, Potassium Sorbate, Polyglycerol-4-oleate, Xanthan Gum, Lecithin, and Water.

Some embodiments of the invention provide a synergistic composition for controlling a target pest comprising Thyme Oil White, Wintergreen Oil, Isopropyl myristate, Potassium Sorbate, Polyglycerol-4-oleate, Xanthan Gum, Lecithin, and Water.

Some embodiments of the invention provide a synergistic composition for controlling a target pest comprising between 1 and 5% Thyme Oil White, between 3 and 12% Wintergreen Oil, between 2 and 10% Isopropyl myristate, between 0.02 and 0.2% Potassium Sorbate, between 0.05 and 0.5% Polyglycerol-4-oleate, between 0.1 and 0.5% Xanthan Gum, between 0.01 and 0.1% Lecithin, and between 60 and 98% Water.

Some embodiments of the invention provide a synergistic composition for controlling a target pest comprising between 2.7 and 3.4% Thyme Oil White, between 6.0 and 7.5% Wintergreen Oil, between 4.5 and 5.7% Isopropyl myristate, between 0.08 and 0.14% Potassium Sorbate, between 0.1 and 0.2% Polyglycerol-4-oleate, between 0.25 and 0.31% Xanthan Gum, between 0.025 and 0.035% Lecithin, and between 76 and 92% Water.

Some embodiments of the invention provide a synergistic composition for controlling a target pest comprising 3.09% Thyme Oil White, 6.77% Wintergreen Oil, 5.15% Isopropyl myristate, 0.11% Potassium Sorbate, 0.15% Polyglycerol-4-oleate, 0.28% Xanthan Gum, 0.03% Lecithin, 84.41% Water.

Some embodiments of the invention provide a synergistic composition for controlling a target pest comprising at least two or three of the group consisting of Potassium Sorbate, Polyglycerol-4-oleate, Xanthan Gum, Lecithin, Water, and Blend 120.

Some embodiments of the invention provide a synergistic composition for controlling a target pest comprising at least four or five of the group consisting of Potassium Sorbate, Polyglycerol-4-oleate, Xanthan Gum, Lecithin, Water, and Blend 120.

Some embodiments of the invention provide a synergistic composition for controlling a target pest comprising Potassium Sorbate, Polyglycerol-4-oleate, Xanthan Gum, Lecithin, Water, and Blend 120.

Some embodiments of the invention provide a synergistic composition for controlling a target pest comprising between 0.05 and 0.2% Potassium Sorbate, between 0.05 and 0.5% Polyglycerol-4-oleate, between 0.1 and 0.5% Xanthan Gum, between 0.01 and 0.1% Lecithin, between 60 and 98% Water, and between 8 and 22% Blend 120.

Some embodiments of the invention provide a synergistic composition for controlling a target pest comprising between 0.09 and 0.13% Potassium Sorbate, between 0.1 and 0.2% Polyglycerol-4-oleate, between 0.25 and 0.31% Xanthan Gum, between 0.025 and 0.043% Lecithin, between 76 and 92% Water, and between 13 and 17% Blend 120.

Some embodiments of the invention provide a synergistic composition for controlling a target pest comprising 0.11% Potassium Sorbate, 0.15% Polyglycerol-4-oleate, 0.28% Xanthan Gum, 0.034% Lecithin, 84.4% Water, and 15.01% Blend 120.

Some embodiments of the invention provide a synergistic composition for controlling a target pest comprising at least two or three of the group consisting of Potassium Sorbate, Polyglycerol-4-oleate, Xanthan Gum, Lecithin, Water, and Blend 120.

Some embodiments of the invention provide a synergistic composition for controlling a target pest comprising at least four or five of the group consisting of Potassium Sorbate, Polyglycerol-4-oleate, Xanthan Gum, Lecithin, Water, and Blend 120.

Some embodiments of the invention provide a synergistic composition for controlling a target pest comprising Potassium Sorbate, Polyglycerol-4-oleate, Xanthan Gum, Lecithin, Water, and Blend 120.

Some embodiments of the invention provide a synergistic composition for controlling a target pest comprising between 0.12% Potassium Sorbate, 0.16% Polyglycerol-4-oleate, 0.29% Xanthan Gum, 0.036% Lecithin, 89.4% Water, 10% Blend 120.

Some embodiments of the invention provide a synergistic composition for controlling a target pest comprising between 0.1 and 0.14% Potassium Sorbate, between 0.12 and 0.18% Polyglycerol-4-oleate, between 0.26 and 0.32% Xanthan Gum, between 0.03 and 0.045% Lecithin, between 80 and 98% Water, and between 8 and 12% Blend 120.

Some embodiments of the invention provide a synergistic composition for controlling a target pest comprising 0.12% Potassium Sorbate, 0.16% Polyglycerol-4-oleate, 0.29% Xanthan Gum, 0.036% Lecithin, 89.4% Water, 10% 120.

Some embodiments of the invention provide a synergistic composition for controlling a target pest comprising CAR-01-097 (McCook) and Blend 10.

Some embodiments of the invention provide a synergistic composition for controlling a target pest comprising between 60 and 90% CAR-01-097 (McCook) and between 10 and 40% Blend 10.

Some embodiments of the invention provide a synergistic composition for controlling a target pest comprising between 70 and 80% CAR-01-097 (McCook) and between 20 and 30% Blend 10.

Some embodiments of the invention provide a synergistic composition for controlling a target pest comprising CAR-01-097 (McCook) with 25% Blend 10.

Some embodiments of the invention provide a synergistic composition for controlling a target pest comprising at least two of the group consisting of Soy Bean Oil, Ethyl Alcohol (denatured), and Blend 10.

Some embodiments of the invention provide a synergistic composition for controlling a target pest comprising Soy Bean Oil, Ethyl Alcohol (denatured), and Blend 10.

A synergistic composition for controlling a target pest comprising between 10 and 30% Soy Bean Oil, between 35 and 65% Ethyl Alcohol (denatured), and between 20 and 40% Blend 10.

Some embodiments of the invention provide a synergistic composition for controlling a target pest comprising between 18 and 22% Soy Bean Oil, between 45 and 55% Ethyl Alcohol (denatured), and between 27 and 33% Blend 10.

Some embodiments of the invention provide a synergistic composition for controlling a target pest comprising 20% Soy Bean Oil, 50% Ethyl Alcohol (denatured), and 30% Blend 10.

Some embodiments of the invention provide a synergistic composition for controlling a target pest comprising at least two or three of the group consisting of Potassium Sorbate, Polyglycerol-4-oleate, Xanthan Gum, Lecithin, Water, and Blend 124.

Some embodiments of the invention provide a synergistic composition for controlling a target pest comprising at least four or five of the group consisting of Potassium Sorbate, Polyglycerol-4-oleate, Xanthan Gum, Lecithin, Water, and Blend 124.

Some embodiments of the invention provide a synergistic composition for controlling a target pest comprising Potassium Sorbate, Polyglycerol-4-oleate, Xanthan Gum, Lecithin, Water, and Blend 124.

Some embodiments of the invention provide a synergistic composition for controlling a target pest comprising between 0.05 and 0.2% Potassium Sorbate, between 0.05 and 0.5% Polyglycerol-4-oleate, between 0.1 and 0.5% Xanthan Gum, between 0.01 and 0.05% Lecithin, between 60 and 98% Water, and between 8 and 25% Blend 124.

Some embodiments of the invention provide a synergistic composition for controlling a target pest comprising between 0.09 and 0.13% Potassium Sorbate, between 0.13 and 0.17% Polyglycerol-4-oleate, between 0.27 and 0.33% Xanthan Gum, between 0.025 and 0.035% Lecithin, between 76 and 92% Water, and between 13 and 17% Blend 124.

Some embodiments of the invention provide a synergistic composition for controlling a target pest comprising 0.11%

Potassium Sorbate, 0.15% Polyglycerol-4-oleate, 0.30% Xanthan Gum, 0.03% Lecithin, 84.4% Water, 15.01% Blend 124.

Some embodiments of the invention provide a synergistic composition for controlling a target pest comprising at least two or three of the group consisting of Potassium Sorbate, Polyglycerol-4-oleate, Xanthan Gum, Lecithin, Water, and Blend 124.

Some embodiments of the invention provide a synergistic composition for controlling a target pest comprising at least four or five of the group consisting of Potassium Sorbate, Polyglycerol-4-oleate, Xanthan Gum, Lecithin, Water, and Blend 124.

Some embodiments of the invention provide a synergistic composition for controlling a target pest comprising Potassium Sorbate, Polyglycerol-4-oleate, Xanthan Gum, Lecithin, Water, and Blend 124.

Some embodiments of the invention provide a synergistic composition for controlling a target pest comprising between 0.05 and 0.5% Potassium Sorbate, between 0.06 and 0.5% Polyglycerol-4-oleate, between 0.1 and 0.5% Xanthan Gum, between 0.01 and 0.1% Lecithin, between 70 and 98% Water, and between 2 and 20% Blend 124.

Some embodiments of the invention provide a synergistic composition for controlling a target pest comprising between 0.1 and 0.14% Potassium Sorbate, between 0.14 and 0.18% Polyglycerol-4-oleate, between 0.27 and 0.33% Xanthan Gum, between 0.03 and 0.042% Lecithin, between 80 and 96% Water, and between 8 and 12% Blend 124.

Some embodiments of the invention provide a synergistic composition for controlling a target pest comprising 0.12% Potassium Sorbate, 0.16% Polyglycerol-4-oleate, 0.30% Xanthan Gum, 0.036% Lecithin, 89.4% Water, 10% Blend 124.

Some embodiments of the invention provide a synergistic composition for controlling a target pest comprising at least two to seven of the group consisting of Citronella Oil, Carbopol 940, Butylated hyrdroxy toluene, Water, Emulsifying Wax, Light Liquid Paraffin, White Soft Paraffin, Sodium Metabisulphate, Propylene Glycol, Cresmer RH40 hydrogenated, Triethanolamine, Vitamin E Acetate, Disodium EDTA, and Blend 7.

Some embodiments of the invention provide a synergistic composition for controlling a target pest comprising at least eight to thirteen of the group consisting of Citronella Oil, Carbopol 940, Butylated hyrdroxy toluene, Water, Emulsifying Wax, Light Liquid Paraffin, White Soft Paraffin, Sodium Metabisulphate, Propylene Glycol, Cresmer RH40 hydrogenated, Triethanolamine, Vitamin E Acetate, Disodium EDTA, and Blend 7.

Some embodiments of the invention provide a synergistic composition for controlling a target pest comprising Citronella Oil, Carbopol 940, Butylated hyrdroxy toluene, Water, Emulsifying Wax, Light Liquid Paraffin, White Soft Paraffin, Sodium Metabisulphate, Propylene Glycol, Cresmer RH40 hydrogenated, Triethanolamine, Vitamin E Acetate, Disodium EDTA, and Blend 7.

Some embodiments of the invention provide a synergistic composition for controlling a target pest comprising between 0.1 and 0.4% Citronella Oil, between 0.1 and 0.4% Carbopol 940, between 0.4 and 0.2% Butylated hyrdroxy toluene, between 40 and 75% Water, between 6 and 25% Emulsifying Wax, between 2 and 8% Light Liquid Paraffin, between 4 and 15% White Soft Paraffin, between 0.1 and 0.5% Sodium Metabisulphate, between 0.8 and 5% Propylene Glycol, between 2 and 10% Cresmer RH40 hydrogenated, between 0.08 and 0.4% Triethanolamine, between 0.01 and 0.05% Vitamin E Acetate, between 0.01 and 0.1% Disodium EDTA, and between 1 and 15% Blend 7.

Some embodiments of the invention provide a synergistic composition for controlling a target pest comprising between 0.18 and 0.22% Citronella Oil, between 0.18 and 0.22% Carbopol 940, between 0.8 and 0.12% Butylated hyrdroxy toluene, between 52 and 66% Water, between 12 and 16% Emulsifying Wax, between 3 and 5% Light Liquid Paraffin, between 7 and 11% White Soft Paraffin, between 0.2 and 0.3% Sodium Metabisulphate, between 1.5 and 2.5% Propylene Glycol, between 4 and 6% Cresmer RH40 hydrogenated, between 0.13 and 0.17% Triethanolamine, between 0.01 and 0.03% Vitamin E Acetate, between 0.04 and 0.06% Disodium EDTA, and between 4 and 6% Blend 7.

Some embodiments of the invention provide a synergistic composition for controlling a target pest comprising 0.20% Citronella Oil, 0.20% Carbopol 940, 0.10% Butylated hyrdroxy toluene, 59.83% Water, 14% Emulsifying Wax, 4.00% Light Liquid Paraffin, 9% White Soft Paraffin, 0.25% Sodium Metabisulphate, 2% Propylene Glycol, 5% Cresmer RH40 hydrogenated, 0.15% Triethanolamine, 0.02% Vitamin E Acetate, 0.05% Disodium EDTA, 5% Blend 7.

Some embodiments of the invention provide a synergistic composition for controlling a target pest comprising at least two of the group consisting of Blend 49, Lemon Grass Oil, and Castor Oil Surfactant.

Some embodiments of the invention provide a synergistic composition for controlling a target pest comprising Blend 49, Lemon Grass Oil, and Castor Oil Surfactant.

Some embodiments of the invention provide a synergistic composition for controlling a target pest comprising between 35 and 65% Blend 49, between 15 and 35% Lemon Grass Oil, and between 15 and 35% Castor Oil Surfactant.

Some embodiments of the invention provide a synergistic composition for controlling a target pest comprising between 45 and 55% Blend 49, between 22 and 28% Lemon Grass Oil, and between 22 and 28% Castor Oil Surfactant.

Some embodiments of the invention provide a synergistic composition for controlling a target pest comprising 50% Blend 49, 25% Lemon Grass Oil, and 25% Castor Oil Surfactant.

Some embodiments of the invention provide a synergistic composition for controlling a target pest comprising at least two of the group consisting of Blend 51, Lemon Grass Oil, and Castor Oil Surfactant.

Some embodiments of the invention provide a synergistic composition for controlling a target pest comprising Blend 51, Lemon Grass Oil, and Castor Oil Surfactant.

Some embodiments of the invention provide a synergistic composition for controlling a target pest comprising between 35 and 65% Blend 51, between 15 and 35% Lemon Grass Oil, and between 15 and 35% Castor Oil Surfactant.

Some embodiments of the invention provide a synergistic composition for controlling a target pest comprising between 45 and 55% Blend 51, between 22 and 28% Lemon Grass Oil, and between 22 and 28% Castor Oil Surfactant.

Some embodiments of the invention provide a synergistic composition for controlling a target pest comprising 50% Blend 51, 25% Lemon Grass Oil, and 25% Castor Oil Surfactant.

Some embodiments of the invention provide a synergistic composition for controlling a target pest comprising at least two of the group consisting of Blend 52, Lemon Grass Oil, and Castor Oil Surfactant.

Some embodiments of the invention provide a synergistic composition for controlling a target pest comprising Blend 52, Lemon Grass Oil, and Castor Oil Surfactant.

Some embodiments of the invention provide a synergistic composition for controlling a target pest comprising between 35 and 65% Blend 52, between 15 and 35% Lemon Grass Oil, and between 15 and 35% Castor Oil Surfactant.

Some embodiments of the invention provide a synergistic composition for controlling a target pest comprising between 45 and 55% Blend 52, between 22 and 28% Lemon Grass Oil, and between 22 and 28% Castor Oil Surfactant.

Some embodiments of the invention provide a synergistic composition for controlling a target pest comprising 50% Blend 52, 25% Lemon Grass Oil, and 25% Castor Oil Surfactant.

Some embodiments of the invention provide a synergistic composition for controlling a target pest comprising at least two of the group consisting of Blend 7, Sodium Lauryl Sulfate, and Water.

Some embodiments of the invention provide a synergistic composition for controlling a target pest comprising Blend 7, Sodium Lauryl Sulfate, and Water.

Some embodiments of the invention provide a synergistic composition for controlling a target pest comprising between 2 and 20% Blend 7, between 0.2 and 2% Sodium Lauryl Sulfate, and between 70 and 99% Water.

Some embodiments of the invention provide a synergistic composition for controlling a target pest comprising between 8 and 12% Blend 7, between 0.8 and 1.2% Sodium Lauryl Sulfate, and between 80 and 98% Water.

Some embodiments of the invention provide a synergistic composition for controlling a target pest comprising 10% Blend 7, 1% Sodium Lauryl Sulfate, 89% Water.

DESCRIPTION OF EXEMPLARY EMBODIMENTS OF THE INVENTION

Figure 1:
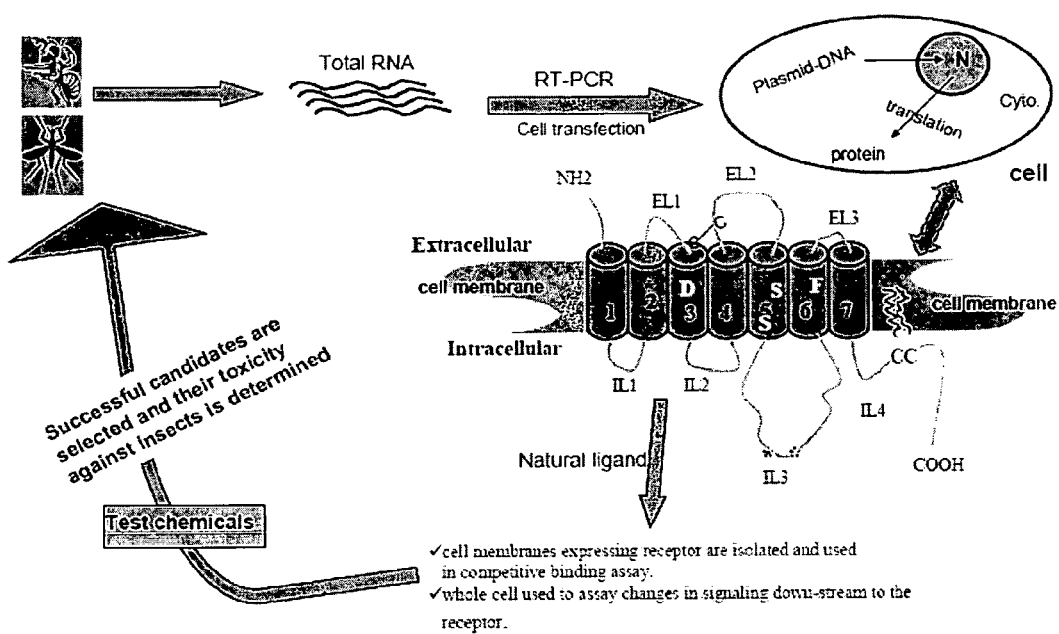
FIG. 1 shows a screening method using a transfected cell lines expressing a receptor of interest, for example, a biogenic amine receptor, such as, a TyR or an octopamine receptor.
Figure 2:
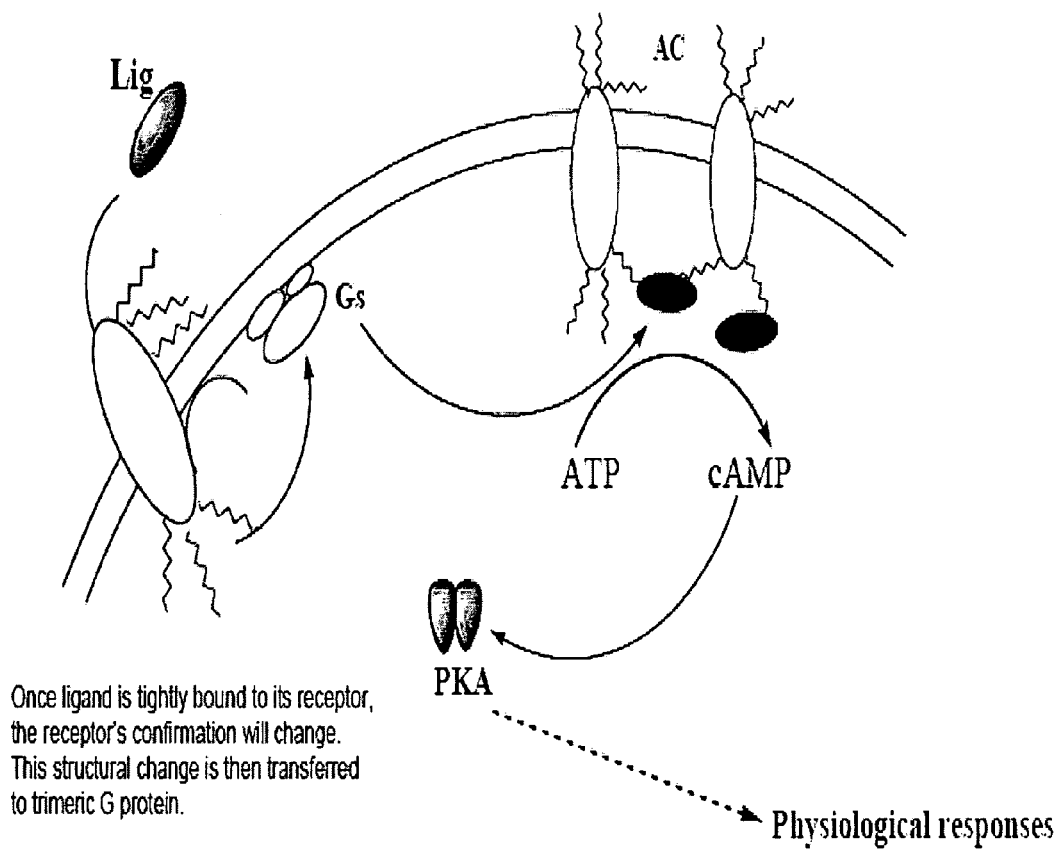
FIG. 2 shows the binding of a ligand to a biogenic amine receptor, resulting in downstream signaling affecting certain physiological responses.
Figure 3:
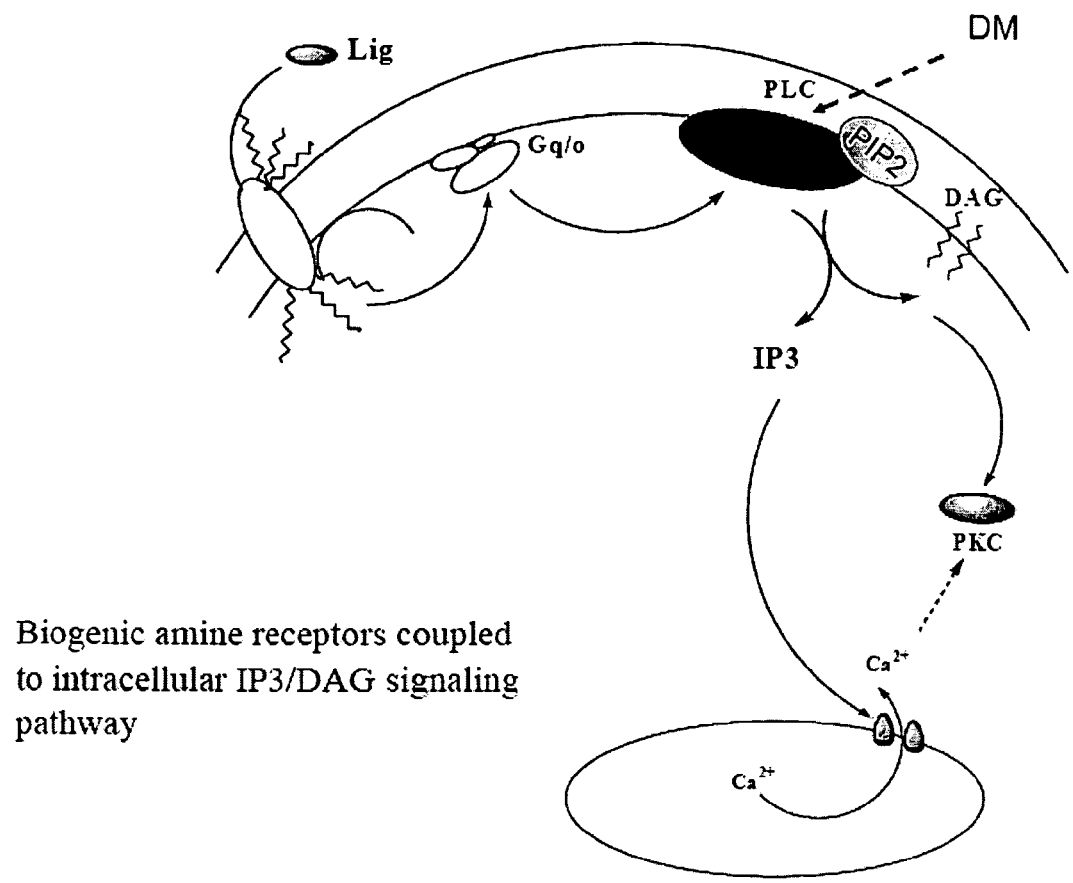
FIG. 3 shows an insect control chemical, deltamethrin (DM), affecting downstream signaling.

Embodiments of the present invention provide compositions for controlling a target pest.

The target pest can be selected from, for example, the group consisting of a fungus, a plant, an animal, a moneran, a protist, and the like. The target pest can be an arthropod species, such as, for example, an insect, an arachnid, or an arachnoid. The target pest can be a species belonging to an animal order, such as, for example, Acari, Anoplura, Araneae, Blattodea, Coleoptera, Collembola, Diptera, Grylloptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, Thysanoptera, and the like.

Embodiments of the invention are directed to methods of screening compositions for pest-control potential, compositions for controlling pests, and methods for using these compositions.

As used herein, "pests" can mean any organism whose existence it can be desirable to control. Pests can include, for example, bacteria, cestodes, fungi, insects, nematodes, parasites, plants, and the like.

As used herein, "pesticidal" can mean, for example, antibacterial, antifungal, antiparasitic, herbicidal, insecticidal, and the like.

Embodiments of the invention include compositions for controlling a target pest, which can include one or more plant essential oils and methods for using these compositions. The plant essential oils, when combined, can have a synergistic effect. The compositions also can include a fixed oil, which is typically a non-volatile non-scented plant oil. Additionally, in some embodiments, these compositions can be made up of generally regarded as safe (GRAS) compounds.

For purposes of simplicity, the term "insect" shall be used in this application; however, it should be understood that the term "insect" refers, not only to insects, but also to mites, spiders, and other arachnids, larvae, and like invertebrates. Also for purposes of this application, the term "insect control" shall refer to having a repellant effect, a pesticidal effect, or both. "Repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition. "Pesticidal effect" is an effect wherein treatment with a composition causes at least about 1% of the insects to die. In this regard, an LC1 to LC100 (lethal concentration) or an LD1 to LD100 (lethal dose) of a composition will cause a pesticidal effect. In some embodiments, the pesticidal effect is an effect wherein treatment with a composition causes at least about 5% of the exposed insects to die. In some embodiments, the target pest is a non-insect, such as a parasite.

Embodiments of the invention can be used to control parasites. As used herein, the term "parasite" includes parasites, such as but not limited to, protozoa, including intestinal protozoa, tissue protozoa, and blood protozoa.

In some embodiments, the pesticidal effect is an effect wherein treatment with a composition causes at least about 10% of the exposed insects to die. In some embodiments, the pesticidal effect is an effect wherein treatment with a composition causes at least about 25% of the insects to die. In some embodiments the pesticidal effect is an effect wherein treatment with a composition causes at least about 50% of the exposed insects to die. In some embodiments the pesticidal effect is an effect wherein treatment with a composition causes at least about 75% of the exposed insects to die. In some embodiments the pesticidal effect is an effect wherein treatment with a composition causes at least about 90% of the exposed insects to die.

In some embodiments of the invention, treatment with compositions of the invention will result in a knockdown of the target pest occurring within a few seconds to a few minutes. "Knockdown" is an effect wherein treatment with a composition causes at least about 1% to display reduced mobility. In some embodiments, the knockdown is an effect wherein treatment with a composition causes at least about 50% of the exposed insects to die.

The compositions of the present invention can be used to control target pest by either treating a host directly, or treating an area in which the host will be located, for example, an indoor living space, outdoor patio or garden. For purposes of this application, host is defined as a plant, human or other animal.

Treatment can include use of a oil-based formulation, a water-based formulation, a residual formulation, and the like. In some embodiments, combinations of formulations can be employed to achieve the benefits of different formulation types.

Embodiments of the invention are directed to compositions for controlling insects and methods for using these compositions. Compositions of the present invention can include any of the following oils, or mixtures thereof.

Embodiments of the invention are directed to compositions for controlling insects and methods for using these compositions. Compositions of the present invention can include any of the following oils, or mixtures thereof.

Methyl salicylate, also known as *betula* oil. Methyl salicylate is a major component of oil of wintergreen and is sometimes referred to interchangeably with oil of wintergreen. It is a natural product of many species of plants, is the methyl ester of salicylic acid, and can be produced chemically from the condensation reaction of salicylic acid and methanol. Some of the plants producing it are called wintergreens, hence the common name. Methyl salicylate can be used by plants as a pheromone to warn other plants of pathogens (Shulaev, et al. (Feb. 20, 1997) *Nature* 385: 718-721). The release of methyl salicylate can also function as an exopheromone aid in the recruitment of beneficial insects to kill the herbivorous insects (James, et al. (August 2004) *J. Chem. Ecol.* 30(8): 1613-1628). Numerous plants produce methyl salicylate including species of the family Pyrolaceae and of the genera *Gaultheria* and *Betula*. It is noted that, where a given blend or formulation or other composition is disclosed herein as containing wintergreen oil, an alternative embodiment, containing methyl salicylate in place of wintergreen oil, is also contemplated. Likewise, where a blend or forumlation of other composition includes methyl salicylate, an alternative embodiment, containing wintergreen oil, is also contemplated.

Thyme Oil is a natural product that can be extracted from certain plants, including species from the Labiatae family; for example, thyme oil can be obtained from *Thymus vulgaris* (also known as, *T. ilerdensis, T. aestivus,* and *T. velantianus*), generally by distillation from the leafy tops and tender stems of the plant. Two commercial varieties of Thyme oil are recognized, the 'red,' the crude distillate, which is deep orange in color, and the 'white,' which is colourless or pale yellow, which is the 'red' rectified by re-distilling. Thyme oil principally contains the phenols thymol and carvacrol, along with borneol, linalool, and cymene, and rosmarinic and ursolic acids. Where an embodiment describes the use of thyme oil white, other embodiments are specifically contemplated in which the thyme oil white is replaced by thyme oil red, thymol, carvacrol, borneol, linalool, cymene, rosmarinic acid, ursolic acid, or a mixture of any of these with each other or with thyme oil white. Particularly preferable are mixtures of thyme oil white and thyme oil red that contain 10% or less thyme oil red, more preferably 5% or less, and most preferably 1%.

Thymol is a monoterpene phenol derivative of cymene, $C_{10}H_{13}OH$, isomeric with carvacrol, found in thyme oil, and extracted as a white crystalline substance. It is also known as hydroxycymene and 5-methyl-2-(1-methylethyl) phenol. Where an embodiment describes the use of thymol, other embodiments are specifically contemplated in which the thymol is replaced by carvacrol, thyme oil white, thyme oil red, or a mixture of any of these with each other or with thyme oil white.

Lime oil is derived from Citrus *aurantifolia* (also known as Citrus *medica* var. *acida* and *C. latifolia*) of the Rutaceae family and is also known as Mexican and West Indian lime, as well as sour lime. Its chief constituents are α-pinene, β-pinene, camphene, myrcene, p-cymene, d-limonene, γ-terpinene, terpinolene, 1,8-ceneole, linalool, terpinene-4-ol, α-terpineol, neral, geraniol, neral acetate, geranyl acetate, caryophyllene, trans-α-bergamotene, β-Bisabolen, borneol, and citral. It can be obtained in several forms, including Lime Oil 410 (an artificial Mexican-exressed lime oil available from Millennium Specialty Chemicals). Where an embodiment describes the use of any form of lime oil, other embodiments are specifically contemplated in which the lime oil is replaced by α-pinene, β-pinene, camphene, myrcene, p-cymene, d-limonene, γ-terpinene, terpinolene, 1,8-ceneole, linalool, terpinene-4-ol, α-terpineol, neral, geraniol, neral acetate, geranyl acetate, caryophyllene, trans-α-bergamotene, β-Bisabolen, borneol, or citral, or a mixture of any of these with each other or with any form of lime oil.

Black seed oil is obtained from the seeds of *Nigella sativa*. Its chief constituents are carvone, α-pinene, sabinene, β-pinene, and p-cymene, as well as the fatty acids myristic acid, palmitic acid, palmitoleic acid, stearic acid, oleic acid, linoleic acid, linolenic acid, and arachidic acid. Where an embodiment describes the use of any form of black seed oil, other embodiments are specifically contemplated in which the black seed oil is replaced by d-carvone, l-carvone, a racemic mixture of d-carvone and l-carvone, α-pinene, sabinene, β-pinene, or p-cymene, or a mixture of any of these with each other, with any of myristic acid, palmitic acid, palmitoleic acid, stearic acid, oleic acid, linoleic acid, linolenic acid, or arachidic acid or with any form of black seed oil.

Linalool is a naturally-occurring terpene alcohol chemical found in many flowers and spice plants. It is also known as 3,7-dimethylocta-1,6-dien-3-ol. It has two stereoisomeric forms: (S)-(+)-linalool (known as licareol) and (R)-(−)-linalool (known as coriandrol). Linalool can be obtained as linalool coeur (a racemic mixture, CAS number 78-70-6), or in preferred derivative forms such as tetrahydrolinalool (the saturated form), ethyl linalool, linalyl acetate, and pseudo linalyl acetate (7-octen-2-ol, 2-methyl-6-methylene:acetate). Where an embodiment describes the use of any form of linalool, other embodiments are specifically contemplated in which the linalool is replaced by licareol, coriandrol, tetrahydrolinalool, ethyl linalool, linalyl acetate, pseudo linalyl acetate, or a mixture of any of these with each other or with any form of linalool. Similarly, where an embodiment describes the use of tetrahydrolinalool, other embodiments are specifically contemplated in which the tetrahydrolinalool is replaced by licareol, coriandrol, racemic linalool, ethyl linalool, linalyl acetate, pseudo linalyl acetate, or a mixture of any of these with each other or with tetrahydrolinalool. Additionally, where an embodiment describes the use of ethyl linalool, other embodiments are specifically contemplated in which the ethyl linalool is replaced by licareol, coriandrol, tetrahydrolinalool, racemic linalool, linalyl acetate, pseudo linalyl acetate, or a mixture of any of these with each other or with ethyl linalool. Finally, where an embodiment describes the use of linalyl acetate, other embodiments are specifically contemplated in which the linalyl acetate is replaced by licareol, coriandrol, tetrahydrolinalool, racemic linalool, ethyl linalool, pseudo linalyl acetate, or a mixture of any of these with each other or with linalyl acetate.

Geraniol, also called rhodinol and 3,7-dimethyl-2,6-octadien-1-ol, is a monoterpenoid and an alcohol. It is the primary part of oil-of-rose and palmarosa oil. It is used in perfumes and as a flavoring. It is also produced by the scent glands of honey bees to help them mark nectar-bearing flowers and locate the entrances to their hives. Geraniol can be obtained in a highly pure form as Geraniol Fine, FCC (Food Chemicals Codex grade), which is 98% minimum pure geraniol and 99% minimum nerol and geraniol. Geraniol can be also be obtained, for example, as Geraniol 60, Geraniol 85, and Geraniol 95. When Geraniol is obtained as Geraniol 60, Geraniol 85, or Geraniol 95, then about forty percent, fifteen percent, or five percent of the oil can be nerol. Nerol is a monoterpene ($C_{10}H_{18}O$), the cis-isomer of geraniol, which can be extracted from attar of roses, oil of orange blossoms and oil of lavender. Citral (3,7-dimethyl-2,6-octadienal or lemonal) is the generic name for the aldehyde form of nerol and geraniol, and can be obtained from lemon myrtly, Litsea cubeba, lemongrass, Lemon verbena, lemon balm, lemon, and orange. The E-isomer of citral is known as geranial or citral A. The Z-isomer is known as neral or citral B. Where an embodiment describes the use of any form of geraniol, other embodiments are specifically contemplated in which the geraniol is replaced by another form of geraniol (such as Geraniol Fine FCC or any geraniol/nerol mixture), nerol, geranial, neral, citral, or a mixture of any of these with each other or with any form of geraniol. Similarly, Where an embodiment describes the use of any form of citral, other embodiments are specifically contemplated in which the citral is replaced by a form of geraniol (such as Geraniol Fine FCC or any gernaiol/nerol mixture), nerol, geranial, neral, or a mixture of any of these with each other or with citral.

Vanillin (also known as methyl vanillin, vanillic aldehyde, vanillin, and 4-hydroxy-3-methoxybenzaldehyde) is the primary component of the extract of the vanilla bean. In addition to vanillin, natural vanilla extract also contains p-hydroxybenzaldehyde, vanillic acid, piperonal, and p-hydroxybenzoic acid. Synthetic vanillin is used as a flavoring agent in foods, beverages, and pharmaceuticals. Where an embodiment describes the use of vanillin, other embodiments are specifically contemplated in which the vanillin is replaced by natural vanilla extract, p-hydroxybenzaldehyde, vanillic acid, piperonal, ethyl vanillin, or p-hydroxybenzoic acid, or a mixture of any of these with each other or with vanillin.

Hercolyn-D is a solvent used to give oils high viscosity; it comprises the methyl esters of hydrogenated rosin acids and is available commercially from Hercules Corporation. Where an embodiment describes the use of Hercolyn D, other embodiments are specifically contemplated in which Hercolyn D may be replaced by other plasticizers such as Hercoflex 900, abalyn, abitol, castor oil, and mineral oil, or a mixture of any of these with each other or with Hercolyn D.

Isopropyl myristate is the ester of isopropanol and myristic acid; it is also known as 1-tetradecanoic acid, methylethyl ester, myristic acid isopropyl ester, and propan-2-yl tetradecanoate. Where an embodiment describes the use of isopropyl myristate, other embodiments are specifically contemplated in which isopropyl myristate may be replaced by similar chemicals such as isopropyl palmitate, isopropyl isothermal, putty stearate, isostearyl neopentonate, myristyl myristate, decyl oleate, octyl sterate, octyl palmitate, isocetyl stearate, or PPG myristyl propionate, or a mixture of any of these with each other or with isopropyl myristate.

Piperonal (heliotropine, protocatechuic aldehyde methylene ether) is an aromatic aldehyde that comes as transparent crystals, $C_8H_6O_3$, and has a floral odor. It is used as flavoring and in perfume. It can be obtained by oxidation of piperonyl alcohol. Where an embodiment describes the use of piperonal, other embodiments are specifically contemplated in which piperonal may be replaced by piperonyl alcohol, 3,4-methylenedioxybenzylamine, 3,4-methylenedioxymandelonitrile, piperonylic acid, piperonyl acetate, piperonylacetone, piperonylideneacetone, piperonyl isobutyrate, piperonyl butoxide, piperonylglycine, or protocatecheuic acid or a mixture of any of these with each other or with piperonal. Similarly, where an embodiment describes the use of piperonyl alcohol, other embodiments are specifically contemplated in which piperonyl alcohol may be replaced by piperonal, 3,4-methylenedioxybenzylamine, 3,4-methylenedioxymandelonitrile, piperonylic acid, piperonyl acetate, piperonylacetone, piperonylideneacetone, piperonyl isobutyrate, piperonyl butoxide, piperonylglycine, or protocatecheuic acid, or a mixture of any of these with each other or with piperonyl alcohol.

Hedione®, also known as methyl dihydrojasmonate and cyclopentaneacetic acid, 3-oxo-2-pentyl-, methyl ester, is a compound developed in 1959 that is frequently used to impart a jasmine scent in perfumes. The most olfactorily active stereoisomer is (+)-cis-Hedione®. Where an embodiment describes the use of Hedione®, other embodiments are specifically contemplated in which Hedione® may be replaced by any of its stereoisomers, or any mixture thereof.

Triethyl citrate (also known as citric acid, triethyl ester; TEC; ethyl citrate; 2-hydroxy-1,2,3-propanetricarboxylic acid, triethyl ester; and Citroflex 2) is used as a high boiling solvent and plasticizer for vinyl resins and cellulose acetates. It is a plasticizer permitted in the field of food additives, food contact materials, medicines, and pharmaceuticals. Where an embodiment describes the use of triethyl citrate, other embodiments are specifically contemplated in which triethyl citrate may be replaced by other citrate plasticiser esters such as tributyl citrate, acetyl tributyl citrate and tri-(2-ethylhexyl)-citrate, or a mixture of any of these with each other or with triethyl citrate.

The terpinenes are isomeric hydrocarbons classified as terpenes. Some members of this group are used in a wide variety of flavor and fragrance compositions, as well as in extensions of citrus oils. Gamma-terpinene is also known as 1-isopropyl-4-methyl-1,4-cyclohexadiene, 4-methyl-1-(1-methylethyl)-1,4-cyclohexadiene, and p-mentha-1,4-diene. Alpha-terpinene is also known as 4-methyl-1-(1-methylethyl)-1,3-cyclohexadiene. Both alpha- and gamma-terpinene have a lemony fragrance. Beta-terpinene, also known as 4-methylene-1-(1-methylethyl)cyclohexene, has been prepared from sabinene. A derivative, terpinene-4-ol, is the primary active ingredient of tea tree oil and the compound of highest concentration in essential oil of nutmeg. Other monoterpene alcohol derivatives of the erpinenes include the α-, β-, and γ-terpineol isomers; the α-terpineol isomer is the major component of the naturally isolated terpineol. Other related compounds are terpinolene (4-Isopropylidene-1-methylcyclohexene; p-Menth-1,4(8)-diene; 1-Methyl-4-(1-methylethylidene)cyclohexene; 1-Methyl-4-propan-2-ylidenecyclohexene), and the isomers α-phellandrene and β-phellandrene. Where an embodiment describes the use of gamma-terpinene, other embodiments are specifically contemplated in which gamma-terpinene may be replaced by other terpinenes or derivatives thereof such as terpinolene, α-phellandrene, β-phellandrene, alpha-terpinene, beta-terpinene, α-terpineol, β-terpineol, γ-terpineol, or terpinene-4-ol, or a mixture of any of these with each other or with gamma-terpinene. Where an embodiment describes the use of alpha-terpinene, other embodiments are specifically contemplated in which alpha-terpinene may be replaced by other terpinenes or derivatives thereof such as terpinolene, α-phellandrene, p-phellandrene, gamma-terpinene, beta-terpinene, α-terpineol, (β-terpineol, γ-terpineol, or terpinene-4-ol, or a mixture of any of these with each other or with alpha-terpinene. Where an embodiment describes the use of terpinene-4-ol, other embodiments are specifically contemplated in which terpinene-4-ol may be replaced by other terpinenes or derivatives thereof such as terpinolene, α-phellandrene, β-phellandrene, alpha-terpinene, beta-terpinene, α-terpineol, (β-terpineol, γ-terpineol, or gamma-terpinene, or a mixture of any of these with each other or with terpinene-4-ol. Where an embodiment describes the use of α-terpineol, other embodiments are specifically contemplated in which α-terpineol may be replaced by other terpinenes or derivatives thereof such as terpinolene, α-phellandrene, β-phellandrene, alpha-terpinene, beta-terpinene, terpinene-4-ol, (β-terpineol, γ-terpineol, or gamma-terpinene, or a mixture of any of these with each other or with α-terpineol. Where an embodiment describes the use of terpinolene, other embodiments are specifically contemplated in which terpinolene may be replaced by other terpinenes or derivatives thereof such as α-terpineol, α-phellandrene, β-phellandrene, alpha-terpinene, beta-terpinene, terpinene-4-ol, β-terpineol, γ-terpineol, or gamma-terpinene, or a mixture of any of these with each other or with terpinolene.

The pinenes encompass the isomeric forms α-pinene and β-pinene; both are important constituents of pine resin. Important pinene derivatives include the bicyclic ketones verbenone and chrysanthone. Where an embodiment describes the use of α-pinene, other embodiments are specifically contemplated in which α-pinene may be replaced by β-pinene, verbenone, or chrysanthone, or a mixture of any of these with each other or with α-pinene. Where an embodiment describes the use of β-pinene, other embodiments are specifically contemplated in which β-pinene may be replaced by α-pinene, verbenone, or chrysanthone, or a mixture of any of these with each other or with β-pinene.

Cymene is a monoterpene-related hydrocarbon, consisting of a benzene ring substituted with a methyl group and an isopropyl group. The para-substituted form occurs naturally and is a component of oil of cumin and thyme. The ortho- and meta-substituted also exist, but are less common. Where an embodiment describes the use of p-cymene, other embodiments are specifically contemplated in which terpinolene may be replaced by o-cymene or m-cymene, or a mixture of any of these with each other or with p-cymene.

Trans-anethole (also known as anethole, p-propenylanisole, anise camphor, isoestragole, or oil of aniseed) is an aromatic unsaturated ether that accounts for the licorice flavor of anise and fennel. It forms white crystals at room temperature and is closely related to estragole, its double-bond isomer, chavicol (p-allylphenol, the phenol analog), and safrole (shikimol), a methylenedioxy analog found in sassafras oil. Where an embodiment describes the use of t-anethole, other embodiments are specifically contemplated in which t-anethole may be replaced by estragole, chavicol, safrole, or a mixture of any of these with each other or with t-anethole.

Citronella oil is classified into two chemotypes. The Ceylon type obtained from *Cymbopogon nardus* Rendle consists of geraniol, limonene, methyl isoeugenol, citronellol, and citronellal. The Java type obtained from *Cymbopogon winterianus* Jowitt consists of citronellal, geraniol, geranyl acetate, and limonene. Where an embodiment describes the use of citronella oil, either they Ceylon type or the Java type may be used. Furthermore, where an embodiment describes the use of citronella oil, other embodiments are specifically contemplated in which citronella oil may be replaced by geraniol, limonene, methyl isoeugenol, citronellol, citronellal, geranyl acetate, or a mixture of any of these with each other or with citronella oil.

Borneol is a terpene and a bicyclic organic compound which exists as two enantiomers, d-borneol and l-borneol. Isoborneol is the exo isomer of borneol. Borneol can be oxidized to the ketone camphor, which exists in the optically active dextro and levo forms. Significant camphor derivatives are norcamphor and camphene. Where an embodiment describes the use of l-borneol, other embodiments are specifically contemplated in which l-borneol may be replaced by d-borneol, racemic borneol, isoborneol, d-camphor, l-camphor, racemic camphor, norcamphor, camphene, or a mixture of any of these with each other or with l-borneol. Where an embodiment describes the use of isoborneol, other embodiments are specifically contemplated in which isoborneol may be replaced by d-borneol, racemic borneol, l-borneol, d-camphor, l-camphor, racemic camphor, norcamphor, camphene, or a mixture of any of these with each other or with isoborneol. Where an embodiment describes the use of d-camphor, other embodiments are specifically contemplated in which d-camphor may be replaced by d-borneol, l-borneol, racemic borneol, isoborneol, l-camphor, racemic camphor, norcamphor, camphene, or a mixture of any of these with each other or with d-camphor. Where an embodiment describes the use of camphene, other embodiments are specifically contemplated in which camphene may be replaced by d-borneol, l-borneol, racemic borneol, isoborneol, d-camphor, l-camphor, racemic camphor, norcamphor, camphene, or a mixture of any of these with each other or with camphene.

Myrcene is a monoterpene that exists in nature as the structural form β-myrcene and is obtained from the essential oils of bay, verbena, and myrcia. The α-myrcene form is a structural isomer not found in nature. Where an embodiment describes the use of myrcene, this signifies the β-myrcene form, but other embodiments are specifically contemplated in which β-myrcene is replaced with α-myrcene or a mixture of α-myrcene and β-myrcene.

Other ingredients, including but not limited to black seed oil, borneol, camphene, carvacrol, β-caryophyllene, triethyl-citrate, p-cymene, hedion, heliotropine, hercolyn D, lilac flower oil, lime oil, limonene, linalool, ethyl-linalool, tetrahydro-linanool, α-pinene, β-pinene, piperonal, piperonyl alcohol, α-terpinene, tert-butyl-p-benzoquinone, α-thujene, and triethyl citrate can also be included in the compositions of the present invention.

In addition, the use of several long-chain aldehydes, such as octanal, nonanal, decanal, and dodecanal. Where an embodiment describes the use of one such aldehyde, other embodiments are specifically contemplated in which the designated aldehyde is replaced with any of the other aldeydes, or a mixture of any of these aldehydes with each other or with the designated aldehyde.

Tocopherols are a class of chemicals consisting of various methylated phenols, some of which have vitamin E activity. These include α-tocopherol, β-tocopherol, γ-tocopherol, and δ-tocopherol. Also belonging to this family are the tocotrienols, including α-tocotrienol, β-tocotrienol, γ-tocotrienol, and δ-tocotrienol. In preferred embodiments, mixtures of these compositions, such as tocopherol gamma tenox or Tenox GT, are employed. Where an embodiment describes the use of one tocopherol, other embodiments are specifically contemplated in which the designated tocopherol is replaced with any of the other tocopherols, or a mixture of any of these tocopherols with each other or with the designated tocopherol.

Certain mixtures of liquefied hydrocarbons, such as propellants A-46, A-70, or 142A may be used as propellants in embodiments of spray mixtures. Where an embodiment describes the use of one propellant, other embodiments are specifically contemplated in which the designated propellant is replaced with any of the other propellant, or a mixture of any of these propellants with each other or with the designated propellant.

In certain exemplary compositions of the invention that include lilac flower oil, one or more of the following compounds can be substituted for the lilac flower oil: tetrahydrolinalool; ethyl linalool; heliotropine; hedion; hercolyn D; and triethyl citrate. In certain exemplary compositions of the invention that include black seed oil, one or more of the following compounds can be substituted for the black seed oil: alpha-thujene: alpha-pinene; Beta-pinene; p-cymene; limonene; and tert-butyl-p-benzoquinone. In certain exemplary compositions of the invention that include thyme oil, one or more of the following compounds can be substituted for the thyme oil: thymol, α-thujone; α-pinene, camphene, β-pinene, p-cymene, α-terpinene, linalool, borneol, β-caryophyllene, and carvacrol. In certain exemplary embodiments of the invention that include methyl salicylate, oil of wintergreen can be substituted for the methyl salicylate. In certain exemplary embodiments of the invention that include oil of wintergreen, methyl salicylate can be substituted for the oil of wintergreen.

D-limonene is the main odour constituent of citrus (plant family Rutaceae), and is found in, among other citrus oils, lemon oil, lime oil, and orange oil. Where an embodiment describes the use of d-limonene, other embodiments are specifically contemplated in which the d-limonene is replaced by lemon oil, orange oil, lime oil, citrus oil, l-limonene, or dipentene (the racemic mixture of d-limonene and l-limonene).

In certain exemplary compositions of the invention that include lilac flower oil, one or more of the following compounds can be substituted for the lilac flower oil: tetrahydrolinalool; ethyl linalool; heliotropine; hedion; hercolyn D; and triethyl citrate. In certain exemplary compositions of the invention that include black seed oil, one or more of the following compounds can be substituted for the black seed oil: alpha-thujene: alpha-pinene; Beta-pinene; p-cymene; limonene; and tert-butyl-p-benzoquinone. In certain exemplary compositions of the invention that include thyme oil, one or more of the following compounds can be substituted for the thyme oil: thymol, α-thujone; α-pinene, camphene, β-pinene, p-cymene, α-terpinene, linalool, borneol, β-caryophyllene, and carvacrol. In certain exemplary embodiments of the invention that include methyl salicylate, oil of wintergreen can be substituted for the methyl salicylate. In certain exemplary embodiments of the invention that include oil of wintergreen, methyl salicylate can be substituted for the oil of wintergreen.

Oils used to prepare the exemplary compositions of the present invention can be obtained, for example, from the following sources: Millennium Specialty Chemical (Jacksonville, Fla.), Ungerer Company (Lincoln Park, N.J.), SAFC (Milwaukee, Wis.), and IFF Inc. (Hazlet, N.J.).

Exemplary embodiments of the invention also can include isopropyl myristate, which is an ester of isopropyl alcohol and myristic acid, is used as a thickening agent and emollient.

In those compositions including more than one oil, each oil can make up between about 0.1%, or less, to about 99%, or more, by weight, of the composition mixture. For example, one composition of the present invention comprises about 1% thymol and about 99% geraniol. Optionally, the compositions can additionally comprise a fixed oil, which is a non-volatile non-scented plant oil. Fixed oils useful in the formulations of the present invention include, but are not limited to, castor oil, corn oil, cumin oil, mineral oil, olive oil, peanut oil, safflower oil, sesame oil, and soy bean oil.

In certain exemplary embodiments, insect control compositions according to the invention include at least one of methyl salicylate, thyme oil, thymol, and/or geraniol. In other exemplary embodiments, insect control compositions include at least two of methyl salicylate, thyme oil, thymol, and/or geraniol. In other exemplary embodiments, insect control compositions according to the invention include methyl salicylate, thymol, and geraniol.

While embodiments of the invention can include active ingredients, carriers, inert ingredients, and other formulation components, preferred embodiments begin with a primary blend. A primary blend is preferably a synergistic combination containing two or more active ingredients and, optionally, additional ingredients. The primary blends can then be combined with other ingredients to produce a formulation. Accordingly, where concentrations, concentration ranges, or amounts, are given herein, such quantities typically are in reference to a primary blend or blends. Thus, when a primary blend is further modified by addition of other ingredients to produce a formulation, the concentrations of the active ingredients are reduced proportional to the presence of other ingredients in the formulation.

In preferred blends, methyl salicylate can be included at a concentration of between 10% or less to 60% or more; at a concentration of between 15%-50%; at a concentration of between 20%-45%; or at a concentration of about 39% by weight.

Thymol can be included at a concentration of between 5% or less to 40% or more; at a concentration of between 15%-25%; or at a concentration of about 20% by weight.

Thyme Oil can be included at a concentration of between 5% or less to 40% or more, at a concentration of between 15%-25%, or at a concentration of about 20% by weight. Geraniol can be included at a concentration of between 5% or less to 40% or more, at a concentration of 15%-25%, or at a concentration of about 20% by weight.

In certain exemplary embodiments, the following active ingredients can be provided at the following concentrations, expressed as a percentage by weight 39% Methyl salicylate; 20% Thymol (crystal); and 20% Geraniol 60. In other exemplary embodiments, the following active ingredients can be provided at the following concentrations: 39% Methyl salicylate; 20% Thyme Oil; and 20% Geraniol 60. In other exemplary embodiments, the following active ingredients can be provided at the following concentrations: 39% Methyl salicylate; 20% Thyme Oil; and 20% Geraniol 85. In other exemplary embodiments, the following active ingredients can be provided at the following concentrations: 39% Methyl salicylate; 20% Thyme Oil; and 20% Geraniol 95. Other exemplary embodiments are shown in the tables provided below.

In exemplary embodiments, the insect control formulation also includes isopropyl myristate at a concentration of between 10-30%, more preferably 15-25%, and most preferably about 20%. Vanillin is included, preferably at a concentration between 0.5 and 4%, most preferably about 1%.

In exemplary embodiments of the invention, thymol is present in crystal form. By using the crystal form, the more volatile components of the insect control composition are stabilized and remain in the area requiring insect control for a longer period. This is explained in U.S. Provisional Application No. 60/799,434, filed May 10, 2006 which is incorporated in its entirety herein by reference. Of course, other components can be included to stabilize the insect control composition. The stabilizer can be a crystal powder, dust, granule or other form which provides an absorption surface area for the insect control composition. Other plant essential oils that are crystalline at room temperature and can be used as stabilizers in formulations of the invention include but are not limited to cinnamic alcohol crystals, salicylic acid crystals, cedrol crystals, piperonal crystals, piperonyl alcohol crystals, (s)-cis-verbenol crystals and DL-menthol crystals which are all crystalline at room temperature. Another stabilizer that can be used is a crystal of Winsense WS-3, cyclohexanecarboxamide, N-methyl-2-(1-methylethyl) and Winsense WE-23, (N-2,3-trimethyl-2-isopropylbutamide) and the like. Another useful stabilizer is talc powder.

In order to produce the stabilized formulation, the stabilizer and the insect-control composition are mixed to allow the stabilizer to become coated with the composition as described in U.S. Provisional Application No. 60/799,434, mentioned above.

The compositions of the present invention can comprise, in admixture with a suitable carrier and optionally with a suitable surface active agent, plant essential oil compounds and/or derivatives thereof, natural and/or synthetic, including racemic mixtures, enantiomers, diastereomers, hydrates, salts, solvates and metabolites, etc.

A suitable carrier can include any carrier in the art known for plant essential oils, provided the carrier does not adversely effect the compositions of the present invention. The term "carrier" as used herein means an inert or fluid material, which can be inorganic or organic and of synthetic or natural origin, with which the active compound is mixed or formulated to facilitate its application to the container or carton or other object to be treated, or to facilitate its storage, transport and/or handling. In general, any of the materials customarily employed in formulating repellents, pesticides, herbicides, or fungicides, are suitable. The compositions of the present invention can be employed alone or in the form of mixtures with such solid and/or liquid dispersible carrier vehicles and/or other known compatible active agents such as other repellants, pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The compositions of the present invention can be formulated or mixed with, if desired, conventional inert pesticide diluents or extenders of the type usable in conventional insect control agents, e.g., conventional dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

The compositions of the present invention can further comprise surface-active agents. Examples of surface-active agents that can be employed with the present invention, include emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents such as lignin, sulfite waste liquors, methyl cellulose, etc.

In some embodiments, water-based formulations are preferred. Although oil-based formulations of insect-control agents are generally more effective, water-based formulations have the advantage that they do not leave behind an oily residue on treated surfaces. Preparation of water-based formulations for insect control are disclosed in U.S. Provisional Application No. 60/747,592, filed May 18, 2006, which is incorporated in its entirety herein by reference.

In certain embodiments, water-based formulations are provided wherein water and a surfactant comprise between about 1% to about 99%, by weight, of the composition mixture. For example, one composition of the present invention comprises about 1% water and surfactant and about 99% of a composition, including: about 39% Methyl salicylate; about 20% Thymol (crystal); about 20% Geraniol 60; and about 1% Vanillin. For another example, one composition of the present invention comprises about 50% water and surfactant and about 50% of a composition, including: about 39% Methyl salicylate; about 20% Thymol (crystal); about 20% Geraniol 60; and about 1% Vanillin.

The surfactant of the water-based formulation is provided to facilitate mixture of the insect-control composition with the water. The surfactant may include an end having a carboxyl group, which will face the water molecules, and a hydrocarbon end, which will face an oil component of the insect-control composition. As such, the surfactant allows the water and the oil component of the composition to be mixed to form an emulsion. Various surfactants may be used in the formulation of the present invention, for example, sodium lauryl sulfate (SLS, anionic), chlorhexidine (CLH, cationic), and Poloxamer 407 (POL407, nonionic), Sodium dodecylsulfate (SDS), Sodium cholate, Sodium deoxycholate, N-Lauroylsarcosine, Lauryldimethylamine-oxide (LDAO), Cetyltrimethylammoniumbromide (CTAB), Bis(2-ethylhexyl)sulfosuccinate, or mixtures thereof.

The solvent of the water-based formulation serves to reduce the water-oil surface tension of the emulsion. By reducing this surface tension, the oil spots are more readily dispersed in the water, and a thin film of the oil-water mixture is allowed to form on the treated surfaces, which surfaces may include areas within a household, outdoor areas, plants and the insects themselves. The solvent may also serve as a carrier and a synergist. The solvent may assist in fast penetration through the cell membrane of an insect being controlled to ensure the arrival of sufficient active ingredients to the site of action. Various solvents may be used, for example, isopar M, isopar C, or mixtures thereof.

To produce the water-based formulation, the insect-control composition containing one or more plant essential oils is mixed with water to create a slurry. The surfactant is then added to create certain embodiments of the water-based formulation. To create other embodiments of the water-based formulation, the solvent is then added. The final concentration of the insect-control composition in the formulation may be, for example, about 10-25%. The final concentration of the surfactant in the formulation may be, for example, about 1-10%. The final concentration of the solvent in the formulation may be, for example, 0 to about 10%. Some embodiments of the present invention are characterized by rapid killing, e.g., kill-on-contact, and some embodiments are characterized by residual effects, i.e., formulation remains on treated surface affecting insect control for an extended period of time. In the case of the embodiment characterized by residual effects, it should be noted that the solvent-component of the formulation is not necessary. In such embodiments of the invention, the formulation includes: water, an insect-control composition, a surfactant, and a stabilizer, such as the one described in the patent application entitled, "Formulations of Insect-Control Compositions having Residual Activity and Methods for Production and Use Thereof," filed on May 10, 2005. Such embodiments may optionally include the solvent described herein.

Once the water-based formulation has been prepared, it may be applied to a desired area to affect insect control in that area. Once applied, it will form a thin film on the treated surfaces, adhering thereto and providing effective insect control. The formulation may be applied to the area in a variety of manners known in the art, for example, the formulation may be prepared as an aerosol or trigger spray.

In certain exemplary embodiments, the present invention encompasses a mixture of an insect control composition including one or more plant essential oils with a carrier. For example, embodiments of the present invention can include a carrier having a surface area, with the insect-control composition coated on the surface area of the carrier. The carrier may be, for example, crystals, powder, dust, granules or the like, which provides an absorption surface area for the insect-control compositions. One example of a carrier that can be used in accordance with the present invention is diatomaceous earth (DE). DE is a naturally occurring sedimentary rock that is easily crumbled into a fine powder. This powder has an abrasive feel, similar to pumice powder, and is very light, due to its high porosity. Diatomaceous earth consists of fossilized remains of diatoms, a type of hard-shelled algae.

To produce certain embodiments of the present invention, the carrier and the insect-control composition are mixed to allow the carrier to become coated with the composition. In some embodiments of the invention, after the carrier has been coated with the insect-control composition to form the formulation, the formulation can be applied to a desired area to affect insect control in that area. Because the carrier reduces the volatility of the insect-control composition, the composition will remain active in the desired area for an amount of time that is greater than the time the composition, alone, i.e., unformulated composition, would remain in the desired area. As such, the formulation continues to provide insect-control after the time by which the composition, alone, would have volatilized.

In certain embodiments, the insect control compositions can be combined with one or more synthetic pesticides such as a pyrethroid, a chloronicotinyl insecticide, and a neonicotinoid. For example, the insect control blends in one embodiment are combined with deltamethrin, clothianidin, or imidacloprid. Delatmethrin is available from AgrEvo Environmental Health, Inc., Montvale, N.J. Clothianidin and imidacloprid are available from Bayer CropScience LP, Research Triangle Park, N.C.

Embodiments of the present invention can be used to control insects by treating an area directly. For example, the area can be treated by spreading the formulation, for example, manually, automatically, with a fertilizer spreader, or the like.

The compositions of the present invention can be used to control insects by either treating a host directly, or treating an area in which the host will be located. For example, the host can be treated directly by using a cream or spray formulation, which can be applied externally or topically, e.g., to the skin of a human. A composition can be applied to the host, for example, in the case of a human, using formulations of a variety of personal products or cosmetics for use on the skin or hair. For example, any of the following can be used: fragrances, colorants, pigments, dyes, colognes, skin creams, skin lotions, deodorants, talcs, bath oils, soaps, shampoos, hair conditioners and styling agents.

The compositions of a select number of specifically contemplated embodiments of the present invention are shown in Table 1. This table lists these blends with a specific Blend Number. These blends can be used as components of other synergistic blends. In embodiments containing other blends as listed herein, Blend Numbers refer to the blends as listed in Table 1.

In some embodiments, the blend of compounds can include at least two of the group consisting of Lilac Flower Oil (LFO), D-Limonene, Thyme Oil White, and Blend 61 (see Table 1).

In some embodiments, the blend of compounds can include at least three of the group consisting of Lilac Flower Oil (LFO), D-Limonene, Thyme Oil White, and Blend 61.

In some embodiments, the blend of compounds can include Lilac Flower Oil (LFO), D-Limonene, Thyme Oil White, and Blend 61.

In some embodiments, the blend of compounds can include between 2 and 8% Lilac Flower Oil (LFO), between 60 and 99% D-Limonene, between 1 and 7% Thyme Oil White, and between 4 and 16% Blend 61.

In some embodiments, the blend of compounds can include between 4 and 5% Lilac Flower Oil (LFO), between 75 and 90% D-Limonene, between 3 and 4% Thyme Oil White, and between 8 and 12% Blend 61.

In some embodiments, the blend of compounds can include 4.40% LFO, 82.3% D-Limonene, 3.3% Thyme Oil White, and 10.0% Blend 61.

In some embodiments, the blend of compounds can include at least two of the group consisting of D-Limonene, Thyme Oil White, Linalool Coeur, Tetrahydrolinalool, Vanillin, Isopropyl myristate, Piperonal (aldehyde), Blend 62 (see Table 1), Geraniol 60, and Triethyl Citrate.

In some embodiments, the blend of compounds can include at least four of the group consisting of D-Limonene, Thyme Oil White, Linalool Coeur, Tetrahydrolinalool, Vanillin, Isopropyl myristate, Piperonal (aldehyde), Blend 62, Geraniol 60, and Triethyl Citrate.

In some embodiments, the blend of compounds can include D-Limonene, Thyme Oil White, Linalool Coeur, Tetrahydrolinalool, Vanillin, Isopropyl myristate, Piperonal (aldehyde), Blend 62, Geraniol 60, and Triethyl Citrate.

In some embodiments, the blend of compounds can include between 60 and 99% D-Limonene, between 1 and 6% Thyme Oil White, between 0.1 and 1.0% Linalool Coeur, between 0.4 and 1.5% Tetrahydrolinalool, between 0.01 and 0.1% Vanillin, between 0.5 and 1.5% Isopropyl myristate, between 0.3 and 1.3% Piperonal (aldehyde), between 5 and 15% Blend 62, between 0.1 and 0.9% Geraniol 60, and between 0.3 and 1.3% Triethyl Citrate.

In some embodiments, the blend of compounds can include between 75 and 90% D-Limonene, between 2.5 and 4% Thyme Oil White, between 0.5 and 0.65% Linalool Coeur, between 0.7 and 0.9% Tetrahydrolinalool, between 0.04 and 0.06% Vanillin, between 0.7 and 0.9% Isopropyl myristate, between 0.7 and 0.9% Piperonal (aldehyde), between 9 and 11% Blend 62, between 0.35 and 0.5% Geraniol 60, and between 0.7 and 0.9% Triethyl Citrate.

In some embodiments, the blend of compounds can include 82.52% D-Limonene, 3.28% Thyme Oil White, 0.57% Linalool Coeur, 0.78% Tetrahydrolinalool, 0.05% Vanillin, 0.80% Isopropyl myristate, 0.80% Piperonal (aldehyde), 9.99% Blend 62, 0.41% Geraniol 60, and 0.80% Triethyl Citrate.

In some embodiments, the blend of compounds can include at least two of the group consisting of Black Seed Oil (BSO), Linalool Coeur, Tetrahydrolinalool, Vanillin, Isopropyl myristate, Piperonal (aldehyde), and Geraniol Fine FCC.

In some embodiments, the blend of compounds can include at least four of the group consisting of Black Seed Oil (hereinafter referred to as BSO), Linalool Coeur, Tetrahydrolinalool, Vanillin, Isopropyl myristate, Piperonal (aldehyde), and Geraniol Fine FCC.

In some embodiments, the blend of compounds can include BSO, Linalool Coeur, Tetrahydrolinalool, Vanillin, Isopropyl myristate, Piperonal (aldehyde), and Geraniol Fine FCC.

In some embodiments, the blend of compounds can include between 10 and 30% BSO, between 5 and 25% Linalool Coeur, between 5 and 30% Tetrahydrolinalool, between 0.8 and 3% Vanillin, between 15 and 30% Isopropyl myristate, between 4 and 10% Piperonal (aldehyde), and between 2 and 20% Geraniol Fine FCC.

In some embodiments, the blend of compounds can include between 15 and 25% BSO, between 10 and 20% Linalool Coeur, between 15 and 23% Tetrahydrolinalool, between 1.5 and 2.5% Vanillin, between 20 and 25% Isopropyl myristate, between 6 and 8% Piperonal (aldehyde), and between 5 and 15% Geraniol Fine FCC.

In some embodiments, the blend of compounds can include 21.50% BSO, 15.90% Linalool Coeur, 19.00% Tetrahydrolinalool, 1.80% Vanillin, 23.50% Isopropyl myristate, 7.80% Piperonal (aldehyde), and 10.50% Geraniol Fine FCC.

In some embodiments, the blend of compounds can include at least two of the group consisting of D-Limonene, BSO, Linalool Coeur, Tetrahydrolinalool, Vanillin, Isopropyl myristate, Piperonal (aldehyde), Geraniol Fine FCC, and Methyl Salicylate 98% Nat.

In some embodiments, the blend of compounds can include at least four of the group consisting of D-Limonene, BSO, Linalool Coeur, Tetrahydrolinalool, Vanillin, Isopropyl myristate, Piperonal (aldehyde), Geraniol Fine FCC, and Methyl Salicylate 98% Nat.

In some embodiments, the blend of compounds can include D-Limonene, BSO, Linalool Coeur, Tetrahydrolinalool, Vanillin, Isopropyl myristate, Piperonal (aldehyde), Geraniol Fine FCC, and Methyl Salicylate 98% Nat.

In some embodiments, the blend of compounds can include between 5 and 15% D-Limonene, between 20 and 35% BSO, between 3 and 10% Linalool Coeur, between 4 and 15% Tetrahydrolinalool, between 0.2 and 1.5% Vanillin, between 5 and 15% Isopropyl myristate, between 1 and 5% Piperonal (aldehyde), between 1 and 10% Geraniol Fine FCC, and between 20 and 45% Methyl Salicylate 98% Nat.

In some embodiments, the blend of compounds can include between 8 and 10% D-Limonene, 24 and 28.5% BSO, 5.5 and 7.0% Linalool Coeur, between 7 and 9% Tetrahydrolinalool, between 0.7 and 0.9% Vanillin, between 8.5 and 10.5% Isopropyl myristate, between 2.8 and 3.6% Piperonal (aldehyde), between 3.8 and 5% Geraniol Fine FCC, and between 29 and 37% Methyl Salicylate 98% Nat.

In some embodiments, the blend of compounds can include 8.80% D-Limonene, 26.20% BSO, 6.40% Linalool Coeur, 7.80% Tetrahydrolinalool, 0.80% Vanillin, 9.50% Isopropyl myristate, 3.20% Piperonal (aldehyde), 4.30% Geraniol Fine FCC, and 33.00% Methyl Salicylate 98% Nat.

In some embodiments, the blend of compounds can include at least two of the group consisting of Thyme Oil White, Wintergreen Oil, Vanillin, and Isopropyl myristate.

In some embodiments, the blend of compounds can include at least three of the group consisting of Thyme Oil White, Wintergreen Oil, Vanillin, and Isopropyl myristate.

In some embodiments, the blend of compounds can include Thyme Oil White, Wintergreen Oil, Vanillin, and Isopropyl myristate.

In some embodiments, the blend of compounds can include between 12 and 30% Thyme Oil White, between 30 and 60% Wintergreen Oil, between 0.5 and 2% Vanillin, and between 25 and 45% Isopropyl myristate.

In some embodiments, the blend of compounds can include between 18 and 23% Thyme Oil White, between 40 and 50% Wintergreen Oil, between 1 and 1.2% Vanillin, and between 30 and 37% Isopropyl myristate.

In some embodiments, the blend of compounds can include 20.50% Thyme Oil White, 45.00% Wintergreen Oil, 1.10% Vanillin, and 33.40% Isopropyl myristate.

In some embodiments, the blend of compounds can include at least one of the group consisting of D-Limonene, Thyme Oil White, and Wintergreen Oil (Technical grade).

In some embodiments, the blend of compounds can include at least two of the group consisting of D-Limonene, Thyme Oil White, and Wintergreen Oil (Technical grade).

In some embodiments, the blend of compounds can include D-Limonene, Thyme Oil White, and Wintergreen Oil (Technical grade).

In some embodiments, the blend of compounds can include between 40 and 70% D-Limonene, between 5 and 20% Thyme Oil White, and between 20 and 40% Wintergreen Oil (Technical grade).

In some embodiments, the blend of compounds can include between 50 and 62% D-Limonene, between 10.5 and 13.5% Thyme Oil White, and between 28 and 35% Wintergreen Oil (Technical grade).

In some embodiments, the blend of compounds can include 56.30% D-Limonene, 12.38% Thyme Oil White, and 31.32% Wintergreen Oil (Technical grade).

In some embodiments, the blend of compounds can include at least two of the group consisting of LFO, D-Limonene, Thyme Oil White, and Blend 61.

In some embodiments, the blend of compounds can include at least three of the group consisting of LFO, D-Limonene, Thyme Oil White, and Blend 61.

In some embodiments, the blend of compounds can include LFO, D-Limonene, Thyme Oil White, and Blend 61.

In some embodiments, the blend of compounds can include between 8 and 18% LFO, between 5 and 12% D-Limonene, between 5 and 15% Thyme Oil White, and between 55 and 80% Blend 61.

In some embodiments, the blend of compounds can include between 11.5 and 14.5% LFO, between 7.9 and 9.5% D-Limonene, between 8.5 and 10.6% Thyme Oil White, and between 61 and 76% Blend 61.

In some embodiments, the blend of compounds can include 12.94% LFO, 8.72% D-Limonene, 9.58% Thyme Oil White, and 68.76% Blend 61.

In some embodiments, the blend of compounds can include at least five of the group consisting of LFO, D-Limonene, Thyme Oil White, between Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include at least ten of the group consisting of LFO, D-Limonene, Thyme Oil White, between Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include LFO, D-Limonene, Thyme Oil White, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include between 7 and 17% LFO, between 35 and 50% D-Limonene, between 5 and 15% Thyme Oil White, between 0.5 and 1.1% Linalool Coeur, between 3 and 10% Citral, between 3 and 10% gamma-terpinene, between 0.7 and 1.9% Alpha-Pinene (98%), between 2 and 6% Alpha-Terpineol, between 2 and 7% Terpinolene, between 0.5 and 2% Para-Cymene, between 1 and 2.5% Linalyl Acetate, between 1.2 and 2.5% Beta Pinene, between 0.02 and 0.3% Camphor Dextro, between 0.02 and 0.15% Terpinene 4 OL, between 1 and 3% Alpha Terpinene, between 0.4 and 1.4% Borneol L, between 0.1 and 0.7% Camphene, between 0.05 and 0.2% Decanal, between 0.04 and 0.16% Dodecanal, between 0.001 and 0.03% Fenchol Alpha, between 0.05 and 0.25% Geranyl Acetate, between 0.1 and 0.5% Isoborneol, between 0.1 and 0.4% 2-Methyl 1,3-cyclohexadiene, between 0.3 and 1.1% Myrcene, between 0.005 and 0.05% Nonanal, between 0.01 and 0.1% Octanal, and between 0.005 and 0.05% Tocopherol Gamma Tenox.

In some embodiments, the blend of compounds can include between 11.5 and 14.5% LFO, between 38 and 46.5% D-Limonene, between 8.5 and 10.6% Thyme Oil White, between 0.76 and 0.92% Linalool Coeur, between 6 and 8% Citral, between 6.5 and 8% gamma-terpinene, between 1.1 and 1.5% Alpha-Pinene (98%), between 4.1 and 5.2% Alpha-Terpineol, between 3.8 and 5% Terpinolene, between 1 and 1.25% Para-Cymene, between 1.6 and 2% Linalyl Acetate, between 1.7 and 2.1% Beta Pinene, between 0.08 and 0.1% Camphor Dextro, between 0.07 and 0.09% Terpinene 4 OL, between 1.7 and 2.1% Alpha Terpinene, between 0.8 and 1.0% Borneol L, between 0.3 and 0.45% Camphene, between 0.10 and 0.14% Decanal, between 0.09 and 0.11% Dodecanal, between 0.005 and 0.015% Fenchol Alpha, between 0.1 and 0.14% Geranyl Acetate, between 0.2 and 0.35% Isoborneol, between 0.24 and 0.28% 2-Methyl 1,3-cyclohexadiene, between 0.7 and 0.85% Myrcene, between 0.015 and 0.025%

Nonanal, between 0.03 and 0.05% Octanal, and between 0.015 and 0.025% Tocopherol Gamma Tenox.

In some embodiments, the blend of compounds can include 12.94% LFO, 42.2% D-Limonene, 9.58% Thyme Oil White, 0.84% Linalool Coeur, 7.02% Citral, 7.23% gamma-terpinene, 1.33% Alpha-Pinene (98%), 4.68% Alpha-Terpineol, 4.33% Terpinolene, 1.11% Para-Cymene, 1.79% Linalyl Acetate, 1.93% Beta Pinene, 0.09% Camphor Dextro, 0.08% Terpinene 4 OL, 1.93% Alpha Terpinene, 0.89% Borneol L, 0.37% Camphene, 0.12% Decanal, 0.10% Dodecanal, 0.01% Fenchol Alpha, 0.12% Geranyl Acetate, 0.28% Isoborneol, 0.26% 2-Methyl 1,3-cyclohexadiene, 0.78% Myrcene, 0.02% Nonanal, 0.04% Octanal, and 0.02% Tocopherol Gamma Tenox.

In some embodiments, the blend of compounds can include at least five of the group consisting of D-Limonene, Thyme Oil White, Blend 61, Linalool Coeur, Tetrahydrolinalool, Vanillin, Isopropyl myristate, Piperonal (aldehyde), Geraniol 60, and Triethyl Citrate.

In some embodiments, the blend of compounds can include at least seven of the group consisting of D-Limonene, Thyme Oil White, Blend 61, Linalool Coeur, Tetrahydrolinalool, Vanillin, Isopropyl myristate, Piperonal (aldehyde), Geraniol 60, and Triethyl Citrate.

In some embodiments, the blend of compounds can include D-Limonene, Thyme Oil White, Blend 61, Linalool Coeur, Tetrahydrolinalool, Vanillin, Isopropyl myristate, Piperonal (aldehyde), Geraniol 60, and Triethyl Citrate.

In some embodiments, the blend of compounds can include between 5 and 15% D-Limonene, between 5 and 15% Thyme Oil White, between 50 and 85% Blend 61, between 1 and 2.5% Linalool Coeur, between 1 and 3.5% Tetrahydrolinalool, between 0.05 and 0.25% Vanillin, between 1 and 3% Isopropyl myristate, between 1 and 3.5% Piperonal (aldehyde), between 0.5 and 2% Geraniol 60, and between 1 and 3.5% Triethyl Citrate.

In some embodiments, the blend of compounds can include between 8.7 and 10.8% D-Limonene, between 7.7 and 9.4% Thyme Oil White, between 62 and 76% Blend 61, between 1.4 and 1.9% Linalool Coeur, between 2 and 2.5% Tetrahydrolinalool, between 0.13 and 0.17% Vanillin, between 2.1 and 2.55% Isopropyl myristate, between 2.1 and 2.55% Piperonal (aldehyde), between 1.08 and 1.35% Geraniol 60, and between 2.1 and 2.55% Triethyl Citrate.

In some embodiments, the blend of compounds can include 9.70% D-Limonene, 8.54% Thyme Oil White, 69.41% Blend 61, 1.66% Linalool Coeur, 2.29% Tetrahydrolinalool, 0.15% Vanillin, 2.35% Isopropyl myristate, 2.35% Piperonal (aldehyde), 1.21% Geraniol 60, and 2.35% Triethyl Citrate.

In some embodiments, the blend of compounds can include at least one of the group consisting of LFO and BSO.

In some embodiments, the blend of compounds can include LFO and BSO.

In some embodiments, the blend of compounds can include between 55 and 99% LFO and between 5 and 35% Black Seed Oil (BSO).

In some embodiments, the blend of compounds can include between 65 and 95% LFO and between 12 and 28% Black Seed Oil (BSO).

In some embodiments, the blend of compounds can include between 72 and 89% LFO and between 18 and 22% Black Seed Oil (BSO).

In some embodiments, the blend of compounds can include 80.09% LFO and 19.91% BSO.

In some embodiments, the blend of compounds can include between 35 and 65% LFO and between 35 and 65% BSO.

In some embodiments, the blend of compounds can include between 45 and 56% LFO and between 45 and 55% BSO.

In some embodiments, the blend of compounds can include 50.13% LFO and 49.87% BSO.

In some embodiments, the blend of compounds can include at least one of the group consisting of Thyme Oil White, Wintergreen Oil, and Isopropyl myristate.

In some embodiments, the blend of compounds can include at least two of the group consisting of Thyme Oil White, Wintergreen Oil, and Isopropyl myristate.

In some embodiments, the blend of compounds can include Thyme Oil White, Wintergreen Oil, and Isopropyl myristate.

In some embodiments, the blend of compounds can include between 2 and 7% Thyme Oil White, between 44 and 70% Wintergreen Oil, and between 25 and 50% Isopropyl myristate.

In some embodiments, the blend of compounds can include between 4.1 and 5.2% Thyme Oil White, between 52 and 64% Wintergreen Oil, and between 33 and 42% Isopropyl myristate.

In some embodiments, the blend of compounds can include 4.60% Thyme Oil White, 57.80% Wintergreen Oil, and 37.60% Isopropyl myristate.

In some embodiments, the blend of compounds can include at least one of the group consisting of D-Limonene, Thyme Oil White, and Wintergreen Oil.

In some embodiments, the blend of compounds can include at least two of the group consisting of D-Limonene, Thyme Oil White, and Wintergreen Oil.

In some embodiments, the blend of compounds can include D-Limonene, Thyme Oil White, and Wintergreen Oil.

In some embodiments, the blend of compounds can include between 20 and 40% D-Limonene, between 2 and 10% Thyme Oil White, and between 50 and 80% Wintergreen Oil.

In some embodiments, the blend of compounds can include between 25 and 31% D-Limonene, between 4 and 5% Thyme Oil White, and between 60 and 72% Wintergreen Oil.

In some embodiments, the blend of compounds can include 28.24% D-Limonene, 4.44% Thyme Oil White, and 67.32% Wintergreen Oil.

In some embodiments, the blend of compounds can include at least three of the group consisting of D-Limonene, Linalool Coeur, Tetrehydrolinalool, Vanillin, Isopropyl myristate, Piperonal (aldehyde), and Geraniol 60.

In some embodiments, the blend of compounds can include at least five of the group consisting of D-Limonene, Linalool Coeur, Tetrehydrolinalool, Vanillin, Isopropyl myristate, Piperonal (aldehyde), and Geraniol 60.

In some embodiments, the blend of compounds can include D-Limonene, Linalool Coeur, Tetrehydrolinalool, Vanillin, Isopropyl myristate, Piperonal (aldehyde), and Geraniol 60.

In some embodiments, the blend of compounds can include between 7 and 15% D-Limonene, between 9 and 20% Linalool Coeur, between 15 and 32% Tetrehydrolinalool, between 1.5 and 3.2% Vanillin, between 15 and 42% Isopropyl myristate, between 5 and 16% Piperonal (aldehyde), and between 5 and 16% Geraniol 60.

In some embodiments, the blend of compounds can include between 8.9 and 11% D-Limonene, between 12.5 and 16% Linalool Coeur, between 21.5 and 27% Tetrahydrolinalool, between 2.2 and 2.7% Vanillin, between 25 and 32% Isopropyl myristate, between 9 and 11% Piperonal (aldehyde), and between 9 and 11.4% Geraniol 60.

In some embodiments, the blend of compounds can include 9.90% D-Limonene, 14.14% Linalool Coeur, 24.29% Tetrehydrolinalool, 2.48% Vanillin, 28.92% Isopropyl myristate, 9.97% Piperonal (aldehyde), and 10.30% Geraniol 60.

In some embodiments, the blend of compounds can include at least three of the group consisting of D-Limonene, Black Seed Oil, Linalool Coeur, Tetrahydrolinalool, Vanillin, Isopropyl myristate, Piperonal (aldehyde), Geraniol Fine FCC, and Methyl Salicylate 98% Nat.

In some embodiments, the blend of compounds can include at least six of the group consisting of D-Limonene, Black Seed Oil, Linalool Coeur, Tetrahydrolinalool, Vanillin, Isopropyl myristate, Piperonal (aldehyde), Geraniol Fine FCC, and Methyl Salicylate 98% Nat.

In some embodiments, the blend of compounds can include D-Limonene, Black Seed Oil, Linalool Coeur, Tetrahydrolinalool, Vanillin, Isopropyl myristate, Piperonal (aldehyde), Geraniol Fine FCC, and Methyl Salicylate 98% Nat.

In some embodiments, the blend of compounds can include between 8.4 and 10.2% D-Limonene, between 29 and 35% Black Seed Oil, between 8.5 and 10.6% Linalool Coeur, between 10 and 12.8% Tetrahydrolinalool, between 1 and 1.35% Vanillin, between 12.5 and 15.5% Isopropyl myristate, between 4.2 and 5.3% Piperonal (aldehyde), between 5.7 and 6.9% Geraniol Fine FCC, and between 10.5 and 13% Methyl Salicylate 98% Nat.

In some embodiments, the blend of compounds can include between 8.4 and 10.2% D-Limonene, between 29 and 35% Black Seed Oil, between 8.5 and 10.6% Linalool Coeur, between 10 and 12.8% Tetrahydrolinalool, between 1 and 1.35% Vanillin, between 12.5 and 15.5% Isopropyl myristate, between 4.2 and 5.3% Piperonal (aldehyde), between 5.7 and 6.9% Geraniol Fine FCC, and between 10.5 and 13% Methyl Salicylate 98% Nat.

In some embodiments, the blend of compounds can include 9.30% D-Limonene, 31.92% Black Seed Oil, 9.48% Linalool Coeur, 11.40% Tetrahydrolinalool, 1.16% Vanillin, 14.04% Isopropyl myristate, 4.68% Piperonal (aldehyde), 6.29% Geraniol Fine FCC, and 11.72% Methyl Salicylate 98% Nat.

In some embodiments, the blend of compounds can include at least five of the group consisting of D-Limonene, Black Seed Oil, Linalool Coeur, Tetrahydrolinalool, Vanillin, Mineral Oil White (USP), Isopropyl myristate, Piperonal (aldehyde), and Geraniol Fine FCC.

In some embodiments, the blend of compounds can include at least seven of the group consisting of D-Limonene, Black Seed Oil, Linalool Coeur, Tetrahydrolinalool, Vanillin, Mineral Oil White (USP), Isopropyl myristate, Piperonal (aldehyde), and Geraniol Fine FCC.

In some embodiments, the blend of compounds can include D-Limonene, Black Seed Oil, Linalool Coeur, Tetrahydrolinalool, Vanillin, Mineral Oil White (USP), Isopropyl myristate, Piperonal (aldehyde), and Geraniol Fine FCC.

In some embodiments, the blend of compounds can include between 5 and 15% D-Limonene, between 16 and 35% Black Seed Oil, between 5 and 15% Linalool Coeur, between 6 and 15% Tetrahydrolinalool, between 0.5 and 2% Vanillin, between 10 and 19% Mineral Oil White (USP), between 10 and 20% Isopropyl myristate, between 3 and 6% Piperonal (aldehyde), and between 4 and 8.5% Geraniol Fine FCC.

In some embodiments, the blend of compounds can include between 8.7 and 10.4% D-Limonene, between 23 and 30% Black Seed Oil, between 8.9 and 10.8% Linalool Coeur, between 10.7 and 12.9% Tetrahydrolinalool, between 1.05 and 1.35% Vanillin, between 13.4 and 16.5% Mineral Oil White (USP), between 13 and 16% Isopropyl myristate, between 4.4 and 5.4% Piperonal (aldehyde), and between 5.9 and 7.2% Geraniol Fine FCC.

In some embodiments, the blend of compounds can include 9.63% D-Limonene, 26.66% BSO, 9.82% Linalool Coeur, 11.81% Tetrahydrolinalool, 1.20% Vanillin, 14.97% Mineral Oil White (USP), 14.54% Isopropyl myristate, 4.85% Piperonal (aldehyde), and 6.51% Geraniol Fine FCC.

In some embodiments, the blend of compounds can include at least three of the group consisting of BSO, Linalool Coeur, Tetrahydrolinalool, Vanillin, Isopropyl myristate, Piperonal (aldehyde), and Geraniol Fine FCC.

In some embodiments, the blend of compounds can include at least five of the group consisting of BSO, Linalool Coeur, Tetrahydrolinalool, Vanillin, Isopropyl myristate, Piperonal (aldehyde), and Geraniol Fine FCC.

In some embodiments, the blend of compounds can include BSO, Linalool Coeur, Tetrahydrolinalool, Vanillin, Isopropyl myristate, Piperonal (aldehyde), and Geraniol Fine FCC.

In some embodiments, the blend of compounds can include between 40 and 65% BSO, between 5 and 15% Linalool Coeur, between 5 and 18% Tetrahydrolinalool, between 0.5 and 2% Vanillin, between 8 and 18% Isopropyl myristate, between 3 and 6% Piperonal (aldehyde), and between 5 and 8.5% Geraniol Fine FCC.

In some embodiments, the blend of compounds can include between 47 and 58% BSO, between 8.7 and 10.5% Linalool Coeur, between 10 and 13% Tetrahydrolinalool, between 1.0 and 1.25% Vanillin, between 12.8 and 15.3% Isopropyl myristate, between 4.3 and 5.2% Piperonal (aldehyde), and between 5.7 and 7% Geraniol Fine FCC.

In some embodiments, the blend of compounds can include 52.28% BSO, 9.63% Linalool Coeur, 11.57% Tetrahydrolinalool, 1.12% Vanillin, 14.26% Isopropyl myristate, 4.75% Piperonal (aldehyde), and 6.38% Geraniol Fine FCC.

In some embodiments, the blend of compounds can include at least two of the group consisting of Thyme Oil White, Wintergreen Oil, Vanillin, and Isopropyl myristate.

In some embodiments, the blend of compounds can include at least three of the group consisting of Thyme Oil White, Wintergreen Oil, Vanillin, and Isopropyl myristate.

In some embodiments, the blend of compounds can include Thyme Oil White, Wintergreen Oil, Vanillin, and Isopropyl myristate.

In some embodiments, the blend of compounds can include between 25 and 50% Thyme Oil White, between 15 and 32% Wintergreen Oil, between 0.5 and 2% Vanillin, and between 25 and 45% Isopropyl myristate.

In some embodiments, the blend of compounds can include between 34 and 42.5% Thyme Oil White, between 22 and 27.5% Wintergreen Oil, between 1.0 and 1.22% Vanillin, and between 32 and 40% Isopropyl myristate.

In some embodiments, the blend of compounds can include 38.21% Thyme Oil White, 24.79% Wintergreen Oil, 1.11% Vanillin, and 35.89% Isopropyl myristate.

In some embodiments, the blend of compounds can include at least one of the group consisting of Thyme Oil White, Wintergreen Oil, and Isopropyl myristate.

In some embodiments, the blend of compounds can include at least two of the group consisting of Thyme Oil White, Wintergreen Oil, and Isopropyl myristate.

In some embodiments, the blend of compounds can include Thyme Oil White, Wintergreen Oil, and Isopropyl myristate.

In some embodiments, the blend of compounds can include between 30 and 50% Thyme Oil White, between 15 and 35% Wintergreen Oil, and between 25 and 45% Isopropyl myristate.

In some embodiments, the blend of compounds can include between 35 and 44% Thyme Oil White, between 22 and 27.2% Wintergreen Oil, and between 32 and 40% Isopropyl myristate.

In some embodiments, the blend of compounds can include 39.24% Thyme Oil White, 24.82% Wintergreen Oil, and 35.94% Isopropyl myristate.

In some embodiments, the blend of compounds can include at least one of the group consisting of Thyme Oil White, Isopropyl myristate, and Wintergreen Oil (Technical grade).

In some embodiments, the blend of compounds can include at least two of the group consisting of Thyme Oil White, Isopropyl myristate, and Wintergreen Oil (Technical grade).

In some embodiments, the blend of compounds can include Thyme Oil White, Isopropyl myristate, and Wintergreen Oil (Technical grade).

In some embodiments, the blend of compounds can include between 30 and 50% Thyme Oil White, between 25 and 45% Isopropyl myristate, and between 17 and 32% Wintergreen Oil (Technical grade).

In some embodiments, the blend of compounds can include between 35 and 44% Thyme Oil White, between 32 and 40% Isopropyl myristate, and between 22 and 27.2% Wintergreen Oil (Technical grade).

In some embodiments, the blend of compounds can include 39.24% Thyme Oil White, 35.94% Isopropyl myristate, and 24.82% Wintergreen Oil (Technical grade).

In some embodiments, the blend of compounds can include at least four of the group consisting of D-Limonene, Linalool Coeur, Tetrahydrolinalool, Vanillin, Isopropyl myristate, Piperonal (aldehyde), Piperonyl Alcohol, and Blend 62.

In some embodiments, the blend of compounds can include at least six of the group consisting of D-Limonene, Linalool Coeur, Tetrahydrolinalool, Vanillin, Isopropyl myristate, Piperonal (aldehyde), Piperonyl Alcohol, and Blend 62.

In some embodiments, the blend of compounds can include D-Limonene, Linalool Coeur, Tetrahydrolinalool, Vanillin, Isopropyl myristate, Piperonal (aldehyde), Piperonyl Alcohol, and Blend 62.

In some embodiments, the blend of compounds can include between 10 and 20% D-Limonene, between 2 and 4% Linalool Coeur, between 3.15 and 3.85% Tetrahydrolinalool, between 0.18 and 0.22% Vanillin, between 3.05 and 3.75% Isopropyl myristate, between 3.2 and 4.0% Piperonal (aldehyde), between 1.25 and 1.55% Piperonyl Alcohol, and between 63 and 78% Blend 62.

In some embodiments, the blend of compounds can include between 13.3 and 16.3% D-Limonene, between 2.6 and 3.2% Linalool Coeur, between 3.15 and 3.85% Tetrahydrolinalool, between 0.18 and 0.22% Vanillin, between 3.05 and 3.75% Isopropyl myristate, between 3.2 and 4.0% Piperonal (aldehyde), between 1.25 and 1.55% Piperonyl Alcohol, and between 63 and 78% Blend 62.

In some embodiments, the blend of compounds can include 14.8% D-Limonene, 2.9% Linalool Coeur, 3.5% Tetrahydrolinalool, 0.2% Vanillin, 3.4% Isopropyl myristate, 3.6% Piperonal (aldehyde), 1.4% Piperonyl Alcohol, and 70.2% Blend 62.

In some embodiments, the blend of compounds can include at least four of the group consisting of D-Limonene, Linalool Coeur, Tetrahydrolinalool, Vanillin, Isopropyl myristate, Piperonal (aldehyde), Piperonyl Alcohol, and Blend 62.

In some embodiments, the blend of compounds can include at least six of the group consisting of D-Limonene, Linalool Coeur, Tetrahydrolinalool, Vanillin, Isopropyl myristate, Piperonal (aldehyde), Piperonyl Alcohol, and Blend 62.

In some embodiments, the blend of compounds can include D-Limonene, Linalool Coeur, Tetrahydrolinalool, Vanillin, Isopropyl myristate, Piperonal (aldehyde), Piperonyl Alcohol, and Blend 62.

In some embodiments, the blend of compounds can include between 50 and 85% D-Limonene, between 2 and 4% Linalool Coeur, between 3 and 5% Tetrahydrolinalool, between 0.1 and 0.3% Vanillin, between 2.5 and 4.55% Isopropyl myristate, between 2.5 and 4.5% Piperonal (aldehyde), between 1 and 2% Piperonyl Alcohol, and between 10 and 20% Blend 62.

In some embodiments, the blend of compounds can include between 62 and 77% D-Limonene, between 2.6 and 3.2% Linalool Coeur, between 3.15 and 3.85% Tetrahydrolinalool, between 0.18 and 0.22% Vanillin, between 3.05 and 3.75% Isopropyl myristate, between 3.25 and 3.95% Piperonal (aldehyde), between 1.25 and 1.55% Piperonyl Alcohol, and between 13.5 and 16.7% Blend 62.

In some embodiments, the blend of compounds can include 69.8% D-Limonene, 2.9% Linalool Coeur, 3.5% Tetrahydrolinalool, 0.2% Vanillin, 3.4% Isopropyl myristate, 3.6% Piperonal (aldehyde), 1.4% Piperonyl Alcohol, and 15.2% Blend 62.

In some embodiments, the blend of compounds can include at least three of the group consisting of Linalool Coeur, Tetrahydrolinalool, Vanillin, Isopropyl myristate, Piperonal (aldehyde), Piperonyl Alcohol, and Blend 62.

In some embodiments, the blend of compounds can include at least five of the group consisting of Linalool Coeur, Tetrahydrolinalool, Vanillin, Isopropyl myristate, Piperonal (aldehyde), Piperonyl Alcohol, and Blend 62.

In some embodiments, the blend of compounds can include Linalool Coeur, Tetrahydrolinalool, Vanillin, Isopropyl myristate, Piperonal (aldehyde), Piperonyl Alcohol, and Blend 62.

In some embodiments, the blend of compounds can include between 4 and 8% Linalool Coeur, between 5 and 9% Tetrahydrolinalool, between 0.2 and 0.6% Vanillin, between 4 and 9% Isopropyl myristate, between 4 and 9% Piperonal (aldehyde), between 2 and 4% Piperonyl Alcohol, and between 55 and 86% Blend 62.

In some embodiments, the blend of compounds can include between 5.1 and 6.3% Linalool Coeur, between 6.2 and 7.6% Tetrahydrolinalool, between 0.36 and 0.44% Vanillin, between 6.1 and 7.5% Isopropyl myristate, between 6.4 and 7.9% Piperonal (aldehyde), between 2.6 and 3.2% Piperonyl Alcohol, and between 63 and 78% Blend 62.

In some embodiments, the blend of compounds can include 5.7% Linalool Coeur, 6.9% Tetrahydrolinalool, 0.4% Vanillin, 6.8% Isopropyl myristate, 7.1% Piperonal (aldehyde), 2.9% Piperonyl Alcohol, and 70.2% Blend 62.

In some embodiments, the blend of compounds can include at least one of the group consisting of LFO, D-Limonene, and Thyme Oil White.

In some embodiments, the blend of compounds can include at least two of the group consisting of LFO, D-Limonene, and Thyme Oil White.

In some embodiments, the blend of compounds can include LFO, D-Limonene, and Thyme Oil White.

In some embodiments, the blend of compounds can include between 30 and 55% LFO, between 20 and 35% D-Limonene, and between 20 and 40% Thyme Oil White.

In some embodiments, the blend of compounds can include between 37 and 45.5% LFO, between 25 and 31% D-Limonene, and between 27.5 and 34% Thyme Oil White.

In some embodiments, the blend of compounds can include 41.4% LFO, 27.9% D-Limonene, and 30.7% Thyme Oil White.

In some embodiments, the blend of compounds can include at least one of the group consisting of D-Limonene, Thyme Oil White, and Blend 59.

In some embodiments, the blend of compounds can include at least two of the group consisting of D-Limonene, Thyme Oil White, and Blend 59.

In some embodiments, the blend of compounds can include D-Limonene, Thyme Oil White, and Blend 59.

In some embodiments, the blend of compounds can include between 20 and 35% D-Limonene, between 23 and 37% Thyme Oil White, and between 33 and 52% Blend 59.

In some embodiments, the blend of compounds can include between 24 and 30% D-Limonene, between 27 and 33% Thyme Oil White, and between 38 and 47% Blend 59.

In some embodiments, the blend of compounds can include 27.35% D-Limonene, 30.08% Thyme Oil White, and 42.57% Blend 59.

In some embodiments, the blend of compounds can include at least five of the group consisting of D-Limonene, Thyme Oil White, Linalool Coeur, Tetrahydrolinalool, Vanillin, Isopropyl myristate, Piperonal (aldehyde), Geraniol 60, and Triethyl Citrate.

In some embodiments, the blend of compounds can include at least seven of the group consisting of D-Limonene, Thyme Oil White, Linalool Coeur, Tetrahydrolinalool, Vanillin, Isopropyl myristate, Piperonal (aldehyde), Geraniol 60, and Triethyl Citrate.

In some embodiments, the blend of compounds can include D-Limonene, Thyme Oil White, Linalool Coeur, Tetrahydrolinalool, Vanillin, Isopropyl myristate, Piperonal (aldehyde), Geraniol 60, and Triethyl Citrate.

In some embodiments, the blend of compounds can include between 20 and 35% D-Limonene, between 23 and 37% Thyme Oil White, between 4 and 8% Linalool Coeur, between 6 and 9.5% Tetrahydrolinalool, between 0.3 and 0.7% Vanillin, between 6 and 10% Isopropyl myristate, between 6 and 10% Piperonal (aldehyde), between 3 and 5.5% Geraniol 60, and between 6.5 and 9.5% Triethyl Citrate.

In some embodiments, the blend of compounds can include between 24 and 31% D-Limonene, between 27 and 33% Thyme Oil White, between 5.1 and 6.3% Linalool Coeur, between 7.1 and 8.8% Tetrahydrolinalool, between 0.45 and 0.55% Vanillin, between 7.3 and 8.9% Isopropyl myristate, between 7.3 and 8.9% Piperonal (aldehyde), between 3.8 and 4.6% Geraniol 60, and between 7.3 and 8.9% Triethyl Citrate.

In some embodiments, the blend of compounds can include 27.4% D-Limonene, 30.1% Thyme Oil White, 5.7% Linalool Coeur, 7.9% Tetrahydrolinalool, 0.5% Vanillin, 8.1% Isopropyl myristate, 8.1% Piperonal (aldehyde), 4.2% Geraniol 60, and 8.1% Triethyl Citrate.

In some embodiments, the blend of compounds can include at least one of the group consisting of LFO, D-Limonene, and Thyme Oil White.

In some embodiments, the blend of compounds can include at least two of the group consisting of LFO, D-Limonene, and Thyme Oil White.

In some embodiments, the blend of compounds can include LFO, D-Limonene, and Thyme Oil White.

In some embodiments, the blend of compounds can include between 34 and 50% LFO, between 20 and 35% D-Limonene, and between 23 and 36% Thyme Oil White.

In some embodiments, the blend of compounds can include between 38 and 47% LFO, between 24 and 31% D-Limonene, and between 27 and 33% Thyme Oil White.

In some embodiments, the blend of compounds can include 42.6% LFO, 27.35% D-Limonene, and 30.08% Thyme Oil White.

In some embodiments, the blend of compounds can include at least three of the group consisting of D-Limonene, Thyme Oil White, Benzyl Alcohol, Isopar M, Water, Blend 59, and 10% SLS Blend.

In some embodiments, the blend of compounds can include at least seven of the group consisting of D-Limonene, Thyme Oil White, Benzyl Alcohol, Isopar M, Water, Blend 59, and 10% SLS Blend.

In some embodiments, the blend of compounds can include D-Limonene, Thyme Oil White, Benzyl Alcohol, Isopar M, Water, Blend 59, and 10% SLS Blend.

In some embodiments, the blend of compounds can include between 3 and 5.5% D-Limonene, between 3 and 6% Thyme Oil White, between 10 and 22% Benzyl Alcohol, between 14 and 27% Isopar M, between 35 and 53% Water, between 5 and 8% Blend 59, and between 2 and 4% of 10% SLS Blend (10% Sodium Lauryl Sulfate, 90.00% Water).

In some embodiments, the blend of compounds can include between 3.6 and 4.45% D-Limonene, between 4 and 4.9% Thyme Oil White, between 15 and 18.4% Benzyl Alcohol, between 18 and 23.5% Isopar M, between 41 and 49% Water, between 5.7 and 7% Blend 59, and between 2.8% and 3.5% of 10% SLS Blend (10% Sodium Lauryl Sulfate, 90.00% Water).

In some embodiments, the blend of compounds can include 4.03% D-Limonene, 4.43% Thyme Oil White, 16.61% Benzyl Alcohol, 20.95% Isopar M, 44.53% Water, 6.27% Blend 59, and 3.18% of 10% SLS Blend (10% Sodium Lauryl Sulfate, 90.00% Water).

In some embodiments, the blend of compounds can include at least seven of the group consisting of D-Limonene, Thyme Oil White, Linalool Coeur, Tetrahydrolinalool, Vanillin, Isopropyl myristate, Piperonal (aldehyde), Geraniol 60, Triethyl Citrate, Benzyl Alcohol, Isopar M, Water, and 10% SLS Blend (10% Sodium Lauryl Sulfate, 90.00% Water).

In some embodiments, the blend of compounds can include at least nine of the group consisting of D-Limonene, Thyme Oil White, Linalool Coeur, Tetrahydrolinalool, Vanillin, Isopropyl myristate, Piperonal (aldehyde), Geraniol 60, Triethyl Citrate, Benzyl Alcohol, Isopar M, Water, and 10% SLS Blend (10% Sodium Lauryl Sulfate, 90.00% Water).

In some embodiments, the blend of compounds can include D-Limonene, Thyme Oil White, Linalool Coeur, Tetrahydrolinalool, Vanillin, Isopropyl myristate, Piperonal (aldehyde), Geraniol 60, Triethyl Citrate, Benzyl Alcohol, Isopar M, Water, and 10% SLS Blend (10% Sodium Lauryl Sulfate, 90.00% Water).

In some embodiments, the blend of compounds can include between 3 and 4% D-Limonene, between 3 and 5% Thyme Oil White, between 0.5 and 1.2% Linalool Coeur, between 0.9 and 1.6% Tetrahydrolinalool, between 0.04 and 0.1% Vanillin, between 0.8 and 1.5% Isopropyl myristate, between 0.8 and 2% Piperonal (aldehyde), between 0.3 and 0.8% Geraniol 60, between 0.8 and 1.6% Triethyl Citrate, between 12 and 21% Benzyl Alcohol, between 14 and 28% Isopar M, between 35 and 53% Water, and between 2.4 and 4% of 10% SLS Blend (10% Sodium Lauryl Sulfate, 90.00% Water).

In some embodiments, the blend of compounds can include between 3.6 and 4.45% D-Limonene, 4.0 and 4.75% Thyme Oil White, between 0.76 and 0.92% Linalool Coeur, between 1.05 and 1.27% Tetrahydrolinalool, between 0.063 and 0.077% Vanillin, between 1.05 and 1.33% Isopropyl myristate, between 1.05 and 1.33% Piperonal (aldehyde), between 0.56 and 0.68% Geraniol 60, between 1.05 and 1.33% Triethyl Citrate, between 15 and 18% Benzyl Alcohol, between 18 and 24.2% Isopar M, between 40 and 49% Water, and between 2.85 and 3.5% of 10% SLS Blend (10% Sodium Lauryl Sulfate, 90.00% Water).

In some embodiments, the blend of compounds can include 4.03% D-Limonene, 4.43% Thyme Oil White, 0.84% Linalool Coeur, 1.16% Tetrahydrolinalool, 0.07% Vanillin, 1.19% Isopropyl myristate, 1.19% Piperonal (aldehyde), 0.62% Geraniol 60, 1.19% Triethyl Citrate, 16.61% Benzyl Alcohol, 20.95% Isopar M, 44.53% Water, and 3.18% of 10% SLS Blend (10% Sodium Lauryl Sulfate, 90.00% Water).

In some embodiments, the blend of compounds can include at least one of the group consisting of D-Limonene, Thyme Oil White, and Blend 59.

In some embodiments, the blend of compounds can include at least two of the group consisting of D-Limonene, Thyme Oil White, and Blend 59.

In some embodiments, the blend of compounds can include D-Limonene, Thyme Oil White, and Blend 59.

In some embodiments, the blend of compounds can include between 20 and 35% D-Limonene, between 22 and 37% Thyme Oil White, and between 34 and 51% Blend 59.

In some embodiments, the blend of compounds can include between 24 and 31% D-Limonene, between 27 and 33% Thyme Oil White, and between 38 and 47% Blend 59.

In some embodiments, the blend of compounds can include 27.35% D-Limonene, 30.08% Thyme Oil White, and 42.57% Blend 59.

In some embodiments, the blend of compounds can include at least two to five of the group consisting of D-Limonene, Thyme Oil White, Linalool Coeur, Tetrahydrolinalool, Vanillin, Isopropyl myristate, Piperonal (aldehyde), Geraniol 60, and Triethyl Citrate.

In some embodiments, the blend of compounds can include at least six to eight of the group consisting of D-Limonene, Thyme Oil White, Linalool Coeur, Tetrahydrolinalool, Vanillin, Isopropyl myristate, Piperonal (aldehyde), Geraniol 60, and Triethyl Citrate.

In some embodiments, the blend of compounds can include D-Limonene, Thyme Oil White, Linalool Coeur, Tetrahydrolinalool, Vanillin, Isopropyl myristate, Piperonal (aldehyde), Geraniol 60, and Triethyl Citrate.

In some embodiments, the blend of compounds can include between 20 and 40% D-Limonene, between 20 and 40% Thyme Oil White, between 2.5 and 10% Linalool Coeur, between 4 and 12% Tetrahydrolinalool, between 0.2 and 1.0% Vanillin, between 5 and 12 Isopropyl myristate, between 5 and 12% Piperonal (aldehyde), between 2 and 6% Geraniol 60, and between 5 and 15% Triethyl Citrate.

In some embodiments, the blend of compounds can include between 24 and 31% D-Limonene, between 27 and 33% Thyme Oil White, between 5.2 and 6.4% Linalool Coeur, between 7 and 8.8% Tetrahydrolinalool, between 0.45 and 0.55% Vanillin, between 7.2 and 8.9% Isopropyl myristate, between 7.2 and 8.9% Piperonal (aldehyde), between 3.7 and 4.6% Geraniol 60, and between 7.3 and 9.0% Triethyl Citrate.

In some embodiments, the blend of compounds can include 27.35% D-Limonene, 30.08% Thyme Oil White, 5.73% Linalool Coeur, 7.88% Tetrahydrolinalool, 0.50% Vanillin, 8.08% Isopropyl myristate, 8.09% Piperonal (aldehyde), 4.18% Geraniol 60, and 8.11% Triethyl Citrate.

In some embodiments, the blend of compounds can include at least two of the group consisting of Lilac Flower Oil, D-Limonene, Thyme Oil White, and Blend 62.

In some embodiments, the blend of compounds can include at least three of the group consisting of Lilac Flower Oil, D-Limonene, Thyme Oil White, and Blend 62.

In some embodiments, the blend of compounds can include Lilac Flower Oil, D-Limonene, Thyme Oil White, and Blend 62.

In some embodiments, the blend of compounds can include between 2 and 8% Lilac Flower Oil, between 60 and 95% D-Limonene, between 1.5 and 6% Thyme Oil White, and between 5 and 16% Blend 62.

In some embodiments, the blend of compounds can include between 4 and 4.9% Lilac Flower Oil, between 76 and 91% D-Limonene, between 2.9 and 3.65% Thyme Oil White, and between 9 and 11% Blend 62.

In some embodiments, the blend of compounds can include 4.4% Lilac Flower Oil, 82.3% D-Limonene, 3.3% Thyme Oil White, and 10.0% Blend 62.

In some embodiments, the blend of compounds can include at least two of the group consisting of Lilac Flower Oil, D-Limonene, Thyme Oil White, and Blend 62.

In some embodiments, the blend of compounds can include at least three of the group consisting of Lilac Flower Oil, D-Limonene, Thyme Oil White, and Blend 62.

In some embodiments, the blend of compounds can include Lilac Flower Oil, D-Limonene, Thyme Oil White, and Blend 62.

In some embodiments, the blend of compounds can include between 6 and 20% Lilac Flower Oil, between 5 and 15% D-Limonene, between 5 and 20% Thyme Oil White, and between 45 and 85% Blend 62.

In some embodiments, the blend of compounds can include between 11.7 and 14.2% Lilac Flower Oil, between 7.9 and 9.6% D-Limonene, between 8.7 and 10.6% Thyme Oil White, and between 61 and 76% Blend 62.

In some embodiments, the blend of compounds can include 12.94% Lilac Flower Oil, 8.72% D-Limonene, 9.58% Thyme Oil White, and 68.76% Blend 62.

In some embodiments, the blend of compounds can include at least two to five of the group consisting of D-Limonene, Thyme Oil White, Linalool Coeur, Tetrahydrolinalool, Vanillin, Piperonal (aldehyde), Blend 62, Geraniol 60, and Triethyl Citrate.

In some embodiments, the blend of compounds can include at least six to eight of the group consisting of D-Limonene, Thyme Oil White, Linalool Coeur, Tetrahydrolinalool, Vanillin, Piperonal (aldehyde), Blend 62, Geraniol 60, and Triethyl Citrate.

In some embodiments, the blend of compounds can include D-Limonene, Thyme Oil White, Linalool Coeur, Tetrahydrolinalool, Vanillin, Piperonal (aldehyde), Blend 62, Geraniol 60, and Triethyl Citrate.

In some embodiments, the blend of compounds can include between 5 and 15% D-Limonene, between 4 and 12% Thyme Oil White, between 0.5 and 4% Linalool Coeur, between 1 and 5% Tetrahydrolinalool, between 0.01 and 0.5% Vanillin, between 1 and 5% Piperonal (aldehyde), between 50 and 90% Blend 62, between 0.5 and 3% Geraniol 60, and between 1 and 5% Triethyl Citrate.

In some embodiments, the blend of compounds can include between 8.8 and 10.8% D-Limonene, between 7.7 and 9.5% Thyme Oil White, between 1.53 and 1.87% Linalool Coeur, between 2.1 and 2.5% Tetrahydrolinalool, between 0.09 and 0.11% Vanillin, between 2.15 and 2.65% Piperonal (aldehyde), between 62 and 77% Blend 62, between 1.05 and 1.35% Geraniol 60, and between 2.15 and 2.55% Triethyl Citrate.

In some embodiments, the blend of compounds can include 9.8% D-Limonene, 8.6% Thyme Oil White, 1.7% Linalool Coeur, 2.3% Tetrahydrolinalool, 0.1% Vanillin, 2.4% Piperonal (aldehyde), 69.3% Blend 62, 1.2% Geraniol 60, and 2.4% Triethyl Citrate.

In some embodiments, the blend of compounds can include at least two of the group consisting of Thyme Oil White, Wintergreen Oil, and Isopropyl myristate.

In some embodiments, the blend of compounds can include Thyme Oil White, Wintergreen Oil, and Isopropyl myristate.

In some embodiments, the blend of compounds can include between 15 and 30% Thyme Oil White, between 30 and 60% Wintergreen Oil, and between 20 and 50% Isopropyl myristate.

In some embodiments, the blend of compounds can include between 18 and 23% Thyme Oil White, between 40 and 50% Wintergreen Oil, and between 31 and 38% Isopropyl myristate.

In some embodiments, the blend of compounds can include 20.6% Thyme Oil White, 45.1% Wintergreen Oil, and 34.3% Isopropyl myristate.

In some embodiments, the blend of compounds can include at least two to four of the group consisting of Black Seed Oil, Linalool Coeur, Tetrahydrolinalool, Vanillin, Isopropyl myristate, Piperonal (aldehyde), and Geraniol Fine FCC.

In some embodiments, the blend of compounds can include at least five or six of the group consisting of Black Seed Oil, Linalool Coeur, Tetrahydrolinalool, Vanillin, Isopropyl myristate, Piperonal (aldehyde), and Geraniol Fine FCC.

In some embodiments, the blend of compounds can include Black Seed Oil, Linalool Coeur, Tetrahydrolinalool, Vanillin, Isopropyl myristate, Piperonal (aldehyde), and Geraniol Fine FCC.

In some embodiments, the blend of compounds can include between 15 and 35% Black Seed Oil, between 10 and 22% Linalool Coeur, between 12 and 28% Tetrahydrolinalool, between 0.5 to 4% Vanillin, between 15 and 32% Isopropyl myristate, between 4 and 12% Piperonal (aldehyde), and between 5 and 15% Geraniol Fine FCC.

In some embodiments, the blend of compounds can include between 19 and 24% Black Seed Oil, between 14 and 17.5% Linalool Coeur, between 17 and 21% Tetrahydrolinalool, between 1.7 and 2.1% Vanillin, between 21 and 26% Isopropyl myristate, between 7 and 8.6% Piperonal (aldehyde), and between 9.5 and 11.6% Geraniol Fine FCC.

In some embodiments, the blend of compounds can include 21.5% Black Seed Oil, 15.8% Linalool Coeur, 19.0% Tetrahydrolinalool, 1.9% Vanillin, 23.4% Isopropyl myristate, 7.8% Piperonal (aldehyde), and 10.5% Geraniol Fine FCC.

In some embodiments, the blend of compounds can include at least two of the group consisting of Linalool Coeur, Soy Bean Oil, Thymol (crystal), and Alpha-Pinene (98%).

In some embodiments, the blend of compounds can include at least three of the group consisting of Linalool Coeur, Soy Bean Oil, Thymol (crystal), and Alpha-Pinene (98%).

In some embodiments, the blend of compounds can include Linalool Coeur, Soy Bean Oil, Thymol (crystal), and Alpha-Pinene (98%).

In some embodiments, the blend of compounds can include between 4 and 10% Linalool Coeur, between 16 and 32% Soy Bean Oil, between 25 and 50% Thymol (crystal), and between 2 and 8% Alpha-Pinene (98%).

In some embodiments, the blend of compounds can include between 6 and 7.4% Linalool Coeur, between 22 and 26% Soy Bean Oil, between 33 and 41% Thymol (crystal), and between 3.3 and 4.2% Alpha-Pinene (98%).

In some embodiments, the blend of compounds can include 6.63% Linalool Coeur, 24.03% Soy Bean Oil, 37.17% Thymol (crystal), and 3.78% Alpha-Pinene (98%).

In some embodiments, the blend of compounds can include at least two of the group consisting of Linalool Coeur, Thymol (crystal), Alpha-Pinene (98%), and Para-Cymene.

In some embodiments, the blend of compounds can include at least three of the group consisting of Linalool Coeur, Thymol (crystal), Alpha-Pinene (98%), and Para-Cymene.

In some embodiments, the blend of compounds can include Linalool Coeur, Thymol (crystal), Alpha-Pinene (98%), and Para-Cymene.

In some embodiments, the blend of compounds can include between 5 and 12% Linalool Coeur, between 30 and 65% Thymol (crystal), between 2.5 and 8% Alpha-Pinene (98%), and between 25 and 55% Para-Cymene.

In some embodiments, the blend of compounds can include between 7.9 and 9.6% Linalool Coeur, between 43 and 53% Thymol (crystal), between 4.5 and 5.5% Alpha-Pinene (98%), and between 33 and 42% Para-Cymene.

In some embodiments, the blend of compounds can include 8.73% Linalool Coeur, 48.93% Thymol (crystal), 4.97% Alpha-Pinene (98%), and 37.37% Para-Cymene.

In some embodiments, the blend of compounds can include at least two to five of the group consisting of D-Limonene, Thyme Oil White, Blend 61, Linalool Coeur, Tetrahydrolinalool, Vanillin, Isopropyl myristate, Piperonal (aldehyde), and Geraniol Fine FCC.

In some embodiments, the blend of compounds can include at least six to eight of the group consisting of D-Limonene, Thyme Oil White, Blend 61, Linalool Coeur, Tetrahydrolinalool, Vanillin, Isopropyl myristate, Piperonal (aldehyde), and Geraniol Fine FCC.

In some embodiments, the blend of compounds can include D-Limonene, Thyme Oil White, Blend 61, Linalool Coeur, Tetrahydrolinalool, Vanillin, Isopropyl myristate, Piperonal (aldehyde), and Geraniol Fine FCC.

In some embodiments, the blend of compounds can include between 5 and 12% D-Limonene, between 6 and 14% Thyme Oil White, between 45 and 85% Blend 61, between 1 and 6% Linalool Coeur, between 1.5 and 8% Tetrahydrolinalool, between 0.1 and 1.0% Vanillin, between 1 and 8% Isopropyl myristate, between 0.5 and 3% Piperonal (aldehyde), and between 0.5 and 4% Geraniol Fine FCC.

In some embodiments, the blend of compounds can include between 7.9 and 9.5% D-Limonene, between 8.6 and 10.5% Thyme Oil White, between 61 and 76% Blend 61, between 2.3 and 2.9% Linalool Coeur, between 2.8 and 3.4% Tetrahydrolinalool, between 0.29 and 0.35% Vanillin, between 3.4 and 4.3% Isopropyl myristate, between 1.16 and 1.42% Piperonal (aldehyde), and between 1.5 and 1.9% Geraniol Fine FCC.

In some embodiments, the blend of compounds can include 8.72% D-Limonene, 9.58% Thyme Oil White, 68.76% Blend 61, 2.61% Linalool Coeur, 3.13% Tetrahydrolinalool, 0.32% Vanillin, 3.86% Isopropyl myristate, 1.29% Piperonal (aldehyde), and 1.73% Geraniol Fine FCC.

In some embodiments, the blend of compounds can include at least two for the group consisting of D-Limonene, Thyme Oil White, and Methyl Salicylate (Synth.).

In some embodiments, the blend of compounds can include D-Limonene, Thyme Oil White, and Methyl Salicylate (Synth.).

In some embodiments, the blend of compounds can include between 20 and 42% D-Limonene, between 2 and 8% Thyme Oil White, and between 45 and 85% Methyl Salicylate (Synth.).

In some embodiments, the blend of compounds can include between 25 and 31% D-Limonene, between 4 and 4.9% Thyme Oil White, and between 60 and 74% Methyl Salicylate (Synth.).

In some embodiments, the blend of compounds can include 28.24% D-Limonene, 4.44% Thyme Oil White, and 67.32% Methyl Salicylate (Synth.).

In some embodiments, the blend of compounds can include at least two of the group consisting of Thyme Oil White, Isopropyl Myristate, and Wintergreen Oil (Technical).

In some embodiments, the blend of compounds can include Thyme Oil White, Isopropyl Myristate, and Wintergreen Oil (Technical).

In some embodiments, the blend of compounds can include between 12 and 30% Thyme Oil White, between 20 and 50% Isopropyl Myristate, and between 30 and 60% Wintergreen Oil (Technical).

In some embodiments, the blend of compounds can include between 18 and 23% Thyme Oil White, between 31 and 37.8% Isopropyl Myristate, and between 40 and 50% Wintergreen Oil (Technical).

In some embodiments, the blend of compounds can include 20.6% Thyme Oil White, 34.3% Isopropyl Myristate, and 45.1% Wintergreen Oil (Technical).

In some embodiments, the blend of compounds can include at least two of the group consisting of Castor Oil hydrogenated—PEO40, Lemon Grass Oil—India, and Blend 7.

In some embodiments, the blend of compounds can include Castor Oil hydrogenated—PEO40, Lemon Grass Oil—India, and Blend 7.

In some embodiments, the blend of compounds can include between 35 and 70% Castor Oil hydrogenated—PEO40, between 15 and 35% Lemon Grass Oil—India, and between 15 and 35% Blend 7.

In some embodiments, the blend of compounds can include between 49 and 60% Castor Oil hydrogenated (PEO40), between 20.7 and 25% Lemon Grass Oil (India), and between 20 and 24.6% Blend 7.

In some embodiments, the blend of compounds can include 54.63% Castor Oil hydrogenated—PEO40, 22.93% Lemon Grass Oil—India, and 22.44% Blend 7.

In some embodiments, the blend of compounds can include at least two of the group consisting of Lilac Flower Oil, D-Limonene, Thyme Oil White, and Black Seed Oil.

In some embodiments, the blend of compounds can include at least three of the group consisting of Lilac Flower Oil, D-Limonene, Thyme Oil White, and Black Seed Oil.

In some embodiments, the blend of compounds can include Lilac Flower Oil, D-Limonene, Thyme Oil White, and Black Seed Oil.

In some embodiments, the blend of compounds can include between 10 and 25% Lilac Flower Oil, between 45 and 90% D-Limonene, between 5 and 18% Thyme Oil White, and between 2.5 and 8% Black Seed Oil.

In some embodiments, the blend of compounds can include between 14.5 and 17.8% Lilac Flower Oil, between 60 and 75% D-Limonene, between 10 and 12.4% Thyme Oil White, and between 4.4 and 5.4% Black Seed Oil.

In some embodiments, the blend of compounds can include 16.18% Lilac Flower Oil, 67.81% D-Limonene, 11.18% Thyme Oil White, and 4.83% Black Seed Oil.

In some embodiments, the blend of compounds can include at least two of the group consisting of Lilac Flower Oil (LFO), D-Limonene, Thyme Oil White, and Black Seed Oil (BSO).

In some embodiments, the blend of compounds can include at least three of the group consisting of Lilac Flower Oil (LFO), D-Limonene, Thyme Oil White, and Black Seed Oil (BSO).

In some embodiments, the blend of compounds can include Lilac Flower Oil (LFO), D-Limonene, Thyme Oil White, and Black Seed Oil (BSO).

In some embodiments, the blend of compounds can include between 10 and 25% Lilac Flower Oil (LFO), between 45 and 90% D-Limonene, between 6 and 16% Thyme Oil White, and between 3 and 9% Black Seed Oil (BSO).

In some embodiments, the blend of compounds can include between 14.4 and 17.6% Lilac Flower Oil (LFO), between 60 and 75% D-Limonene, between 10.4 and 12.7% Thyme Oil White, and between 4.8 and 5.8% Black Seed Oil (BSO).

In some embodiments, the blend of compounds can include 16.01% LFO, 67.09% D-Limonene, 11.59% Thyme Oil White, and 5.31% BSO.

In some embodiments, the blend of compounds can include at least two to four of the group consisting of D-Limonene, Thyme Oil White, Blend 61, Linalool Coeur, Tetrahydrolinalool, Vanillin, Isopropyl myristate, Piperonal (aldehyde), Geraniol 60, Triethyl Citrate, and Isopar M.

In some embodiments, the blend of compounds can include at least five to seven of the group consisting of D-Limonene, Thyme Oil White, Blend 61, Linalool Coeur, Tetrahydrolinalool, Vanillin, Isopropyl myristate, Piperonal (aldehyde), Geraniol 60, Triethyl Citrate, and Isopar M.

In some embodiments, the blend of compounds can include at least eight to ten of the group consisting of D-Limonene, Thyme Oil White, Blend 61, Linalool Coeur, Tetrahydrolinalool, Vanillin, Isopropyl myristate, Piperonal (aldehyde), Geraniol 60, Triethyl Citrate, and Isopar M.

In some embodiments, the blend of compounds can include D-Limonene, Thyme Oil White, Blend 61, Linalool Coeur, Tetrahydrolinalool, Vanillin, Isopropyl myristate, Piperonal (aldehyde), Geraniol 60, Triethyl Citrate, and Isopar M.

In some embodiments, the blend of compounds can include between 5 and 12% D-Limonene, between 5 and 15% Thyme Oil White, between 40 and 70% Blend 61, between 0.5 and 4% Linalool Coeur, between 1 and 5% Tetrahydrolinalool, between 0.05 and 0.5% Vanillin, between 1 and 5% Isopropyl myristate, between 1 and 5% Piperonal (aldehyde), between 0.5 and 4% Geraniol 60, between 1 and 6% Triethyl Citrate, and between 8 and 18% Isopar M.

In some embodiments, the blend of compounds can include between 8 and 9.6% D-Limonene, between 8.8 and 10.6% Thyme Oil White, between 50 and 60% Blend 61, between 1.5 and 1.85% Linalool Coeur, between 2.1 and 2.5% Tetrahydrolinalool, between 0.135 and 0.165% Vanillin, between 2.1 and 2.5% Isopropyl myristate, between 2.1 and 2.6% Piperonal (aldehyde), between 1.1 and 1.35% Geraniol 60, between 2.1 and 2.6% Triethyl Citrate, and between 12.5 and 15.3% Isopar M.

In some embodiments, the blend of compounds can include 8.83% D-Limonene, 9.71% Thyme Oil White, 55.17% Blend 61, 1.68% Linalool Coeur, 2.31% Tetrahydrolinalool, 0.15% Vanillin, 2.37% Isopropyl myristate, 2.37% Piperonal (aldehyde), 1.23% Geraniol 60, 2.38% Triethyl Citrate, and 13.80% Isopar M.

In some embodiments, the blend of compounds can include at least two to four of the group consisting of D-Limonene, Thyme Oil White, Blend 61, Linalool Coeur, Tetrahydrolinalool, Vanillin, Isopropyl myristate, Piperonal (aldehyde), Geraniol 60, and Triethyl Citrate.

In some embodiments, the blend of compounds can include at least five to seven of the group consisting of D-Limonene, Thyme Oil White, Blend 61, Linalool Coeur, Tetrahydrolinalool, Vanillin, Isopropyl myristate, Piperonal (aldehyde), Geraniol 60, and Triethyl Citrate.

In some embodiments, the blend of compounds can include at least eight or nine of the group consisting of D-Limonene, Thyme Oil White, Blend 61, Linalool Coeur, Tetrahydrolinalool, Vanillin, Isopropyl myristate, Piperonal (aldehyde), Geraniol 60, and Triethyl Citrate.

In some embodiments, the blend of compounds can include D-Limonene, Thyme Oil White, Blend 61, Linalool Coeur, Tetrahydrolinalool, Vanillin, Isopropyl myristate, Piperonal (aldehyde), Geraniol 60, and Triethyl Citrate.

In some embodiments, the blend of compounds can include between 5 and 15% D-Limonene, between 5 and 15% Thyme Oil White, between 45 and 85% Blend 61, between 0.8 and 3% Linalool Coeur, between 1 and 5% Tetrahydrolinalool, between 0.5 and 0.5% Vanillin, between 1 and 5% Isopropyl myristate, between 1 and 5% Piperonal (aldehyde), between 0.5 and 2.5% Geraniol 60, and between 1 and 5% Triethyl Citrate.

In some embodiments, the blend of compounds can include between 7.9 and 9.5% D-Limonene, between 8.6 and 10.5% Thyme Oil White, between 62 and 76% Blend 61, between 1.5 and 1.82% Linalool Coeur, between 2 and 2.5% Tetrahydrolinalool, between 0.14 and 0.16% Vanillin, between 2.1 and 2.6% Isopropyl myristate, between 2.1 and 2.6% Piperonal (aldehyde), between 1.1 and 1.32% Geraniol 60, and between 2.1 and 2.6% Triethyl Citrate.

In some embodiments, the blend of compounds can include 8.72% D-Limonene, 9.59% Thyme Oil White, 69.35% Blend 61, 1.66% Linalool Coeur, 2.28% Tetrahydrolinalool, 0.15% Vanillin, 2.34% Isopropyl myristate, 2.34% Piperonal (aldehyde), 1.21% Geraniol 60, and 2.35% Triethyl Citrate.

In some embodiments, the blend of compounds can include at least two of the group consisting of LFO, D-Limonene, Thyme Oil White, and Blend 61.

In some embodiments, the blend of compounds can include at least three of the group consisting of LFO, D-Limonene, Thyme Oil White, and Blend 61.

In some embodiments, the blend of compounds can include LFO, D-Limonene, Thyme Oil White, and Blend 61.

In some embodiments, the blend of compounds can include between 10 and 22% LFO, between 50 and 85% D-Limonene, between 2.5 and 8% Thyme Oil White, and between 5 and 16% Blend 61.

In some embodiments, the blend of compounds can include between 14.7 and 18% LFO, between 61 and 76% D-Limonene, between 4.8 and 5.9% Thyme Oil White, and between 9 and 11% Blend 61.

In some embodiments, the blend of compounds can include 16.31% LFO, 68.34% D-Limonene, 5.37% Thyme Oil White, and 9.98% Blend 61.

In some embodiments, the blend of compounds can include at least two or three of the group consisting of Linalool Coeur, Thymol (crystal), Alpha-Pinene (98%), Para-Cymene, and Trans-anethole.

In some embodiments, the blend of compounds can include at least four of the group consisting of Linalool Coeur, Thymol (crystal), Alpha-Pinene (98%), Para-Cymene, and Trans-anethole.

In some embodiments, the blend of compounds can include Linalool Coeur, Thymol (crystal), Alpha-Pinene (98%), Para-Cymene, and Trans-anethole.

In some embodiments, the blend of compounds can include between 3 and 8% Linalool Coeur, between 25 and 55% Thymol (crystal), between 1 and 4% Alpha-Pinene (98%), between 25 and 50% Para-Cymene, and between 12 and 26% Trans-anethole.

In some embodiments, the blend of compounds can include between 4.2 and 5.2% Linalool Coeur, between 36 and 45% Thymol (crystal), between 1.7 and 2.1% Alpha-Pinene (98%), between 31 and 38% Para-Cymene, and between 16 and 20% Trans-anethole.

In some embodiments, the blend of compounds can include 4.7% Linalool Coeur, 40.8% Thymol (crystal), 1.9% Alpha-Pinene (98%), 34.49% Para-Cymene, and 18.2% Trans-anethole.

In some embodiments, the blend of compounds can include at least two or three of the group consisting of Linalool Coeur, Soy Bean Oil, Thymol (crystal), Alpha-Pinene (98%), and Para-Cymene.

In some embodiments, the blend of compounds can include at least four of the group consisting of Linalool Coeur, Soy Bean Oil, Thymol (crystal), Alpha-Pinene (98%), and Para-Cymene.

In some embodiments, the blend of compounds can include Linalool Coeur, Soy Bean Oil, Thymol (crystal), Alpha-Pinene (98%), and Para-Cymene.

In some embodiments, the blend of compounds can include between 4 and 10% Linalool Coeur, between 16 and 30% Soy Bean Oil, between 25 and 55% Thymol (crystal), between 1.5 and 6% Alpha-Pinene (98%), and between 18 and 40% Para-Cymene.

In some embodiments, the blend of compounds can include between 6 and 7.4% Linalool Coeur, between 21.5 and 26.5% Soy Bean Oil, between 33 and 41% Thymol (crystal), between 3.4 and 4.2% Alpha-Pinene (98%), and between 25 and 31% Para-Cymene.

In some embodiments, the blend of compounds can include 6.6% Linalool Coeur, 24.0% Soy Bean Oil, 37.2% Thymol (crystal), 3.8% Alpha-Pinene (98%), and 28.39% Para-Cymene.

In some embodiments, the blend of compounds can include at least two or three of the group consisting of Linalool Coeur, Thymol (crystal), Alpha-Pinene (98%), Para-Cymene, and Trans-anethole.

In some embodiments, the blend of compounds can include at least four of the group consisting of Linalool Coeur, Thymol (crystal), Alpha-Pinene (98%), Para-Cymene, and Trans-anethole.

In some embodiments, the blend of compounds can include Linalool Coeur, Thymol (crystal), Alpha-Pinene (98%), Para-Cymene, and Trans-anethole.

In some embodiments, the blend of compounds can include between 30 and 55% Linalool Coeur, between 25 and 45% Thymol (crystal), between 3 and 8% Alpha-Pinene (98%), between 1 and 4% Para-Cymene, and between 12 and 26% Trans-anethole.

In some embodiments, the blend of compounds can include between 36 and 45% Linalool Coeur, between 31 and 37.5% Thymol (crystal), between 4.2 and 5.2% Alpha-Pinene (98%), between 1.7 and 2.1% Para-Cymene, and between 16.5 and 20% Trans-anethole.

In some embodiments, the blend of compounds can include 40.8% Linalool Coeur, 34.4% Thymol (crystal), 4.7% Alpha-Pinene (98%), 1.9% Para-Cymene, and 18.20% Trans-anethole.

In some embodiments, the blend of compounds can include at least two of the group consisting of Linalool Coeur, Thymol (crystal), Alpha-Pinene (98%), and Para-Cymene.

In some embodiments, the blend of compounds can include at least three of the group consisting of Linalool Coeur, Thymol (crystal), Alpha-Pinene (98%), and Para-Cymene.

In some embodiments, the blend of compounds can include Linalool Coeur, Thymol (crystal), Alpha-Pinene (98%), and Para-Cymene.

In some embodiments, the blend of compounds can include between 6 and 14% Linalool Coeur, between 30 and 65% Thymol (crystal), between 5 and 14% Alpha-Pinene (98%), and between 22.5 and 45% Para-Cymene.

In some embodiments, the blend of compounds can include between 8.5 and 10.5% Linalool Coeur, between 42 and 53% Thymol (crystal), between 8.5 and 10.4% Alpha-Pinene (98%), and between 30 and 36.5% Para-Cymene.

In some embodiments, the blend of compounds can include 9.49% Linalool Coeur, 47.87% Thymol (crystal), 9.46% Alpha-Pinene (98%), and 33.18% Para-Cymene.

In some embodiments, the blend of compounds can include at least two or three of the group consisting of Linalool Coeur, Tetrahydrolinalool, Vanillin, Isopropyl myristate, Piperonal (aldehyde), and Geraniol Fine FCC.

In some embodiments, the blend of compounds can include at least four or five of the group consisting of Linalool Coeur, Tetrahydrolinalool, Vanillin, Isopropyl myristate, Piperonal (aldehyde), and Geraniol Fine FCC.

In some embodiments, the blend of compounds can include Linalool Coeur, Tetrahydrolinalool, Vanillin, Isopropyl myristate, Piperonal (aldehyde), and Geraniol Fine FCC.

In some embodiments, the blend of compounds can include between 15 and 25% Linalool Coeur, between 18 and 32% Tetrahydrolinalool, between 1 and 5% Vanillin, between 18 and 40% Isopropyl myristate, between 5 and 16% Piperonal (aldehyde), and between 8 and 18% Geraniol Fine FCC.

In some embodiments, the blend of compounds can include between 18 and 22.3% Linalool Coeur, between 22 and 27% Tetrahydrolinalool, between 2.2 and 2.7% Vanillin, between 26 and 33% Isopropyl myristate, between 9 and 11% Piperonal (aldehyde), and between 12 and 14.6% Geraniol Fine FCC.

In some embodiments, the blend of compounds can include 20.15% Linalool Coeur, 24.23% Tetrahydrolinalool, 2.47% Vanillin, 29.84% Isopropyl myristate, 9.95% Piperonal (aldehyde), and 13.36% Geraniol Fine FCC.

In some embodiments, the blend of compounds can include at least two to five of the group consisting of Tetrahydrolinalool, Vanillin, Hercolyn D, Isopropyl myristate, Piperonal (aldehyde), Ethyl Linalool, Hedione, Triethyl Citrate, and Dipropylene glycol (DPG).

In some embodiments, the blend of compounds can include at least six to eight of the group consisting of Tetrahydrolinalool, Vanillin, Hercolyn D, Isopropyl myristate, Piperonal (aldehyde), Ethyl Linalool, Hedione, Triethyl Citrate, and Dipropylene glycol (DPG).

In some embodiments, the blend of compounds can include Tetrahydrolinalool, Vanillin, Hercolyn D, Isopropyl myristate, Piperonal (aldehyde), Ethyl Linalool, Hedione, Triethyl Citrate, and Dipropylene glycol (DPG).

In some embodiments, the blend of compounds can include between 15 and 30% Tetrahydrolinalool, between 0.5 and 3% Vanillin, between 2 and 8% Hercolyn D, between 10 and 20% Isopropyl myristate, between 4 and 12% Piperonal (aldehyde), between 15 and 32% Ethyl Linalool, between 4 and 10% Hedione, between 6 and 14% Triethyl Citrate, and between 5 and 14% Dipropylene glycol (DPG).

In some embodiments, the blend of compounds can include between 20 and 26% Tetrahydrolinalool, between 1.0 and 1.4% Vanillin, between 4 and 4.9% Hercolyn D, between 13.5 and 16.6% Isopropyl myristate, between 6.8 and 8.3% Piperonal (aldehyde), between 20 and 25.2% Ethyl Linalool, between 6 and 7.3% Hedione, between 9 and 11.2% Triethyl Citrate, and between 8.1 and 10% Dipropylene glycol (DPG).

In some embodiments, the blend of compounds can include 22.98% Tetrahydrolinalool, 1.17% Vanillin, 4.44% Hercolyn D, 15.10% Isopropyl myristate, 7.55% Piperonal (aldehyde), 22.91% Ethyl Linalool, 6.67% Hedione, 10.10% Triethyl Citrate, and 9.09% Dipropylene glycol (DPG).

In some embodiments, the blend of compounds can include at least two to four of the group consisting of Linalool Coeur, Tetradyrdolinalool, Vanillin, Isopropyl myristate, Piperonal (aldehyde), Geraniol 60, and Triethyl Citrate.

In some embodiments, the blend of compounds can include at least five or six of the group consisting of Linalool Coeur, Tetradyrdolinalool, Vanillin, Isopropyl myristate, Piperonal (aldehyde), Geraniol 60, and Triethyl Citrate.

In some embodiments, the blend of compounds can include Linalool Coeur, Tetradyrdolinalool, Vanillin, Isopropyl myristate, Piperonal (aldehyde), Geraniol 60, and Triethyl Citrate.

In some embodiments, the blend of compounds can include between 10 and 18% Linalool Coeur, between 12 and 25% Tetradyrdolinalool, between 0.5 and 2.5% Vanillin, between 12 and 28% Isopropyl myristate, between 12 and 30% Piperonal (aldehyde), between 6 and 14% Geraniol 60, and between 15 and 28% Triethyl Citrate.

In some embodiments, the blend of compounds can include between 12.2 and 14.8% Linalool Coeur, between 16.9 and 20.1% Tetradyrdolinalool, 1.08 and 1.32% Vanillin, between 17 and 21% Isopropyl myristate, between 17 and 21% Piperonal (aldehyde), between 8.8 and 10.8% Geraniol 60, and between 17 and 21% Triethyl Citrate.

In some embodiments, the blend of compounds can include 13.5% Linalool Coeur, 18.5% Tetradyrdolinalool, 1.2% Vanillin, 19.0% Isopropyl myristate, 19.0% Piperonal (aldehyde), 9.8% Geraniol 60, and 19.1% Triethyl Citrate.

In some embodiments, the blend of compounds can include at least two or three of the group consisting of Linalool Coeur, Tetrahydrolinalool, Vanillin, Isopropyl myristate, Piperonal (aldehyde), and Piperonyl Alcohol.

In some embodiments, the blend of compounds can include at least four or five of the group consisting of Linalool Coeur, Tetrahydrolinalool, Vanillin, Isopropyl myristate, Piperonal (aldehyde), and Piperonyl Alcohol.

In some embodiments, the blend of compounds can include Linalool Coeur, Tetrahydrolinalool, Vanillin, Isopropyl myristate, Piperonal (aldehyde), and Piperonyl Alcohol.

In some embodiments, the blend of compounds can include between 14 and 26% Linalool Coeur, between 16 and 32% Tetrahydrolinalool, between 0.5 and 3% Vanillin, between 16 and 32% Isopropyl myristate, between 16 and 32% Piperonal (aldehyde), and between 6 and 14% Piperonyl Alcohol.

In some embodiments, the blend of compounds can include between 17 and 21% Linalool Coeur, between 21 and 25.5% Tetrahydrolinalool, between 1.08 and 1.32% Vanillin, between 20.6 and 25.2% Isopropyl myristate, between 21 and 26% Piperonal (aldehyde), and between 8.6 and 10.5% Piperonyl Alcohol.

In some embodiments, the blend of compounds can include 19.2% Linalool Coeur, 23.2% Tetrahydrolinalool, 1.2% Vanillin, 22.9% Isopropyl myristate, 23.8% Piperonal (aldehyde), and 9.6% Piperonyl Alcohol.

In some embodiments, the blend of compounds can include of at least two to five of the group consisting of D-Limonene, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include of at least six to nine of the group consisting of D-Limonene, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include of at least ten to thirteen of the group consisting of D-Limonene, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include of at least fourteen to seventeen of the group consisting of D-Limonene, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include of at least eighteen to twenty-one of the group consisting of D-Limonene, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include of at least twenty-two to twenty-four of the group consisting of D-Limonene, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include D-Limonene, Linalool Coeur, Citral, gamma-terpinene, Alpha-Pinene (98%), Alpha-Terpineol, Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include between 38 and 60% D-Limonene, between 0.5 and 2.5% Linalool Coeur, between 6 and 14% Citral, between 6 and 16% gamma-terpinene, between 0.5 and 4% Alpha-Pinene (98%), between 3 and 10% Alpha-Terpineol, between 3 and 10% Terpinolene, between 0.5 and 4% Para-Cymene, between 1 and 5% Linalyl Acetate, between 1.2 and 5.5% Beta Pinene, between 0.05 and 0.4% Camphor Dextro, between 0.05 and 0.5% Terpinene 4 OL, between 1 and 6% Alpha Terpinene, between 0.5 and 2.5% Borneol L, between 0.2 and 1% Camphene, between 0.08 and 0.4% Decanal, between 0.08 and 0.4% Dodecanal, between 0.001 and 0.05% Fenchol Alpha, between 0.1 and 0.4% Geranyl Acetate, between 0.2 and 0.8% Isoborneol, between 0.1 and 0.8% 2-Methyl 1,3-cyclohexadiene, between 0.5 and 4% Myrcene, between 0.01 and 0.08% Nonanal, between 0.01 and 0.15% Octanal, and between 0.01 and 0.1% Tocopherol Gamma Tenox.

In some embodiments, the blend of compounds can include between 43 and 54% D-Limonene, between 1.1 and 1.34% Linalool Coeur, between 9.2 and 11.3% Citral, between 9.4 and 11.6% gamma-terpinene, between 1.7 and 2.13% Alpha-Pinene (98%), between 6.1 and 7.5% Alpha-Terpineol, between 5.6 and 7.0% Terpinolene, between 1.45 and 1.76% Para-Cymene, between 2.34 and 2.86% Linalyl Acetate, between 2.5 and 3.1% Beta Pinene, between 0.12 and 0.14% Camphor Dextro, between 0.1 and 0.12% Terpinene 4 OL, between 2.5 and 3.1% Alpha Terpinene, between 1.17 and 1.43% Borneol L, between 0.49 and 0.61% Camphene, between 0.155 and 0.185% Decanal, between 0.13 and 0.15% Dodecanal, between 0.009 and 0.011% Fenchol Alpha, between 0.16 and 0.20% Geranyl Acetate, between 0.37 and 0.45% Isoborneol, between 0.34 and 0.42% 2-Methyl 1,3-cyclohexadiene, between 1.03 and 1.25% Myrcene, between 0.027 and 0.033% Nonanal, between 0.054 and 0.066% Octanal, and between 0.027 and 0.033% Tocopherol Gamma Tenox.

In some embodiments, the blend of compounds can include 48.58% D-Limonene, 1.22% Linalool Coeur, 10.21% Citral, 10.51% gamma-terpinene, 1.94% Alpha-Pinene (98%), 6.80% Alpha-Terpineol, 6.30% Terpinolene, 1.61% Para-Cymene, 2.60% Linalyl Acetate, 2.80% Beta Pinene, 0.13% Camphor Dextro, 0.11% Terpinene 4 OL, 2.80% Alpha Terpinene, 1.30% Borneol L, 0.54% Camphene, 0.17% Decanal, 0.14% Dodecanal, 0.01% Fenchol Alpha, 0.18% Geranyl Acetate, 0.41% Isoborneol, 0.38% 2-Methyl 1,3-cyclohexadiene, 1.14% Myrcene, 0.03% Nonanal, 0.06% Octanal, and 0.03% Tocopherol Gamma Tenox.

In some embodiments, the blend of compounds can include at least two to six of the group consisting of D-Limonene, Linalool Coeur, gamma-terpinene, Alpha-Pinene (98%), Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include at least seven to ten of the group consisting of D-Limonene, Linalool Coeur, gamma-terpinene, Alpha-Pinene (98%), Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include at least eleven to fourteen of the group consisting of D-Limonene, Linalool Coeur, gamma-terpinene, Alpha-Pinene (98%), Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include at least fifteen to eighteen of the group consisting of D-Limonene, Linalool Coeur, gamma-terpinene, Alpha-Pinene (98%), Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include at least nineteen to twenty-two of the group consisting of D-Limonene, Linalool Coeur, gamma-terpinene, Alpha-Pinene (98%), Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include D-Limonene, Linalool Coeur, gamma-terpinene, Alpha-Pinene (98%), Terpinolene, Para-Cymene, Linalyl Acetate, Beta Pinene, Camphor Dextro, Terpinene 4 OL, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, and Tocopherol Gamma Tenox.

In some embodiments, the blend of compounds can include between 42 and 75% D-Limonene, between 0.5 and 4% Linalool Coeur, between 6 and 18% gamma-terpinene, between 1 and 5% Alpha-Pinene (98%), between 3 and 14% Terpinolene, between 0.5 and 4% Para-Cymene, between 1 and 6% Linalyl Acetate, between 1 and 6% Beta Pinene, between 0.01 and 0.5% Camphor Dextro, between 0.001 and 0.5% Terpinene 4 OL, between 1 and 6% Alpha Terpinene, between 0.5 and 4% Borneol L, between 0.1 and 2% Camphene, between 0.05 and 0.5% Decanal, between 0.05 and 0.5% Dodecanal, between 0.001 and 0.1% Fenchol Alpha, between 0.05 and 0.5% Geranyl Acetate, between 0.1 and 1% Isoborneol, between 0.1 and 1% 2-Methyl 1,3-cyclohexadiene, between 0.5 and 4% Myrcene, between 0.01 and 0.1% Nonanal, between 0.01 and 0.25% Octanal, and between 0.01 and 0.1% Tocopherol Gamma Tenox.

In some embodiments, the blend of compounds can include between 52 and 65% D-Limonene, between 1.3 and 1.61% Linalool Coeur, between 11.4 and 13.9% gamma-terpinene, between 2.1 and 2.6% Alpha-Pinene (98%), between 6.8 and 8.5% Terpinolene, between 1.7 and 2.2% Para-Cymene, between 2.8 and 2.45% Linalyl Acetate, between 3 and 3.7% Beta Pinene, between 0.145 and 0.176% Camphor Dextro, between 0.12 and 0.14% Terpinene 4 OL, between 3 and 3.7% Alpha Terpinene, between 1.42 and 1.72% Borneol L, between 0.59 and 0.71% Camphene, between 0.18 and 0.22% Decanal, between 0.155 and 0.185% Dodecanal, between 0.009 and 0.011% Fenchol Alpha, 0.2 and 0.24% Geranyl Acetate, between 0.44 and 0.54% Isoborneol, between 0.42 and 0.5% 2-Methyl 1,3-cyclohexadiene, between 1.24 and 1.5% Myrcene, between 0.036 and 0.044% Nonanal, between 0.06 and 0.08% Octanal, and between 0.036 and 0.044% Tocopherol Gamma Tenox.

In some embodiments, the blend of compounds can include 58.54% D-Limonene, 1.47% Linalool Coeur, 12.66% gamma-terpinene, 2.34% Alpha-Pinene (98%), 7.59% Terpinolene, 1.94% Para-Cymene, 3.13% Linalyl Acetate, 3.37% Beta Pinene, 0.16% Camphor Dextro, 0.13% Terpinene 4 OL, 3.37% Alpha Terpinene, 1.57% Borneol L, 0.65% Camphene, 0.20% Decanal, 0.17% Dodecanal, 0.01% Fenchol Alpha, 0.22% Geranyl Acetate, 0.49% Isoborneol, 0.46% 2-Methyl 1,3-cyclohexadiene, 1.37% Myrcene, 0.04% Nonanal, 0.07% Octanal, and 0.04% Tocopherol Gamma Tenox.

In some embodiments, the blend of compounds can include at least two to four of the group consisting of D-Limonene, Linalool Coeur, Alpha-Pinene (98%), Terpinolene, Para-Cymene, Linalyl Acetate, Beta Pinene, Alpha Terpinene, Camphene, and Myrcene.

In some embodiments, the blend of compounds can include at least five to seven of the group consisting of D-Limonene, Linalool Coeur, Alpha-Pinene (98%), Terpinolene, Para-Cymene, Linalyl Acetate, Beta Pinene, Alpha Terpinene, Camphene, and Myrcene.

In some embodiments, the blend of compounds can include at least eight or nine of the group consisting of D-Limonene, Linalool Coeur, Alpha-Pinene (98%), Terpinolene, Para-Cymene, Linalyl Acetate, Beta Pinene, Alpha Terpinene, Camphene, and Myrcene.

In some embodiments, the blend of compounds can include D-Limonene, Linalool Coeur, Alpha-Pinene (98%), Terpinolene, Para-Cymene, Linalyl Acetate, Beta Pinene, Alpha Terpinene, Camphene, and Myrcene.

In some embodiments, the blend of compounds can include between 25 and 45% D-Limonene, between 6 and 14% Linalool Coeur, between 2 and 8% Alpha-Pinene (98%), between 6 and 14% Terpinolene, between 6 and 14% Para-Cymene, between 2.5 and 8% Linalyl Acetate, between 2 and 8% Beta Pinene, between 2 and 8% Alpha Terpinene, between 2.5 and 9% Camphene, and between 6 and 15% Myrcene.

In some embodiments, the blend of compounds can include between 31 and 38% D-Limonene, between 9 and 11.1% Linalool Coeur, between 4.5 and 5.5% Alpha-Pinene (98%), between 9 and 11.2% Terpinolene, between 9 and 11.1% Para-Cymene, between 2.8 and 5.9% Linalyl Acetate, between 4.5 and 5.8% Beta Pinene, between 4.3 and 5.4% Alpha Terpinene, between 5.2 and 6.4% Camphene, and between 8.3 and 10.2% Myrcene.

In some embodiments, the blend of compounds can include 34.50% D-Limonene, 10.05% Linalool Coeur, 5.01% Alpha-Pinene (98%), 10.10% Terpinolene, 10.04% Para-Cymene, 5.30% Linalyl Acetate, 5.02% Beta Pinene, 4.88% Alpha Terpinene, 5.84% Camphene, and 9.26% Myrcene.

In some embodiments, the blend of compounds can include Blend 41 and Blend 105 (10% Sodium Lauryl Sulfate, 90.00% Water).

In some embodiments, the blend of compounds can include between 70 and 99% Blend 41 and between 5 and 15% Blend 105 (10% Sodium Lauryl Sulfate, 90.00% Water).

In some embodiments, the blend of compounds can include between 81 and 99% Blend 41 and between 9 and 11% Blend 105 (10% Sodium Lauryl Sulfate, 90.00% Water).

In some embodiments, the blend of compounds can include 90% Blend 41 and 10% Blend 105 (10% Sodium Lauryl Sulfate, 90.00% Water).

In some embodiments, the blend of compounds can include at least two of the group consisting of Polyglycerol-4-oleate, Lecithin, Water, and Blend 41.

In some embodiments, the blend of compounds can include at least three of the group consisting of Polyglycerol-4-oleate, Lecithin, Water, and Blend 41.

In some embodiments, the blend of compounds can include Polyglycerol-4-oleate, Lecithin, Water, and Blend 41.

In some embodiments, the blend of compounds can include between 0.6 and 1.4% Polyglycerol-4-oleate, between 0.05 and 0.5% Lecithin, between 6 and 16% Water, and between 70 and 99% Blend 41.

In some embodiments, the blend of compounds can include between 0.8 and 1.0% Polyglycerol-4-oleate, between 0.18 and 0.22% Lecithin, between 8.8 and 10.8% Water, and between 80 and 98% Blend 41.

In some embodiments, the blend of compounds can include 0.90% Polyglycerol-4-oleate, 0.20% Lecithin, 9.8% Water, and 89.1% Blend 41.

In some embodiments, the blend of compounds can include at least two of the group consisting of Potassium sorbate, Xanthan Gum, Water, and Blend 65.

In some embodiments, the blend of compounds can include at least three of the group consisting of Potassium sorbate, Xanthan Gum, Water, and Blend 65.

In some embodiments, the blend of compounds can include Potassium sorbate, Xanthan Gum, Water, and Blend 65.

In some embodiments, the blend of compounds can include 0.2 and 2.5% Potassium sorbate, between 0.1 and 0.8% Xanthan Gum, between 60 and 95% Water, and between 10 and 22% Blend 65.

In some embodiments, the blend of compounds can include between 0.9 and 1.1% Potassium sorbate, between 0.25 and 0.31% Xanthan Gum, between 73 and 89% Water, and between 15.3 and 18.4% Blend 65.

In some embodiments, the blend of compounds can include 1.00% Potassium sorbate, 0.28% Xanthan Gum, 81.82% Water, and 16.90% Blend 65.

In some embodiments, the blend of compounds can include at least two or three of the group consisting of Potassium sorbate, Polyglycerol-4-oleate, Xanthan Gum, Lecithin, Water, and Blend 41.

In some embodiments, the blend of compounds can include at least four or five of the group consisting of Potassium sorbate, Polyglycerol-4-oleate, Xanthan Gum, Lecithin, Water, and Blend 41.

In some embodiments, the blend of compounds can include Potassium sorbate, Polyglycerol-4-oleate, Xanthan Gum, Lecithin, Water, and Blend 41.

In some embodiments, the blend of compounds can include between 0.05 and 0.2% Potassium sorbate, between 0.05 and 0.25% Polyglycerol-4-oleate, between 0.1 and 0.5% Xanthan Gum, between 0.01 and 0.1% Lecithin, between 50 and 95% Water, and between 5 and 20% Blend 41.

In some embodiments, the blend of compounds can include between 0.10 and 0.12% Potassium sorbate, between 0.135 and 0.165% Polyglycerol-4-oleate, between 0.25 and 0.31% Xanthan Gum, between 0.030 and 0.038% Lecithin, between 76 and 92% Water, and between 13.5 and 16.5% Blend 41.

In some embodiments, the blend of compounds can include 0.11% Potassium sorbate, 0.15% Polyglycerol-4-oleate, 0.28% Xanthan Gum, 0.034% Lecithin, 84.4% Water, and 15% Blend 41.

In some embodiments, the blend of compounds can include at least two to four of the group consisting of Thyme Oil White, Wintergreen Oil, Isopropyl myristate, Potassium sorbate, Polyglycerol-4-oleate, Xanthan Gum, Lecithin, and Water.

In some embodiments, the blend of compounds can include at least five to seven of the group consisting of Thyme Oil White, Wintergreen Oil, Isopropyl myristate, Potassium sorbate, Polyglycerol-4-oleate, Xanthan Gum, Lecithin, and Water.

In some embodiments, the blend of compounds can include Thyme Oil White, Wintergreen Oil, Isopropyl myristate, Potassium sorbate, Polyglycerol-4-oleate, Xanthan Gum, Lecithin, and Water.

In some embodiments, the blend of compounds can include between 1.5 and 5% Thyme Oil White, between 3 and 10% Wintergreen Oil, between 2 and 8% Isopropyl myristate, between 0.05 and 0.5% Potassium sorbate, between 0.05 and 0.5% Polyglycerol-4-oleate, between 0.1 and 0.5% Xanthan Gum, between 0.01 and 0.1% Lecithin, and between 50 and 95% Water.

In some embodiments, the blend of compounds can include 2.7 and 3.4% Thyme Oil White, between 6 and 7.5% Wintergreen Oil, between 4.5 and 5.7% Isopropyl myristate, between 0.1 and 0.12% Potassium sorbate, between 0.135 and 0.165% Polyglycerol-4-oleate, between 0.25 and 0.31% Xanthan Gum, between 0.027 and 0.033% Lecithin, and between 76 and 91% Water.

In some embodiments, the blend of compounds can include 3.09% Thyme Oil White, 6.77% Wintergreen Oil, 5.15% Isopropyl myristate, 0.11% Potassium sorbate, 0.15% Polyglycerol-4-oleate, 0.28% Xanthan Gum, 0.03% Lecithin, and 84.41% Water.

In some embodiments, the blend of compounds can include at least two of the group consisting of Polyglycerol-4-oleate, Lecithin, Water, and Blend 18.

In some embodiments, the blend of compounds can include at least three of the group consisting of Polyglycerol-4-oleate, Lecithin, Water, and Blend 18.

In some embodiments, the blend of compounds can include Polyglycerol-4-oleate, Lecithin, Water, and Blend 18.

In some embodiments, the blend of compounds can include between 0.5 and 2% Polyglycerol-4-oleate, between 0.1 and 0.5% Lecithin, between 2 and 20% Water, and between 50 and 98% Blend 18.

In some embodiments, the blend of compounds can include 0.8 and 1.0% Polyglycerol-4-oleate, between 0.18 and 0.22% Lecithin, between 8 and 12% Water, and between 80 and 95% Blend 18.

In some embodiments, the blend of compounds can include 0.90% Polyglycerol-4-oleate, 0.20% Lecithin, 9.8% Water, and 89.10% Blend 18.

In some embodiments, the blend of compounds can include at least two of the group consisting of Water, Blend 65, and Blend 104 (1% Potassium Sorbate, 2.50% Xanthan Gum, 96.50% Water).

In some embodiments, the blend of compounds can include Water, Blend 65, and Blend 104 (1% Potassium Sorbate, 2.50% Xanthan Gum, 96.50% Water).

In some embodiments, the blend of compounds can include between 1 and 6% Water, between 50 and 95% Blend 65, and between 5 and 20% Blend 104 (1% Potassium Sorbate, 2.50% Xanthan Gum, 96.50% Water).

In some embodiments, the blend of compounds can include between 2.7 and 3.4% Water, between 76 and 92% Blend 65, and between 11.5 and 14% Blend 104 (1% Potassium Sorbate, 2.50% Xanthan Gum, 96.50% Water).

In some embodiments, the blend of compounds can include 3.1% Water, 84.2% Blend 65, and 12.7% Blend 104 (1% Potassium Sorbate, 2.50% Xanthan Gum, 96.50% Water).

In some embodiments, the blend of compounds can include at least two to four of the group consisting of Thyme Oil White, Wintergreen Oil, Isopropyl myristate, Potassium sorbate, Polyglycerol-4-oleate, Xanthan Gum, Lecithin, and Water.

In some embodiments, the blend of compounds can include at least five to seven of the group consisting of Thyme Oil White, Wintergreen Oil, Isopropyl myristate, Potassium sorbate, Polyglycerol-4-oleate, Xanthan Gum, Lecithin, and Water.

In some embodiments, the blend of compounds can include Thyme Oil White, Wintergreen Oil, Isopropyl myristate, Potassium sorbate, Polyglycerol-4-oleate, Xanthan Gum, Lecithin, and Water.

In some embodiments, the blend of compounds can include between 8 and 25% Thyme Oil White, between 20 and 50% Wintergreen Oil, between 15 and 40% Isopropyl myristate, between 0.05 and 0.5% Potassium sorbate, between 0.1 and 2% Polyglycerol-4-oleate, between 0.1 and 0.6% Xanthan Gum, between 0.05 and 0.4% Lecithin, and between 10 and 40% Water.

In some embodiments, the blend of compounds can include between 14 and 17% Thyme Oil White, between 30 and 37% Wintergreen Oil, between 23 and 27.5% Isopropyl myristate, between 0.115 and 0.145% Potassium sorbate, between 0.7 and 0.83% Polyglycerol-4-oleate, between 0.29 and 0.36% Xanthan Gum, between 0.15 and 0.19% Lecithin, and between 21 and 26% Water.

In some embodiments, the blend of compounds can include 15.5% Thyme Oil White, 33.8% Wintergreen Oil, 25.7% Isopropyl myristate, 0.13% Potassium sorbate, 0.76% Polyglycerol-4-oleate, 0.32% Xanthan Gum, 0.17% Lecithin, and 23.6% Water.

In some embodiments, the blend of compounds can include at least two of the group consisting of Water, Blend 65, and Blend 104 (1% Potassium Sorbate, 2.50% Xanthan Gum, 96.50% Water).

In some embodiments, the blend of compounds can include Water, Blend 65, and Blend 104 (1% Potassium Sorbate, 2.50% Xanthan Gum, 96.50% Water).

In some embodiments, the blend of compounds can include between 5 and 20% Water, between 50 and 95% Blend 65, and between 5 and 20% Blend 104 (1% Potassium Sorbate, 2.50% Xanthan Gum, 96.50% Water).

In some embodiments, the blend of compounds can include between 8 and 12% Water, between 70 and 88% Blend 65, and between 10.5 and 13.2% Blend 104 (1% Potassium Sorbate, 2.50% Xanthan Gum, 96.50% Water).

In some embodiments, the blend of compounds can include 9.2% Water, 78.87% Blend 65, and 11.90% Blend 104 (1% Potassium Sorbate, 2.50% Xanthan Gum, 96.50% Water).

In some embodiments, the blend of compounds can include at least two or three of the group consisting of Potassium sorbate, Polyglycerol-4-oleate, Xanthan gum, Lecithin, Water, and Blend 41.

In some embodiments, the blend of compounds can include at least four or five of the group consisting of Potassium sorbate, Polyglycerol-4-oleate, Xanthan gum, Lecithin, Water, and Blend 41.

In some embodiments, the blend of compounds can include Potassium sorbate, Polyglycerol-4-oleate, Xanthan gum, Lecithin, Water, and Blend 41.

In some embodiments, the blend of compounds can include between 0.05 and 0.25% Potassium sorbate, between 0.4 and 1.5% Polyglycerol-4-oleate, between 0.1 and 1% Xanthan gum, between 0.05 and 0.5% Lecithin, between 10 and 40% Water, and between 40 and 90% Blend 41.

In some embodiments, the blend of compounds can include between 0.11 and 0.15% Potassium sorbate, between 0.7 and 0.84% Polyglycerol-4-oleate, between 0.29 and 0.36% Xanthan gum, between 0.15 and 0.19% Lecithin, between 25 and 32% Water, and between 63 and 77% Blend 41.

In some embodiments, the blend of compounds can include 0.13% Potassium sorbate, 0.76% Polyglycerol-4-oleate, 0.32% Xanthan gum, 0.17% Lecithin, 28.6% Water, and 70% Blend 41.

In some embodiments, the blend of compounds can include at least two of the group consisting of Water, Blend 69, and Blend 104 (1% Potassium Sorbate, 2.50% Xanthan Gum, 96.50% Water).

In some embodiments, the blend of compounds can include Water, Blend 69, and Blend 104 (1% Potassium Sorbate, 2.50% Xanthan Gum, 96.50% Water).

In some embodiments, the blend of compounds can include between 1 and 6% Water, between 50 and 95% Blend 69, and between 5 and 20% Blend 104 (1% Potassium Sorbate, 2.50% Xanthan Gum, 96.50% Water).

In some embodiments, the blend of compounds can include between 2.8 and 3.4% Water, between 76 and 92% Blend 69, and between 11.5 and 14% Blend 104 (1% Potassium Sorbate, 2.50% Xanthan Gum, 96.50% Water).

In some embodiments, the blend of compounds can include 3.1% Water, 84.2% Blend 69, and 12.7% Blend 104 (1% Potassium Sorbate, 2.50% Xanthan Gum, 96.50% Water).

In some embodiments, the blend of compounds can include at least two of the group consisting Potassium sorbate, Xanthan gum, Water, and Blend 69.

In some embodiments, the blend of compounds can include at least three of the group consisting Potassium sorbate, Xanthan gum, Water, and Blend 69.

In some embodiments, the blend of compounds can include Potassium sorbate, Xanthan gum, Water, and Blend 69.

In some embodiments, the blend of compounds can include between 0.5 and 2% Potassium sorbate, between 0.1 and 0.6% Xanthan gum, between 50 and 95% Water, and between 5 and 30% Blend 69.

In some embodiments, the blend of compounds can include between 0.9 and 1.1% Potassium sorbate, between 0.25 and 0.31% Xanthan gum, between 73 and 90% Water, and between 15.3 and 18.5% Blend 69.

In some embodiments, the blend of compounds can include 1% Potassium sorbate, 0.28% Xanthan gum, 81.8% Water, and 16.9% Blend 69.

In some embodiments, the blend of compounds can include at least two of the group consisting of Polyglycerol-4-oleate, Lecithin, Water, and Blend 47.

In some embodiments, the blend of compounds can include at least three of the group consisting of Polyglycerol-4-oleate, Lecithin, Water, and Blend 47.

In some embodiments, the blend of compounds can include Polyglycerol-4-oleate, Lecithin, Water, and Blend 47.

In some embodiments, the blend of compounds can include between 0.5 and 2.5% Polyglycerol-4-oleate, between 0.1 and 0.5% Lecithin, between 2 and 15% Water, and between 50 and 98% Blend 47.

In some embodiments, the blend of compounds can include between 0.8 and 1.0% Polyglycerol-4-oleate, between 0.18 and 0.22% Lecithin, between 8.9 and 11% Water, and between 80 and 92% Blend 47.

In some embodiments, the blend of compounds can include 0.90% Polyglycerol-4-oleate, 0.20% Lecithin, 9.8% Water, and 89.10% Blend 47.

In some embodiments, the blend of compounds can include at least two of the group consisting of Potassium sorbate, Xanthan gum, Water, and Blend 77.

In some embodiments, the blend of compounds can include at least three of the group consisting of Potassium sorbate, Xanthan gum, Water, and Blend 77.

In some embodiments, the blend of compounds can include Potassium sorbate, Xanthan gum, Water, and Blend 77.

In some embodiments, the blend of compounds can include between 0.5 and 2.5% Potassium sorbate, between 0.1 and 1% Xanthan gum, between 50 and 95% Water, and between 5 and 30% Blend 77.

In some embodiments, the blend of compounds can include between 0.9 and 1.1% Potassium sorbate, between 0.25 and 0.31% Xanthan gum, between 73 and 90% Water, and between 15.3 and 17.5% Blend 77.

In some embodiments, the blend of compounds can include 1.00% Potassium sorbate, 0.28% Xanthan gum, 81.82% Water, and 16.9% Blend 77.

In some embodiments, the blend of compounds can include at least two to five of the group consisting of Citronella Oil, Carbopol 940, BHT, Water, Emulsifying Wax, Light liquid paraffin, White Soft Paraffin, Sodium metabisulfate, Propylene glycol, Methyl paraben, Propyl paraben, Cresmer RH40 hydrogenated, Triethanolamine, Vitamin E acetate, Disodium EDTA, and Blend 7.

In some embodiments, the blend of compounds can include at least six to nine of the group consisting of Citronella Oil, Carbopol 940, BHT, Water, Emulsifying Wax, Light liquid paraffin, White Soft Paraffin, Sodium metabisulfate, Propylene glycol, Methyl paraben, Propyl paraben, Cresmer RH40 hydrogenated, Triethanolamine, Vitamin E acetate, Disodium EDTA, and Blend 7.

In some embodiments, the blend of compounds can include at least ten to fourteen of the group consisting of Citronella Oil, Carbopol 940, BHT, Water, Emulsifying Wax, Light liquid paraffin, White Soft Paraffin, Sodium metabisulfate, Propylene glycol, Methyl paraben, Propyl paraben, Cresmer RH40 hydrogenated, Triethanolamine, Vitamin E acetate, Disodium EDTA, and Blend 7.

In some embodiments, the blend of compounds can include Citronella Oil, Carbopol 940, BHT, Water, Emulsifying Wax, Light liquid paraffin, White Soft Paraffin, Sodium metabisulfate, Propylene glycol, Methyl paraben, Propyl paraben, Cresmer RH40 hydrogenated, Triethanolamine, Vitamin E acetate, Disodium EDTA, and Blend 7.

In some embodiments, the blend of compounds can include between 0.1 and 0.5% Citronella Oil, between 0.1 and 0.5% Carbopol 940, between 0.05 and 0.5% BHT, between 40 and 80% Water, between 8 and 25% Emulsifying Wax, between 2 and 8% Light liquid paraffin, between 5 and 15% White Soft Paraffin, between 0.1 and 0.5% Sodium metabisulfate, between 1 and 5% Propylene glycol, between 0.05 and 0.5% Methyl paraben, between 0.01 and 0.1% Propyl paraben, between 2 and 10% Cresmer RH40 hydrogenated, between 0.01 and 0.5% Triethanolamine, between 0.005 and 0.05% Vitamin E acetate, between 0.005 and 0.5% Disodium EDTA, and between 2 and 10% Blend 7.

In some embodiments, the blend of compounds can include between 0.18 and 0.22% Citronella Oil, between 0.18 and 0.22% Carbopol 940, between 0.9 and 0.11% BHT, between 54 and 66% Water, between 12.5 and 16% Emulsifying Wax, between 3.6 and 4.4% Light liquid paraffin, between 8.1 and 9.9% White Soft Paraffin, between 0.22 and 0.28% Sodium metabisulfate, between 1.8 and 2.2% Propylene glycol, between 0.13 and 0.17% Methyl paraben, between 0.045 and 0.055% Propyl paraben, between 4.5 and 5.5% Cresmer RH40 hydrogenated, between 0.13 and 0.17% Triethanolamine, between 0.018 and 0.022% Vitamin E acetate, between 0.045 and 0.055% Disodium EDTA, and between 4.5 and 5.5% Blend 7.

In some embodiments, the blend of compounds can include 0.20% Citronella Oil, 0.20% Carbopol 940, 0.10% BHT, 59.83% Water, 14.00% Emulsifying Wax, 4.00% Light liquid paraffin, 9.00% White Soft Paraffin, 0.25% Sodium metabisulfate, 2.00% Propylene glycol, 0.15% Methyl paraben, 0.05% Propyl paraben, 5.00% Cresmer RH40 hydrogenated, 0.15% Triethanolamine, 0.02% Vitamin E acetate, 0.05% Disodium EDTA, and 5.00% Blend 7.

In some embodiments, the blend of compounds can include at least two to four of the group consisting of Span 80, Sodium benzoate, Isopar M, A46 Propellant, Water, Isopropyl alcohol, and Blend 6.

In some embodiments, the blend of compounds can include at least five or six of the group consisting of Span 80, Sodium benzoate, Isopar M, A46 Propellant, Water, Isopropyl alcohol, and Blend 6.

In some embodiments, the blend of compounds can include Span 80, Sodium benzoate, Isopar M, A46 Propellant, Water, Isopropyl alcohol, and Blend 6.

In some embodiments, the blend of compounds can include between 0.005 and 0.5% Span 80, between 0.05 and 0.5% Sodium benzoate, between 15 and 40% Isopar M, between 8 and 25% A46 Propellant, between 20 and 60% Water, between 0.5 and 3% Isopropyl alcohol, and between 5 and 20% Blend 6.

In some embodiments, the blend of compounds can include between 0.045 and 0.055% Span 80, between 0.18 and 0.22% Sodium benzoate, between 26 and 32% Isopar M, between 13 and 16% A46 Propellant, between 38 and 46% Water, between 1.3 and 1.7% Isopropyl alcohol, and between 11.2 and 13.7% Blend 6.

In some embodiments, the blend of compounds can include 0.05% Span 80, 0.20% Sodium benzoate, 29% Isopar M, 14.5% A46 Propellant, 42.25% Water, 1.50% Isopropyl alcohol, and 12.5% Blend 6.

In some embodiments, the blend of compounds can include at least two of the group consisting of Isopar M, A46 propellant, Isopropyl alcohol, and Blend 36.

In some embodiments, the blend of compounds can include at least three of the group consisting of Isopar M, A46 propellant, Isopropyl alcohol, and Blend 36.

In some embodiments, the blend of compounds can include Isopar M, A46 propellant, Isopropyl alcohol, and Blend 36.

In some embodiments, the blend of compounds can include between 30 and 70% Isopar M, between 25 and 55% A46 propellant, between 1 and 6% Isopropyl alcohol, and between 3 and 12% Blend 36.

In some embodiments, the blend of compounds can include between 46 and 56% Isopar M, between 36 and 44% A46 propellant, between 2.7 and 3.3% Isopropyl alcohol, and between 5.4 and 6.6% Blend 36.

In some embodiments, the blend of compounds can include 51.0% Isopar M, 40.0% A46 propellant, 3.0% Isopropyl alcohol, and 6.0% Blend 36.

In some embodiments, the blend of compounds can include at least two or three of the group consisting of Isopar M, A46 propellant, Bifenthrin, Isopropyl alcohol, and Blend 36.

In some embodiments, the blend of compounds can include at least four of the group consisting of Isopar M, A46 propellant, Bifenthrin, Isopropyl alcohol, and Blend 36.

In some embodiments, the blend of compounds can include Isopar M, A46 propellant, Bifenthrin, Isopropyl alcohol, and Blend 36.

In some embodiments, the blend of compounds can include between 30 and 70% Isopar M, between 25 and 60% A46 propellant, between 0.005 and 0.1% Bifenthrin, between 1 and 6% Isopropyl alcohol, and between 3 and 12% Blend 36.

In some embodiments, the blend of compounds can include between 46 and 56% Isopar M, between 36 and 44% A46 propellant, between 0.045 and 0.055% Bifenthrin, between 2.7 and 3.3% Isopropyl alcohol, and between 5.4 and 6.6% Blend 36.

In some embodiments, the blend of compounds can include 51.0% Isopar M, 40.0% A46 propellant, 0.05% Bifenthrin, 3.0% Isopropyl alcohol, and 6.0% Blend 36.

In some embodiments, the blend of compounds can include at least two of the group consisting of Isopar M, A46 propellant, and Blend 31.

In some embodiments, the blend of compounds can include Isopar M, A46 propellant, and Blend 31.

In some embodiments, the blend of compounds can include between 25 and 70% Isopar M, between 20 and 65% A46 propellant, and between 3 and 12% Blend 31.

In some embodiments, the blend of compounds can include between 49 and 60% Isopar M, between 36 and 44% A46 propellant, and between 5.4 and 6.6% Blend 31.

In some embodiments, the blend of compounds can include 54.0% Isopar M, 40.0% A46 propellant, and 6.0% Blend 31.

In some embodiments, the blend of compounds can include at least two to four of the group consisting of Thyme Oil White, Wintergreen Oil, Isopropyl myristate, Potassium Sorbate, Polyclycerol-4-oleate, Xanthan Gum, Lecithin, and Water.

In some embodiments, the blend of compounds can include at least five to seven of the group consisting of Thyme Oil White, Wintergreen Oil, Isopropyl myristate, Potassium Sorbate, Polyclycerol-4-oleate, Xanthan Gum, Lecithin, and Water.

In some embodiments, the blend of compounds can include Thyme Oil White, Wintergreen Oil, Isopropyl myristate, Potassium Sorbate, Polyclycerol-4-oleate, Xanthan Gum, Lecithin, and Water.

In some embodiments, the blend of compounds can include between 1 and 4% Thyme Oil White, between 2 and 8% Wintergreen Oil, between 1.5 and 5% Isopropyl myristate, between 0.01 and 0.5% Potassium Sorbate, between 0.05 and 0.5% Polyclycerol-4-oleate, between 0.1 and 0.6% Xanthan Gum, between 0.005 and 0.1% Lecithin, and between 60 and 99% Water.

In some embodiments, the blend of compounds can include between 1.8 and 2.3% Thyme Oil White, between 4 and 5% Wintergreen Oil, between 3.1 and 3.75% Isopropyl myristate, between 0.10 and 0.12% Potassium Sorbate, between 0.135 and 0.165% Polyclycerol-4-oleate, between 0.25 and 0.31% Xanthan Gum, between 0.027 and 0.033% Lecithin, and between 80 and 98% Water.

In some embodiments, the blend of compounds can include 2.06% Thyme Oil White, 4.51% Wintergreen Oil, 3.43% Isopropyl myristate, 0.11% Potassium Sorbate, 0.15% Polyclycerol-4-oleate, 0.28% Xanthan Gum, 0.03% Lecithin, and 89.42% Water.

In some embodiments, the blend of compounds can include at least two to four of the group consisting of Thyme Oil White, Wintergreen Oil, Isopropyl myristate, Potassium Sorbate, Polyglycerol-4-oleate, Xanthan Gum, Lecithin, and Water.

In some embodiments, the blend of compounds can include at least five to seven of the group consisting of Thyme Oil White, Wintergreen Oil, Isopropyl myristate, Potassium Sorbate, Polyglycerol-4-oleate, Xanthan Gum, Lecithin, and Water.

In some embodiments, the blend of compounds can include Thyme Oil White, Wintergreen Oil, Isopropyl myristate, Potassium Sorbate, Polyglycerol-4-oleate, Xanthan Gum, Lecithin, and Water.

In some embodiments, the blend of compounds can include between 0.5 and 2% Thyme Oil White, between 1 and 5% Wintergreen Oil, between 0.5 and 4% Isopropyl myristate, between 0.05 and 0.5% Potassium Sorbate, between 0.05 and 0.5% Polyglycerol-4-oleate, between 0.1 and 0.6% Xanthan Gum, between 0.005 and 0.1% Lecithin, and between 60 and 99% Water.

In some embodiments, the blend of compounds can include between 0.9 and 1.15% Thyme Oil White, between 2 and 2.5% Wintergreen Oil, between 1.55 and 1.89% Isopropyl myristate, between 0.1 and 0.12% Potassium Sorbate, between 0.13 and 0.17% Polyglycerol-4-oleate, between 0.25 and 0.31% Xanthan Gum, between 0.027 and 0.033% Lecithin, and between 85 and 98% Water.

In some embodiments, the blend of compounds can include 1.03% Thyme Oil White, 2.26% Wintergreen Oil, 1.72% Isopropyl myristate, 0.11% Potassium Sorbate, 0.15% Polyglycerol-4-oleate, 0.28% Xanthan Gum, 0.03% Lecithin, and 94.43% Water.

In some embodiments, the blend of compounds can include at least two of the group consisting of Soya Lecithin, Polyglycerol-4-oleate, Water, and Blend 18.

In some embodiments, the blend of compounds can include at least three of the group consisting of Soya Lecithin, Polyglycerol-4-oleate, Water, and Blend 18.

In some embodiments, the blend of compounds can include Soya Lecithin, Polyglycerol-4-oleate, Water, and Blend 18.

In some embodiments, the blend of compounds can include between 0.1 and 0.5% Soya Lecithin, between 0.5 and 2.5% Polyglycerol-4-oleate, between 5 and 20% Water, and between 60 and 99% Blend 18.

In some embodiments, the blend of compounds can include between 0.18 and 0.22% Soya Lecithin, between 0.8 and 1.0% Polyglycerol-4-oleate, between 8.8 and 10.8% Water, and between 80 and 98% Blend 18.

In some embodiments, the blend of compounds can include 0.20% Soya Lecithin, 0.90% Polyglycerol-4-oleate, 9.80% Water, and 89.10% Blend 18.

In some embodiments, the blend of compounds can include at least two or three of the group consisting of Thyme Oil White, Isopropyl myristate, Soya Lecithin, Polyglycerol-4-oleate, Water, and Wintergreen Oil (Technical grade).

In some embodiments, the blend of compounds can include at least four or five of the group consisting of Thyme Oil White, Isopropyl myristate, Soya Lecithin, Polyglycerol-4-oleate, Water, and Wintergreen Oil (Technical grade).

In some embodiments, the blend of compounds can include Thyme Oil White, Isopropyl myristate, Soya Lecithin, Polyglycerol-4-oleate, Water, and Wintergreen Oil (Technical grade).

In some embodiments, the blend of compounds can include between 25 and 50% Thyme Oil White, between 20 and 45% Isopropyl myristate, between 0.1 and 0.5% Soya Lecithin, between 0.5 and 2.5% Polyglycerol-4-oleate, between 5 and 20% Water, and between 10 and 40% Wintergreen Oil (Technical grade).

In some embodiments, the blend of compounds can include between 32 and 38% Thyme Oil White, between 29 and 35% Isopropyl myristate, between 0.18 and 0.22% Soya Lecithin, between 0.8 and 1.0% Polyglycerol-4-oleate, between 8.8 and 10.8% Water, and between 20 and 24% Wintergreen Oil (Technical grade).

In some embodiments, the blend of compounds can include 35.0% Thyme Oil White, 32.0% Isopropyl myristate, 0.20% Soya Lecithin, 0.90% Polyglycerol-4-oleate, 9.80% Water, and 22.1% Wintergreen Oil (Technical grade).

In some embodiments, the blend of compounds can include at least two of the group consisting of Soya Lecithin, Polyglycerol-4-oleate, Water, and Blend 5.

In some embodiments, the blend of compounds can include at least three of the group consisting of Soya Lecithin, Polyglycerol-4-oleate, Water, and Blend 5.

In some embodiments, the blend of compounds can include Soya Lecithin, Polyglycerol-4-oleate, Water, and Blend 5.

In some embodiments, the blend of compounds can include between 0.05 and 0.5% Soya Lecithin, between 0.5 and 2.5% Polyglycerol-4-oleate, between 5 and 20% Water, and between 60 and 99% Blend 5.

In some embodiments, the blend of compounds can include between 0.09 and 0.11% Soya Lecithin, between 0.8 and 1.0% Polyglycerol-4-oleate, between 8.9 and 10.9% Water, and between 80 and 98% Blend 5.

In some embodiments, the blend of compounds can include 0.10% Soya Lecithin, 0.90% Polyglycerol-4-oleate, 9.90% Water, and 89.1% Blend 5.

In some embodiments, the blend of compounds can include at least two to four of the group consisting of Thyme Oil White, Wintergreen Oil, Vanillin, Isopropyl myristate, Soya Lecithin, Polyglycerol-4-oleate, and Water.

In some embodiments, the blend of compounds can include at least five or six of the group consisting of Thyme Oil White, Wintergreen Oil, Vanillin, Isopropyl myristate, Soya Lecithin, Polyglycerol-4-oleate, and Water.

In some embodiments, the blend of compounds can include Thyme Oil White, Wintergreen Oil, Vanillin, Isopropyl myristate, Soya Lecithin, Polyglycerol-4-oleate, and Water.

In some embodiments, the blend of compounds can include between 10 and 30% Thyme Oil White, between 30 and 55% Wintergreen Oil, between 0.5 and 2.5% Vanillin, between 20 and 40% Isopropyl myristate, between 0.01 and 0.5% Soya Lecithin, between 0.5 and 2.5% Polyglycerol-4-oleate, and between 5 and 20% Water.

In some embodiments, the blend of compounds can include between 16 and 20.5% Thyme Oil White, between 36 and 44% Wintergreen Oil, between 0.89 and 1.08% Vanillin, between 26.5 and 33% Isopropyl myristate, between 0.09 and 0.11% Soya Lecithin, between 0.8 and 1.0% Polyglycerol-4-oleate, and between 8.9 and 10.9% Water.

In some embodiments, the blend of compounds can include 18.27% Thyme Oil White, 40.10% Wintergreen Oil, 0.98% Vanillin, 29.76% Isopropyl myristate, 0.10% Soya Lecithin, 0.90% Polyglycerol-4-oleate, and 9.90% Water.

In some embodiments, the blend of compounds can include at least two of the group consisting of Polyglycerol-4-oleate, Water, and Blend 18.

In some embodiments, the blend of compounds can include Polyglycerol-4-oleate, Water, and Blend 18.

In some embodiments, the blend of compounds can include between 1 and 4% Polyglycerol-4-oleate, between 5 and 20% Water, and between 60 and 99% Blend 18.

In some embodiments, the blend of compounds can include between 1.7 and 2.1% Polyglycerol-4-oleate, between 8 and 10% Water, and between 80 and 98% Blend 18.

In some embodiments, the blend of compounds can include 1.90% Polyglycerol-4-oleate, 9.00% Water, and 89.10% Blend 18.

In some embodiments, the blend of compounds can include at least two or three of the group consisting of Thyme Oil White, Isopropyl myristate, Polyglycerol-4-oleate, Water, and Wintergreen Oil (Technical).

In some embodiments, the blend of compounds can include at least four of the group consisting of Thyme Oil White, Isopropyl myristate, Polyglycerol-4-oleate, Water, and Wintergreen Oil (Technical).

In some embodiments, the blend of compounds can include Thyme Oil White, Isopropyl myristate, Polyglycerol-4-oleate, Water, and Wintergreen Oil (Technical).

In some embodiments, the blend of compounds can include between 25 and 50% Thyme Oil White, between 20 and 45% Isopropyl myristate, between 1 and 5% Polyglycerol-4-oleate, between 5 and 20% Water, and between 15 and 30% Wintergreen Oil (Technical).

In some embodiments, the blend of compounds can include 31.5 and 38.5% Thyme Oil White, between 29 and 35% Isopropyl myristate, between 1.7 and 2.1% Polyglycerol-4-oleate, between 8 and 10% Water, and between 20 and 24% Wintergreen Oil (Technical).

In some embodiments, the blend of compounds can include 35.0% Thyme Oil White, 32.0% Isopropyl myristate, 1.90% Polyglycerol-4-oleate, 9.00% Water, and 22.1% Wintergreen Oil (Technical).

In some embodiments, the blend of compounds can include at least two or three of the group consisting of Potassium Sorbate, Polyglycerol-4-oleate, Xanthan Gum, Water, and Blend 88.

In some embodiments, the blend of compounds can include at least four of the group consisting of Potassium Sorbate, Polyglycerol-4-oleate, Xanthan Gum, Water, and Blend 88.

In some embodiments, the blend of compounds can include Potassium Sorbate, Polyglycerol-4-oleate, Xanthan Gum, Water, and Blend 88.

In some embodiments, the blend of compounds can include between 0.05 and 0.25% Potassium Sorbate, between 1 and 4% Polyglycerol-4-oleate, between 0.1 and 0.6% Xanthan Gum, between 60 and 98% Water, and between 5 and 20% Blend 88.

In some embodiments, the blend of compounds can include between 0.10 and 0.12% Potassium Sorbate, between 1.7 and 2.1% Polyglycerol-4-oleate, between 0.24 and 0.31% Xanthan Gum, between 78 and 94% Water, and between 10 and 12.5% Blend 88.

In some embodiments, the blend of compounds can include 0.11% Potassium Sorbate, 1.90% Polyglycerol-4-oleate, 0.275% Xanthan Gum, 86.410% Water, and 11.30% Blend 88.

In some embodiments, the blend of compounds can include at least two to four of the group consisting of D-Limonene, Thyme Oil White, Soya Lecithin, Potassium Sorbate, Polyglycerol-4-oleate, Xanthan Gum, Water, and Wintergreen Oil (Technical).

In some embodiments, the blend of compounds can include at least five to seven of the group consisting of D-Limonene, Thyme Oil White, Soya Lecithin, Potassium Sorbate, Polyglycerol-4-oleate, Xanthan Gum, Water, and Wintergreen Oil (Technical).

In some embodiments, the blend of compounds can include D-Limonene, Thyme Oil White, Soya Lecithin, Potassium Sorbate, Polyglycerol-4-oleate, Xanthan Gum, Water, and Wintergreen Oil (Technical).

In some embodiments, the blend of compounds can include between 2 and 10% D-Limonene, between 0.5 and 5% Thyme Oil White, between 0.001 and 0.1% Soya Lecithin, between 0.01 and 1% Potassium Sorbate, between 0.5 and 5% Polyglycerol-4-oleate, between 0.5 and 1% Xanthan Gum, between 40 and 99% Water, and between 1 and 10% Wintergreen Oil (Technical).

In some embodiments, the blend of compounds can include between 4 and 7% D-Limonene, between 1 and 2% Thyme Oil White, between 0.005 and 0.05% Soya Lecithin, between 0.05 and 0.2% Potassium Sorbate, between 1 and 3% Polyglycerol-4-oleate, between 0.2 and 0.5% Xanthan Gum, between 80 and 95% Water, and between 2.5 and 5% Wintergreen Oil (Technical).

In some embodiments, the blend of compounds can include 5.67% D-Limonene, 1.25% Thyme Oil White, 0.011% Soya Lecithin, 0.11% Potassium Sorbate, 2.002% Polyglycerol-4-oleate, 0.275% Xanthan Gum, 87.529% Water, and 3.15% Wintergreen Oil (Technical).

In some embodiments, the blend of compounds can include at least two of the group consisting of Potassium Sorbate, Xanthan Gum, Water, and blend 86.

In some embodiments, the blend of compounds can include at least three of the group consisting of Potassium Sorbate, Xanthan Gum, Water, and blend 86.

In some embodiments, the blend of compounds can include Potassium Sorbate, Xanthan Gum, Water, and blend 86.

In some embodiments, the blend of compounds can include between 0.05 and 0.5% Potassium Sorbate, between 0.1 and 0.5% Xanthan Gum, between 50 and 99% Water, and between 5 and 20% Blend 86.

In some embodiments, the blend of compounds can include between 0.1 and 0.12% Potassium Sorbate, between 0.24 and 0.31% Xanthan Gum, between 80 and 97% Water, and between 10 and 12.6% Blend 86.

In some embodiments, the blend of compounds can include 0.11% Potassium Sorbate, 0.275% Xanthan Gum, 88.315% Water, and 11.30% Blend 86.

In some embodiments, the blend of compounds can include at least two to four of the group consisting of Thyme Oil White, Isopropyl myristate, Soya Lecithin, Potassium Sorbate, Polyglycerol-4-oleate, Xanthan Gum, Water, and Wintergreen Oil (Technical).

In some embodiments, the blend of compounds can include at least five to seven of the group consisting of Thyme Oil White, Isopropyl myristate, Soya Lecithin, Potassium Sorbate, Polyglycerol-4-oleate, Xanthan Gum, Water, and Wintergreen Oil (Technical).

In some embodiments, the blend of compounds can include Thyme Oil White, Isopropyl myristate, Soya Lecithin, Potassium Sorbate, Polyglycerol-4-oleate, Xanthan Gum, Water, and Wintergreen Oil (Technical).

In some embodiments, the blend of compounds can include between 2 and 10% Thyme Oil White, between 2 and 10% Isopropyl myristate, between 0.005 and 0.1% Soya Lecithin, between 0.001 and 0.5% Potassium Sorbate, between 0.01 and 0.5% Polyglycerol-4-oleate, between 0.1 and 0.5% Xanthan Gum, between 50 and 99% Water, and between 1 and 5% Wintergreen Oil (Technical).

In some embodiments, the blend of compounds can include between 3 and 5% Thyme Oil White, between 3.2 and 4% Isopropyl myristate, between 0.01 and 0.05% Soya Lecithin, between 0.01 and 0.0.1% Potassium Sorbate, between 0.9 and 0.115% Polyglycerol-4-oleate, between 0.25 and 0.30% Xanthan Gum, between 80 and 95% Water, and between 2 and 3% Wintergreen Oil (Technical).

In some embodiments, the blend of compounds can include 3.95% Thyme Oil White, 3.62% Isopropyl myristate, 0.023% Soya Lecithin, 0.11% Potassium Sorbate, 0.102% Polyglycerol-4-oleate, 0.275% Xanthan Gum, 89.422% Water, and 2.50% Wintergreen Oil (Technical).

In some embodiments, the blend of compounds can include at two of the group consisting of Potassium Sorbate, Xanthan Gum, Water, and Blend 90.

In some embodiments, the blend of compounds can include at three of the group consisting of Potassium Sorbate, Xanthan Gum, Water, and Blend 90.

In some embodiments, the blend of compounds can include Potassium Sorbate, Xanthan Gum, Water, and Blend 90.

In some embodiments, the blend of compounds can include between 0.01 and 0.5% Potassium Sorbate, between 0.1 and 0.5% Xanthan Gum, between 50 and 99% Water, and between 5 and 20% Blend 90.

In some embodiments, the blend of compounds can include between 0.1 and 0.12% Potassium Sorbate, between 0.25 and 0.30% Xanthan Gum, between 80 and 95% Water, and between 10 and 12.6% Blend 90.

In some embodiments, the blend of compounds can include 0.11% Potassium Sorbate, 0.275% Xanthan Gum, 88.315% Water, and 11.30% Blend 90.

In some embodiments, the blend of compounds can include at least two to four of the group consisting of Thyme Oil White, Wintergreen Oil, Isopropyl myristate, Potassium Sorbate, Polyglycerol-4-oleate, Xanthan Gum, and Water.

In some embodiments, the blend of compounds can include at least five or six of the group consisting of Thyme Oil White, Wintergreen Oil, Isopropyl myristate, Potassium Sorbate, Polyglycerol-4-oleate, Xanthan Gum, and Water.

In some embodiments, the blend of compounds can include Thyme Oil White, Wintergreen Oil, Isopropyl myristate, Potassium Sorbate, Polyglycerol-4-oleate, Xanthan Gum, and Water.

In some embodiments, the blend of compounds can include between 1 and 10% Thyme Oil White, between 1 and 10% Wintergreen Oil, between 1 and 10% Isopropyl myristate, between 0.01 and 0.5% Potassium Sorbate, between 0.05 and 0.5% Polyglycerol-4-oleate, between 0.1 and 0.5% Xanthan Gum, and between 50 and 99% Water.

In some embodiments, the blend of compounds can include between 2 and 5% Thyme Oil White, between 2 and 5% Wintergreen Oil, between 2 and 5% Isopropyl myristate, between 0.1 and 0.12% Potassium Sorbate, between 0.18 and 0.23% Polyglycerol-4-oleate, between 0.25 and 0.30% Xanthan Gum, and between 80 and 95% Water.

In some embodiments, the blend of compounds can include 3.95% Thyme Oil White, 2.50% Wintergreen Oil, 3.62% Isopropyl myristate, 0.11% Potassium Sorbate, 0.21% Polyglycerol-4-oleate, 0.275% Xanthan Gum, and 89.332% Water.

In some embodiments, the blend of compounds can include Potassium Sorbate, Xanthan Gum, and Water In some embodiments, the blend of compounds can include between 0.9 and 1.1% Potassium Sorbate, between 2.2 and 2.8% Xanthan Gum, and between 87 and 100% Water.

In some embodiments, the blend of compounds can include 1.00% Potassium Sorbate, 2.500% Xanthan Gum, and 96.500% Water.

In some embodiments, the blend of compounds can include Sodium Benzoate and Water.

In some embodiments, the blend of compounds can include between 1.8 and 2.2% Sodium Benzoate and between 89 and 100% Water.

In some embodiments, the blend of compounds can include 2% Sodium Benzoate and 98% Water.

In some embodiments, the blend of compounds can include at least two or three of the group consisting of Span 80, Tween 80, Isopar M, Water, Blend 6, and Blend 99 (2% Sodium Benzoate, 98% Water).

In some embodiments, the blend of compounds can include at least four or five of the group consisting of Span 80, Tween 80, Isopar M, Water, Blend 6, and Blend 99 (2% Sodium Benzoate, 98% Water).

In some embodiments, the blend of compounds can include Span 80, Tween 80, Isopar M, Water, Blend 6, and Blend 99 (2% Sodium Benzoate, 98% Water).

In some embodiments, the blend of compounds can include between 0.1 and 5% Span 80, between 0.1 and 2.5% Tween 80, between 10 and 20% Isopar M, between 40 and 90% Water, between 1 and 5% Blend 6, and between 5 and 20% Blend 99 (2% Sodium Benzoate; 2% Sodium Benzoate, 98% Water).

In some embodiments, the blend of compounds can include between 1.05 and 1.32% Span 80, between 1.5 and 1.8% Tween 80, between 13 and 15.4% Isopar M, between 60 and 76% Water, between 2.5 and 3.2% Blend 6, and between 10 and 12.5% Blend 99 (2% Sodium Benzoate; 2% Sodium Benzoate, 98% Water).

In some embodiments, the blend of compounds can include 1.20% Span 80, 1.65% Tween 80, 14.20% Isopar M, 68.75% Water, 2.84% Blend 6, and 11.36% Blend 99 (2% Sodium Benzoate; 2% Sodium Benzoate, 98% Water).

In some embodiments, the blend of compounds can include at least two to four of the group consisting of D-Limonene, Thyme Oil White, Wintergreen Oil, Span 80, Tween 80, Sodium Benzoate, Isopar M, and Water.

In some embodiments, the blend of compounds can include at least five to seven of the group consisting of D-Limonene, Thyme Oil White, Wintergreen Oil, Span 80, Tween 80, Sodium Benzoate, Isopar M, and Water.

In some embodiments, the blend of compounds can include D-Limonene, Thyme Oil White, Wintergreen Oil, Span 80, Tween 80, Sodium Benzoate, Isopar M, and Water.

In some embodiments, the blend of compounds can include between 0.5 and 5% D-Limonene, between 0.1 and 1% Thyme Oil White, between 0.1 and 2% Wintergreen Oil, between 0.5 and 2% Span 80, between 0.5 and 5% Tween 80, between 0.1 and 0.5% Sodium Benzoate, between 5 and 20% Isopar M, and between 50 and 95% Water.

In some embodiments, the blend of compounds can include between 1.4 and 1.8% D-Limonene, between 0.32 and 0.38% Thyme Oil White, between 0.8 and 0.98% Wintergreen Oil, between 1.1 and 1.3% Span 80, between 1.5 and 1.8% Tween 80, between 0.2 and 0.26% Sodium Benzoate, between 13 and 15.4% Isopar M, and between 71 and 88% Water.

In some embodiments, the blend of compounds can include 1.60% D-Limonene, 0.35% Thyme Oil White, 0.89% Wintergreen Oil, 1.20% Span 80, 1.65% Tween 80, 0.23% Sodium Benzoate, 14.20% Isopar M, and 79.88% Water.

In some embodiments, the blend of compounds can include Propellent A70 and Blend 100.

In some embodiments, the blend of compounds can include between 5 and 50% Propellent A70 and between 50 and 95% Blend 100.

In some embodiments, the blend of compounds can include between 20 and 24% Propellent A70 and between 70 and 86% Blend 100.

In some embodiments, the blend of compounds can include 22% Propellent A70 and 78% Blend 100.

In some embodiments, the blend of compounds can include at least two to five of the group consisting of D-Limonene, Thyme Oil White, Wintergreen Oil, Span 80, Tween 80, Sodium Benzoate, Isopar M, Water, and Propellent A70.

In some embodiments, the blend of compounds can include at least six to eight of the group consisting of D-Limonene, Thyme Oil White, Wintergreen Oil, Span 80, Tween 80, Sodium Benzoate, Isopar M, Water, and Propellent A70.

In some embodiments, the blend of compounds can include D-Limonene, Thyme Oil White, Wintergreen Oil, Span 80, Tween 80, Sodium Benzoate, Isopar M, Water, and Propellent A70.

In some embodiments, the blend of compounds can include between 0.5 and 5% D-Limonene, between 0.1 and 0.5% Thyme Oil White, between 0.3 and 1% Wintergreen Oil, between 0.5 and 2% Span 80, between 0.5 and 2.5% Tween 80, between 0.1 and 0.5% Sodium Benzoate, between 5 and 20% Isopar M, between 30 and 80% Water, and between 10 and 50% Propellent A70.

In some embodiments, the blend of compounds can include between 1.1 and 1.4% D-Limonene, between 0.24 and 0.3% Thyme Oil White, between 0.62 and 0.76% Wintergreen Oil, between 0.85 and 1.04% Span 80, between 1.1 and 1.48% Tween 80, between 0.16 and 0.20% Sodium Benzoate, between 10 and 12.2% Isopar M, between 56 and 69% Water, and between 20 and 24% Propellent A70.

In some embodiments, the blend of compounds can include 1.25% D-Limonene, 0.27% Thyme Oil White, 0.69% Wintergreen Oil, 0.94% Span 80, 1.29% Tween 80, 0.18% Sodium Benzoate, 11.08% Isopar M, 62.31% Water, and 22.0% Propellent A70.

In some embodiments, the blend of compounds can include at least two to four of the group consisting of Potassium Sorbate, Polyglycerol-4-oleate, Xanthan Gum, Lecithin, Water, and Blend 41.

In some embodiments, the blend of compounds can include at least five or six of the group consisting of Potassium Sorbate, Polyglycerol-4-oleate, Xanthan Gum, Lecithin, Water, and Blend 41.

In some embodiments, the blend of compounds can include Potassium Sorbate, Polyglycerol-4-oleate, Xanthan Gum, Lecithin, Water, and Blend 41.

In some embodiments, the blend of compounds can include between 0.5 and 2.5% Potassium Sorbate, between 0.05 and 0.5% Polyglycerol-4-oleate, between 0.1 and 0.5% Xanthan Gum, between 0.01 and 0.1% Lecithin, between 50 and 98% Water, and between 10 and 20% Blend 41.

In some embodiments, the blend of compounds can include between 0.9 and 1.1% Potassium Sorbate, between 0.13 and 0.17% Polyglycerol-4-oleate, between 0.25 and 0.31% Xanthan Gum, between 0.030 and 0.037% Lecithin, between 75 and 91% Water, and between 13.5 and 16.6% Blend 41.

In some embodiments, the blend of compounds can include 1.0% Potassium Sorbate, 0.15% Polyglycerol-4-oleate, 0.28% Xanthan Gum, 0.034% Lecithin, 83.5% Water, and 15.1% Blend 41.

In some embodiments, the blend of compounds can include Water and Blend 66.

In some embodiments, the blend of compounds can include between 15 and 75% Water and between 25 and 85% Blend 66.

In some embodiments, the blend of compounds can include between 30 and 37% Water and between 59 and 74% Blend 66.

In some embodiments, the blend of compounds can include 33.40% Water and 66.60% Blend 66.

In some embodiments, the blend of compounds can include at least two to four of the group consisting of D-Limonene, Thyme Oil White, Benzyl Alcohol, Isopar M, Water, Blend 59, and Blend 105 (10% Sodium Lauryl Sulfate, 90% Water).

In some embodiments, the blend of compounds can include at least five or six of the group consisting of D-Limonene, Thyme Oil White, Benzyl Alcohol, Isopar M, Water, Blend 59, and Blend 105 (10% Sodium Lauryl Sulfate, 90% Water).

In some embodiments, the blend of compounds can include D-Limonene, Thyme Oil White, Benzyl Alcohol, Isopar M, Water, Blend 59, and Blend 105 (10% Sodium Lauryl Sulfate, 90% Water).

In some embodiments, the blend of compounds can include between 2 and 10% D-Limonene, between 2 and 10% Thyme Oil White, between 10 and 30% Benzyl Alcohol, between 10 and 30% Isopar M, between 30 and 60% Water, between 3 and 12% Blend 59, and between 1 and 8% Blend 105 (Stock 10% SLS Blend; 10% Sodium Lauryl Sulfate, 90% Water).

In some embodiments, the blend of compounds can include between 3.6 and 4.5% D-Limonene, between 4 and 4.9%

Thyme Oil White, between 15 and 18.2% Benzyl Alcohol, between 18 and 23.5% Isopar M, between 44 and 49% Water, between 5.6 and 7.0% Blend 59, and between 2.5 and 4% Blend 105 (Stock 10% SLS Blend; 10% Sodium Lauryl Sulfate, 90% Water).

In some embodiments, the blend of compounds can include 4.03% D-Limonene, 4.43% Thyme Oil White, 16.61% Benzyl Alcohol, 20.95% Isopar M, 44.53% Water, 6.27% Blend 59, and 3.18% Blend 105 (Stock 10% SLS Blend; 10% Sodium Lauryl Sulfate, 90% Water).

In some embodiments, the blend of compounds can include at least two to four of the group consisting of D-Limonene, Thyme Oil White, Benzyl Alcohol, Isopar M, Water, Bifenthrin, Blend 59, and Blend 105 (Stock 10% SLS Blend; 10% Sodium Lauryl Sulfate, 90% Water).

In some embodiments, the blend of compounds can include at least five to seven of the group consisting of D-Limonene, Thyme Oil White, Benzyl Alcohol, Isopar M, Water, Bifenthrin, Blend 59, and Blend 105 (Stock 10% SLS Blend; 10% Sodium Lauryl Sulfate, 90% Water).

In some embodiments, the blend of compounds can include D-Limonene, Thyme Oil White, Benzyl Alcohol, Isopar M, Water, Bifenthrin, Blend 59, and Blend 105 (Stock 10% SLS Blend; 10% Sodium Lauryl Sulfate, 90% Water).

In some embodiments, the blend of compounds can include between 2 and 10% D-Limonene, between 2 and 10% Thyme Oil White, between 10 and 30% Benzyl Alcohol, between 10 and 40% Isopar M, between 30 and 60% Water, between 0.01 and 0.1% Bifenthrin, between 3 and 10% Blend 59, and between 1 and 10% Blend 105 (Stock 10% SLS Blend; 10% Sodium Lauryl Sulfate, 90% Water In some embodiments, the blend of compounds can include between 3.6 and 4.45% D-Limonene, between 4.0 and 4.9% Thyme Oil White, between 15 and 18.4% Benzyl Alcohol, between 18 and 23.4% Isopar M, between 40 and 49% Water, between 0.045 and 0.055% Bifenthrin, between 5.6 and 7.0% Blend 59, and between 2.5 and 4% Blend 105 (Stock 10% SLS Blend; 10% Sodium Lauryl Sulfate, 90% Water).

In some embodiments, the blend of compounds can include 4.028% D-Limonene, 4.428% Thyme Oil White, 16.60% Benzyl Alcohol, 20.94% Isopar M, 44.51% Water, 0.05% Bifenthrin, 6.267% Blend 59, and 3.178% Blend 105 (Stock 10% SLS Blend; 10% Sodium Lauryl Sulfate, 90% Water).

In some embodiments, the blend of compounds can include at least two to four of the group consisting of Thyme Oil White, Wintergreen Oil, Isopropyl myristate, Span 80, Isopar M, Water, and Bifenthrin.

In some embodiments, the blend of compounds can include at least five or six of the group consisting of Thyme Oil White, Wintergreen Oil, Isopropyl myristate, Span 80, Isopar M, Water, and Bifenthrin.

In some embodiments, the blend of compounds can include Thyme Oil White, Wintergreen Oil, Isopropyl myristate, Span 80, Isopar M, Water, and Bifenthrin.

In some embodiments, the blend of compounds can include between 1 and 5% Thyme Oil White, between 2 and 10% Wintergreen Oil, between 2 and 8% Isopropyl myristate, between 0.2 and 1% Span 80, between 6 and 25% Isopar M, between 40 and 95% Water, and between 0.02 and 0.1% Bifenthrin.

In some embodiments, the blend of compounds can include between 1.8 and 2.3% Thyme Oil White, between 4.0 and 5.0% Wintergreen Oil, between 3.1 and 3.8% Isopropyl myristate, between 0.45 and 0.55% Span 80, between 13.5 and 16.5% Isopar M, between 67 and 82% Water, and between 0.045 and 0.055% Bifenthrin.

In some embodiments, the blend of compounds can include 2.06% Thyme Oil White, 4.51% Wintergreen Oil, 3.43% Isopropyl myristate, 0.50% Span 80, 15% Isopar M, 74.45% Water, and 0.05% Bifenthrin.

In some embodiments, the blend of compounds can include at least two or three of the group consisting of Thyme Oil White, Wintergreen Oil, Isopropyl myristate, Sodium Lauryl Sulfate, and Water.

In some embodiments, the blend of compounds can include at least four of the group consisting of Thyme Oil White, Wintergreen Oil, Isopropyl myristate, Sodium Lauryl Sulfate, and Water.

In some embodiments, the blend of compounds can include Thyme Oil White, Wintergreen Oil, Isopropyl myristate, Sodium Lauryl Sulfate, and Water.

In some embodiments, the blend of compounds can include between 0.2 and 1% Thyme Oil White, between 0.5 and 2% Wintergreen Oil, between 0.3 and 2% Isopropyl myristate, between 0.005 and 0.1% Sodium Lauryl Sulfate, and between 50 and 99% Water.

In some embodiments, the blend of compounds can include between 0.36 and 0.45% Thyme Oil White, between 0.8 and 1.0% Wintergreen Oil, between 0.6 and 0.76% Isopropyl myristate, between 0.018 and 0.022% Sodium Lauryl Sulfate, and between 88 and 99% Water.

In some embodiments, the blend of compounds can include 0.41% Thyme Oil White, 0.90% Wintergreen Oil, 0.69% Isopropyl myristate, 0.02% Sodium Lauryl Sulfate, and 97.98% Water.

In some embodiments, the blend of compounds can include at least three of the group consisting of Thyme Oil White, Wintergreen Oil, Isopropyl myristate, and AgSorb.

In some embodiments, the blend of compounds can include at least two of the group consisting of Thyme Oil White, Wintergreen Oil, Isopropyl myristate, and AgSorb.

In some embodiments, the blend of compounds can include Thyme Oil White, Wintergreen Oil, Isopropyl myristate, and AgSorb.

In some embodiments, the blend of compounds can include between 0.5 and 3% Thyme Oil White, between 1 and 5% Wintergreen Oil, between 0.5 and 5% Isopropyl myristate, and between 50 and 99% AgSorb.

In some embodiments, the blend of compounds can include between 0.9 and 1.15% Thyme Oil White, between 2.0 and 2.5% Wintergreen Oil, between 1.5 and 1.9% Isopropyl myristate, and between 85 and 98% AgSorb.

In some embodiments, the blend of compounds can include 1.03% Thyme Oil White, 2.26% Wintergreen Oil, 1.71% Isopropyl myristate, and 95.00% AgSorb.

In some embodiments, the blend of compounds can include at least two of the group consisting of Thyme Oil White, Wintergreen Oil, Isopropyl myristate, and DG Light.

In some embodiments, the blend of compounds can include at least three of the group consisting of Thyme Oil White, Wintergreen Oil, Isopropyl myristate, and DG Light.

In some embodiments, the blend of compounds can include Thyme Oil White, Wintergreen Oil, Isopropyl myristate, and DG Light.

In some embodiments, the blend of compounds can include between 0.5 and 2.5% Thyme Oil White, between 1 and 5% Wintergreen Oil, between 0.5 and 5% Isopropyl myristate, and between 50 and 99% DG Light.

In some embodiments, the blend of compounds can include between 0.9 and 1.16% Thyme Oil White, between 2.0 and 2.5% Wintergreen Oil, between 1.5 and 1.9% Isopropyl myristate, and between 85 and 98% DG Light.

In some embodiments, the blend of compounds can include 1.03% Thyme Oil White, 2.26% Wintergreen Oil, 1.71% Isopropyl myristate, and 95.0% DG Light.

In some embodiments, the blend of compounds can include at least two or three of the group consisting of Thyme Oil White, Wintergreen Oil, Isopropyl myristate, Sodium Lauryl Sulfate, and Water.

In some embodiments, the blend of compounds can include at least four of the group consisting of Thyme Oil White, Wintergreen Oil, Isopropyl myristate, Sodium Lauryl Sulfate, and Water.

In some embodiments, the blend of compounds can include Thyme Oil White, Wintergreen Oil, Isopropyl myristate, Sodium Lauryl Sulfate, and Water.

In some embodiments, the blend of compounds can include between 0.2 and 1% Thyme Oil White, between 0.5 and 2% Wintergreen Oil, between 0.3 and 2% Isopropyl myristate, between 0.005 and 0.1% Sodium Lauryl Sulfate, and between 50 and 99% Water.

In some embodiments, the blend of compounds can include between 0.36 and 0.45% Thyme Oil White, between 0.8 and 1.0% Wintergreen Oil, between 0.6 and 0.78% Isopropyl myristate, between 0.018 and 0.022% Sodium Lauryl Sulfate, and between 87 and 99% Water.

In some embodiments, the blend of compounds can include 0.41% Thyme Oil White, 0.90% Wintergreen Oil, 0.69% Isopropyl myristate, 0.02% Sodium Lauryl Sulfate, and 97.98% Water.

In some embodiments, the blend of compounds can include at least 2 to 4 of the group consisting of D-Limonene, Thyme Oil White, Linalool Coeur, Tetrahydrolinalool, Vanillin, Isopropyl myristate, Piperonal (aldehyde), Blend 62, Geraniol 60, Triethyl Citrate, Water, and Blend 105 (10% Sodium Lauryl Sulfate; 90% Water).

In some embodiments, the blend of compounds can include at least 5 to 7 of the group consisting of D-Limonene, Thyme Oil White, Linalool Coeur, Tetrahydrolinalool, Vanillin, Isopropyl myristate, Piperonal (aldehyde), Blend 62, Geraniol 60, Triethyl Citrate, Water, and Blend 105 (10% Sodium Lauryl Sulfate; 90% Water).

In some embodiments, the blend of compounds can include at least 8 to 10 of the group consisting of D-Limonene, Thyme Oil White, Linalool Coeur, Tetrahydrolinalool, Vanillin, Isopropyl myristate, Piperonal (aldehyde), Blend 62, Geraniol 60, Triethyl Citrate, Water, and Blend 105 (10% Sodium Lauryl Sulfate; 90% Water).

In some embodiments, the blend of compounds can include D-Limonene, Thyme Oil White, Linalool Coeur, Tetrahydrolinalool, Vanillin, Isopropyl myristate, Piperonal (aldehyde), Blend 62, Geraniol 60, Triethyl Citrate, Water, and Blend 105 (10% Sodium Lauryl Sulfate; 90% Water).

In some embodiments, the blend of compounds can include between 10 and 40% D-Limonene, between 0.5 and 2% Thyme Oil White, between 0.05 and 0.5% Linalool Coeur, between 0.1 and 0.5% Tetrahydrolinalool, between 0.005 and 0.1% Vanillin, between 0.1 and 0.5% Isopropyl myristate, between 0.1 and 0.5% Piperonal (aldehyde), between 1 and 5% Blend 62, between 0.05 and 0.5% Geraniol 60, between 0.1 and 0.5% Triethyl Citrate, between 30 and 90% Water, and between 1.5 and 5% Blend 105 (Stock 10% SLS Blend; 10% Sodium Lauryl Sulfate; 90% Water).

In some embodiments, the blend of compounds can include between 22 and 27% D-Limonene, between 0.89 and 1.1% Thyme Oil White, between 0.15 and 0.19% Linalool Coeur, between 0.2 and 0.26% Tetrahydrolinalool, between 0.018 and 0.022% Vanillin, between 0.22 and 0.26% Isopropyl myristate, between 0.215 and 0.265% Piperonal (aldehyde), between 2.7 and 3.3% Blend 62, between 0.11 and 0.13% Geraniol 60, between 0.22 and 0.26% Triethyl Citrate, between 60 and 74% Water, and between 2.7 and 3.3% Blend 105 (Stock 10% SLS Blend; 10% Sodium Lauryl Sulfate; 90% Water).

In some embodiments, the blend of compounds can include 24.76% D-Limonene, 0.98% Thyme Oil White, 0.17% Linalool Coeur, 0.23% Tetrahydrolinalool, 0.02% Vanillin, 0.24% Isopropyl myristate, 0.24% Piperonal (aldehyde), 3.00% Blend 62, 0.12% Geraniol 60, 0.24% Triethyl Citrate, 67% Water, and 3% Blend 105 (Stock 10% SLS Blend; 10% Sodium Lauryl Sulfate; 90% Water).

In some embodiments, the blend of compounds can include at least two to four of the group consisting of Thyme Oil White, Wintergreen Oil, Isopropyl myristate, Potassium Sorbate, Xanthan Gum, Water, and Blend 65.

In some embodiments, the blend of compounds can include at least five or six of the group consisting of Thyme Oil White, Wintergreen Oil, Isopropyl myristate, Potassium Sorbate, Xanthan Gum, Water, and Blend 65.

In some embodiments, the blend of compounds can include Thyme Oil White, Wintergreen Oil, Isopropyl myristate, Potassium Sorbate, Xanthan Gum, Water, and Blend 65.

In some embodiments, the blend of compounds can include between 10 and 30% Thyme Oil White, between 25 and 60% Wintergreen Oil, between 20 and 50% Isopropyl myristate, between 0.1 and 2% Potassium Sorbate, between 0.05 and 0.5% Xanthan Gum, between 50 and 99% Water, and between 10 and 30% Blend 65.

In some embodiments, the blend of compounds can include between 18 and 23% Thyme Oil White, between 40 and 50% Wintergreen Oil, between 31 and 38% Isopropyl myristate, between 0.9 and 1.1% Potassium Sorbate, between 0.25 and 0.31% Xanthan Gum, between 72 and 89% Water, between 15 and 17.6% Blend 65.

In some embodiments, the blend of compounds can include 20.6% Thyme Oil White, 45.1% Wintergreen Oil, 34.3% Isopropyl myristate, 1% Potassium Sorbate, 0.28% Xanthan Gum, 81.82% Water, and 16.90% Blend 65.

In some embodiments, the blend of compounds can include Miracle Gro (Sterile), and Blend 41.

In some embodiments, the blend of compounds can include between 80 and 99% Miracle Gro (Sterile), and 1 to 20% Blend 41.

In some embodiments, the blend of compounds can include between 90 and 98% Miracle Gro (Sterile), and between 2 and 10% Blend 41.

In some embodiments, the blend of compounds can include 95% Miracle Gro (Sterile), and 5% Blend 41.

In some embodiments, the blend of compounds can include at least two to four of the group consisting of Thyme Oil White, Wintergreen Oil, Isopropyl myristate, Span 80, Isopar M, Water, and Bifenthrin.

In some embodiments, the blend of compounds can include at least five or six of the group consisting of Thyme Oil White, Wintergreen Oil, Isopropyl myristate, Span 80, Isopar M, Water, and Bifenthrin.

In some embodiments, the blend of compounds can include Thyme Oil White, Wintergreen Oil, Isopropyl myristate, Span 80, Isopar M, Water, and Bifenthrin.

In some embodiments, the blend of compounds can include between 0.2 and 1% Thyme Oil White, between 0.5 and 2.5% Wintergreen Oil, between 0.5 and 2% Isopropyl myristate, between 0.2 and 1% Span 80, between 5 and 20% Isopar M, between 50 and 95% Water, and between 0.005 and 0.1% Bifenthrin In some embodiments, the blend of compounds can include between 0.45 and 0.56% Thyme Oil White, between 1.0 and 1.3% Wintergreen Oil, between 0.78 and 0.95% Isopropyl myristate, between 0.45 and 0.55% Span 80, between 13.5 and 16.5% Isopar M, between 73 and 90% Water, and between 0.045 and 0.055% Bifenthrin.

In some embodiments, the blend of compounds can include 0.51% Thyme Oil White, 1.13% Wintergreen Oil, 0.86% Isopropyl myristate, 0.50% Span 80, 15% Isopar M, 81.95% Water, and 0.05% Bifenthrin.

In some embodiments, a formulation can include a carrier such as diatomaceous earth and a blend of compounds including blackseed oil and geranium oil.

In some embodiments, a carrier-based formulation can include between 5 and 35% blackseed oil.

In some embodiments, the carrier-based formulation can include between 25 and 55% geranium oil.

In some embodiments, a formulation can include a carrier such as diatomaceous earth and a blend of compounds including blackseed oil, geranium oil and piperonal. The concentration of blackseed oil can be between 5 and 35%. The concentration of geranium oil can be between 25 and 55%. The concentration of piperonal can be between 5 and 35%.

In some embodiments, a formulation can include a carrier such as diatomaceous earth and a blend of compounds including blackseed oil, geranium oil piperonal, and linalool. The concentration of blackseed oil can be between 5% and 35%. The concentration of geranium oil can be between 25% and 55%. The concentration of piperonal can be between 5% and 35%. The concentration of linalool can be between 5% and 35%.

In some embodiments, the blend of compounds can include at least one of the group consisting of Thyme Oil White, Methyl Salicylate, and Isopropyl myristate.

In some embodiments, the blend of compounds can include at least two of the group consisting of Thyme Oil White, Methyl Salicylate, and Isopropyl myristate.

In some embodiments, the blend of compounds can include Thyme Oil White, Methyl Salicylate, and Isopropyl myristate.

In some embodiments, the blend of compounds can include between 10 and 30% Thyme Oil White, between 30 and 60% Methyl Salicylate, and between 20 and 48% Isopropyl myristate.

In some embodiments, the blend of compounds can include between 18 and 23% Thyme Oil White, between 40 and 50% Methyl Salicylate, and between 30 and 38% Isopropyl myristate.

In some embodiments, the blend of compounds can include 20.6% Thyme Oil White, 45.1% Methyl Salicylate, and 34.3% Isopropyl myristate.

In some embodiments, the blend of compounds can include at least one of the group consisting of Isopropyl myristate, Wintergreen Oil, and Thyme Oil White containing 1% Thyme Oil Red.

In some embodiments, the blend of compounds can include at least two of the group consisting of % Isopropyl myristate, Wintergreen Oil, and Thyme Oil White containing 1% Thyme Oil Red.

In some embodiments, the blend of compounds can include Isopropyl myristate, Wintergreen Oil, and Thyme Oil White containing 1% Thyme Oil Red.

In some embodiments, the blend of compounds can include between 25 and 48% Isopropyl myristate, 30 and 60% Wintergreen Oil, and between 10 and 30% Thyme Oil White containing 1% Thyme Oil Red.

In some embodiments, the blend of compounds can include between 30 and 38% Isopropyl myristate, 40 and 50% Wintergreen Oil, and between 18 and 23% Thyme Oil White containing 1% Thyme Oil Red.

In some embodiments, the blend of compounds can include 34.3% Isopropyl myristate, 45.1% Wintergreen Oil, and 20.6% Thyme Oil White containing 1% Thyme Oil Red.

In some embodiments, the blend of compounds can include at least one of the group consisting of Wintergreen Oil, Isopropyl myristate, and Thyme Oil Red.

In some embodiments, the blend of compounds can include at least two of the group consisting of Wintergreen Oil, Isopropyl myristate, and Thyme Oil Red.

In some embodiments, the blend of compounds can include Wintergreen Oil, Isopropyl myristate, and Thyme Oil Red.

In some embodiments, the blend of compounds can include between 30 and 60% Wintergreen Oil, between 20 and 48% Isopropyl myristate, and between 10 and 30% Thyme Oil Red.

In some embodiments, the blend of compounds can include between 40 and 50% Wintergreen Oil, between 30 and 38% Isopropyl myristate, and between 18 and 23% Thyme Oil Red.

In some embodiments, the blend of compounds can include 45.10% Wintergreen Oil, 34.3% Isopropyl myristate, and 20.6% Thyme Oil Red.

In some embodiments, the blend of compounds can include at least one of the group consisting of Isopropyl myristate, Wintergreen Oil (Technical grade), and Thyme Oil White containing 1% Thyme Oil Red.

In some embodiments, the blend of compounds can include at least two of the group consisting of Isopropyl myristate, Wintergreen Oil (Technical grade), and Thyme Oil White containing 1% Thyme Oil Red In some embodiments, the blend of compounds can include Isopropyl myristate, Wintergreen Oil (Technical grade), and Thyme Oil White containing 1% Thyme Oil Red.

In some embodiments, the blend of compounds can include between 20 and 48% Isopropyl myristate, between 30 and 60% Wintergreen Oil (Technical grade), and between 10 and 30% Thyme Oil White containing 1% Thyme Oil Red.

In some embodiments, the blend of compounds can include between 30 and 38% Isopropyl myristate, between 40 and 50% Wintergreen Oil (Technical grade), and between 18 and 23% Thyme Oil White containing 1% Thyme Oil Red.

In some embodiments, the blend of compounds can include 34.3% Isopropyl myristate, 45.10% Wintergreen Oil (Technical grade), and 20.6% Thyme Oil White containing 1% Thyme Oil Red.

In some embodiments, the blend of compounds can include at least two of the group consisting of Thyme Oil White, Wintergreen Oil, Isopropyl myristate, and Vanillin In some embodiments, the blend of compounds can include at least three of the group consisting of Thyme Oil White, Wintergreen Oil, Isopropyl myristate, and Vanillin.

In some embodiments, the blend of compounds can include Thyme Oil White, Wintergreen Oil, Isopropyl myristate, and Vanillin.

In some embodiments, the blend of compounds can include between 10 and 30% Thyme Oil White, between 30 and 60% Wintergreen Oil, between 20 and 48% Isopropyl myristate, and between 0.01 and 0.3% Vanillin.

In some embodiments, the blend of compounds can include between 18 and 23% Thyme Oil White, between 40 and 50% Wintergreen Oil, between 30 and 38% Isopropyl myristate, and between 0.05 and 0.15% Vanillin.

In some embodiments, the blend of compounds can include 20.6% Thyme Oil White, 45.1% Wintergreen Oil, 34.2% Isopropyl myristate, and 0.1% Vanillin.

In some embodiments, the blend of compounds can include at least two of the group consisting of Thyme Oil Red, Wintergreen Oil, Isopropyl myristate, and Vanillin In some embodiments, the blend of compounds can include at least three of the group consisting of Thyme Oil Red, Wintergreen Oil, Isopropyl myristate, and Vanillin.

In some embodiments, the blend of compounds can include Thyme Oil Red, Wintergreen Oil, Isopropyl myristate, and Vanillin.

In some embodiments, the blend of compounds can include 10 and 30% Thyme Oil Red, between 30 and 60% Wintergreen Oil, between 20 and 48% Isopropyl myristate, and between 0.01 and 0.3% Vanillin.

In some embodiments, the blend of compounds can include 18 and 23% Thyme Oil Red, 40 and 50% Wintergreen Oil, and between 30 and 38% Isopropyl myristate, and between 0.05 and 0.15% Vanillin.

In some embodiments, the blend of compounds can include 20.6% Thyme Oil Red, 45.1% Wintergreen Oil, 34.2% Isopropyl myristate, and 0.1% Vanillin.

In some embodiments, the blend of compounds can include at least one of the group consisting of Thyme Oil White, Isopropyl myristate, and Geraniol Fine, FCC.

In some embodiments, the blend of compounds can include at least two of the group consisting of Thyme Oil White, Isopropyl myristate, and Geraniol Fine, FCC.

In some embodiments, the blend of compounds can include Thyme Oil White, Isopropyl myristate, and Geraniol Fine, FCC.

In some embodiments, the blend of compounds can include between 30 and 55% Thyme Oil White, between 28 and 50% Isopropyl myristate, and between 15 and 26% Geraniol Fine, FCC.

In some embodiments, the blend of compounds can include between 36 and 46% Thyme Oil White, between 34 and 42% Isopropyl myristate, and between 18 and 22% Geraniol Fine, FCC.

In some embodiments, the blend of compounds can include 41.86% Thyme Oil White, 38.34% Isopropyl myristate, and 19.80% Geraniol Fine, FCC.

In some embodiments, the blend of compounds can include at least one of the group consisting of Thyme Oil White, Isopropyl myristate, and Geraniol Fine, FCC.

In some embodiments, the blend of compounds can include at least two of the group consisting of Thyme Oil White, Isopropyl myristate, and Geraniol Fine, FCC.

In some embodiments, the blend of compounds can include Thyme Oil White, Isopropyl myristate, and Geraniol Fine, FCC.

In some embodiments, the blend of compounds can include between 12 and 30% Thyme Oil White, between 45 and 75% Isopropyl myristate, and between 12 and 30% Geraniol Fine, FCC.

In some embodiments, the blend of compounds can include 18 and 24% Thyme Oil White, between 53 and 65% Isopropyl myristate, and between 18 and 23% Geraniol Fine, FCC.

In some embodiments, the blend of compounds can include 21.30% Thyme Oil White, 58.54% Isopropyl myristate, and 20.16% Geraniol Fine, FCC.

In some embodiments, the blend of compounds can include at least one of the group consisting of Thyme Oil White, Isopropyl myristate, and Geraniol Fine, FCC.

In some embodiments, the blend of compounds can include at least two of the group consisting of Thyme Oil White, Isopropyl myristate, and Geraniol Fine, FCC.

In some embodiments, the blend of compounds can include Thyme Oil White, Isopropyl myristate, and Geraniol Fine, FCC.

In some embodiments, the blend of compounds can include between 22 and 40% Thyme Oil White, between 28 and 50% Isopropyl myristate, and between 20 and 40% Geraniol Fine, FCC.

In some embodiments, the blend of compounds can include between 28 and 35% Thyme Oil White, between 34 and 43% Isopropyl myristate, and between 26 and 33% Geraniol Fine, FCC.

In some embodiments, the blend of compounds can include 31.57% Thyme Oil White, 38.56% Isopropyl myristate, 29.87% Geraniol Fine, FCC.

In some embodiments, the blend of compounds can include at least one of the group consisting of Thyme Oil White, Isopropyl myristate, and Geraniol Fine, FCC.

In some embodiments, the blend of compounds can include at least two of the group consisting of Thyme Oil White, Isopropyl myristate, and Geraniol Fine, FCC.

In some embodiments, the blend of compounds can include Thyme Oil White, Isopropyl myristate, and Geraniol Fine, FCC.

In some embodiments, the blend of compounds can include 36.85% Thyme Oil White, 48.21% Isopropyl myristate, 14.94% Geraniol Fine, FCC.

In some embodiments, the blend of compounds can include 36.85% Thyme Oil White, 48.21% Isopropyl myristate, 14.94% Geraniol Fine, FCC.

In some embodiments, the blend of compounds can include 36.85% Thyme Oil White, 48.21% Isopropyl myristate, 14.94% Geraniol Fine, FCC.

In some embodiments, the blend of compounds can include at least one of the group consisting of Thyme Oil White containing 1% Thyme Oil Red, Isopropyl myristate, and Geraniol Fine, FCC.

In some embodiments, the blend of compounds can include at least two of the group consisting of Thyme Oil White containing 1% Thyme Oil Red, Isopropyl myristate, and Geraniol Fine, FCC.

In some embodiments, the blend of compounds can include Thyme Oil White containing 1% Thyme Oil Red, Isopropyl myristate, and Geraniol Fine, FCC.

In some embodiments, the blend of compounds can include between 25 and 50% Thyme Oil White containing 1% Thyme Oil Red, between 35 and 65% Isopropyl myristate, and between 8 and 25% Geraniol Fine, FCC.

In some embodiments, the blend of compounds can include between 33 and 40% Thyme Oil White containing 1% Thyme Oil Red, between 44 and 55% Isopropyl myristate, and between 13 and 17% Geraniol Fine, FCC.

In some embodiments, the blend of compounds can include 36.85% Thyme Oil White containing 1% Thyme Oil Red, 48.21% Isopropyl myristate, 14.94% Geraniol Fine, FCC.

In some embodiments, the blend of compounds can include at least two or three of the group consisting of Potassium Sorbate, Polyglycerol-4-oleate, Xanthan Gum, Lecithin, Water, and Blend 41.

In some embodiments, the blend of compounds can include at least four of the group consisting of Potassium Sorbate, Polyglycerol-4-oleate, Xanthan Gum, Lecithin, Water, and Blend 41.

In some embodiments, the blend of compounds can include Potassium Sorbate, Polyglycerol-4-oleate, Xanthan Gum, Lecithin, Water, and Blend 41.

In some embodiments, the blend of compounds can include between 0.01 and 0.25% Potassium Sorbate, between 0.05 and 0.5% Polyglycerol-4-oleate, between 0.1 and 0.6% Xanthan Gum, between 0.01 and 0.1% Lecithin, between 60 and 98% Water, and between 5 and 25% Blend 41.

In some embodiments, the blend of compounds can include between 0.05 and 0.16% Potassium Sorbate, between 0.1 and 0.2% Polyglycerol-4-oleate, between 0.2 and 0.36% Xanthan Gum, between 0.03 and 0.04% Lecithin, between 76 and 94% Water, and between 13 and 17% Blend 41.

In some embodiments, the blend of compounds can include 0.11% Potassium Sorbate, 0.15% Polyglycerol-4-oleate, 0.28% Xanthan Gum, 0.034% Lecithin, 84.4% Water, and 15.01% Blend 41.

In some embodiments, the blend of compounds can include at least three to five of the group consisting of Thyme Oil White, Wintergreen Oil, Isopropyl myristate, Potassium Sorbate, Polyglycerol-4-oleate, Xanthan Gum, Lecithin, and Water.

In some embodiments, the blend of compounds can include at least six or seven of the group consisting of Thyme Oil White, Wintergreen Oil, Isopropyl myristate, Potassium Sorbate, Polyglycerol-4-oleate, Xanthan Gum, Lecithin, and Water.

In some embodiments, the blend of compounds can include Thyme Oil White, Wintergreen Oil, Isopropyl myristate, Potassium Sorbate, Polyglycerol-4-oleate, Xanthan Gum, Lecithin, and Water.

In some embodiments, the blend of compounds can include between 1 and 5% Thyme Oil White, between 3 and 12% Wintergreen Oil, between 2 and 10% Isopropyl myristate, between 0.02 and 0.2% Potassium Sorbate, between 0.05 and 0.5% Polyglycerol-4-oleate, between 0.1 and 0.5% Xanthan Gum, between 0.01 and 0.1% Lecithin, and between 60 and 98% Water.

In some embodiments, the blend of compounds can include between 2.7 and 3.4% Thyme Oil White, between 6.0 and 7.5% Wintergreen Oil, between 4.5 and 5.7% Isopropyl myristate, between 0.08 and 0.14% Potassium Sorbate, between 0.1 and 0.2% Polyglycerol-4-oleate, between 0.25 and 0.31% Xanthan Gum, between 0.025 and 0.035% Lecithin, and between 76 and 92% Water.

In some embodiments, the blend of compounds can include 3.09% Thyme Oil White, 6.77% Wintergreen Oil, 5.15% Isopropyl myristate, 0.11% Potassium Sorbate, 0.15% Polyglycerol-4-oleate, 0.28% Xanthan Gum, 0.03% Lecithin, 84.41% Water.

In some embodiments, the blend of compounds can include at least two or three of the group consisting of Potassium Sorbate, Polyglycerol-4-oleate, Xanthan Gum, Lecithin, Water, and Blend 120.

In some embodiments, the blend of compounds can include at least four or five of the group consisting of Potassium Sorbate, Polyglycerol-4-oleate, Xanthan Gum, Lecithin, Water, and Blend 120.

In some embodiments, the blend of compounds can include Potassium Sorbate, Polyglycerol-4-oleate, Xanthan Gum, Lecithin, Water, and Blend 120.

In some embodiments, the blend of compounds can include between 0.05 and 0.2% Potassium Sorbate, between 0.05 and 0.5% Polyglycerol-4-oleate, between 0.1 and 0.5% Xanthan Gum, between 0.01 and 0.1% Lecithin, between 60 and 98% Water, and between 8 and 22% Blend 120.

In some embodiments, the blend of compounds can include between 0.09 and 0.13% Potassium Sorbate, between 0.1 and 0.2% Polyglycerol-4-oleate, between 0.25 and 0.31% Xanthan Gum, between 0.025 and 0.043% Lecithin, between 76 and 92% Water, and between 13 and 17% Blend 120.

In some embodiments, the blend of compounds can include 0.11% Potassium Sorbate, 0.15% Polyglycerol-4-oleate, 0.28% Xanthan Gum, 0.034% Lecithin, 84.4% Water, and 15.01% Blend 120.

In some embodiments, the blend of compounds can include at least two or three of the group consisting of Potassium Sorbate, Polyglycerol-4-oleate, Xanthan Gum, Lecithin, Water, and Blend 120.

In some embodiments, the blend of compounds can include at least four or five of the group consisting of Potassium Sorbate, Polyglycerol-4-oleate, Xanthan Gum, Lecithin, Water, and Blend 120.

In some embodiments, the blend of compounds can include Potassium Sorbate, Polyglycerol-4-oleate, Xanthan Gum, Lecithin, Water, and Blend 120.

In some embodiments, the blend of compounds can include between 0.12% Potassium Sorbate, 0.16% Polyglycerol-4-oleate, 0.29% Xanthan Gum, 0.036% Lecithin, 89.4% Water, 10% Blend 120.

In some embodiments, the blend of compounds can include between 0.1 and 0.14% Potassium Sorbate, between 0.12 and 0.18% Polyglycerol-4-oleate, between 0.26 and 0.32% Xanthan Gum, between 0.03 and 0.045% Lecithin, between 80 and 98% Water, and between 8 and 12% Blend 120.

In some embodiments, the blend of compounds can include 0.12% Potassium Sorbate, 0.16% Polyglycerol-4-oleate, 0.29% Xanthan Gum, 0.036% Lecithin, 89.4% Water, 10% 120.

In some embodiments, the blend of compounds can include CAR-01-097 (McCook) and Blend 10.

In some embodiments, the blend of compounds can include between 60 and 90% CAR-01-097 (McCook) and between 10 and 40% Blend 10.

In some embodiments, the blend of compounds can include between 70 and 80% CAR-01-097 (McCook) and between 20 and 30% Blend 10.

In some embodiments, the blend of compounds can include CAR-01-097 (McCook) with 25% Blend 10.

In some embodiments, the blend of compounds can include at least two of the group consisting of Soy Bean Oil, Ethyl Alcohol (denatured), and Blend 10.

In some embodiments, the blend of compounds can include Soy Bean Oil, Ethyl Alcohol (denatured), and Blend 10.

In some embodiments, the blend of compounds can include between 10 and 30% Soy Bean Oil, between 35 and 65% Ethyl Alcohol (denatured), and between 20 and 40% Blend 10.

In some embodiments, the blend of compounds can include between 18 and 22% Soy Bean Oil, between 45 and 55% Ethyl Alcohol (denatured), and between 27 and 33% Blend 10.

In some embodiments, the blend of compounds can include 20% Soy Bean Oil, 50% Ethyl Alcohol (denatured), and 30% Blend 10.

In some embodiments, the blend of compounds can include at least two or three of the group consisting of Potassium Sorbate, Polyglycerol-4-oleate, Xanthan Gum, Lecithin, Water, and Blend 124.

In some embodiments, the blend of compounds can include at least four or five of the group consisting of Potassium Sorbate, Polyglycerol-4-oleate, Xanthan Gum, Lecithin, Water, and Blend 124.

In some embodiments, the blend of compounds can include Potassium Sorbate, Polyglycerol-4-oleate, Xanthan Gum, Lecithin, Water, and Blend 124.

In some embodiments, the blend of compounds can include between 0.05 and 0.2% Potassium Sorbate, between 0.05 and 0.5% Polyglycerol-4-oleate, between 0.1 and 0.5% Xanthan Gum, between 0.01 and 0.05% Lecithin, between 60 and 98% Water, and between 8 and 25% Blend 124.

In some embodiments, the blend of compounds can include between 0.09 and 0.13% Potassium Sorbate, between 0.13 and 0.17% Polyglycerol-4-oleate, between 0.27 and 0.33% Xanthan Gum, between 0.025 and 0.035% Lecithin, between 76 and 92% Water, and between 13 and 17% Blend 124.

In some embodiments, the blend of compounds can include 0.11% Potassium Sorbate, 0.15% Polyglycerol-4-oleate, 0.30% Xanthan Gum, 0.03% Lecithin, 84.4% Water, 15.01% Blend 124.

In some embodiments, the blend of compounds can include at least two or three of the group consisting of Potassium Sorbate, Polyglycerol-4-oleate, Xanthan Gum, Lecithin, Water, and Blend 124.

In some embodiments, the blend of compounds can include at least four or five of the group consisting of Potassium Sorbate, Polyglycerol-4-oleate, Xanthan Gum, Lecithin, Water, and Blend 124.

In some embodiments, the blend of compounds can include Potassium Sorbate, Polyglycerol-4-oleate, Xanthan Gum, Lecithin, Water, and Blend 124.

In some embodiments, the blend of compounds can include between 0.05 and 0.5% Potassium Sorbate, between 0.06 and 0.5% Polyglycerol-4-oleate, between 0.1 and 0.5% Xanthan Gum, between 0.01 and 0.1% Lecithin, between 70 and 98% Water, and between 2 and 20% Blend 124.

In some embodiments, the blend of compounds can include between 0.1 and 0.14% Potassium Sorbate, between 0.14 and 0.18% Polyglycerol-4-oleate, between 0.27 and 0.33% Xanthan Gum, between 0.03 and 0.042% Lecithin, between 80 and 96% Water, and between 8 and 12% Blend 124.

In some embodiments, the blend of compounds can include 0.12% Potassium Sorbate, 0.16% Polyglycerol-4-oleate, 0.30% Xanthan Gum, 0.036% Lecithin, 89.4% Water, 10% Blend 124.

In some embodiments, the blend of compounds can include at least two to seven of the group consisting of Citronella Oil, Carbopol 940, Butylated hyrdroxy toluene, Water, Emulsifying Wax, Light Liquid Paraffin, White Soft Paraffin, Sodium Metabisulphate, Propylene Glycol, Cresmer RH40 hydrogenated, Triethanolamine, Vitamin E Acetate, Disodium EDTA, and Blend 7.

In some embodiments, the blend of compounds can include at least eight to thirteen of the group consisting of Citronella Oil, Carbopol 940, Butylated hydroxy toluene, Water, Emulsifying Wax, Light Liquid Paraffin, White Soft Paraffin, Sodium Metabisulphate, Propylene Glycol, Cresmer RH40 hydrogenated, Triethanolamine, Vitamin E Acetate, Disodium EDTA, and Blend 7.

In some embodiments, the blend of compounds can include Citronella Oil, Carbopol 940, Butylated hyrdroxy toluene, Water, Emulsifying Wax, Light Liquid Paraffin, White Soft Paraffin, Sodium Metabisulphate, Propylene Glycol, Cresmer RH40 hydrogenated, Triethanolamine, Vitamin E Acetate, Disodium EDTA, and Blend 7.

In some embodiments, the blend of compounds can include between 0.1 and 0.4% Citronella Oil, between 0.1 and 0.4% Carbopol 940, between 0.4 and 0.2% Butylated hyrdroxy toluene, between 40 and 75% Water, between 6 and 25% Emulsifying Wax, between 2 and 8% Light Liquid Paraffin, between 4 and 15% White Soft Paraffin, between 0.1 and 0.5% Sodium Metabisulphate, between 0.8 and 5% Propylene Glycol, between 2 and 10% Cresmer RH40 hydrogenated, between 0.08 and 0.4% Triethanolamine, between 0.01 and 0.05% Vitamin E Acetate, between 0.01 and 0.1% Disodium EDTA, and between 1 and 15% Blend 7.

In some embodiments, the blend of compounds can include between 0.18 and 0.22% Citronella Oil, between 0.18 and 0.22% Carbopol 940, between 0.8 and 0.12% Butylated hyrdroxy toluene, between 52 and 66% Water, between 12 and 16% Emulsifying Wax, between 3 and 5% Light Liquid Paraffin, between 7 and 11% White Soft Paraffin, between 0.2 and 0.3% Sodium Metabisulphate, between 1.5 and 2.5% Propylene Glycol, between 4 and 6% Cresmer RH40 hydrogenated, between 0.13 and 0.17% Triethanolamine, between 0.01 and 0.03% Vitamin E Acetate, between 0.04 and 0.06% Disodium EDTA, and between 4 and 6% Blend 7.

In some embodiments, the blend of compounds can include 0.20% Citronella Oil, 0.20% Carbopol 940, 0.10% Butylated hyrdroxy toluene, 59.83% Water, 14% Emulsifying Wax, 4.00% Light Liquid Paraffin, 9% White Soft Paraffin, 0.25% Sodium Metabisulphate, 2% Propylene Glycol, 5% Cresmer RH40 hydrogenated, 0.15% Triethanolamine, 0.02% Vitamin E Acetate, 0.05% Disodium EDTA, 5% Blend 7.

In some embodiments, the blend of compounds can include at least two of the group consisting of Blend 49, Lemon Grass Oil, and Castor Oil Surfactant.

In some embodiments, the blend of compounds can include Blend 49, Lemon Grass Oil, and Castor Oil Surfactant.

In some embodiments, the blend of compounds can include between 35 and 65% Blend 49, between 15 and 35% Lemon Grass Oil, and between 15 and 35% Castor Oil Surfactant.

In some embodiments, the blend of compounds can include between 45 and 55% Blend 49, between 22 and 28% Lemon Grass Oil, and between 22 and 28% Castor Oil Surfactant.

In some embodiments, the blend of compounds can include 50% Blend 49, 25% Lemon Grass Oil, and 25% Castor Oil Surfactant.

In some embodiments, the blend of compounds can include at least two of the group consisting of Blend 51, Lemon Grass Oil, and Castor Oil Surfactant.

In some embodiments, the blend of compounds can include Blend 51, Lemon Grass Oil, and Castor Oil Surfactant.

In some embodiments, the blend of compounds can include between 35 and 65% Blend 51, between 15 and 35% Lemon Grass Oil, and between 15 and 35% Castor Oil Surfactant.

In some embodiments, the blend of compounds can include between 45 and 55% Blend 51, between 22 and 28% Lemon Grass Oil, and between 22 and 28% Castor Oil Surfactant.

In some embodiments, the blend of compounds can include 50% Blend 51, 25% Lemon Grass Oil, and 25% Castor Oil Surfactant.

In some embodiments, the blend of compounds can include at least two of the group consisting of Blend 52, Lemon Grass Oil, and Castor Oil Surfactant.

In some embodiments, the blend of compounds can include Blend 52, Lemon Grass Oil, and Castor Oil Surfactant.

In some embodiments, the blend of compounds can include between 35 and 65% Blend 52, between 15 and 35% Lemon Grass Oil, and between 15 and 35% Castor Oil Surfactant.

In some embodiments, the blend of compounds can include between 45 and 55% Blend 52, between 22 and 28% Lemon Grass Oil, and between 22 and 28% Castor Oil Surfactant.

In some embodiments, the blend of compounds can include 50% Blend 52, 25% Lemon Grass Oil, and 25% Castor Oil Surfactant.

In some embodiments, the blend of compounds can include at least two of the group consisting of Blend 7, Sodium Lauryl Sulfate, and Water.

In some embodiments, the blend of compounds can include Blend 7, Sodium Lauryl Sulfate, and Water.

In some embodiments, the blend of compounds can include between 2 and 20% Blend 7, between 0.2 and 2% Sodium Lauryl Sulfate, and between 70 and 99% Water.

In some embodiments, the blend of compounds can include between 8 and 12% Blend 7, between 0.8 and 1.2% Sodium Lauryl Sulfate, and between 80 and 98% Water.

In some embodiments, the blend of compounds can include 10% Blend 7, 1% Sodium Lauryl Sulfate, 89% Water.

The composition of exemplary synergistic blends is listed in the following table:

TABLE 1

BLENDS OF COMPOUNDS

| | Compounds | CAS Registry Number | Vol/Vol | Wt/Wt |
|---|---|---|---|---|
| Blend 1 (B-5000) | LFO (LFO), (IFF) | | 4.0% | 4% |
| | D-Limonene (Millennium) | 5989-27-5 | 83.0% | 82% |
| | Thyme Oil White (Ungerer) | 8007-46-3 | 3.0% | 3% |
| | Blend 61 | | 10.0% | 10% |
| Blend 2 | Tetrahydrolinalool FCC | 78-69-3 | 0.80% | 0.78% |
| | Isopropyl Myristate | 110-27-0 | 0.80% | 0.80% |
| | Piperonal (aldehyde) | 120-57-0 | 0.80% | 0.80% |
| | Triethyl Citrate | 77-93-0 | 0.60% | 0.80% |
| | Linalool Coeur | 78-70-6 | 0.56% | 0.57% |
| | Geraniol 60 | 106-24-1 | 0.40% | 0.41% |
| | Vanillin | 121-33-5 | 0.04% | 0.05% |
| | D-Limonene (Millennium) | 5989-27-5 | 83.0% | 85.5% |
| | Blend 61 | | 10.0% | 10.0% |
| | Thyme Oil White (Ungerer) | 8007-46-3 | 3.0% | 3.3% |
| Blend 3 | Isopropyl myristate | 110-27-0 | 24.0% | 23.5% |
| | Tetrahydrolinalool FCC | 78-69-3 | 20.0% | 19.0% |
| | Linalool Coeur | 78-70-6 | 16.0% | 15.9% |
| | Geraniol Fine FCC | 106-24-1 | 10.4% | 10.5% |
| | Piperonal (aldehyde) | 120-57-0 | 8.0% | 7.8% |
| | Vanillin | 121-33-5 | 1.6% | 1.8% |
| | Black Seed Oil (BSO) | 8014-13-9 | 20.0% | 21.5% |
| Blend 4 | Isopropyl myristate | 110-27-0 | 10.8% | 9.6% |
| | Tetrahydrolinalool FCC | 78-69-3 | 9.0% | 7.8% |
| | Linalool Synthetic | 78-70-6 | 7.2% | 6.5% |
| | Geraniol Fine FCC | 106-24-1 | 4.7% | 4.3% |
| | Piperonal (aldehyde) | 120-57-0 | 3.6% | 3.2% |
| | Vanillin | 121-33-5 | 0.7% | 0.8% |
| | BSO | 8014-13-9 | 27.0% | 26.3% |
| | Methyl Salicylate 98% Nat | 119-36-8 | 27.0% | 33.0% |
| | D-Limonene (Millennium) | 5989-27-5 | 10.0% | 8.8% |
| Blend 5 | Thyme Oil White (Ungerer) | 8007-46-3 | 22.0% | 20.6% |
| | Wintergreen Oil | 68-917-75-9 | 38.0% | 45.0% |
| | Isopropyl Myristate | 110-27-0 | 39.0% | 33.4% |
| | Vanillin | 121-33-5 | 1.0% | 1.1% |
| Blend 6 | D-Limonene (Millennium) | 5989-27-5 | 62.5% | 56.3% |
| | Thyme Oil White (Ungerer) | 8007-46-3 | 12.5% | 12.4% |
| | Wintergreen Oil | 68-917-75-9 | 25.0% | 31.3% |
| Blend 7 | LFO (IFF) | | 12.0% | 12.94% |
| | D-Limonene (Millennium) | 5989-27-5 | 9.0% | 8.72% |
| | Thyme Oil White (Ungerer) | 8007-46-3 | 9.0% | 9.58% |
| | Blend 61 | | 70.0% | 68.76% |
| Blend 8 | Tetrahydrolinalool FCC | 78-69-3 | 2.40% | 2.29% |
| | Isopropyl Myristate | 110-27-0 | 2.40% | 2.35% |
| | Piperonal (aldehyde) | 120-57-0 | 2.40% | 2.35% |
| | Triethyl Citrate | 77-93-0 | 1.80% | 2.35% |
| | Linalool Coeur | 78-70-6 | 1.68% | 1.66% |
| | Geraniol 60 | 106-24-1 | 1.20% | 1.21% |

TABLE 1-continued

| | BLENDS OF COMPOUNDS | | | |
|---|---|---|---|---|
| | Compounds | CAS Registry Number | Vol/Vol | Wt/Wt |
| | Vanillin | 121-33-5 | 0.12% | 0.15% |
| | Blend 61 | | 70.0% | 69.4% |
| | D-Limonene (Millennium) | 5989-27-5 | 10.0% | 9.70% |
| | Thyme Oil White (Ungerer) | 8007-46-3 | 8.0% | 8.54% |
| Blend 9 | LFO (IFF) | | 80.0% | 80.09% |
| | BSO | 8014-13-9 | 20.0% | 19.91% |
| Blend 10 | LFO (IFF) | | 50.0% | 50.13% |
| | BSO | 8014-13-9 | 50.0% | 49.87% |
| Blend 11 | Thyme Oil White | 8007-46-3 | 5.0% | 4.60% |
| | Wintergreen Oil | 68-917-75-9 | 50.0% | 57.80% |
| | Isopropyl Myristate | 110-27-0 | 45.0% | 37.60% |
| Blend 12 | d-Limonene | 5989-27-5 | 35.0% | 28.24% |
| | Thyme Oil White | 8007-46-3 | 5.0% | 4.44% |
| | Wintergreen Oil | 68-917-75-9 | 60.0% | 67.33% |
| Blend 13 (B-5011; CL4) | d-Limonene | 5989-27-5 | 10.0% | 9.90% |
| | Linalool Coeur | 78-70-6 | 14.0% | 14.14% |
| | Geraniol 60 | 106-24-1 | 10.0% | 10.30% |
| | Tetrahydrolinalool | 78-69-3 | 25.0% | 24.29% |
| | Isopropyl Myristate | 110-27-0 | 29.0% | 28.92% |
| | Piperonal | 120-57-0 | 10.0% | 9.97% |
| | Vanillin | 121-33-5 | 2.0% | 2.48% |
| Blend 14 | Methyl Salicylate 98% Nat | 119-36-8 | 9.0% | 11.73% |
| | Linalool Coeur | 78-70-6 | 10.0% | 9.49% |
| | Geraniol Fine | 106-24-1 | 6.5% | 6.29% |
| | Tetrahydrolinalool | 78-69-3 | 12.5% | 11.40% |
| | Isopropyl Myristate | 110-27-0 | 15.0% | 14.04% |
| | Piperonal (aldehyde) | 120-57-0 | 5.0% | 4.68% |
| | Vanillin | 121-33-5 | 1.0% | 1.16% |
| | BSO | 8014-13-9 | 31.0% | 31.92% |
| | d-Limonene | 5989-27-5 | 10.0% | 9.30% |
| Blend 15 | Isopropyl myristate | 110-27-0 | 15.0% | 14.54% |
| | Tetrahydrolinalool FCC | 78-69-3 | 12.5% | 11.81% |
| | Linalool Coeur | 78-70-6 | 10.0% | 9.82% |
| | Geraniol Fine FCC | 106-24-1 | 6.5% | 6.51% |
| | Piperonal (aldehyde) | 120-57-0 | 5.0% | 4.85% |
| | Vanillin | 121-33-5 | 1.0% | 1.20% |
| | Mineral Oil | 8042-47-5 | 15.0% | 14.97% |
| | BSO | 8014-13-9 | 25.0% | 26.66% |
| | d-Limonene | 5989-27-5 | 10.0% | 9.63% |
| Blend 16 | Isopropyl myristate | 110-27-0 | 15.0% | 14.26% |
| | Tetrahydrolinalool FCC | 78-69-3 | 12.5% | 11.57% |
| | Linalool Synthetic | 78-70-6 | 10.0% | 9.63% |
| | Geraniol Fine FCC | 106-24-1 | 6.5% | 6.38% |
| | Piperonal (aldehyde) | 120-57-0 | 5.0% | 4.75% |
| | Vanillin | 121-33-5 | 1.0% | 1.12% |
| | BSO | 8014-13-9 | 50.0% | 52.28% |
| Blend 17 | Thyme Oil White | 110-27-0 | 39.0% | 38.21% |
| | Wintergreen Oil | 78-69-3 | 20.0% | 24.79% |
| | Vanillin | 121-33-5 | 1.0% | 1.11% |
| | Isopropyl Myristate | 8014-13-9 | 40.0% | 35.89% |
| Blend 18 | Thyme Oil White | 110-27-0 | 40.0% | 39.24% |
| | Wintergreen Oil | 78-69-3 | 20.0% | 24.82% |
| | Isopropyl Myristate | 8014-13-9 | 40.0% | 35.94% |
| Blend 19 (B-7000) | Linalool Coeur | 78-70-6 | 5.0% | 4.7% |
| | Thymol (crystal) | 89-83-8 | 39.0% | 40.8% |
| | Alpha-Pinene, 98% | 80-56-8 | 2.0% | 1.9% |
| | Para-Cymene | 99-87-6 | 37.0% | 34.5% |
| | trans-Anethole | 4180-23-8 | 17.0% | 18.2% |
| Blend 20 | Thyme Oil White (Ungerer) | 8007-46-3 | | 22% |
| | Methyl Salicylate Nat Wintergreen extract | 68917-75-9 | | 38% |
| | Isopropyl Myristate | 110-27-0 | | 39% |
| | Vanillin | 121-33-5 | | 1.0% |
| Blend 21 | D-Limonene (Millennium) | 5989-27-5 | | 62.5% |
| | Thyme Oil White (Ungerer) | 8007-46-3 | | 12.5% |
| | Methyl Salicylate Nat Wintergreen extract | 68917-75-9 | | 25.0% |

TABLE 1-continued

| | BLENDS OF COMPOUNDS | | | |
|---|---|---|---|---|
| | Compounds | CAS Registry Number | Vol/Vol | Wt/Wt |
| Blend 22 | Methyl Salicylate | 119-36-8 | | 39% |
| | Thymol (crystal) | 89-83-8 | | 20% |
| | Geraniol 60 | 106-24-1 | | 20% |
| | Isopropyl Myristate | 110-27-0 | | 20% |
| | Vanillin | 121-33-5 | | 1% |
| Blend 23 | LFO | 5989-27-5 | | 42.6% |
| | D-Limonene (Millennium) | 5989-27-5 | | 27.35% |
| | Thyme Oil White (Ungerer) | 8007-46-3 | | 30.08% |
| Blend 24 (B-5001) | D-Limonene | 5989-27-5 | | 82.52% |
| | Thyme Oil White | 8007-46-3 | | 3.28% |
| | Linalool Coeur | 78-70-6 | | 0.57% |
| | Tetrahydrolinalool | 78-69-3 | | 0.78% |
| | Vanillin | 121-33-5 | | 0.05% |
| | Isopropyl myristate | 110-27-0 | | 0.80% |
| | Piperonal (aldehyde) | 120-57-0 | | 0.80% |
| | Blend 62 | | | 9.99% |
| | Geraniol 60 | 106-24-1 | | 0.41% |
| | Triethyl Citrate | 77-93-0 | | 0.80% |
| Blend 25 | Thyme Oil White | 8007-46-3 | | 12.38% |
| | Wintergreen Oil (Technical grade) | | | 31.32% |
| | D-Limonene | 5989-27-5 | | 56.30% |
| Blend 26 | Fenchol Alpha | 512-13-0 | | 0.01% |
| | Nonanal | 124-19-6 | | 0.02% |
| | Tocopherol Gamma Tenox | 54-28-4 | | 0.02% |
| | Octanal | 124-13-0 | | 0.04% |
| | Terpinene 4 OL | 562-74-3 | | 0.08% |
| | Camphor Dextro | 464-49-3 | | 0.09% |
| | Dodecanal | 112-54-9 | | 0.10% |
| | Decanal | 112-31-2 | | 0.12% |
| | Geranyl Acetate | 105-87-3 | | 0.12% |
| | 2-Methyl 1,3-cyclohexadiene | 30640-46-1, 1888-90-0 | | 0.26% |
| | Isoborneol | 124-76-5 | | 0.28% |
| | Camphene | 79-92-5 | | 0.37% |
| | Myrcene | 123-35-3 | | 0.78% |
| | Linalool Coeur | 78-70-6 | | 0.84% |
| | Borneol L | 507-70-0 | | 0.89% |
| | Para-Cymene | 99-87-6 | | 1.11% |
| | Alpha-Pinene, 98% | 80-56-8 | | 1.33% |
| | Linalyl Acetate | 115-95-7 | | 1.79% |
| | Beta Pinene | 127-91-3 | | 1.93% |
| | Alpha Terpinene | 99-86-5 | | 1.93% |
| | Terpinolene | 586-62-9 | | 4.33% |
| | alpha-Terpineol | 98-55-5 | | 4.68% |
| | Citral | 5392-40-5 | | 7.02% |
| | gamma-terpinene | 99-85-4 | | 7.23% |
| | Thyme Oil White | 8007-46-3 | | 9.58% |
| | LFO | | | 12.94% |
| | D-Limonene | 5989-27-5 | | 42.12% |
| Blend 27 | Wintergreen Oil (Technical grade) | | | 24.82% |
| | Isopropyl myristate | 110-27-0 | | 35.94% |
| | Thyme Oil White | 8007-46-3 | | 39.24% |
| Blend 28 | Vanillin | 121-33-5 | | 0.2% |
| | Piperonyl Alcohol | 495-76-1 | | 1.4% |
| | Linalool Coeur | 78-70-6 | | 2.9% |
| | Isopropyl myristate | 110-27-0 | | 3.4% |
| | Tetrahydrolinalool | 78-69-3 | | 3.5% |
| | Piperonal (aldehyde) | 120-57-0 | | 3.6% |
| | D-Limonene | 5989-27-5 | | 14.8% |
| | Blend 62 | | | 70.2% |
| Blend 29 | Vanillin | 121-33-5 | | 0.2% |
| | Piperonyl Alcohol | 495-76-1 | | 1.4% |
| | Linalool Coeur | 78-70-6 | | 2.9% |
| | Isopropyl myristate | 110-27-0 | | 3.4% |
| | Tetrahydrolinalool | 78-69-3 | | 3.5% |
| | Piperonal (aldehyde) | 120-57-0 | | 3.6% |
| | Blend 62 | | | 15.2% |
| | D-Limonene | 5989-27-5 | | 69.8% |
| Blend 30 | Vanillin | 121-33-5 | | 0.4% |
| | Piperonyl Alcohol | 495-76-1 | | 2.9% |
| | Linalool Coeur | 78-70-6 | | 5.7% |

TABLE 1-continued

BLENDS OF COMPOUNDS

| | Compounds | CAS Registry Number | Vol/Vol | Wt/Wt |
|---|---|---|---|---|
| | Isopropyl myristate | 110-27-0 | | 6.8% |
| | Tetrahydrolinalool | 78-69-3 | | 6.9% |
| | Piperonal (aldehyde) | 120-57-0 | | 7.1% |
| | Blend 62 | | | 70.2% |
| Blend 31 | D-Limonene | 5989-27-5 | | 27.35% |
| | Thyme Oil White | 8007-46-3 | | 30.08% |
| | LFO3 | | | 42.57% |
| Blend 32 | Vanillin | 121-33-5 | | 0.5% |
| | Geraniol 60 | 106-24-1 | | 4.2% |
| | Linalool Coeur | 78-70-6 | | 5.7% |
| | Tetrahydrolinalool | 78-69-3 | | 7.9% |
| | Isopropyl myristate | 110-27-0 | | 8.1% |
| | Piperonal (aldehyde) | 120-57-0 | | 8.1% |
| | Triethyl Citrate | 77-93-0 | | 8.1% |
| | D-Limonene | 5989-27-5 | | 27.4% |
| | Thyme Oil White | 8007-46-3 | | 30.1% |
| Blend 33 | D-Limonene | 5989-27-5 | | 27.35% |
| (B-5021A; HL1) | Thyme Oil White | 8007-46-3 | | 30.08% |
| | LFO | | | 42.6% |
| Blend 34 | Stock 10% SLS Solution | | | 3.18% |
| | D-Limonene | 5989-27-5 | | 4.03% |
| | Thyme Oil White | 8007-46-3 | | 4.43% |
| | LFO3 | | | 6.27% |
| | Benzyl Alcohol | 100-51-6 | | 16.61% |
| | Isopar M | 64742-47-8 | | 20.95% |
| | Water | 7732-18-5 | | 44.53% |
| Blend 35 | Vanillin | 121-33-5 | | 0.07% |
| | Geraniol 60 | 106-24-1 | | 0.62% |
| | Linalool Coeur | 78-70-6 | | 0.84% |
| | Tetrahydrolinalool | 78-69-3 | | 1.16% |
| | Isopropyl myristate | 110-27-0 | | 1.19% |
| | Piperonal (aldehyde) | 120-57-0 | | 1.19% |
| | Triethyl Citrate | 77-93-0 | | 1.19% |
| | Stock 10% SLS Solution | | | 3.18% |
| | D-Limonene | 5989-27-5 | | 4.03% |
| | Thyme Oil White | 8007-46-3 | | 4.43% |
| | Benzyl Alcohol | 100-51-6 | | 16.61% |
| | Isopar M | 64742-47-8 | | 20.95% |
| | Water | 7732-18-5 | | 44.53% |
| Blend 36 | D-Limonene | 5989-27-5 | | 27.35% |
| | Thyme Oil White | 8007-46-3 | | 30.08% |
| | LFO3 | | | 42.57% |
| Blend 37 | Vanillin | 121-33-5 | | 0.50% |
| | Geraniol 60 | 106-24-1 | | 4.18% |
| | Linalool Coeur | 78-70-6 | | 5.73% |
| | Tetrahydrolinalool | 78-69-3 | | 7.88% |
| | Isopropyl myristate | 110-27-0 | | 8.08% |
| | Piperonal (aldehyde) | 120-57-0 | | 8.09% |
| | Triethyl Citrate | 77-93-0 | | 8.11% |
| | D-Limonene | 5989-27-5 | | 27.35% |
| | Thyme Oil White | 8007-46-3 | | 30.08% |
| Blend 38 | Thyme Oil White | 8007-46-3 | | 3.3% |
| | LFO | | | 4.4% |
| | Blend 62 | | | 10.0% |
| | D-Limonene | 5989-27-5 | | 82.3% |
| Blend 39 | D-Limonene | 5989-27-5 | | 8.72% |
| | Thyme Oil White | 8007-46-3 | | 9.58% |
| | LFO | | | 12.94% |
| | Blend 62 | | | 68.76% |
| Blend 40 | Vanillin | 121-33-5 | | 0.1% |
| | Geraniol 60 | 106-24-1 | | 1.2% |
| | Linalool Coeur | 78-70-6 | | 1.7% |
| | Tetrahydrolinalool | 78-69-3 | | 2.3% |
| | Piperonal (aldehyde) | 120-57-0 | | 2.4% |
| | Triethyl Citrate | 77-93-0 | | 2.4% |
| | Thyme Oil White | 8007-46-3 | | 8.6% |
| | D-Limonene | 5989-27-5 | | 9.8% |
| | Blend 62 | | | 69.3% |
| Blend 41 | Thyme Oil White | 8007-46-3 | | 20.6% |
| (B-5028) | Isopropyl myristate | 110-27-0 | | 34.3% |
| | Wintergreen Oil | 68917-75-9 | | 45.1% |
| Blend 42 | Vanillin | 121-33-5 | | 1.9% |
| | Piperonal (aldehyde) | 120-57-0 | | 7.8% |
| | Geraniol Fine FCC | 106-24-1 | | 10.5% |

TABLE 1-continued

BLENDS OF COMPOUNDS

| | Compounds | CAS Registry Number | Vol/Vol | Wt/Wt |
|---|---|---|---|---|
| | Linalool Coeur | 78-70-6 | | 15.8% |
| | Tetrahydrolinalool | 78-69-3 | | 19.0% |
| | BSO | 977017-84-7 | | 21.5% |
| | Isopropyl myristate | 110-27-0 | | 23.4% |
| Blend 43 | Alpha-Pinene, 98% | 80-56-8 | | 3.78% |
| | Linalool Coeur | 78-70-6 | | 6.63% |
| | Soy Bean Oil | 8016-70-4 | | 24.03% |
| | Para-Cymene | 99-87-6 | | 28.39% |
| | Thymol (crystal) | 89-83-8 | | 37.17% |
| Blend 44 | Alpha-Pinene, 98% | 80-56-8 | | 4.97% |
| | Linalool Coeur | 78-70-6 | | 8.73% |
| | Para-Cymene | 99-87-6 | | 37.37% |
| | Thymol (crystal) | 89-83-8 | | 48.93% |
| Blend 45 | Vanillin | 121-33-5 | | 0.32% |
| | Piperonal (aldehyde) | 120-57-0 | | 1.29% |
| | Geraniol Fine FCC | 106-24-1 | | 1.73% |
| | Linalool Coeur | 78-70-6 | | 2.61% |
| | Tetrahydrolinalool | 78-69-3 | | 3.13% |
| | Isopropyl myristate | 110-27-0 | | 3.86% |
| | D-Limonene | 5989-27-5 | | 8.72% |
| | Thyme Oil White | 8007-46-3 | | 9.58% |
| | Blend 61 | | | 68.76% |
| Blend 46 | Thyme Oil White | 8007-46-3 | | 4.44% |
| | D-Limonene | 5989-27-5 | | 28.24% |
| | Methyl Salicylate Synth | | | 67.32% |
| Blend 47 | Thyme Oil White | 8007-46-3 | | 20.6% |
| | Isopropyl myristate | 110-27-0 | | 34.3% |
| | Wintergreen Oil (Technical grade) | | | 45.1% |
| Blend 48 | CIK Formula | | | 22.44% |
| | Lemon Grass Oil-India | | | 22.93% |
| | Castor Oil hydrogenated-PEO40 | | | 54.63% |
| Blend 49 | BSO | 977017-84-7 | | 4.83% |
| | Thyme Oil White | 8007-46-3 | | 11.18% |
| | LFO | | | 16.18% |
| | D-Limonene | 5989-27-5 | | 67.81% |
| Blend 50 | BSO | 977017-84-7 | | 5.31% |
| | Thyme Oil White | 8007-46-3 | | 11.59% |
| | LFO | | | 16.01% |
| | D-Limonene | 5989-27-5 | | 67.09% |
| Blend 51 | Vanillin | 121-33-5 | | 0.15% |
| | Geraniol 60 | 106-24-1 | | 1.23% |
| | Linalool Coeur | 78-70-6 | | 1.68% |
| | Tetrahydrolinalool | 78-69-3 | | 2.31% |
| | Isopropyl myristate | 110-27-0 | | 2.37% |
| | Piperonal (aldehyde) | 120-57-0 | | 2.37% |
| | Triethyl Citrate | 77-93-0 | | 2.38% |
| | D-Limonene | 5989-27-5 | | 8.83% |
| | Thyme Oil White | 8007-46-3 | | 9.71% |
| | Isopar M | 64742-47-8 | | 13.80% |
| | Blend 61 | | | 55.17% |
| Blend 52 | Vanillin | 121-33-5 | | 0.15% |
| | Geraniol 60 | 106-24-1 | | 1.21% |
| | Linalool Coeur | 78-70-6 | | 1.66% |
| | Tetrahydrolinalool | 78-69-3 | | 2.28% |
| | Isopropyl myristate | 110-27-0 | | 2.34% |
| | Piperonal (aldehyde) | 120-57-0 | | 2.34% |
| | Triethyl Citrate | 77-93-0 | | 2.35% |
| | D-Limonene | 5989-27-5 | | 8.72% |
| | Thyme Oil White | 8007-46-3 | | 9.59% |
| | Blend 61 | | | 69.35% |
| Blend 53 | Thyme Oil White | 8007-46-3 | | 5.37% |
| | Blend 61 | | | 9.98% |
| | LFO | | | 16.31% |
| | D-Limonene | 5989-27-5 | | 68.34% |
| Blend 54 (B-7001; Armor Blend) | Alpha-Pinene, 98% | 80-56-8 | | 3.8% |
| | Linalool Coeur | 78-70-6 | | 6.6% |
| | Soy Bean Oil | 8016-70-4 | | 24.0% |
| | Para-Cymene | 99-87-6 | | 28.39% |
| | Thymol (crystal) | 89-83-8 | | 37.2% |
| Blend 55 | Para-Cymene | 99-87-6 | | 1.90% |
| | Alpha-Pinene, 98% | 80-56-8 | | 4.70% |

TABLE 1-continued

BLENDS OF COMPOUNDS

| | Compounds | CAS Registry Number | Vol/Vol | Wt/Wt |
|---|---|---|---|---|
| | Trans-Anethole | 4180-23-8 | | 18.20% |
| | Thymol (crystal) | 89-83-8 | | 34.40% |
| | Linalool Coeur | 78-70-6 | | 40.80% |
| Blend 56 | Alpha-Pinene, 98% | 80-56-8 | | 9.46% |
| | Linalool Coeur | 78-70-6 | | 9.49% |
| | Para-Cymene | 99-87-6 | | 33.18% |
| | Thymol (crystal) | 89-83-8 | | 47.87% |
| Blend 57 | Vanillin | 121-33-5 | | 2.47% |
| | Piperonal (aldehyde) | 120-57-0 | | 9.95% |
| | Geraniol Fine FCC | 106-24-1 | | 13.36% |
| | Linalool Coeur | 78-70-6 | | 20.15% |
| | Tetrahydrolinalool | 78-69-3 | | 24.23% |
| | Isopropyl myristate | 110-27-0 | | 29.84% |
| Blend 58 | Vanillin | 121-33-5 | | 1.17% |
| | Hercolyn D | 8050-15-5 | | 4.44% |
| | Hedione | 24851-98-7 | | 6.67% |
| | Piperonal (aldehyde) | 120-57-0 | | 7.55% |
| | Dipropylene glycol (DPG) | 246-770-3 | | 9.09% |
| | Triethyl Citrate | 77-93-0 | | 10.10% |
| | Isopropyl myristate | 110-27-0 | | 15.10% |
| | Ethyl Linalool | 10339-55-6 | | 22.91% |
| | Tetrahydrolinalool | 78-69-3 | | 22.98% |
| Blend 59 | Vanillin | 121-33-5 | | 1.2% |
| | Geraniol 60 | 106-24-1 | | 9.8% |
| | Linalool Coeur | 78-70-6 | | 13.5% |
| | Tetrahydrolinalool | 78-69-3 | | 18.5% |
| | Isopropyl myristate | 110-27-0 | | 19.0% |
| | Piperonal (aldehyde) | 120-57-0 | | 19.0% |
| | Triethyl Citrate | 77-93-0 | | 19.1% |
| Blend 60 | Vanillin | 121-33-5 | | 1.2% |
| | Piperonyl Alcohol | 495-76-1 | | 9.6% |
| | Linalool Coeur | 78-70-6 | | 19.2% |
| | Isopropyl myristate | 110-27-0 | | 22.9% |
| | Tetrahydrolinalool | 78-69-3 | | 23.2% |
| | Piperonal (aldehyde) | 120-57-0 | | 23.8% |
| Blend 61 | Fenchol Alpha | 512-13-0 | | 0.01% |
| | Nonanal | 124-19-6 | | 0.03% |
| | Tocopherol Gamma Tenox | 54-28-4 | | 0.03% |
| | Octanal | 124-13-0 | | 0.06% |
| | Terpinene 4 OL | 562-74-3 | | 0.11% |
| | Camphor Dextro | 464-49-3 | | 0.13% |
| | Dodecanal | 112-54-9 | | 0.14% |
| | Decanal | 112-31-2 | | 0.17% |
| | Geranyl Acetate | 105-87-3 | | 0.18% |
| | 2-Methyl 1,3-cyclohexadiene | 30640-46-1, 1888-90-0 | | 0.38% |
| | Isoborneol | 124-76-5 | | 0.41% |
| | Camphene | 79-92-5 | | 0.54% |
| | Myrcene | 123-35-3 | | 1.14% |
| | Linalool Coeur | 78-70-6 | | 1.22% |
| | Borneol L | 507-70-0 | | 1.30% |
| | Para-Cymene | 99-87-6 | | 1.61% |
| | Alpha-Pinene, 98% | 80-56-8 | | 1.94% |
| | Linalyl Acetate | 115-95-7 | | 2.60% |
| | Beta Pinene | 127-91-3 | | 2.80% |
| | Alpha Terpinene | 99-86-5 | | 2.80% |
| | Terpinolene | 586-62-9 | | 6.30% |
| | alpha-Terpineol | 98-55-5 | | 6.80% |
| | Citral | 5392-40-5 | | 10.21% |
| | gamma-terpinene | 99-85-4 | | 10.51% |
| | D-Limonene | 5989-27-5 | | 48.58% |
| Blend 62 | Fenchol Alpha | 512-13-0 | | 0.01% |
| | Nonanal | 124-19-6 | | 0.04% |
| | Tocopherol Gamma Tenox | 54-28-4 | | 0.04% |
| | Octanal | 124-13-0 | | 0.07% |
| | Terpinene 4 OL | 562-74-3 | | 0.13% |
| | Camphor Dextro | 464-49-3 | | 0.16% |
| | Dodecanal | 112-54-9 | | 0.17% |
| | Decanal | 112-31-2 | | 0.20% |
| | Geranyl Acetate | 105-87-3 | | 0.22% |
| | 2-Methyl 1,3-cyclohexadiene | 30640-46-1, 1888-90-0 | | 0.46% |
| | Isoborneol | 124-76-5 | | 0.49% |

TABLE 1-continued

BLENDS OF COMPOUNDS

| | Compounds | CAS Registry Number | Vol/Vol | Wt/Wt |
|---|---|---|---|---|
| | Camphene | 79-92-5 | | 0.65% |
| | Myrcene | 123-35-3 | | 1.37% |
| | Linalool Coeur | 78-70-6 | | 1.47% |
| | Borneol L | 507-70-0 | | 1.57% |
| | Para-Cymene | 99-87-6 | | 1.94% |
| | Alpha-Pinene, 98% | 80-56-8 | | 2.34% |
| | Linalyl Acetate | 115-95-7 | | 3.13% |
| | Beta Pinene | 127-91-3 | | 3.37% |
| | Alpha Terpinene | 99-86-5 | | 3.37% |
| | Terpinolene | 586-62-9 | | 7.59% |
| | gamma-terpinene | 99-85-4 | | 12.66% |
| | D-Limonene | 5989-27-5 | | 58.54% |
| Blend 63 | Alpha Terpinene | 99-86-5 | | 4.88% |
| | Alpha-Pinene, 98% | 80-56-8 | | 5.01% |
| | Beta Pinene | 127-91-3 | | 5.02% |
| | Linalyl Acetate | 115-95-7 | | 5.30% |
| | Camphene | 79-92-5 | | 5.84% |
| | Myrcene | 123-35-3 | | 9.26% |
| | Para-Cymene | 99-87-6 | | 10.04% |
| | Linalool Coeur | 78-70-6 | | 10.05% |
| | Terpinolene | 586-62-9 | | 10.10% |
| | D-Limonene | 5989-27-5 | | 34.50% |
| Blend 64 | Stock 10% SLS Solution | | | 10% |
| | Blend 41 | | | 90% |
| Blend 65 | Lecithin | 8002-43-5 | | 0.20% |
| | Polyglycerol-4-oleate | 9007-48-1 | | 0.90% |
| | Water | 7732-18-5 | | 9.8% |
| | Blend 41 | | | 89.1% |
| Blend 66 | Xanthan Gum | 11138-66-2 | | 0.28% |
| | Potassium Sorbate | 590-00-1 or 24634-61-5 | | 1.00% |
| | Blend 65 | | | 16.90% |
| | Water | 7732-18-5 | | 81.82% |
| Blend 67 | Lecithin | 8002-43-5 | | 0.034% |
| | Potassium Sorbate | 590-00-1 or 24634-61-5 | | 0.11% |
| | Polyglycerol-4-oleate | 9007-48-1 | | 0.15% |
| | Xanthan Gum | 11138-66-2 | | 0.28% |
| | Blend 41 | | | 15% |
| | Water | 7732-18-5 | | 84.4% |
| Blend 68 | Lecithin | 8002-43-5 | | 0.03% |
| | Potassium Sorbate | 590-00-1 or 24634-61-5 | | 0.11% |
| | Polyglycerol-4-oleate | 9007-48-1 | | 0.15% |
| | Xanthan Gum | 11138-66-2 | | 0.28% |
| | Thyme Oil White | 8007-46-3 | | 3.09% |
| | Isopropyl myristate | 110-27-0 | | 5.15% |
| | Wintergreen Oil | 68917-75-9 | | 6.77% |
| | Water | 7732-18-5 | | 84.41% |
| Blend 69 | Lecithin | 8002-43-5 | | 0.20% |
| | Polyglycerol-4-oleate | 9007-48-1 | | 0.90% |
| | Water | 7732-18-5 | | 9.8% |
| | Blend 18 | | | 89.10% |
| Blend 70 | Stock 2.5% Xanthan-1% Ksorbate | | | 12.7% |
| | Blend 65 | | | 84.2% |
| | Water | 7732-18-5 | | 3.1% |
| Blend 71 | Potassium Sorbate | 590-00-1 or 24634-61-5 | | 0.13% |
| | Lecithin | 8002-43-5 | | 0.17% |
| | Xanthan Gum | 11138-66-2 | | 0.32% |
| | Polyglycerol-4-oleate | 9007-48-1 | | 0.76% |
| | Thyme Oil White | 8007-46-3 | | 15.5% |
| | Water | 7732-18-5 | | 23.6% |
| | Isopropyl myristate | 110-27-0 | | 25.7% |
| | Wintergreen Oil | 68917-75-9 | | 33.8% |
| Blend 72 | Water | 7732-18-5 | | 9.2% |
| | Stock 2.5% Xanthan-1% Ksorbate | | | 11.90% |
| | Blend 65 | | | 78.87% |
| Blend 73 | Potassium Sorbate | 590-00-1 or 24634-61-5 | | 0.13% |
| | Lecithin | 8002-43-5 | | 0.17% |
| | Xanthan Gum | 11138-66-2 | | 0.32% |
| | Polyglycerol-4-oleate | 9007-48-1 | | 0.76% |

TABLE 1-continued

| | BLENDS OF COMPOUNDS | | | |
|---|---|---|---|---|
| | Compounds | CAS Registry Number | Vol/Vol | Wt/Wt |
| | Water | 7732-18-5 | | 28.6% |
| | Blend 41 | | | 70% |
| Blend 74 | Water | 7732-18-5 | | 3.1% |
| | Stock 2.5% Xanthan-1% Ksorbate | | | 12.7% |
| | Blend 69 | | | 84.2% |
| Blend 75 | Xanthan Gum | 11138-66-2 | | 0.28% |
| | Potassium Sorbate | 590-00-1 or 24634-61-5 | | 1% |
| | Blend 69 | | | 16.90% |
| | Water | 7732-18-5 | | 81.8% |
| Blend 76 | CIK Formula | | | 2.50% |
| Blend 77 | Lecithin | 8002-43-5 | | 0.20% |
| | Polyglycerol-4-oleate | 9007-48-1 | | 0.90% |
| | Water | 7732-18-5 | | 9.8% |
| | Blend 47 | | | 89.10% |
| Blend 78 | Xanthan Gum | 11138-66-2 | | 0.28% |
| | Potassium Sorbate | 590-00-1 or 24634-61-5 | | 1.00% |
| | Blend 77 | | | 16.90% |
| | Water | 7732-18-5 | | 81.82% |
| Blend 79 | Vitamin E Acetate | [58-95-7] | | 0.02% |
| | Propyl Paraben | [94-13-3] | | 0.05% |
| | Disodium EDTA | [139-33-3] | | 0.05% |
| | BHT | 128-37-0 | | 0.10% |
| | Methyl Paraben | [99-76-3] | | 0.15% |
| | Triethanolamine | [102-71-6] | | 0.15% |
| | Citronella Oil | 106-22-9 | | 0.20% |
| | Carbopol 940 | [9003-01-4] | | 0.20% |
| | Sodium Metabisulphate | [7681-57-4] | | 0.25% |
| | Propylene Glycol | [57-55-6] | | 2.00% |
| | Light Liquid Paraffin | 8012-95-1 | | 4.00% |
| | CIK Formula | | | 5.00% |
| | Cresmer RH40 hydrogenated castor oil | [61791-12-6] | | 5.00% |
| | White Soft Paraffin | [8009-03-8] | | 9.00% |
| | Emulsifying Wax | 67762-27-0, 9005-67-8 | | 14.00% |
| | Water | 7732-18-5 | | 59.83% |
| Blend 80 | Span 80 | | | 0.05% |
| | Sodium Benzoate | | | 0.20% |
| | Isopropyl alcohol | 67-63-0 | | 1.50% |
| | Blend 6 | | | 12.50% |
| | A46 Propellent | | | 14.50% |
| | Isopar M | 64742-47-8 | | 29% |
| | Water | 7732-18-5 | | 42.25% |
| Blend 81 | Isopropyl alcohol | 67-63-0 | | 3.0% |
| | Blend 36 | | | 6.0% |
| | A46 Propellent | | | 40.0% |
| | Isopar M | 64742-47-8 | | 51.0% |
| Blend 82 | Isopropyl alcohol | 67-63-0 | | 3.0% |
| | Blend 36 | | | 6.0% |
| | A46 Propellent | | | 40.0% |
| | Isopar M | 64742-47-8 | | 51.0% |
| Blend 83 | HL1 | | | 6.0% |
| | A46 Propellent | | | 40.0% |
| | Isopar M | 64742-47-8 | | 54.0% |
| Blend 84 | Bifenthrin | 83657-04-3 | | 0.05% |
| | Lecithin | 8002-43-5 | | 0.03% |
| | Potassium Sorbate | 590-00-1 or 24634-61-5 | | 0.11% |
| | Polyglycerol-4-oleate | 9007-48-1 | | 0.15% |
| | Xanthan Gum | 11138-66-2 | | 0.28% |
| | Thyme Oil White | 8007-46-3 | | 2.06% |
| | Isopropyl myristate | 110-27-0 | | 3.43% |
| | Wintergreen Oil | 68917-75-9 | | 4.51% |
| | Water | 7732-18-5 | | 89.42% |
| Blend 85 | Lecithin | 8002-43-5 | | 0.03% |
| | Potassium Sorbate | 590-00-1 or 24634-61-5 | | 0.11% |
| | Polyglycerol-4-oleate | 9007-48-1 | | 0.15% |
| | Xanthan Gum | 11138-66-2 | | 0.28% |
| | Thyme Oil White | 8007-46-3 | | 1.03% |
| | Isopropyl myristate | 110-27-0 | | 1.72% |

TABLE 1-continued

| | BLENDS OF COMPOUNDS | | | |
|---|---|---|---|---|
| | Compounds | CAS Registry Number | Vol/Vol | Wt/Wt |
| | Wintergreen Oil | 68917-75-9 | | 2.26% |
| | Water | 7732-18-5 | | 94.43% |
| Blend 86 | Lecithin, Soya | 8030-76-0 | | 0.20% |
| | Polyglycerol-4-oleate | 9007-48-1 | | 0.90% |
| | Water | 7732-18-5 | | 9.80% |
| | Blend 18 | | | 89.10% |
| Blend 87 | Lecithin, Soya | 8030-76-0 | | 0.20% |
| | Polyglycerol-4-oleate | 9007-48-1 | | 0.90% |
| | Water | 7732-18-5 | | 9.80% |
| | Wintergreen Oil (Technical grade) | | | 22.1% |
| | Isopropyl myristate | 110-27-0 | | 32.0% |
| | Thyme Oil White | 8007-46-3 | | 35.0% |
| Blend 88 | Lecithin, Soya | 8030-76-0 | | 0.10% |
| | Polyglycerol-4-oleate | 9007-48-1 | | 0.90% |
| | Water | 7732-18-5 | | 9.90% |
| | Blend 5 | | | 89.1% |
| Blend 89 | Lecithin, Soya | 8030-76-0 | | 0.10% |
| | Polyglycerol-4-oleate | 9007-48-1 | | 0.90% |
| | Water | 7732-18-5 | | 9.90% |
| | Isopropyl myristate | 110-27-0 | | 29.76% |
| | Thyme Oil White | 8007-46-3 | | 18.27% |
| | Wintergreen Oil | 68917-75-9 | | 40.10% |
| | Vanillin | 121-33-5 | | 0.98% |
| Blend 90 | Polyglycerol-4-oleate | 9007-48-1 | | 1.90% |
| | Water | 7732-18-5 | | 9.00% |
| | Blend 18 | | | 89.10% |
| Blend 91 | Polyglycerol-4-oleate | 9007-48-1 | | 1.90% |
| | Water | 7732-18-5 | | 9.00% |
| | Wintergreen Oil (Technical grade) | | | 22.1% |
| | Isopropyl myristate | 110-27-0 | | 32.0% |
| | Thyme Oil White | 8007-46-3 | | 35.0% |
| Blend 92 | Potassium Sorbate | 590-00-1 or 24634-61-5 | | 0.11% |
| | Xanthan Gum | 11138-66-2 | | 0.275% |
| | Polyglycerol-4-oleate | 9007-48-1 | | 1.90% |
| | Blend 88 | | | 11.30% |
| | Water | 7732-18-5 | | 86.410% |
| Blend 93 | Lecithin, Soya | 8030-76-0 | | 0.011% |
| | Potassium Sorbate | 590-00-1 or 24634-61-5 | | 0.11% |
| | Xanthan Gum | 11138-66-2 | | 0.275% |
| | Thyme Oil White | 8007-46-3 | | 1.25% |
| | Polyglycerol-4-oleate | 9007-48-1 | | 2.002% |
| | Wintergreen Oil (Technical grade) | | | 3.15% |
| | D-Limonene | 5989-27-5 | | 5.67% |
| | Water | 7732-18-5 | | 87.529% |
| Blend 94 | Potassium Sorbate | 590-00-1 or 24634-61-5 | | 0.11% |
| | Xanthan Gum | 11138-66-2 | | 0.275% |
| | Blend 86 | | | 11.30% |
| | Water | 7732-18-5 | | 88.315% |
| Blend 95 | Lecithin, Soya | 8030-76-0 | | 0.023% |
| | Polyglycerol-4-oleate | 9007-48-1 | | 0.102% |
| | Potassium Sorbate | 590-00-1 or 24634-61-5 | | 0.11% |
| | Xanthan Gum | 11138-66-2 | | 0.275% |
| | Wintergreen Oil (Technical grade) | | | 2.50% |
| | Isopropyl myristate | 110-27-0 | | 3.62% |
| | Thyme Oil White | 8007-46-3 | | 3.95% |
| | Water | 7732-18-5 | | 89.422% |
| Blend 96 | Potassium Sorbate | 24634-61-5 | | 0.11% |
| | Xanthan Gum | 11138-66-2 | | 0.275% |
| | Blend 90 | | | 11.30% |
| | Water | 7732-18-5 | | 88.315% |
| Blend 97 | Potassium Sorbate | 24634-61-5 | | 0.11% |
| | Polyglycerol-4-oleate | 9007-48-1 | | 0.21% |
| | Xanthan Gum | 11138-66-2 | | 0.275% |
| | Wintergreen Oil | 68917-75-9 | | 2.50% |
| | Isopropyl myristate | 110-27-0 | | 3.62% |
| | Thyme Oil White | 8007-46-3 | | 3.95% |
| | Water | 7732-18-5 | | 89.332% |

TABLE 1-continued

| | BLENDS OF COMPOUNDS | | | |
|---|---|---|---|---|
| | Compounds | CAS Registry Number | Vol/Vol | Wt/Wt |
| Blend 98 | Potassium Sorbate | 24634-61-5 | | 1.00% |
| | Xanthan Gum | 11138-66-2 | | 2.500% |
| | Water | 7732-18-5 | | 96.500% |
| Blend 99 | Sodium Benzoate | | | 2% |
| | Water | 7732-18-5 | | 98% |
| Blend 100 | Span 80 | | | 1.20% |
| | Tween 80 | | | 1.65% |
| | Blend 6 | | | 2.84% |
| | Blend 99 | | | 11.36% |
| | Isopar M | 64742-47-8 | | 14.20% |
| | Water | 7732-18-5 | | 68.75% |
| Blend 101 | Span 80 | | | 1.20% |
| | Tween 80 | | | 1.65% |
| | Isopar M | 64742-47-8 | | 14.20% |
| | Water | 7732-18-5 | | 79.88% |
| | Sodium Benzoate | | | 0.23% |
| | Wintergreen Oil | 68917-75-9 | | 0.89% |
| | Thyme Oil White | 8007-46-3 | | 0.35% |
| | D-Limonene | 5989-27-5 | | 1.60% |
| Blend 102 | Propellent A70 | | | 22% |
| | Blend 100 | | | 78% |
| Blend 103 | Propellent A70 | | | 22.0% |
| | Span 80 | | | 0.94% |
| | Tween 80 | | | 1.29% |
| | Isopar M | 64742-47-8 | | 11.08% |
| | Water | 7732-18-5 | | 62.31% |
| | Sodium Benzoate | | | 0.18% |
| | Wintergreen Oil | 68917-75-9 | | 0.69% |
| | Thyme Oil White | 8007-46-3 | | 0.27% |
| | D-Limonene | 5989-27-5 | | 1.25% |
| Blend 104 | Potassium Sorbate | 590-00-1 or 24634-61-5 | | 1% |
| | Xanthan Gum | 11138-66-2 | | 2.50% |
| | Water | 7732-18-5 | | 96.50% |
| Blend 105 | Sodium Lauryl Sulfate | 151-21-3 | | 10% |
| | Water | 7732-18-5 | | 90.00% |
| Blend 106 | Water | 7732-18-5 | | 83.5% |
| | Potassium Sorbate | 590-00-1 or 24634-61-5 | | 1.0% |
| | Xanthan Gum | 11138-66-2 | | 0.28% |
| | Polyglycerol-4-oleate | 9007-48-1 | | 0.15% |
| | Lecithin | 8002-43-5 | | 0.034% |
| | Blend 41 | | | 15.1% |
| Blend 107 | Water | 7732-18-5 | | 33.40% |
| | 15% B-5028 RTU in BLF | | | 66.60% |
| Blend 108 | Stock 10% SLS Solution | | | 3.18% |
| | D-Limonene | 5989-27-5 | | 4.03% |
| | Thyme Oil White | 8007-46-3 | | 4.43% |
| | LFO3 | | | 6.27% |
| | Benzyl Alcohol | 100-51-6 | | 16.61% |
| | Isopar M | 64742-47-8 | | 20.95% |
| | Water | 7732-18-5 | | 44.53% |
| Blend 109 | Bifenthrin | 83657-04-3 | | 0.05% |
| | Stock 10% SLS Solution | | | 3.178% |
| | D-Limonene | 5989-27-5 | | 4.028% |
| | Thyme Oil White | 8007-46-3 | | 4.428% |
| | LFO3 | | | 6.267% |
| | Benzyl Alcohol | 100-51-6 | | 16.60% |
| | Isopar M | 64742-47-8 | | 20.94% |
| | Water | 7732-18-5 | | 44.51% |
| Blend 110 | Bifenthrin | 83657-04-3 | | 0.05% |
| | Span 80 | | | 0.50% |
| | Isopar M | 64742-47-8 | | 15% |
| | Water | 7732-18-5 | | 74.45% |
| | Thyme Oil White | 8007-46-3 | | 2.06% |
| | Wintergreen Oil | 68917-75-9 | | 4.51% |
| | Isopropyl myristate | 110-27-0 | | 3.43% |
| Blend 111 | Sodium Lauryl Sulfate | 151-21-3 | | 0.02% |
| | Water | 7732-18-5 | | 97.98% |
| | Thyme Oil White | 8007-46-3 | | 0.41% |
| | Wintergreen Oil | 68917-75-9 | | 0.90% |
| | Isopropyl myristate | 110-27-0 | | 0.69% |

TABLE 1-continued

| | BLENDS OF COMPOUNDS | | | |
|---|---|---|---|---|
| | Compounds | CAS Registry Number | Vol/Vol | Wt/Wt |
| Blend 112 | AgSorb | | | 95.00% |
| | Thyme Oil White | 8007-46-3 | | 1.03% |
| | Wintergreen Oil | 68917-75-9 | | 2.26% |
| | Isopropyl myristate | 110-27-0 | | 1.71% |
| Blend 113 | DG Light | | | 95.0% |
| | Thyme Oil White | 8007-46-3 | | 1.03% |
| | Wintergreen Oil | 68917-75-9 | | 2.26% |
| | Isopropyl myristate | 110-27-0 | | 1.71% |
| Blend 114 | Sodium Lauryl Sulfate | 151-21-3 | | 0.02% |
| | Thyme Oil White | 8007-46-3 | | 0.41% |
| | Isopropyl myristate | 110-27-0 | | 0.69% |
| | Wintergreen Oil | 68917-75-9 | | 0.90% |
| | Water | 7732-18-5 | | 97.98% |
| Blend 115 | Vanillin | 121-33-5 | | 0.02% |
| | Geraniol 60 | 106-24-1 | | 0.12% |
| | Linalool Coeur | 78-70-6 | | 0.17% |
| | Tetrahydrolinalool | 78-69-3 | | 0.23% |
| | Isopropyl myristate | 110-27-0 | | 0.24% |
| | Piperonal (aldehyde) | 120-57-0 | | 0.24% |
| | Triethyl Citrate | 77-93-0 | | 0.24% |
| | Thyme Oil White | 8007-46-3 | | 0.98% |
| | Blend 62 | | | 3.00% |
| | Stock 10% SLS Solution | | | 3% |
| | D-Limonene | 5989-27-5 | | 24.76% |
| | Water | 7732-18-5 | | 67% |
| Blend 116 | Xanthan Gum | 11138-66-2 | | 0.28% |
| | Potassium Sorbate | 590-00-1 or 24634-61-5 | | 1% |
| | Blend 65 | | | 16.90% |
| | Thyme Oil White | 8007-46-3 | | 20.6% |
| | Isopropyl myristate | 110-27-0 | | 34.3% |
| | Wintergreen Oil | 68917-75-9 | | 45.1% |
| | Water | 7732-18-5 | | 81.82% |
| Blend 117 | Blend 41 | | | 5% |
| | Miracle Gro (Sterile) | | | 95% |
| Blend 118 | Bifenthrin | 83657-04-3 | | 0.05% |
| | Span 80 | | | 0.50% |
| | Thyme Oil White | 8007-46-3 | | 0.51% |
| | Isopropyl myristate | 110-27-0 | | 0.86% |
| | Wintergreen Oil | 68917-75-9 | | 1.13% |
| | Isopar M | 64742-47-8 | | 15% |
| | Water | 7732-18-5 | | 81.95% |
| Blend 119 | Thyme Oil White | 8007-46-3 | | 20.6% |
| | Methyl Salicylate | 119-36-8 | | 45.1% |
| | Isopropyl myristate | 110-27-0 | | 34.3% |
| Blend 120 | Isopropyl myristate | 110-27-0 | | 34.3% |
| | Wintergreen Oil | 68917-75-9 | | 45.1% |
| | Thyme Oil White with 1% Thyme Oil Red | 8007-46-3 | | 20.6% |
| Blend 121 | Thyme Oil Red | 8007-46-3 | | 20.6% |
| | Wintergreen Oil | 68917-75-9 | | 45.1% |
| | Isopropyl myristate | 110-27-0 | | 34.3% |
| Blend 122 | Isopropyl myristate | 110-27-0 | | 34.3% |
| | Wintergreen Oil (Technical Grade) | 68917-75-9 | | 45.1% |
| | Thyme Oil White containing 1% Thyme Oil Red | 8007-46-3 | | 20.6% |
| Blend 123 | Thyme Oil White | 8007-46-3 | | 20.6% |
| | Wintergreen Oil | 68917-75-9 | | 45.1% |
| | Isopropyl myristate | 110-27-0 | | 34.2% |
| | Vanillin | 121-33-5 | | 0.1% |
| Blend 124 | Thyme Oil Red | 8007-46-3 | | 20.6% |
| | Wintergreen Oil | 68917-75-9 | | 45.1% |
| | Isopropyl myristate | 110-27-0 | | 34.2% |
| | Vanillin | 121-33-5 | | 0.1% |
| Blend 125 | Thyme Oil White | 8007-46-3 | | 41.86% |
| | Isopropyl myristate | 110-27-0 | | 38.34% |
| | Geraniol Fine, FCC | 106-24-1 | | 19.80% |
| Blend 126 | Thyme Oil White | 8007-46-3 | | 21.30% |
| | Isopropyl myristate | 110-27-0 | | 58.54% |
| | Geraniol Fine, FCC | 106-24-1 | | 20.16% |
| Blend 127 | Thyme Oil White | 8007-46-3 | | 31.57% |
| | Isopropyl myristate | 110-27-0 | | 38.56% |
| | Geraniol Fine, FCC | 106-24-1 | | 29.87% |

TABLE 1-continued

| | BLENDS OF COMPOUNDS | | | |
|---|---|---|---|---|
| | Compounds | CAS Registry Number | Vol/Vol | Wt/Wt |
| Blend 128 | Thyme Oil White | 8007-46-3 | | 36.85% |
| | Isopropyl myristate | 110-27-0 | | 48.21% |
| | Geraniol Fine, FCC | 106-24-1 | | 14.94% |
| Blend 129 | Thyme Oil White containing 1% Thyme Oil Red | 8007-46-3 | | 36.85% |
| | Isopropyl myristate | 110-27-0 | | 48.21% |
| | Geraniol Fine, FCC | 106-24-1 | | 14.94% |
| Blend 130 | Potassium Sorbate | 24634-61-5 | | 0.11% |
| | Polyglycerol-4-oleate | 9007-48-1 | | 0.15% |
| | Xanthan Gum | 11138-66-2 | | 0.30% |
| | Lecithin | 8002-43-5 | | 0.03% |
| | Water | 7732-18-5 | | 84.4% |
| | Blend 41 | | | 15.01% |
| Blend 131 | Thyme Oil White | 8007-46-3 | | 3.09% |
| | Wintergreen Oil | 68917-75-9 | | 6.77% |
| | Isopropyl myristate | 110-27-0 | | 5.15% |
| | Potassium Sorbate | 24634-61-5 | | 0.11% |
| | Polyglycerol-4-oleate | 9007-48-1 | | 0.15% |
| | Xanthan Gum | 11138-66-2 | | 0.28% |
| | Lecithin | 8002-43-5 | | 0.03% |
| | Water | 7732-18-5 | | 84.41% |
| Blend 132 | Potassium Sorbate | 24634-61-5 | | 0.11% |
| | Polyglycerol-4-oleate | 9007-48-1 | | 0.15% |
| | Xanthan Gum | 11138-66-2 | | 0.28% |
| | Lecithin | 8002-43-5 | | 0.034% |
| | Water | 7732-18-5 | | 84.4% |
| | Blend 120 | | | 15.01% |
| Blend 133 | Potassium Sorbate | 24634-61-5 | | 0.12% |
| | Polyglycerol-4-oleate | 9007-48-1 | | 0.16% |
| | Xanthan Gum | 11138-66-2 | | 0.29% |
| | Lecithin | 8002-43-5 | | 0.036% |
| | Water | 7732-18-5 | | 89.4% |
| | Blend 120 | | | 10% |
| Blend 134 | (Blend # unassigned) | | | |
| Blend 135 | Potassium Sorbate | 24634-61-5 | | 0.11% |
| | Polyglycerol-4-oleate | 9007-48-1 | | 0.15% |
| | Xanthan Gum | 11138-66-2 | | 0.30% |
| | Lecithin | 8002-43-5 | | 0.03% |
| | Water | 7732-18-5 | | 84.4% |
| | Blend 124 | | | 15.01% |
| Blend 136 | Potassium Sorbate | 24634-61-5 | | 0.12% |
| | Polyglycerol-4-oleate | 9007-48-1 | | 0.16% |
| | Xanthan Gum | 11138-66-2 | | 0.30% |
| | Lecithin | 8002-43-5 | | 0.036% |
| | Water | 7732-18-5 | | 89.4% |
| | Blend 124 | | | 10% |
| Blend 137 | Soy Bean Oil | 8016-70-4 | | 20% |
| | Ethyl Alcohol (denatured) | | | 50% |
| | Blend 10 | | | 30% |
| Blend 138 | Citronella Oil | 106-22-9 | | 0.20% |
| | Carbopol 940 | [9003-01-4] | | 0.20% |
| | Butylated hydroxy toluene | 128-37-0 | | 0.10% |
| | Water | 7732-18-5 | | 59.83% |
| | Emulsifying Wax | 67762-27-0, 9005-67-8 | | 14% |
| | Light Liquid Paraffin | 8012-95-1 | | 4.00% |
| | White Soft Paraffin | [8009-03-8] | | 9% |
| | Sodium Metabisulphate | 7681-57-4 | | 0.25% |
| | Propylene Glycol | [57-55-6] | | 2% |
| | Cresmer RH40 hydrogenated | [61791-12-6] | | 5% |
| | Triethanolamine | [102-71-6] | | 0.15% |
| | Blend 7 | | | 5% |
| | Disodium EDTA | [139-33-3] | | 0.05% |
| | Vitamin E Acetate | [58-95-7] | | 0.02% |
| Blend 139 | Blend 49 | | | 50% |
| | Lemon Grass Oil | 8007-02-1 | | 25% |
| | Castor Oil Surfactant | 61791-12-6 | | 25% |
| Blend 140 | Blend 51 | | | 50% |
| | Lemon Grass Oil | 8007-02-1 | | 25% |
| | Castor Oil Surfactant | 61791-12-6 | | 25% |

TABLE 1-continued

BLENDS OF COMPOUNDS

| | Compounds | CAS Registry Number | Vol/Vol | Wt/Wt |
|---|---|---|---|---|
| Blend 141 | Blend 52 | | | 50% |
| | Lemon Grass Oil | 8007-02-1 | | 25% |
| | Castor Oil Surfactant | 61791-12-6 | | 25% |
| Blend 142 | Blend 7 | | | 10% |
| | Water | 7732-18-5 | | 89% |
| | Sodium Lauryl Sulfate | 151-21-3 | | 1% |

The present invention comprises compositions for controlling insects and methods for using these compositions. The present invention comprises compositions for controlling insects, which comprise one or more plant essential oils and methods for using these compositions. The plant essential oils, when combined, can have a synergistic effect. The compositions of the present invention can include any of the following oils listed below, or mixtures thereof:

| | | |
|---|---|---|
| trans-anethole | lime oil | piperonyl |
| Black seed oil (BSO) | d-limonene | piperonyl acetate |
| camphene | linalyl anthranilate | piperonyl alcohol |
| carvacrol | linalool | piperonyl amine quinone |
| d-carvone | lindenol | sabinene |
| l-carvone | methyl citrate | α-terpinene |
| 1,8-cineole | methyl di-hydrojasmonate | terpinene 900 |
| p-cymene | myrcene | α-terpineol |
| diethyl phthalate | perillyl alcohol | gamma-terpineol |
| eugenol | phenyl acetaldehyde | 2-tert-butyl-p-quinone |
| geraniol | phenylethyl alcohol | α-thujone |
| isopropyl citrate | phenylethyl propionate | thyme oil |
| lemon grass oil | α-pinene | thymol |
| lilac flower oil (LFO) | β-pinene | |
| | piperonal | |

The compositions of the present invention may also include any of the following oils listed below, or mixtures thereof:

| | | |
|---|---|---|
| Allyl sulfide | β-elemene | Menthyl salicylate |
| Allyl trisulfide | gamma-elemene | Myrtenal |
| Allyl-disulfide | Elmol | Neraldimethyl acetate |
| Anethole | Estragole | Nerolidol |
| Artemisia alcohol acetate | 2-ethyl-2-hexen-1-ol | Nonanone |
| Benzyl acetate | Eugenol acetate | 1-octanol |
| Benzyl alcohol | α-farnesene | E ocimenone |
| Bergamotene | (Z,E)-α-farnesene | Z ocimenone |
| β-bisabolene | E-β-farnesene | 3-octanone |
| Bisabolene oxide | Fenchone | Ocimene |
| α-bisabolol | Forskolin | Octyl acetate |
| Bisabolol oxide | Furanodiene Furanoeudesma-1,3-diene | PD 98059 |
| Bisobolol oxide β | | Peppermint oil |
| Bornyl acetate | Furanoeudesma-1,4-diene | Permethrin |
| β-bourbonene | Furano germacra 1,10(15)-diene-6-one | α-phellandrene |
| α-cadinol | | β-phellandrene |
| Camphene | Furanosesquiterpene | piperonal |
| α-campholene | Geraniol | Prenal |
| α-campholene aldehyde | Geraniol acetate | Propargite |
| camphor | Germacrene D | Pulegone |
| carbaryl | Germacrene B | Pyrethrum |
| Caryophyllene oxide | α-gurjunene | Sabinene |
| Chamazulene | α-humulene | Sabinyl acetate |
| Chrysanthemate ester | α-ionone | α-santalene |
| Chrysanthemic acid | β-ionone | Santalol |
| Chrysanthemyl alcohol | Isoborneol | Sativen |
| Cinnamaldehyde | Isofuranogermacrene | δ-selinene |
| Cis-verbenol | Iso-menthone | β-sesquphelandrene |
| Citral A | Iso-pulegone | Spathulenol |
| Citral B | Jasmone | Tagetone |
| Citronellal | cis-jasmone | Tamoxifen |
| Citronellol | Lavandustin A | Tebufenozide |
| Citronellyl acetate | Lilac flower oil | α-terpinene |
| Citronellyl formate | Limonene | 4-terpineol |
| α-copaene | Linalool | α-terpinolene |
| cornmint oil | Linalyl acetate | α-terpinyl acetate |
| β-costol | Lindestrene | tetrahydrofurfuryl alcohol. |
| Cryptone | Methyl-allyl-trisulfide | α-thujene |
| Curzerenone | Menthol | Thymyl methyl ether |
| d-Carvone | 2-methoxy furanodiene | Trans-caryophyllene |
| l-Carvone | menthone | Trans-pinocarveol |
| Davanone | Methyl acetate | Trans-verbenol |

| | | |
|---|---|---|
| Diallyl tetrasulfide | Menthyl salicylate | Verbenone |
| dihydropyrocurzerenone | Methyl cinnamate | Yomogi alcohol |
| | | Zingiberene |
| | | Dihydrotagentone |

In those compositions including more than one oil, each oil can make up between about 1% to about 99%, by weight, of the composition mixture. For example, one composition of the present invention comprises about 1% thymol and about 99% geraniol. Optionally, the compositions can additionally comprise a fixed oil, which is a non-volatile non-scented plant oil. For example, the composition could include one or more of the following fixed oils listed below:

| | | |
|---|---|---|
| castor oil | mineral oil | safflower oil |
| corn oil | olive oil | sesame oil |
| cumin oil | peanut oil | soy bean oil |

For example, one composition of the present invention includes about 1% thymol, about 50% geraniol and about 49% mineral oil. Additionally, it is contemplated that these compositions may be made up of generally regarded as safe (GRAS) compounds, for example: thyme oil, geraniol, lemon grass oil, lilac flower oil, black seed oil, lime oil, eugenol, castor oil, mineral oil, and safflower oil.

In addition, embodiments are specifically contemplated in which any of the ingredients of the above lists are combined, with the proviso that the ingredients do not comprise alpha-terpineol or pyrethrum. Furthermore, embodiments are specifically contemplated in which any of the ingredients listed in Table 1 are combined, with the proviso that the ingredients do not comprise alpha-terpineol or pyrethrum. Moreover, embodiments are specifically contemplated in which any of the ingredients listed in any one of Blends 1-142 of Table 1 are combined, with the proviso that the ingredients do not comprise alpha-terpineol or pyrethrum.

In addition, embodiments are specifically contemplated in which any of the ingredients of the above lists are combined, with the proviso that the ingredients do not comprise benzyl alcohol or eugenol. Furthermore, embodiments are specifically contemplated in which any of the ingredients listed in Table 1 are combined, with the proviso that the ingredients do not comprise benzyl alcohol or eugenol. Moreover, embodiments are specifically contemplated in which any of the ingredients listed in any one of Blends 1-142 of Table 1 are combined, with the proviso that the ingredients do not comprise benzyl alcohol or eugenol.

In addition, embodiments are specifically contemplated in which any of the ingredients of the above lists are combined, with the proviso that the ingredients do not comprise benzyl alcohol or cis-jasmone. Furthermore, embodiments are specifically contemplated in which any of the ingredients listed in Table 1 are combined, with the proviso that the ingredients do not comprise benzyl alcohol or cis-jasmone. Moreover, embodiments are specifically contemplated in which any of the ingredients listed in any one of Blends 1-142 of Table 1 are combined, with the proviso that the ingredients do not comprise benzyl alcohol or cis-jasmone.

In addition, embodiments are specifically contemplated in which any of the ingredients of the above lists are combined, with the proviso that the ingredients do not comprise benzyl alcohol or jasmone. Furthermore, embodiments are specifically contemplated in which any of the ingredients listed in Table 1 are combined, with the proviso that the ingredients do not comprise benzyl alcohol or jasmone. Moreover, embodiments are specifically contemplated in which any of the ingredients listed in any one of Blends 1-142 of Table 1 are combined, with the proviso that the ingredients do not comprise benzyl alcohol or jasmone.

In addition, embodiments are specifically contemplated in which any of the ingredients of the above lists are combined, with the proviso that the ingredients do not comprise benzyl alcohol or tetrahydrofurfuryl alcohol. Furthermore, embodiments are specifically contemplated in which any of the ingredients listed in Table 1 are combined, with the proviso that the ingredients do not comprise benzyl alcohol or tetrahydrofurfuryl alcohol. Moreover, embodiments are specifically contemplated in which any of the ingredients listed in any one of Blends 1-142 of Table 1 are combined, with the proviso that the ingredients do not comprise benzyl alcohol or tetrahydrofurfuryl alcohol.

In addition, embodiments are specifically contemplated in which any of the ingredients of the above lists are combined, with the proviso that the ingredients do not comprise eugenol or pyrethrum. Furthermore, embodiments are specifically contemplated in which any of the ingredients listed in Table 1 are combined, with the proviso that the ingredients do not comprise eugenol or pyrethrum. Moreover, embodiments are specifically contemplated in which any of the ingredients listed in any one of Blends 1-142 of Table 1 are combined, with the proviso that the ingredients do not comprise eugenol or pyrethrum.

In addition, embodiments are specifically contemplated in which any of the ingredients of the above lists are combined, with the proviso that the ingredients do not comprise thyme oil or pyrethrum. Furthermore, embodiments are specifically contemplated in which any of the ingredients listed in Table 1 are combined, with the proviso that the ingredients do not comprise thyme oil or pyrethrum. Moreover, embodiments are specifically contemplated in which any of the ingredients listed in any one of Blends 1-142 of Table 1 are combined, with the proviso that the ingredients do not comprise thyme oil or pyrethrum.

In addition, embodiments are specifically contemplated in which any of the ingredients of the above lists are combined, with the proviso that the ingredients do not comprise thymol or carbaryl. Furthermore, embodiments are specifically contemplated in which any of the ingredients listed in Table 1 are combined, with the proviso that the ingredients do not comprise thymol or carbaryl. Moreover, embodiments are specifically contemplated in which any of the ingredients listed in any one of Blends 1-142 of Table 1 are combined, with the proviso that the ingredients do not comprise thymol or carbaryl.

In addition, embodiments are specifically contemplated in which any of the ingredients of the above lists are combined, with the proviso that the ingredients do not comprise thymol or chrysanthemate ester. Furthermore, embodiments are specifically contemplated in which any of the ingredients listed in Table 1 are combined, with the proviso that the ingredients do not comprise thymol or chrysanthemate ester. Moreover, embodiments are specifically contemplated in which any of the ingredients listed in any one of Blends 1-142 of Table 1 are combined, with the proviso that the ingredients do not comprise thymol or chrysanthemate ester.

In addition, embodiments are specifically contemplated in which any of the ingredients of the above lists are combined, with the proviso that the ingredients do not comprise thymol or chrysanthemyl alcohol or chrysanthemic acid. Furthermore, embodiments are specifically contemplated in which any of the ingredients listed in Table 1 are combined, with the proviso that the ingredients do not comprise thymol or chrysanthemyl alcohol or chrysanthemic acid. Moreover, embodiments are specifically contemplated in which any of the ingredients listed in any one of Blends 1-142 of Table 1 are combined, with the proviso that the ingredients do not comprise thymol or chrysanthemyl alcohol or chrysanthemic acid.

In addition, embodiments are specifically contemplated in which any of the ingredients of the above lists are combined, with the proviso that the ingredients do not comprise thymol or eugenol or trans-anethole, or alpha-terpineol, or citronellal, or propargite. Furthermore, embodiments are specifically contemplated in which any of the ingredients listed in Table 1 are combined, with the proviso that the ingredients do not comprise thymol or eugenol or trans-anethole, or alpha-terpineol, or citronellal, or propargite. Moreover, embodiments are specifically contemplated in which any of the ingredients listed in any one of Blends 1-142 of Table 1 are combined, with the proviso that the ingredients do not comprise thymol or eugenol or trans-anethole, or alpha-terpineol, or citronellal, or propargite.

In addition, embodiments are specifically contemplated in which any of the ingredients of the above lists are combined, with the proviso that the ingredients do not comprise thymol or eugenol or trans-anethole, or alpha-terpineol, or citronellal, or pyrethrum. Furthermore, embodiments are specifically contemplated in which any of the ingredients listed in Table 1 are combined, with the proviso that the ingredients do not comprise thymol or eugenol or trans-anethole, or alpha-terpineol, or citronellal, or pyrethrum. Moreover, embodiments are specifically contemplated in which any of the ingredients listed in any one of Blends 1-142 of Table 1 are combined, with the proviso that the ingredients do not comprise thymol or eugenol or trans-anethole, or alpha-terpineol, or citronellal, or pyrethrum.

In addition, embodiments are specifically contemplated in which any of the ingredients of the above lists are combined, with the proviso that the ingredients do not comprise thymol or eugenol or trans-anethole, or alpha-terpineol, or citronellal, or tebufenozide. Furthermore, embodiments are specifically contemplated in which any of the ingredients listed in Table 1 are combined, with the proviso that the ingredients do not comprise thymol or eugenol or trans-anethole, or alpha-terpineol, or citronellal, or tebufenozide. Moreover, embodiments are specifically contemplated in which any of the ingredients listed in any one of Blends 1-142 of Table 1 are combined, with the proviso that the ingredients do not comprise thymol or eugenol or trans-anethole, or alpha-terpineol, or citronellal, or tebufenozide.

In addition, embodiments are specifically contemplated in which any of the ingredients of the above lists are combined, with the proviso that the ingredients do not comprise thymol or cis-jasmone. Furthermore, embodiments are specifically contemplated in which any of the ingredients listed in Table 1 are combined, with the proviso that the ingredients do not comprise thymol or cis-jasmone. Moreover, embodiments are specifically contemplated in which any of the ingredients listed in any one of Blends 1-142 of Table 1 are combined, with the proviso that the ingredients do not comprise thymol or cis-jasmone.

In addition, embodiments are specifically contemplated in which any of the ingredients of the above lists are combined, with the proviso that the ingredients do not comprise thymol or deltamethrin. Furthermore, embodiments are specifically contemplated in which any of the ingredients listed in Table 1 are combined, with the proviso that the ingredients do not comprise thymol or deltamethrin. Moreover, embodiments are specifically contemplated in which any of the ingredients listed in any one of Blends 1-142 of Table 1 are combined, with the proviso that the ingredients do not comprise thymol or deltamethrin.

In addition, embodiments are specifically contemplated in which any of the ingredients of the above lists are combined, with the proviso that the ingredients do not comprise thymol or lavandustin A. Furthermore, embodiments are specifically contemplated in which any of the ingredients listed in Table 1 are combined, with the proviso that the ingredients do not comprise thymol or lavandustin A. Moreover, embodiments are specifically contemplated in which any of the ingredients listed in any one of Blends 1-142 of Table 1 are combined, with the proviso that the ingredients do not comprise thymol or lavandustin A.

In addition, embodiments are specifically contemplated in which any of the ingredients of the above lists are combined, with the proviso that the ingredients do not comprise thymol or PD 98059. Furthermore, embodiments are specifically contemplated in which any of the ingredients listed in Table 1 are combined, with the proviso that the ingredients do not comprise thymol or PD 98059. Moreover, embodiments are specifically contemplated in which any of the ingredients listed in any one of Blends 1-142 of Table 1 are combined, with the proviso that the ingredients do not comprise thymol or PD 98059.

In addition, embodiments are specifically contemplated in which any of the ingredients of the above lists are combined, with the proviso that the ingredients do not comprise thymol or permethrin. Furthermore, embodiments are specifically contemplated in which any of the ingredients listed in Table 1 are combined, with the proviso that the ingredients do not comprise thymol or permethrin. Moreover, embodiments are specifically contemplated in which any of the ingredients listed in any one of Blends 1-142 of Table 1 are combined, with the proviso that the ingredients do not comprise thymol or permethrin.

In addition, embodiments are specifically contemplated in which any of the ingredients of the above lists are combined, with the proviso that the ingredients do not comprise thymol or pyrethrum. Furthermore, embodiments are specifically contemplated in which any of the ingredients listed in Table 1 are combined, with the proviso that the ingredients do not comprise thymol or pyrethrum. Moreover, embodiments are specifically contemplated in which any of the ingredients listed in any one of Blends 1-142 of Table 1 are combined, with the proviso that the ingredients do not comprise thymol or pyrethrum.

In addition, embodiments are specifically contemplated in which any of the ingredients of the above lists are combined, with the proviso that the ingredients do not comprise benzyl alcohol or pyrethrum. Furthermore, embodiments are specifically contemplated in which any of the ingredients listed in Table 1 are combined, with the proviso that the ingredients do not comprise benzyl alcohol or pyrethrum. Moreover, embodiments are specifically contemplated in which any of the ingredients listed in any one of Blends 1-142 of Table 1 are combined, with the proviso that the ingredients do not comprise benzyl alcohol or pyrethrum.

In addition, embodiments are specifically contemplated in which any of the ingredients of the above lists are combined, with the proviso that the ingredients do not comprise benzyl alcohol or chrysanthemate ester. Furthermore, embodiments are specifically contemplated in which any of the ingredients listed in Table 1 are combined, with the proviso that the ingredients do not comprise benzyl alcohol or chrysanthemate ester. Moreover, embodiments are specifically contemplated in which any of the ingredients listed in any one of Blends 1-142 of Table 1 are combined, with the proviso that the ingredients do not comprise benzyl alcohol or chrysanthemate ester.

In addition, embodiments are specifically contemplated in which any of the ingredients of the above lists are combined, with the proviso that the ingredients do not comprise benzyl alcohol, or chrysanthemyl alcohol, or chrysanthemic acid. Furthermore, embodiments are specifically contemplated in which any of the ingredients listed in Table 1 are combined, with the proviso that the ingredients do not comprise benzyl alcohol, or chrysanthemyl alcohol, or chrysanthemic acid. Moreover, embodiments are specifically contemplated in which any of the ingredients listed in any one of Blends 1-142 of Table 1 are combined, with the proviso that the ingredients do not comprise benzyl alcohol, or chrysanthemyl alcohol, or chrysanthemic acid.

In addition, embodiments are specifically contemplated in which any of the ingredients of the above lists are combined, with the proviso that the ingredients do not comprise benzyl alcohol or trans-anethole. Furthermore, embodiments are specifically contemplated in which any of the ingredients listed in Table 1 are combined, with the proviso that the ingredients do not comprise benzyl alcohol or trans-anethole. Moreover, embodiments are specifically contemplated in which any of the ingredients listed in any one of Blends 1-142 of Table 1 are combined, with the proviso that the ingredients do not comprise benzyl alcohol or trans-anethole.

In addition, embodiments are specifically contemplated in which any of the ingredients of the above lists are combined, with the proviso that the ingredients do not comprise benzyl alcohol, or tetrahydrofurfuryl alcohol, or PD 98059, or trans-anethole, or chrysanthemate ester. Furthermore, embodiments are specifically contemplated in which any of the ingredients listed in Table 1 are combined, with the proviso that the ingredients do not comprise benzyl alcohol, or tetrahydrofurfuryl alcohol, or PD 98059, or trans-anethole, or chrysanthemate ester. Moreover, embodiments are specifically contemplated in which any of the ingredients listed in any one of Blends 1-142 of Table 1 are combined, with the proviso that the ingredients do not comprise benzyl alcohol, or tetrahydrofurfuryl alcohol, or PD 98059, or trans-anethole, or chrysanthemate ester.

In addition, embodiments are specifically contemplated in which any of the ingredients of the above lists are combined, with the proviso that the ingredients do not comprise benzyl alcohol, or tetrahydrofurfuryl alcohol, or PD 98059, or trans-anethole, or pyrethrum. Furthermore, embodiments are specifically contemplated in which any of the ingredients listed in Table 1 are combined, with the proviso that the ingredients do not comprise benzyl alcohol, or tetrahydrofurfuryl alcohol, or PD 98059, or trans-anethole, or pyrethrum. Moreover, embodiments are specifically contemplated in which any of the ingredients listed in any one of Blends 1-142 of Table 1 are combined, with the proviso that the ingredients do not comprise benzyl alcohol, or tetrahydrofurfuryl alcohol, or PD 98059, or trans-anethole, or pyrethrum.

In addition, embodiments are specifically contemplated in which any of the ingredients of the above lists are combined, with the proviso that the ingredients do not comprise eugenol, or phenylethyl propionate, or menthyl salicylate. Furthermore, embodiments are specifically contemplated in which any of the ingredients listed in Table 1 are combined, with the proviso that the ingredients do not comprise eugenol, or phenylethyl propionate, or menthyl salicylate. Moreover, embodiments are specifically contemplated in which any of the ingredients listed in any one of Blends 1-142 of Table 1 are combined, with the proviso that the ingredients do not comprise eugenol, or phenylethyl propionate, or menthyl salicylate.

In addition, embodiments are specifically contemplated in which any of the ingredients of the above lists are combined, with the proviso that the ingredients do not comprise phenylethyl alcohol, or alpha-terpineol, or benzyl alcohol. Furthermore, embodiments are specifically contemplated in which any of the ingredients listed in Table 1 are combined, with the proviso that the ingredients do not comprise phenylethyl alcohol, or alpha-terpineol, or benzyl alcohol. Moreover, embodiments are specifically contemplated in which any of the ingredients listed in any one of Blends 1-142 of Table 1 are combined, with the proviso that the ingredients do not comprise phenylethyl alcohol, or alpha-terpineol, or benzyl alcohol.

In addition, embodiments are specifically contemplated in which any of the ingredients of the above lists are combined, with the proviso that the ingredients do not comprise phenylethyl alcohol, or alpha-terpineol, or benzyl alcohol, or phenylethyl propionate. Furthermore, embodiments are specifically contemplated in which any of the ingredients listed in Table 1 are combined, with the proviso that the ingredients do not comprise phenylethyl alcohol, or alpha-terpineol, or benzyl alcohol, or phenylethyl propionate. Moreover, embodiments are specifically contemplated in which any of the ingredients listed in any one of Blends 1-142 of Table 1 are combined, with the proviso that the ingredients do not comprise phenylethyl alcohol, or alpha-terpineol, or benzyl alcohol, or phenylethyl propionate.

In addition, embodiments are specifically contemplated in which any of the ingredients of the above lists are combined, with the proviso that the ingredients do not comprise phenylethyl alcohol, or alpha-terpineol, or benzyl alcohol, or phenylethyl propionate, or eugenol. Furthermore, embodiments are specifically contemplated in which any of the ingredients listed in Table 1 are combined, with the proviso that the ingredients do not comprise phenylethyl alcohol, or alpha-terpineol, or benzyl alcohol, or phenylethyl propionate, or eugenol. Moreover, embodiments are specifically contemplated in which any of the ingredients listed in any one of Blends 1-142 of Table 1 are combined, with the proviso that the ingredients do not comprise phenylethyl alcohol, or alpha-terpineol, or benzyl alcohol, or phenylethyl propionate, or eugenol.

In addition, embodiments are specifically contemplated in which any of the ingredients of the above lists are combined, with the proviso that the ingredients do not comprise tamoxifen or forskolin. Furthermore, embodiments are specifically contemplated in which any of the ingredients listed in Table 1 are combined, with the proviso that the ingredients do not comprise tamoxifen or forskolin. Moreover, embodiments are specifically contemplated in which any of the ingredients listed in any one of Blends 1-142 of Table 1 are combined, with the proviso that the ingredients do not comprise tamoxifen or forskolin.

In addition, embodiments are specifically contemplated in which any of the ingredients of the above lists are combined, with the proviso that the ingredients do not comprise thymol or benzyl alcohol. Furthermore, embodiments are specifically contemplated in which any of the ingredients listed in Table 1 are combined, with the proviso that the ingredients do not comprise thymol or benzyl alcohol. Moreover, embodiments are specifically contemplated in which any of the ingredients listed in any one of Blends 1-142 of Table 1 are combined, with the proviso that the ingredients do not comprise thymol or benzyl alcohol.

In addition, embodiments are specifically contemplated in which any of the ingredients of the above lists are combined, with the proviso that the ingredients do not comprise thymol, or eugenol, or trans-anethole, or alpha-terpineol, or citronellal, or chrysanthemate ester. Furthermore, embodiments are specifically contemplated in which any of the ingredients listed in Table 1 are combined, with the proviso that the ingredients do not comprise thymol, or eugenol, or trans-anethole, or alpha-terpineol, or citronellal, or chrysanthemate ester. Moreover, embodiments are specifically contemplated in which any of the ingredients listed in any one of Blends 1-142 of Table 1 are combined, with the proviso that the ingredients do not comprise thymol, or eugenol, or trans-anethole, or alpha-terpineol, or, citronellal, or chrysanthemate ester.

In addition, embodiments are specifically contemplated in which any of the ingredients of the above lists are combined, with the proviso that the ingredients do not comprise thymol, or eugenol, or trans-anethole, or alpha-terpineol, or citronellal, or chrysanthemic acid. Furthermore, embodiments are specifically contemplated in which any of the ingredients listed in Table 1 are combined, with the proviso that the ingredients do not comprise thymol, or eugenol, or trans-anethole, or alpha-terpineol, or citronellal, or chrysanthemic acid. Moreover, embodiments are specifically contemplated in which any of the ingredients listed in any one of Blends 1-142 of Table 1 are combined, with the proviso that the ingredients do not comprise thymol, or eugenol, or trans-anethole, or alpha-terpineol, or, citronellal, or chrysanthemic acid.

In addition, embodiments are specifically contemplated in which any of the ingredients of the above lists are combined, with the proviso that the ingredients do not comprise thymol, or eugenol, or trans-anethole, or alpha-terpineol, or citronellal, or chrysanthemyl alcohol. Furthermore, embodiments are specifically contemplated in which any of the ingredients listed in Table 1 are combined, with the proviso that the ingredients do not comprise thymol, or eugenol, or trans-anethole, or alpha-terpineol, or citronellal, or chrysanthemyl alcohol. Moreover, embodiments are specifically contemplated in which any of the ingredients listed in any one of Blends 1-142 of Table 1 are combined, with the proviso that the ingredients do not comprise thymol, or eugenol, or trans-anethole, or alpha-terpineol, or, citronellal, or chrysanthemyl alcohol.

In addition, embodiments are specifically contemplated in which any of the ingredients of the above lists are combined, with the proviso that the ingredients do not comprise thymol, or eugenol, or trans-anethole, or alpha-terpineol, or citronellal, or cis-jasmone. Furthermore, embodiments are specifically contemplated in which any of the ingredients listed in Table 1 are combined, with the proviso that the ingredients do not comprise thymol, or eugenol, or trans-anethole, or alpha-terpineol, or citronellal, or cis-jasmone. Moreover, embodiments are specifically contemplated in which any of the ingredients listed in any one of Blends 1-142 of Table 1 are combined, with the proviso that the ingredients do not comprise thymol, or eugenol, or trans-anethole, or alpha-terpineol, or, citronellal, or cis-jasmone.

In certain embodiments wherein the composition includes Lilac Flower Oil (LFO), one or more of the following compounds can be substituted for the LFO: Tetrahydrolinalool, Ethyl Linalool, Heliotropine, Hedion, Hercolyn D, and Triethyl Citrate. In certain embodiments wherein the composition includes LFO, a blend of the following compounds can be substituted for the LFO: Isopropyl myristate, Tetrahydrolinalool FCC, Linalool, Geraniol Fine FCC, Piperonal (aldehyde), and Vanillin. In certain embodiments wherein the composition includes LFO, a blend of the following compounds can be substituted for the LFO: Isopropyl myristate, Tetrahydrolinalool, Linalool, Geraniol, Piperonal (aldehyde), Vanillin, Methyl Salicylate, and D-limonene.

In certain embodiments wherein the composition includes Black Seed Oil (BSO), one or more of the following compounds can be substituted for the BSO: alpha-thujene: alpha-pinene; beta-pinene; p-cymene; limonene; and tert-butyl-p-benzoquinone.

In certain exemplary embodiments wherein the composition includes Thyme Oil, one or more of the following compounds can be substituted for the Thyme Oil: thymol, α-thujone; α-pinene, camphene, β-pinene, p-cymene, α-terpinene, linalool, borneol, β-caryophyllene, and carvacrol. Compounds used to prepare the exemplary compositions of the present invention can be obtained, for example, from the following sources: Millennium Chemicals, Inc. (Jacksonville, Fla.), Ungerer Company (Lincoln Park, N.J.), SAFC (Milwaukee, Wis.), and IFF Inc. (Hazlet, N.J.).

In some embodiments of the compositions, it can be desirable to include compounds each having a purity of about 60%, 65%, 70%, 75%, 80%, 85%, 90%, or 95%. For example, in some embodiments of the compositions that include geraniol, it can be desirable to include a geraniol that is at least about 60%, 85% or 95% pure. In some embodiments, it can be desirable to include a specific type of geraniol. For example, in some embodiments, the compositions can include: geraniol 60, geraniol 85, or geraniol 95. When geraniol is obtained as geraniol 60, geraniol 85, or geraniol 95, then forty percent, fifteen percent, or five percent of the oil can be Nerol. Nerol is a monoterpene (C10H18O), that can be extracted from attar of roses, oil of orange blossoms and oil of lavender. Embodiments of the present invention can include art-recognised ingredients normally used in such formulations. These ingredients can include, for example, antifoaming agents, anti-microbial agents, anti-oxidants, anti-redeposition agents, bleaches, colorants, emulsifiers, enzymes, fats, fluorescent materials, fungicides, hydrotropes, moisturizers, optical brighteners, perfume carriers, perfume, preservatives, proteins, silicones, soil release agents, solubilisers, sugar derivatives, sun screens, surfactants, vitamins waxes, and the like.

In certain embodiments, embodiments of the present invention can also contain other adjuvants or modifiers such as one or more therapeutically or cosmetically active ingredients. Exemplary therapeutic or cosmetically active ingredients useful in the compositions of the invention can include, for example, fungicides, sunscreening agents, sunblocking agents, vitamins, tanning agents, plant extracts, anti-inflammatory agents, anti-oxidants, radical scavenging agents, retinoids, alpha-hydroxy acids, emollients, antiseptics, antibiotics, antibacterial agents, antihistamines, and the like, and can be present in an amount effective for achieving the therapeutic or cosmetic result desired.

In some embodiments, compositions of this invention can include one or more materials that can function as an antioxidant, such as reducing agents and free radical scavengers. Suitable materials that can function as an antioxidant can include, for example: acetyl cysteine, ascorbic acid, t-butyl hydroquinone, cysteine, diamylhydroquinone, erythorbic acid, ferulic acid, hydroquinone, p-hydroxyanisole, hydroxylamine sulfate, magnesium ascorbate, magnesium ascorbyl phosphate, octocrylene, phloroglucinol, potassium ascorbyl tocopheryl phosphate, potassium sulfite, rutin, sodium ascorbate, sodium sulfite, sodium thloglycolate, thiodiglycol, thiodiglycolamide, thioglycolic acid, thiosalicylic acid, tocopherol, tocopheryl acetate, tocopheryl linoleate, tris(nonylphenyl)phosphite, and the like.

Embodiments of the invention can also include one or more materials that can function as a chelating agent to complex with metallic ions. This action can help to inactivate the metallic ions for the purpose of preventing their adverse effects on the stability or appearance of a formulated composition. Chelating agents suitable for use in an embodiment of this invention can include, for example, aminotrimethylene phosphonic acid, beta-alanine diacetic acid, calcium disodium EDTA, citric acid, cyclodextrin, cyclohexanediamine tetraacetic acid, diammonium citrate, diammonium EDTA, dipotassium EDTA, disodium azacycloheptane diphosphonate, disodium EDTA, disodium pyrophosphate, EDTA (ethylene diamine tetra acetic acid), gluconic acid, HEDTA (hydroxyethyl ethylene diamine triacetic acid), methyl cyclodextrin, pentapotassium triphosphate, pentasodium aminotrimethylene phosphonate, pentasodium triphosphate, pentetic acid, phytic acid, potassium citrate, potassium gluconate, sodium citrate, sodium diethylenetriamine pentamethylene phosphonate, sodium dihydroxyethylglycinate, sodium gluconate, sodium metaphosphate, sodium metasilicate, sodium phytate, triethanolamine ("TEA")-EDTA, TEA-polyphosphate, tetrahydroxypropyl ethylenediamine, tetrapotassium pyrophosphate, tetrasodium EDTA, tetrasodium pyrophosphate, tripotassium EDTA, trisodium EDTA, trisodium HEDTA, trisodium phosphate, and the like.

Embodiments of the invention can also include one or more materials that can function as a humectant. A humectant is added to a composition to retard moisture loss during use, which effect is accomplished, in general, by the presence therein of hygroscopic materials.

The following table (table 2) provides exemplary compositions of embodiments of the invention:

TABLE 2

| Ingredients | Exemplified form | % Range 1 | | % Range 2 | | % Range 3 | | % Range 4 | | Exemplified % (w/w) |
|---|---|---|---|---|---|---|---|---|---|---|
| Example 1 - Ingredient Family 1 | | | | | | | | | | |
| Limonene | D-Limonene | 8.25% | 99.00% | 41.25% | 99.00% | 61.88% | 99.00% | 74.25% | 90.75% | 82.50% |
| Thyme Oil | Thyme Oil White | 0.33% | 9.84% | 1.64% | 4.92% | 2.46% | 4.10% | 2.95% | 3.61% | 3.28% |
| Linalool | Linalool Coeur | 0.06% | 5.00% | 0.29% | 0.86% | 0.43% | 0.71% | 0.51% | 0.63% | 0.57% |
| Tetrahydrolinalool | Tetrahydrolinalool | 0.08% | 5.00% | 0.39% | 1.17% | 0.59% | 0.98% | 0.70% | 0.86% | 0.78% |
| Vanillin | Vanillin | 0.01% | 5.00% | 0.03% | 0.08% | 0.04% | 0.06% | 0.05% | 0.06% | 0.05% |
| Isopropyl Myristate | Isopropyl Myristate | 0.08% | 5.00% | 0.40% | 1.20% | 0.60% | 1.00% | 0.72% | 0.88% | 0.80% |
| Piperonal | Piperonal (aldehyde) | 0.08% | 5.00% | 0.40% | 1.20% | 0.60% | 1.00% | 0.72% | 0.88% | 0.80% |
| Lime Oil | Lime Oil 410 Minus | 1.00% | 30.00% | 5.00% | 15.00% | 7.50% | 12.50% | 9.00% | 11.00% | 10.00% |
| Geraniol | Geraniol 60 | 0.04% | 5.00% | 0.21% | 0.62% | 0.31% | 0.51% | 0.37% | 0.45% | 0.41% |
| Triethyl Citrate | Triethyl Citrate | 0.08% | 5.00% | 0.40% | 1.20% | 0.60% | 1.00% | 0.72% | 0.88% | 0.80% |
| Example 2 - Ingredient Family 2 | | | | | | | | | | |
| Thyme Oil | Thyme Oil White | 2.05% | 61.50% | 10.25% | 30.75% | 15.38% | 25.63% | 18.45% | 22.55% | 20.50% |
| Wintergreen Oil | Wintergreen Oil | 4.50% | 99.00% | 22.50% | 67.50% | 33.75% | 56.25% | 40.50% | 49.50% | 45% |
| Vanillin | Vanillin | 0.11% | 5.00% | 0.55% | 1.65% | 0.83% | 1.38% | 0.99% | 1.21% | 1.10% |
| Isopropyl myristate | Isopropyl myristate | 3.34% | 99.00% | 16.70% | 50.10% | 25.05% | 41.75% | 30.06% | 36.74% | 33.40% |
| Example 3 - Ingredient Family 3 | | | | | | | | | | |
| Lilac Flower Oil (LFO) | LFO | 1.29% | 38.70% | 6.45% | 19.35% | 9.68% | 16.13% | 11.61% | 14.19% | 12.90% |
| Limonene | D-Limonene | 0.87% | 26.10% | 4.35% | 13.05% | 6.53% | 10.88% | 7.83% | 9.57% | 8.70% |
| Thyme Oil | Thyme Oil White | 0.96% | 28.80% | 4.80% | 14.40% | 7.20% | 12.00% | 8.64% | 10.56% | 9.60% |
| Lime Oil | Lime Oil 410 | 6.88% | 99.00% | 34.40% | 99.00% | 51.60% | 86.00% | 61.92% | 75.68% | 68.80% |
| Example 4 - Ingredient Family 4 | | | | | | | | | | |
| LFO | LFO | 5.01% | 99.00% | 25.05% | 75.15% | 37.58% | 62.63% | 45.09% | 55.11% | 50.10% |
| BSO (Black Seed Oil) | BSO | 4.99% | 99.00% | 24.95% | 74.85% | 37.43% | 62.38% | 44.91% | 54.89% | 49.90% |
| Example 5 - Ingredient Family 5 | | | | | | | | | | |
| Limonene | D-Limonene | 0.99% | 29.70% | 4.95% | 14.85% | 7.43% | 12.38% | 8.91% | 10.89% | 9.90% |
| Linalool | Linalool Coeur | 1.41% | 42.42% | 7.07% | 21.21% | 10.61% | 17.68% | 12.73% | 15.55% | 14.14% |
| Tetrahydrolinalool | Tetrahydrolinalool | 2.43% | 72.87% | 12.15% | 36.44% | 18.22% | 30.36% | 21.86% | 26.72% | 24.29% |
| Vanillin | Vanillin | 0.25% | 7.44% | 1.24% | 3.72% | 1.86% | 3.10% | 2.23% | 2.73% | 2.48% |
| Isopropyl myristate | Isopropyl myristate | 2.89% | 86.76% | 14.46% | 43.38% | 21.69% | 36.15% | 26.03% | 31.81% | 28.92% |

TABLE 2-continued

| Ingredients | Exemplified form | % Range 1 | | % Range 2 | | % Range 3 | | % Range 4 | | Exemplified % (w/w) |
|---|---|---|---|---|---|---|---|---|---|---|
| Piperonal | Piperonal (aldehyde) | 1.00% | 29.91% | 4.99% | 14.96% | 7.48% | 12.46% | 8.97% | 10.97% | 9.97% |
| Geraniol | Geraniol 60 | 1.03% | 30.90% | 5.15% | 15.45% | 7.73% | 12.88% | 9.27% | 11.33% | 10.30% |
| Example 6 - Ingredient Family 6 | | | | | | | | | | |
| Thyme Oil | Thyme Oil White | 3.93% | 99.00% | 19.65% | 58.95% | 29.48% | 49.13% | 35.37% | 43.23% | 39.30% |
| Wintergreen Oil | Wintergreen Oil | 2.48% | 74.40% | 12.40% | 37.20% | 18.60% | 31.00% | 22.32% | 27.28% | 24.80% |
| Isopropyl Myristate | Isopropyl Myristate | 3.59% | 99.00% | 17.95% | 53.85% | 26.93% | 44.88% | 32.31% | 39.49% | 35.90% |
| Example 7 - Ingredient Family 7 | | | | | | | | | | |
| Limonene | D-Limonene | 2.74% | 82.20% | 13.70% | 41.10% | 20.55% | 34.25% | 24.66% | 30.14% | 27.40% |
| Thyme Oil | Thyme Oil White | 3.01% | 90.30% | 15.05% | 45.15% | 22.58% | 37.63% | 27.09% | 33.11% | 30.10% |
| Linalool | Linalool Coeur | 0.57% | 17.10% | 2.85% | 8.55% | 4.28% | 7.13% | 5.13% | 6.27% | 5.70% |
| Tetrahydrolinalool | Tetrahydrolinalool | 0.79% | 23.70% | 3.95% | 11.85% | 5.93% | 9.88% | 7.11% | 8.69% | 7.90% |
| Vanillin | Vanillin | 0.05% | 5.00% | 0.25% | 0.75% | 0.38% | 0.63% | 0.45% | 0.55% | 0.50% |
| Isopropyl myristate | Isopropyl myristate | 0.81% | 24.30% | 4.05% | 12.15% | 6.08% | 10.13% | 7.29% | 8.91% | 8.10% |
| Piperonal | Piperonal (aldehyde) | 0.81% | 24.30% | 4.05% | 12.15% | 6.08% | 10.13% | 7.29% | 8.91% | 8.10% |
| Geraniol | Geraniol 60 | 0.42% | 12.60% | 2.10% | 6.30% | 3.15% | 5.25% | 3.78% | 4.62% | 4.20% |
| Triethyl Citrate | Triethyl Citrate | 0.81% | 24.30% | 4.05% | 12.15% | 6.08% | 10.13% | 7.29% | 8.91% | 8.10% |
| Example 8 - Ingredient Family 8 | | | | | | | | | | |
| Limonene | D-Limonene | 0.40% | 12.09% | 2.02% | 6.05% | 3.02% | 5.04% | 3.63% | 4.43% | 4.03% |
| Thyme Oil | Thyme Oil White | 0.44% | 13.29% | 2.22% | 6.65% | 3.32% | 5.54% | 3.99% | 4.87% | 4.43% |
| Linalool | Linalool Coeur | 0.08% | 5.00% | 0.42% | 1.26% | 0.63% | 1.05% | 0.76% | 0.92% | 0.84% |
| Tetrahydrolinalool | Tetrahydrolinalool | 0.12% | 5.00% | 0.58% | 1.74% | 0.87% | 1.45% | 1.04% | 1.28% | 1.16% |
| Vanillin | Vanillin | 0.01% | 5.00% | 0.04% | 0.11% | 0.05% | 0.09% | 0.06% | 0.08% | 0.07% |
| Isopropyl myristate | Isopropyl myristate | 0.12% | 5.00% | 0.60% | 1.79% | 0.89% | 1.49% | 1.07% | 1.31% | 1.19% |
| Piperonal | Piperonal (aldehyde) | 0.12% | 5.00% | 0.60% | 1.79% | 0.89% | 1.49% | 1.07% | 1.31% | 1.19% |
| Geraniol | Geraniol 60 | 0.06% | 5.00% | 0.31% | 0.93% | 0.47% | 0.78% | 0.56% | 0.68% | 0.62% |
| Triethyl Citrate | Triethyl Citrate | 0.12% | 5.00% | 0.60% | 1.79% | 0.89% | 1.49% | 1.07% | 1.31% | 1.19% |
| Benzyl Alcohol | Benzyl Alcohol | 1.66% | 49.83% | 8.31% | 24.92% | 12.46% | 20.76% | 14.95% | 18.27% | 16.61% |
| Isopar | Isopar M | 2.10% | 62.85% | 10.48% | 31.43% | 15.71% | 26.19% | 18.86% | 23.05% | 20.95% |
| Water | Water | 4.45% | 99.00% | 22.27% | 66.80% | 33.40% | 55.66% | 40.08% | 48.98% | 44.53% |
| Example 9 - Ingredient Family 9 | | | | | | | | | | |
| Limonene | D-Limonene | 2.74% | 82.05% | 13.68% | 41.03% | 20.51% | 34.19% | 24.62% | 30.09% | 27.35% |
| Thyme Oil | Thyme Oil White | 3.01% | 90.24% | 15.04% | 45.12% | 22.56% | 37.60% | 27.07% | 33.09% | 30.08% |
| Linalool | Linalool Coeur | 0.57% | 17.19% | 2.87% | 8.60% | 4.30% | 7.16% | 5.16% | 6.30% | 5.73% |
| Tetrahydrolinalool | Tetrahydrolinalool | 0.79% | 23.64% | 3.94% | 11.82% | 5.91% | 9.85% | 7.09% | 8.67% | 7.88% |
| Vanillin | Vanillin | 0.05% | 5.00% | 0.25% | 0.75% | 0.38% | 0.63% | 0.45% | 0.55% | 0.50% |
| Isopropyl myristate | Isopropyl myristate | 0.81% | 24.24% | 4.04% | 12.12% | 6.06% | 10.10% | 7.27% | 8.89% | 8.08% |
| Piperonal | Piperonal (aldehyde) | 0.81% | 24.27% | 4.05% | 12.14% | 6.07% | 10.11% | 7.28% | 8.90% | 8.09% |
| Geraniol | Geraniol 60 | 0.42% | 12.54% | 2.09% | 6.27% | 3.14% | 5.23% | 3.76% | 4.60% | 4.18% |
| Triethyl Citrate | Triethyl Citrate | 0.81% | 24.33% | 4.06% | 12.17% | 6.08% | 10.14% | 7.30% | 8.92% | 8.11% |
| Example 10 - Ingredient Family 10 | | | | | | | | | | |
| Thyme Oil | Thyme Oil White | 2.06% | 61.80% | 10.30% | 30.90% | 15.45% | 25.75% | 18.54% | 22.66% | 20.60% |
| Wintergreen Oil | Wintergreen Oil | 4.51% | 99.00% | 22.55% | 67.65% | 33.83% | 56.38% | 40.59% | 49.61% | 45.10% |
| Isopropyl myristate | Isopropyl myristate | 3.43% | 99.00% | 17.15% | 51.45% | 25.73% | 42.88% | 30.87% | 37.73% | 34.30% |
| Example 11 - Ingredient Family 11 | | | | | | | | | | |
| Thyme Oil | Thyme Oil White | 2.06% | 61.80% | 10.30% | 30.90% | 15.45% | 25.75% | 18.54% | 22.66% | 20.60% |
| Methyl Salicylate | Methyl Salicylate | 4.51% | 99.00% | 22.55% | 67.65% | 33.83% | 56.38% | 40.59% | 49.61% | 45.10% |
| Isopropyl myristate | Isopropyl myristate | 3.43% | 99.00% | 17.15% | 51.45% | 25.73% | 42.88% | 30.87% | 37.73% | 34.30% |
| Example 12 - Ingredient Family 12 | | | | | | | | | | |
| LFO | LFO | 1.62% | 48.54% | 8.09% | 24.27% | 12.14% | 20.23% | 14.56% | 17.80% | 16.18% |
| Limonene | D-Limonene | 6.78% | 99.00% | 33.91% | 99.00% | 50.86% | 84.76% | 61.03% | 74.59% | 67.81% |
| Thyme Oil | Thyme Oil White | 1.12% | 33.54% | 5.59% | 16.77% | 8.39% | 13.98% | 10.06% | 12.30% | 11.18% |
| BSO | BSO | 0.48% | 14.49% | 2.42% | 7.25% | 3.62% | 6.04% | 4.35% | 5.31% | 4.83% |
| Example 13 - Ingredient Family 13 | | | | | | | | | | |
| Limonene | D-Limonene | 0.88% | 26.49% | 4.42% | 13.25% | 6.62% | 11.04% | 7.95% | 9.71% | 8.83% |
| Thyme Oil | Thyme Oil White | 0.97% | 29.13% | 4.86% | 14.57% | 7.28% | 12.14% | 8.74% | 10.68% | 9.71% |
| Lime Oil | Lime Oil 410 | 5.52% | 99.00% | 27.59% | 82.76% | 41.38% | 68.96% | 49.65% | 60.69% | 55.17% |
| Linalool | Linalool Coeur | 0.17% | 5.04% | 0.84% | 2.52% | 1.26% | 2.10% | 1.51% | 1.85% | 1.68% |
| Tetrahydrolinalool | Tetrahydrolinalool | 0.23% | 6.93% | 1.16% | 3.47% | 1.73% | 2.89% | 2.08% | 2.54% | 2.31% |
| Vanillin | Vanillin | 0.02% | 5.00% | 0.08% | 0.23% | 0.11% | 0.19% | 0.14% | 0.17% | 0.15% |
| Isopropyl myristate | Isopropyl myristate | 0.24% | 7.11% | 1.19% | 3.56% | 1.78% | 2.96% | 2.13% | 2.61% | 2.37% |
| Piperonal | Piperonal (aldehyde) | 0.24% | 7.11% | 1.19% | 3.56% | 1.78% | 2.96% | 2.13% | 2.61% | 2.37% |
| Geraniol | Geraniol 60 | 0.12% | 5.00% | 0.62% | 1.85% | 0.92% | 1.54% | 1.11% | 1.35% | 1.23% |
| Triethyl Citrate | Triethyl Citrate | 0.24% | 7.14% | 1.19% | 3.57% | 1.79% | 2.98% | 2.14% | 2.62% | 2.38% |
| Isopar | Isopar M | 1.38% | 41.40% | 6.90% | 20.70% | 10.35% | 17.25% | 12.42% | 15.18% | 13.80% |

TABLE 2-continued

| Ingredients | Exemplified form | % Range 1 | | % Range 2 | | % Range 3 | | % Range 4 | | Exemplified % (w/w) |
|---|---|---|---|---|---|---|---|---|---|---|
| Example 14 - Ingredient Family 14 | | | | | | | | | | |
| Limonene | D-Limonene | 0.87% | 26.16% | 4.36% | 13.08% | 6.54% | 10.90% | 7.85% | 9.59% | 8.72% |
| Thyme Oil | Thyme Oil White | 0.96% | 28.77% | 4.80% | 14.39% | 7.19% | 11.99% | 8.63% | 10.55% | 9.59% |
| Lime Oil | Lime Oil 410 | 6.94% | 99.00% | 34.68% | 99.00% | 52.01% | 86.69% | 62.42% | 76.29% | 69.35% |
| Linalool | Linalool Coeur | 0.17% | 5.00% | 0.83% | 2.49% | 1.25% | 2.08% | 1.49% | 1.83% | 1.66% |
| Tetrahydrolinalool | Tetrahydrolinalool | 0.23% | 6.84% | 1.14% | 3.42% | 1.71% | 2.85% | 2.05% | 2.51% | 2.28% |
| Vanillin | Vanillin | 0.02% | 5.00% | 0.08% | 0.23% | 0.11% | 0.19% | 0.14% | 0.17% | 0.15% |
| Isopropyl myristate | Isopropyl myristate | 0.23% | 7.02% | 1.17% | 3.51% | 1.76% | 2.93% | 2.11% | 2.57% | 2.34% |
| Piperonal | Piperonal (aldehyde) | 0.23% | 7.02% | 1.17% | 3.51% | 1.76% | 2.93% | 2.11% | 2.57% | 2.34% |
| Geraniol | Geraniol 60 | 0.12% | 5.00% | 0.61% | 1.82% | 0.91% | 1.51% | 1.09% | 1.33% | 1.21% |
| Triethyl Citrate | Triethyl Citrate | 0.24% | 7.05% | 1.18% | 3.53% | 1.76% | 2.94% | 2.12% | 2.59% | 2.35% |
| Example 15 - Ingredient Family 15 | | | | | | | | | | |
| Thyme Oil | Thyme Oil 99% White 1% Red | 2.06% | 61.80% | 10.30% | 30.90% | 15.45% | 25.75% | 18.54% | 22.66% | 20.60% |
| Wintergreen Oil | Wintergreen Oil | 4.51% | 99.00% | 22.55% | 67.65% | 33.83% | 56.38% | 40.59% | 49.61% | 45.10% |
| Isopropyl myristate | Isopropyl myristate | 3.43% | 99.00% | 17.15% | 51.45% | 25.73% | 42.88% | 30.87% | 37.73% | 34.30% |
| Example 16 - Ingredient Family 16 | | | | | | | | | | |
| Thyme Oil | Thyme Oil Red | 2.06% | 61.80% | 10.30% | 30.90% | 15.45% | 25.75% | 18.54% | 22.66% | 20.60% |
| Wintergreen Oil | Wintergreen Oil | 4.51% | 99.00% | 22.55% | 67.65% | 33.83% | 56.38% | 40.59% | 49.61% | 45.10% |
| Isopropyl myristate | Isopropyl myristate | 3.43% | 99.00% | 17.15% | 51.45% | 25.73% | 42.88% | 30.87% | 37.73% | 34.30% |
| Example 17 - Ingredient Family 17 | | | | | | | | | | |
| Thyme Oil | Thyme Oil White | 2.06% | 61.80% | 10.30% | 30.90% | 15.45% | 25.75% | 18.54% | 22.66% | 20.60% |
| Wintergreen Oil | Wintergreen Oil | 4.51% | 99.00% | 22.55% | 67.65% | 33.83% | 56.38% | 40.59% | 49.61% | 45.10% |
| Isopropyl myristate | Isopropyl myristate | 3.42% | 99.00% | 17.10% | 51.30% | 25.65% | 42.75% | 30.78% | 37.62% | 34.20% |
| Vanillin | Vanillin | 0.01% | 5.00% | 0.05% | 0.15% | 0.08% | 0.13% | 0.09% | 0.11% | 0.10% |
| Example 18 - Ingredient Family 18 | | | | | | | | | | |
| Thyme Oil | Thyme Oil Red | 2.06% | 61.80% | 10.30% | 30.90% | 15.45% | 25.75% | 18.54% | 22.66% | 20.60% |
| Wintergreen Oil | Wintergreen Oil | 4.51% | 99.00% | 22.55% | 67.65% | 33.83% | 56.38% | 40.59% | 49.61% | 45.10% |
| Isopropyl myristate | Isopropyl myristate | 3.42% | 99.00% | 17.10% | 51.30% | 25.65% | 42.75% | 30.78% | 37.62% | 34.20% |
| Vanillin | Vanillin | 0.01% | 5.00% | 0.05% | 0.15% | 0.08% | 0.13% | 0.09% | 0.11% | 0.10% |
| Example 19 - Ingredient Family 19 | | | | | | | | | | |
| Thyme Oil | Thyme Oil White | 4.19% | 99.00% | 20.93% | 62.79% | 31.40% | 52.33% | 37.67% | 46.05% | 41.86% |
| Isopropyl myristate | Isopropyl myristate | 3.83% | 99.00% | 19.17% | 57.51% | 28.76% | 47.93% | 34.51% | 42.17% | 38.34% |
| Geraniol | Geraniol Fine FCC | 1.98% | 59.40% | 9.90% | 29.70% | 14.85% | 24.75% | 17.82% | 21.78% | 19.80% |
| Example 20 - Ingredient Family 20 | | | | | | | | | | |
| Thyme Oil | Thyme Oil White | 2.13% | 63.90% | 10.65% | 31.95% | 15.98% | 26.63% | 19.17% | 23.43% | 21.30% |
| Isopropyl myristate | Isopropyl myristate | 5.85% | 99.00% | 29.27% | 87.81% | 43.91% | 73.18% | 52.69% | 64.39% | 58.54% |
| Geraniol | Geraniol Fine FCC | 2.02% | 60.48% | 10.08% | 30.24% | 15.12% | 25.20% | 18.14% | 22.18% | 20.16% |
| Example 21 - Ingredient Family 21 | | | | | | | | | | |
| Thyme Oil | Thyme Oil White | 3.16% | 94.71% | 15.79% | 47.36% | 23.68% | 39.46% | 28.41% | 34.73% | 31.57% |
| Isopropyl myristate | Isopropyl myristate | 3.86% | 99.00% | 19.28% | 57.84% | 28.92% | 48.20% | 34.70% | 42.42% | 38.56% |
| Geraniol | Geraniol Fine FCC | 2.99% | 89.61% | 14.94% | 44.81% | 22.40% | 37.34% | 26.88% | 32.86% | 29.87% |
| Example 22 - Ingredient Family 22 | | | | | | | | | | |
| Thyme Oil | Thyme Oil White | 3.69% | 99.00% | 18.43% | 55.28% | 27.64% | 46.06% | 33.17% | 40.54% | 36.85% |
| Isopropyl myristate | Isopropyl myristate | 4.82% | 99.00% | 24.11% | 72.32% | 36.16% | 60.26% | 43.39% | 53.03% | 48.21% |
| Geraniol | Geraniol Fine FCC | 1.49% | 44.82% | 7.47% | 22.41% | 11.21% | 18.68% | 13.45% | 16.43% | 14.94% |
| Example 23 - Ingredient Family 23 | | | | | | | | | | |
| Thyme Oil | Thyme Oil 99% White 1% Red | 3.69% | 99.00% | 18.43% | 55.28% | 27.64% | 46.06% | 33.17% | 40.54% | 36.85% |
| Isopropyl myristate | Isopropyl myristate | 4.82% | 99.00% | 24.11% | 72.32% | 36.16% | 60.26% | 43.39% | 53.03% | 48.21% |
| Geraniol | Geraniol Fine FCC | 1.49% | 44.82% | 7.47% | 22.41% | 11.21% | 18.68% | 13.45% | 16.43% | 14.94% |
| Example 24 - Ingredient Family 24 | | | | | | | | | | |
| Linalool | Linalool Coeur | 0.66% | 19.80% | 3.30% | 9.90% | 4.95% | 8.25% | 5.94% | 7.26% | 6.60% |
| Base Oil | Soy Bean Oil | 2.40% | 72.00% | 12.00% | 36.00% | 18.00% | 30.00% | 21.60% | 26.40% | 24.00% |
| Thymol | Thymol (crystal) | 3.72% | 99.00% | 18.60% | 55.80% | 27.90% | 46.50% | 33.48% | 40.92% | 37.20% |
| Pinene | Alpha-Pinene, 98% | 0.38% | 11.40% | 1.90% | 5.70% | 2.85% | 4.75% | 3.42% | 4.18% | 3.80% |
| Cymene | Para-Cymene | 2.84% | 85.17% | 14.20% | 42.59% | 21.29% | 35.49% | 25.55% | 31.23% | 28.39% |
| Example 25 - Ingredient Family 25 | | | | | | | | | | |
| Linalool | Linalool Coeur | 4.08% | 99.00% | 20.40% | 61.20% | 30.60% | 51.00% | 36.72% | 44.88% | 40.80% |
| Thymol | Thymol (crystal) | 3.44% | 99.00% | 17.20% | 51.60% | 25.80% | 43.00% | 30.96% | 37.84% | 34.40% |
| Pinene | Alpha-Pinene, 98% | 0.47% | 14.10% | 2.35% | 7.05% | 3.53% | 5.88% | 4.23% | 5.17% | 4.70% |

TABLE 2-continued

| Ingredients | Exemplified form | % Range 1 | | % Range 2 | | % Range 3 | | % Range 4 | | Exemplified % (w/w) |
|---|---|---|---|---|---|---|---|---|---|---|
| Cymene | Para-Cymene | 0.19% | 5.70% | 0.95% | 2.85% | 1.43% | 2.38% | 1.71% | 2.09% | 1.90% |
| Anethole | Trans-Anethole | 1.82% | 54.60% | 9.10% | 27.30% | 13.65% | 22.75% | 16.38% | 20.02% | 18.20% |
| Example 26 - Ingredient Family 26 | | | | | | | | | | |
| Potassium Sorbate | Potassium Sorbate | 0.01% | 5.00% | 0.06% | 0.17% | 0.08% | 0.14% | 0.10% | 0.12% | 0.11% |
| Polyglycerol-4-oleate | Polyglycerol-4-oleate | 0.02% | 5.00% | 0.08% | 0.23% | 0.11% | 0.19% | 0.14% | 0.17% | 0.15% |
| Xanthan Gum | Xanthan Gum | 0.03% | 5.00% | 0.15% | 0.45% | 0.23% | 0.38% | 0.27% | 0.33% | 0.30% |
| Lecithin | Lecithin | 0.00% | 5.00% | 0.02% | 0.05% | 0.02% | 0.04% | 0.03% | 0.03% | 0.03% |
| Water | Water | 8.44% | 99.00% | 42.20% | 99.00% | 63.30% | 99.00% | 75.96% | 92.84% | 84.40% |
| Blend 41 | Blend 41 | 1.50% | 45.03% | 7.51% | 22.52% | 11.26% | 18.76% | 13.51% | 16.51% | 15.01% |
| Example 27 - Ingredient Family 27 | | | | | | | | | | |
| Potassium Sorbate | Potassium Sorbate | 0.01% | 5.00% | 0.06% | 0.17% | 0.08% | 0.14% | 0.10% | 0.12% | 0.11% |
| Polyglycerol-4-oleate | Polyglycerol-4-oleate | 0.02% | 5.00% | 0.08% | 0.23% | 0.11% | 0.19% | 0.14% | 0.17% | 0.15% |
| Xanthan Gum | Xanthan Gum | 0.03% | 5.00% | 0.15% | 0.45% | 0.23% | 0.38% | 0.27% | 0.33% | 0.30% |
| Lecithin | Lecithin | 0.00% | 5.00% | 0.02% | 0.05% | 0.02% | 0.04% | 0.03% | 0.03% | 0.03% |
| Water | Water | 8.44% | 99.00% | 42.20% | 99.00% | 63.30% | 99.00% | 75.96% | 92.84% | 84.40% |
| Blend 120 | Blend 120 | 1.50% | 45.03% | 7.51% | 22.52% | 11.26% | 18.76% | 13.51% | 16.51% | 15.01% |
| Example 28 - Ingredient Family 28 | | | | | | | | | | |
| Potassium Sorbate | Potassium Sorbate | 0.01% | 5.00% | 0.06% | 0.18% | 0.09% | 0.15% | 0.11% | 0.13% | 0.12% |
| Polyglycerol-4-oleate | Polyglycerol-4-oleate | 0.02% | 5.00% | 0.08% | 0.24% | 0.12% | 0.20% | 0.14% | 0.18% | 0.16% |
| Xanthan Gum | Xanthan Gum | 0.03% | 5.00% | 0.15% | 0.44% | 0.22% | 0.36% | 0.26% | 0.32% | 0.29% |
| Lecithin | Lecithin | 0.00% | 5.00% | 0.02% | 0.05% | 0.03% | 0.05% | 0.03% | 0.04% | 0.04% |
| Water | Water | 8.94% | 99.00% | 44.70% | 99.00% | 67.05% | 99.00% | 80.46% | 98.34% | 89.40% |
| Blend 120 | Blend 120 | 1.00% | 30.00% | 5.00% | 15.00% | 7.50% | 12.50% | 9.00% | 11.00% | 10% |
| Example 29 - Ingredient Family 29 | | | | | | | | | | |
| Soy Bean Oil | Soy Bean Oil | 2.00% | 60.00% | 10.00% | 30.00% | 15.00% | 25.00% | 18.00% | 22.00% | 20% |
| Ethyl Alcohol | Ethyl Alcohol, denatured | 5.00% | 99.00% | 25.00% | 75.00% | 37.50% | 62.50% | 45.00% | 55.00% | 50% |
| Blend 10 | Blend 10 | 3.00% | 99.00% | 15.00% | 45.00% | 22.50% | 37.50% | 27.00% | 33.00% | 30% |
| Example 30 - Ingredient Family 30 | | | | | | | | | | |
| Potassium Sorbate | Potassium Sorbate | 0.01% | 5.00% | 0.06% | 0.17% | 0.08% | 0.14% | 0.10% | 0.12% | 0.11% |
| Polyglycerol-4-oleate | Polyglycerol-4-oleate | 0.02% | 5.00% | 0.08% | 0.23% | 0.11% | 0.19% | 0.14% | 0.17% | 0.15% |
| Xanthan Gum | Xanthan Gum | 0.03% | 5.00% | 0.15% | 0.45% | 0.23% | 0.38% | 0.27% | 0.33% | 0.30% |
| Lecithin | Lecithin | 0.00% | 5.00% | 0.02% | 0.05% | 0.02% | 0.04% | 0.03% | 0.03% | 0.03% |
| Water | Water | 8.44% | 99.00% | 42.20% | 99.00% | 63.30% | 99.00% | 75.96% | 92.84% | 84.40% |
| Blend PB-5048 | Blend PB-5048 | 1.50% | 45.03% | 7.51% | 22.52% | 11.26% | 18.76% | 13.51% | 16.51% | 15.01% |
| Example 31 - Ingredient Family 31 | | | | | | | | | | |
| Potassium Sorbate | Potassium Sorbate | 0.01% | 5.00% | 0.06% | 0.18% | 0.09% | 0.15% | 0.11% | 0.13% | 0.12% |
| Polyglycerol-4-oleate | Polyglycerol-4-oleate | 0.02% | 5.00% | 0.08% | 0.24% | 0.12% | 0.20% | 0.14% | 0.18% | 0.16% |
| Xanthan Gum | Xanthan Gum | 0.03% | 5.00% | 0.15% | 0.44% | 0.22% | 0.36% | 0.26% | 0.32% | 0.29% |
| Lecithin | Lecithin | 0.00% | 5.00% | 0.02% | 0.05% | 0.03% | 0.05% | 0.03% | 0.04% | 0.04% |
| Water | Water | 8.94% | 99.00% | 44.70% | 99.00% | 67.05% | 99.00% | 80.46% | 98.34% | 89.40% |
| Blend PB-5048 | Blend PB-5048 | 1.00% | 30.00% | 5.00% | 15.00% | 7.50% | 12.50% | 9.00% | 11.00% | 10% |
| Example 32 - Ingredient Family 32 | | | | | | | | | | |
| B-5038/B-5040/B-5041 | B-5038/B-5040/B-5041 | 5.00% | 99.00% | 25.00% | 75.00% | 37.50% | 62.50% | 45.00% | 55.00% | 50% |
| Lemon Grass Oil | Lemon Grass Oil | 2.50% | 75.00% | 12.50% | 37.50% | 18.75% | 31.25% | 22.50% | 27.50% | 25% |
| Castor Oil | Castor Oil, Surfactant | 2.50% | 75.00% | 12.50% | 37.50% | 18.75% | 31.25% | 22.50% | 27.50% | 25% |
| Example 33 - Ingredient Family 33 | | | | | | | | | | |
| Blend 7 | Blend 7 | 1.00% | 30.00% | 5.00% | 15.00% | 7.50% | 12.50% | 9.00% | 11.00% | 10% |
| Sodium Lauryl Sulfate | Sodium Lauryl Sulfate | 0.10% | 5.00% | 0.50% | 1.50% | 0.75% | 1.25% | 0.90% | 1.10% | 1% |
| Water | Water | 8.90% | 99.00% | 44.50% | 99.00% | 66.75% | 99.00% | 80.10% | 97.90% | 89% |
| Example 34 - Ingredient Family 34 | | | | | | | | | | |
| Blend 7 | Blend 7 | 0.50% | 15.00% | 2.50% | 7.50% | 3.75% | 6.25% | 4.50% | 5.50% | 5.00% |
| Citronella Oil | Citronella Oil | 0.02% | 5.00% | 0.10% | 0.30% | 0.15% | 0.25% | 0.18% | 0.22% | 0.20% |
| Paraffin | Light Liquid paraffin | 0.40% | 12.00% | 2.00% | 6.00% | 3.00% | 5.00% | 3.60% | 4.40% | 4% |
| Emulsifying wax | Emulsifying wax | 1.40% | 42.00% | 7.00% | 21.00% | 10.50% | 17.50% | 12.60% | 15.40% | 14% |
| Butylated hydroxy toluene | Butylated hydroxy toluene | 0.01% | 5.00% | 0.05% | 0.15% | 0.08% | 0.13% | 0.09% | 0.11% | 0.10% |

TABLE 2-continued

| Ingredients | Exemplified form | % Range 1 | | % Range 2 | | % Range 3 | | % Range 4 | | Exemplified % (w/w) |
|---|---|---|---|---|---|---|---|---|---|---|
| Paraffin | White soft Paraffin | 0.90% | 27.00% | 4.50% | 13.50% | 6.75% | 11.25% | 8.10% | 9.90% | 9% |
| Sodium Metabisulphate | Sodium Metabisulphate | 0.03% | 5.00% | 0.13% | 0.38% | 0.19% | 0.31% | 0.23% | 0.28% | 0.25% |
| Propylene Glycol | Propylene Glycol | 0.20% | 6.00% | 1.00% | 3.00% | 1.50% | 2.50% | 1.80% | 2.20% | 2% |
| Methyl Paraben | Methyl Paraben | 0.02% | 5.00% | 0.08% | 0.23% | 0.11% | 0.19% | 0.14% | 0.17% | 0.15% |
| Propyl Paraben | Propyl Paraben | 0.01% | 5.00% | 0.03% | 0.08% | 0.04% | 0.06% | 0.05% | 0.06% | 0.05% |
| Hydrogenated castor oil | Hydrogenated castor oil | 0.50% | 15.00% | 2.50% | 7.50% | 3.75% | 6.25% | 4.50% | 5.50% | 5% |
| Carbopol | Carbopol 940 | 0.02% | 5.00% | 0.10% | 0.30% | 0.15% | 0.25% | 0.18% | 0.22% | 0.20% |
| Triethanolamine | Triethanolamine | 0.02% | 5.00% | 0.08% | 0.23% | 0.11% | 0.19% | 0.14% | 0.17% | 0.15% |
| Vitamin E acetate | Vitamin E acetate | 0.00% | 5.00% | 0.01% | 0.03% | 0.02% | 0.03% | 0.02% | 0.02% | 0.02% |
| Disodium EDTA | Disodium EDTA | 0.01% | 5.00% | 0.03% | 0.08% | 0.04% | 0.06% | 0.05% | 0.06% | 0.05% |
| Water | Purified water | 5.98% | 99.00% | 29.92% | 89.75% | 44.87% | 74.79% | 53.85% | 65.81% | 59.83% |

In some other embodiments, each compound can make up between about 1% to about 99%, by weight (wt/wt %) or by volume (vol/vol %), of the composition. For example, one composition of the present invention comprises about 2% alpha-Pinene and about 98% D-limonene. As used herein, percent amounts, by weight or by volume, of compounds are to be understood as referring to relative amounts of the compounds. As such, for example, a composition including 7% linalool, 35% thymol, 4% alpha-pinene, 30% para-cymene, and 24% soy bean oil (vol/vol %) can be said to include a ratio of 7 to 35 to 4 to 30 to 24 linalool, thymol, alpha-pinene, para-cymene, and soy bean oil, respectively (by volume). As such, if one compound is removed from the composition, or additional compounds or other ingredients are added to the composition, it is contemplated that the remaining compounds can be provided in the same relative amounts. For example, if soy bean oil were removed from the exemplary composition, the resulting composition would include 7 to 35 to 4 to 40 linalool, thymol, alpha-pinene, and para-cymene, respectively (by volume). This resulting composition would include 9.21% linalool, 46.05% thymol, 5.26% alpha-pinene, and 39.48% para-cymene (vol/vol %). For another example, if safflower oil were added to the original composition to yield a final composition containing 40% (vol/vol) safflower oil, then the resulting composition would include 4.2% linalool, 21% thymol, 2.4% alpha-pinene, 18% para-cymene, 14.4% soy bean oil, and 40% safflower oil (vol/vol %). One having ordinary skill in the art would understand that volume percentages are easily converted to weight percentages based the known or measured specific gravity of the substance.

In certain embodiments, it can be desirable to include a naturally-occurring version or a synthetic version of a compound. For example, in certain embodiments it can be desirable to include Blend 61, a synthetic lime oil that can be obtained, for example, from Millennium Chemicals, Inc. In certain exemplary compositions, it can be desirable to include a compound that is designated as meeting Food Chemical Codex (FCC), for example, Geraniol Fine FCC or Tetrahydrolinalool FCC, which compounds can be obtained, for example, from Millennium Chemicals, Inc.

In certain embodiments, it can be desirable to combine an insect control blend as described herein with a synthetic insecticide such as pyrethroid compound, a nitroguanidine compound or a chloronicotinyl compound. For example, in certain embodiments it can be desirable to combine a blend with delatamethrin, clothianidin or imidacloprid, or a combination thereof. Delatamethrin is available for example from AgrEvo Environmental Health, Inc., of Montvale, N.J. Clothianidin and imidacloprid are available from Bayer CropScience LP of Research Triangle Park, N.C.

In embodiments of the invention that include at least one blend of compounds of a plant origin, the compounds of plant origin can be tested for their precise chemical composition using, for example, High-Pressure Liquid Chromatography (HPLC), Mass Spectrometry (MS), gas chromatography, or the like.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "substantially," as used herein, means at least about 80%, preferably at least about 90%, more preferably at least about 99%, for example at least about 99.9%. In some embodiments, the term "substantially" can mean completely, or about 100%.

Embodiments of the invention can include at least one oil, such as, for example, "Superior oil," highly-refined oils, and the like.

In the case of an animal, human or non-human, the host can also be treated directly by using a formulation of a composition that is delivered orally. For example, a composition can be enclosed within a liquid capsule and ingested.

An area can be treated with a composition of the present invention, for example, by using a spray formulation, such as an aerosol or a pump spray, or a burning formulation, such as a candle or a piece of incense containing the composition. Of course, various treatment methods can be used without departing from the spirit and scope of the present invention. For example, compositions can be comprised in household products such as: air fresheners (including heated air fresheners in which insect repellent substances are released upon heating, e.g., electrically, or by burning); hard surface cleaners; or laundry products (e.g., laundry detergent-containing compositions, conditioners).

Synergistic Properties of Blends

Surprisingly, by blending certain compounds in certain relative amounts, the resulting composition demonstrates a repellant or pesticidal effect that exceeds the repellant or pesticidal effect of any component of the composition. As used herein, "component of a composition" refers to a compound, or a subset of compounds included in a composition, e.g., the complete composition minus at least one compound. As used herein, "repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition. As used herein, "pesticidal effect" is an effect wherein treatment with a composition causes at least about 1% of the insects to die. In this regard, when a first effect and a second effect are compared, the first effect can indicate a greater pesticidal or repellant efficacy if it exceeds the second effect. For example, when the effect being measured is a % killing of target insects, a greater % killing is a pesticidal effect that exceeds a lesser % killing. Effects that can be measured include, but are not limited to: time to kill a given percentage of a target insect, or repellency as to a given percentage of a target insect.

Surprisingly, by combining certain insect control chemicals, and compounds or blends of the present invention, insect control activity of the resulting compositions can be enhanced, i.e., a synergistic effect on insect control activity is achieved when a certain chemical or chemicals, and a certain compound or compounds are combined. In other words, the compositions including certain combinations of at least one chemical, and at least one compound or at least one blend of compounds can have an enhanced ability to control target pests, as compared to each of the chemicals or compounds taken alone.

In embodiments of the present invention, "synergy" can refer to any substantial enhancement, in a combination of at least two ingredients, of a measurable effect, when compared with the effect of one active ingredient alone, or when compared with the effect of the complete combination minus at least one ingredient. Synergy is a specific feature of a combination of ingredients, and is above any background level of enhancement that would be due solely to, e.g., additive effects of any random combination of ingredients. Effects include but are not limited to: repellant effect of the composition; pesticidal effect of the composition; perturbation of a cell message or cell signal such as, e.g., calcium, cyclic-AMP, and the like; and diminution of activity or downstream effects of a molecular target.

As used herein, "synergy" and "synergistic effect" can refer to any substantial enhancement, in a composition of at least two compounds, of a measurable effect, e.g., an antiparasitic effect, when compared with the effect of a component of the composition, e.g., one active compound alone, or the complete blend of compounds minus at least one compound. Synergy is a specific feature of a blend of compounds, and is above any background level of enhancement that would be due solely to, e.g., additive effects of any random combination of ingredients.

In some embodiments, a substantial enhancement of a measurable effect can be expressed as a coefficient of synergy. A coefficient of synergy is an expression of a comparison between measured effects of a composition and measured effects of a comparison composition. The comparison composition can be a component of the composition. In some embodiments, the synergy coefficient can be adjusted for differences in concentration of the complete blend and the comparison composition.

Synergy coefficients can be calculated as follows. An activity ratio (R) can be calculated by dividing the % effect of the composition ($A_B$) by the % effect of the comparison composition ($X_n$), as follows:

$$R = A_B/X_n \quad \text{Formula 1}$$

A concentration adjustment factor (F) can be calculated based on the concentration ($C_n$), i.e., % (wt/wt) or % (vol/vol), of the comparison composition in the composition, as follows:

$$F = 100/Cn \quad \text{Formula 2}$$

The synergy coefficient (S) can then be calculated by multiplying the activity ratio (R) and the concentration adjustment factor (F), as follows:

$$S = (R)(F) \quad \text{Formula 3}$$

As such, the synergy coefficient (S) can also by calculated, as follows:

$$S = [(AB/Xn)(100)]/Cn \quad \text{Formula 4}$$

In Formula 4, AB is expressed as % effect of the blend, Xn is expressed as % effect of the comparison composition (Xn), and Cn is expressed as % (wt/wt) or % (vol/vol) concentration of the comparison composition in the blend.

In some embodiments, a coefficient of synergy of about 1.1, 1.2, 1.3, 1.4, or 1.5 can be substantial and commercially desirable. In other embodiments, the coefficient of synergy can be from about 1.6 to about 5, including but not limited to about 1.8, 2.0, 2.5, 3.0, 3.5, 4.0, and 4.5. In other embodiments, the coefficient of synergy can be from about 5 to 50, including but not limited to about 10, 15, 20, 25, 30, 35, 40, and 45. In other embodiments, the coefficient of synergy can be from about 50 to about 500, or more, including but not limited to about 50, 75, 100, 125, 150, 200, 250, 300, 350, 400, and 450. Any coefficient of synergy above 500 is also contemplated within embodiments of the compositions.

Given that a broad range of synergies can be found in various embodiments described herein, it is expressly noted that a coefficient of synergy can be described as being "greater than" a given number and therefore not necessarily limited to being within the bounds of a range having a lower and an upper numerical limit. Likewise, in some embodiments described herein, certain low synergy coefficients, or lower ends of ranges, are expressly excluded. Accordingly, in some embodiments, synergy can be expressed as being "greater than" a given number that constitutes a lower limit of synergy for such an embodiment. For example, in some embodiments, the synergy coefficient is equal to or greater than 25; in such an embodiment, all synergy coefficients below 25, even though substantial, are expressly excluded.

In some embodiments, synergy or synergistic effect associated with a composition can be determined using calculations similar to those described in Colby, S. R., "Calculating Synergistic and Antagonistic Responses of Herbicide Combinations," Weeds, 1967 15:1, pp. 20-22, which is incorporated herein by reference. In this regard, the following formula can be used to express percent effect (E) of a composition including two compounds, Compound X and Compound Y:

$$E = X + Y - (X*Y/100) \quad \text{Formula 5}$$

In Formula 5, X is the measured actual percent effect of Compound X in the composition, and Y is the measured actual percent effect of Compound Y in the composition. The expected percent effect (E) of the composition is then compared to a measured actual percent effect (A) of the composition. If the actual percent effect (A) that is measured differs from the expected percent effect (E) as calculated by the formula, then the difference is due to an interaction of the compounds. Thus, the composition has synergy (a positive interaction of the compounds) when A>E. Further, there is a negative interaction (antagonism) when A<E.

Formula 5 can be extended to account for any number of compounds in a composition; however it becomes more complex as it is expanded, as is illustrated by the following formula for a composition including three compounds, Compound X, Compound Y, and Compound Z:

$$E = X+Y+Z-((XY+XZ+YZ)/100)+(X*Y*Z/1000) \quad \text{Formula 6}$$

An easy-to-use formula that accommodates compositions with any number of compounds can be provided by modifying Formulas 5 and 6. Such a modification of the formula will now be described. When using Formulas 5 and 6, an untreated control value (untreated with composition or compound) is set at 100%, e.g., if the effect being measured is the amount of target insects killed, the control value would be set at 100% survival of the target insect. In this regard, if treatment with compound A results in 80% killing of the target insect, then the treatment with compound A can be said to result in a 20% survival, or 20% of the control value. The relationship between values expressed as a percent effect and values expressed as a percent-of-control are set forth in the following formulas, where E' is the expected percent of control of the composition, $X_n$ is the measured actual % effect of an individual compound (Compound $X_n$) of the composition, $X_n'$ is the percent of control of an individual compound of the composition, and A' is the actual measured percent of control of the composition.

$$E = 100 - E' \quad \text{Formula 7}$$

$$X_n = 100 - X_n' \quad \text{Formula 8}$$

$$A = 100 - A' \quad \text{Formula 9}$$

By substituting the percent-of-control values for the percent effect values of Formulas 5 and 6, and making modifications to accommodate any number (n) of compounds, the following formula is provided for calculating the expected % of control (E') of the composition:

$$E' = \frac{\left(\prod_{i=1}^{n} X_i'\right)}{100^{n-1}} \quad \text{Formula 10}$$

According to Formula 10, the expected % of control (E') for the composition is calculated by dividing the product of the measured actual % of control values ($X_n'$) for each compound of the composition by $100^{n-1}$. The expected % of control (E') of the composition is then compared to the measured actual % of control (A') of the composition. If the actual % of control (A') that is measured differs from the expected % of control (E') as calculated by the Formula 10, then the difference is due to an interaction of the compounds. Thus, the composition has synergy (a positive interaction of the compounds) when A'<E'. Further, there is a negative interaction (antagonism) when A'>E'.

Compositions containing two or more compounds in certain ratios or relative amounts can be tested for a synergistic effect by comparing the pesticidal effect of a particular composition of compounds to the pesticidal effect of a component of the composition. Additional information related to making a synergy determination can be found in the examples set forth in this document. While synergy has been described in terms of a coefficient of synergy and in terms of the Colby synergy calculations, it is noted that synergy by other measures or determinations known in the art is, in some embodiments, also within the meaning of synergy as described and claimed herein.

Exemplary methods that can be used to determine the synergistic effect of a particular composition are set forth in the following applications, each of which is incorporated in its entirety herein by reference: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; and U.S. application Ser. No. 11/870,385, entitled COMPOSITIONS AND METHODS FOR CONTROLLING INSECTS.

Screening of Compositions

In some embodiments of the invention, the screening method for pest control potential can target a molecule of an insect olfactory receptor protein. In some embodiments of the invention, the screening method for pest control potential can target an insect olfactory receptor protein. The insect olfactory system includes more than 60 identified olfactory receptors. These receptors are generally members of a large family of G protein coupled receptors (GPCRs).

As used herein, a "receptor" is an entity on the cell membrane or within the cell, cytoplasm, or cell nucleus that can bind to a specific molecule (a ligand), such as, for example, a neurotransmitter, hormone, or the like, and initiates the cellular response to the ligand. Ligand-induced changes in the behavior of receptor proteins can result in physiological changes that constitute the biological actions of the ligands.

In accordance with the present disclosure, receptors such as G protein-coupled receptors may be classified on the basis of binding affinity of the receptor to an active ingredient. This may also be expressed as the binding affinity of the active ingredient for the receptor. The binding affinity of an active ingredient for a receptor, or the binding affinity of a receptor for an active ingredient, may be measured in accordance with methods disclosed herein or methods known to those of skill in the art. As used in the present disclosure, a "low" affinity indicates that a high concentration of the active ingredient relative to the receptor is required to maximally occupy the binding site of the receptor and trigger a physiological response, while a "high" affinity indicates that that a low concentration of the active ingredient relative to the receptor is adequate to maximally occupy the binding site of the receptor and trigger a physiological response. A "high" affinity may correspond to, for example, an active ingredient concentration of two or more orders of magnitude less than the concentration of the receptor that is effective to trigger the physiological response, while a "low" affinity may correspond to an active ingredient concentration of one or more orders of magnitude greater than the concentration of the receptor that is effective to trigger the physiological response.

Any insect cell or cell line can be used for the screening assay. Exemplary insect cell lines include but are not limited to SF9, SF21, T.ni, *Drosophila* S2 cells, and the like. Methods of culturing the insect cells are known in the art, and are described, for example, in Lynn et al., J. Insect Sci. 2002; 2:

9, incorporated herein by reference in its entirety. Methods of starting a new insect cell culture from a desired insect cell are described, for example, in Lynn et al. Cytotechnology. 1996; 20:3-11, which is incorporated herein by reference in its entirety.

Further discussion of various approaches to screening, preparing, evaluating, and using insect control formulations are disclosed in the following applications, each of which is incorporated by reference in its entirety: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; U.S. Provisional Application 60/807,600, entitled COMPOSITIONS AND METHODS FOR CONTROLLING INSECTS; U.S. Provisional Application 60/805,963, entitled COMPOSITIONS FOR TREATING PARASITIC INFECTIONS AND METHODS OF SCREENING FOR SAME; U.S. Provisional Application 60/718,570, entitled COMPOSITIONS HAVING INSECT CONTROL ACTIVITY AND METHODS FOR USE THEREOF.

In embodiments of the present invention, a *Drosophila* Schneider 2 (S2) cell line is stably transfected with a G protein-coupled receptor that is amplified from *Drosophila melanogaster* head cDNA phage library. The cell line can be used to screen potential active ingredients, as described below.

Receptor binding can result in cellular changes down stream to the receptor. The subsequent cellular changes may include altered intracellular cAMP levels, calcium levels or both.

In some embodiments of the invention, the screening method for insect control activity can target an insect olfactory receptor protein. The insect olfactory system includes more than 60 identified olfactory receptors. These receptors are generally members of a large family of G protein coupled receptors (GPCRs).

In *Drosophila melanogaster*, the olfactory receptors are located in two pairs of appendages located on the head of the fly. The family of *Drosophila* chemoreceptors includes approximately 62 odorant receptor (Or) and 68 gustatory receptor (Gr) proteins, encoded by families of approximately 60 Or and 60 Gr genes through alternative splicing. Some of these receptor proteins have been functionally characterized, while others have been identified by sequence homology to other sequences but have not been fully characterized. Other insects have similar olfactory receptor proteins.

In certain embodiments, the insect olfactory receptor protein targeted by the screening or insect control method of the invention is the tyramine receptor (tyrR). In additional embodiments, the insect olfactory receptor protein is the insect olfactory receptor protein Or83b or Or43a. In additional embodiments, the targeted protein can be any of the insect olfactory protein receptors.

Additionally, other components of the insect olfactory receptor cascade can be targeted using the method of the invention in order to identify useful insect control compounds. Exemplary insect olfactory cascade components that can be targeted by methods of the invention include but are not limited to serotonin receptor, Or22a, Or22b, Gr5a, Gr21a, Gr61a, beta-arrestin receptor, GRK2 receptor, and tyramine beta-hydroxylase receptor, and the like.

With reference to FIG. 1, an exemplary screening method for identifying effective pestcontrol compositions can make use of one or more transfected cell lines expressing a receptor of interest, for example, a biogenic amine receptor, such as, a TyR or an octopamine receptor.

In some embodiments of the invention, isolated cell membranes expressing the receptor of interest can be used in competitive binding assays. Whole cells can be used to study changes in signaling down-stream to the receptor, in response to treatment with a test composition.

Embodiments of the invention can utilize prokaryotic and eukaryotic cells including, for example, bacterial cells, yeast cells, fungal cells, insect cells, nematode cells, plant cells, animal cells, and the like. Suitable animal cells can include, for example, HEK cells, HeLa cells, COS cells, U20S cells, CHO-K1 cells, various primary mammalian cells, and the like. An animal model expressing one or more conjugates of an arrestin and a marker molecule, for example, throughout its tissues, within a particular organ or tissue type, or the like, can be used.

The potential for insect control activity can be identified by measuring the affinity of the test compositions for the receptor in the cell lines expressing a TyrR, Or83b, and/or Or43a. The potential for insect control activity can also be identified by measuring the change in intracellular cAMP and/or $Ca2+$ in the cell lines expressing TyrR, Or83b, and/or Or43a following treatment with the test compositions. The gene sequences of the TyrR, the Or 83b receptor and the Or 43a receptor have substantial similarity between various insect species. As such, the *Drosophila* Schneider cell lines expressing these receptors can be used to screen for compositions having insect control activity in various insect species.

The methods of embodiments of the invention can used to control any type of target pest, such as an insect. Exemplary insects that can be controlled include but are not limited to beetles, cockroaches, flies, ants, insect larvae, bees, lice, fleas, mosquitoes, moths, and the like. Exemplary insect orders can include but are not limited to orders Acari, Anoplura, Araneae, Blattodea, Coleoptera, Collembola, Diptera, Gryloptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, and Thysanoptera and the like.

Embodiments of the present invention can be used to control, for example, the insects set forth in the following table (Table 3), or the like.

TABLE 3

INSECTS SUBJECT TO CONTROL BY EMBODIMENTS OF THE INVENTION

| Scientific Name | English Common Name | Order | Family |
|---|---|---|---|
| *Abgrallaspis ithacae* (Ferris) | hemlock scale | Homoptera | Diaspididae |
| *Acalitus essigi* (Hassan) | redberry mite | Acari | Eriophyidae |
| *Acalitus rudis* (Can.) | birch budgall mite | Acari | Eriophyidae |

TABLE 3-continued

INSECTS SUBJECT TO CONTROL BY EMBODIMENTS OF THE INVENTION

| Scientific Name | English Common Name | Order | Family |
|---|---|---|---|
| *Acalitus vaccinii* (Keif.) | blueberry bud mite | Acari | Eriophyidae |
| *Acalymma vittatum* (F.) | striped cucumber beetle | Coleoptera | Chrysomelidae |
| *Acantholyda erythrocephala* (L.) | pine false webworm | Hymenoptera | Pamphiliidae |
| *Acantholyda zappei* (Roh.) | nesting pine sawfly | Hymenoptera | Pamphiliidae |
| *Acanthomyops interjectus* (Mayr) | larger yellow ant | Hymenoptera | Formicidae |
| *Acanthoscelides obtectus* (Say) | bean weevil | Coleoptera | Bruchidae |
| *Acarus siro* L. | grain mite | Acari | Acaridae |
| *Aceria campestricola* (Frauen.) | elm leafgall mite | Acari | Eriophyidae |
| *Aceria dispar* (Nal.) | aspen leaf mite | Acari | Eriophyidae |
| *Aceria elongatus* (Hodg.) | crimson erineum mite | Acari | Eriophyidae |
| *Aceria fraxiniflora* (Felt) | ash flower gall mite | Acari | Eriophyidae |
| *Aceria parapopuli* (Keif.) | poplar budgall mite | Acari | Eriophyidae |
| *Aceria tosichella* Keif. | wheat curl mite | Acari | Eriophyidae |
| *Acericecis ocellaris* (O.S.) | ocellate gall midge | Diptera | Cecidomyiidae |
| *Achaearanea tepidariorum* (Koch) | European house spider | Araneae | Theridiidae |
| *Acheta domesticus* (L.) | house cricket | Grylloptera | Gryllidae |
| *Achyra rantalis* (Gn.) | garden webworm | Lepidoptera | Pyralidae |
| *Acleris chalybeana* (Fern.) | lesser maple leafroller | Lepidoptera | Tortricidae |
| *Acleris comariana* (Zell.) | strawberry tortrix | Lepidoptera | Tortricidae |
| *Acleris fuscana* (B. & Bsk.) | small aspen leaftier | Lepidoptera | Tortricidae |
| *Acleris gloverana* (Wlsm.) | western blackheaded budworm | Lepidoptera | Tortricidae |
| *Acleris logiana* (Cl.) | blackheaded birch leaffolder | Lepidoptera | Tortricidae |
| *Acleris minuta* (Rob.) | yellowheaded fireworm | Lepidoptera | Tortricidae |
| *Acleris variana* (Fern.) | eastern blackheaded budworm | Lepidoptera | Tortricidae |
| *Acossus centerensis* (Lint.) | poplar carpenterworm | Lepidoptera | Cossidae |
| *Acossus populi* (Wlk.) | aspen carpenterworm | Lepidoptera | Cossidae |
| *Acrobasis betulella* Hulst | birch tubemaker | Lepidoptera | Pyralidae |
| *Acrobasis caryae* Grt. | hickory shoot borer | Lepidoptera | Pyralidae |
| *Acrobasis comptoniella* Hulst | sweetfern leaf casebearer | Lepidoptera | Pyralidae |
| *Acrobasis juglandis* (LeB.) | pecan leaf casebearer | Lepidoptera | Pyralidae |
| *Acrobasis rubrifasciella* Pack. | alder tubemaker | Lepidoptera | Pyralidae |
| *Acrobasis sylviella* Ely | ironwood tubemaker | Lepidoptera | Pyralidae |
| *Acrobasis vaccinii* Riley | cranberry fruitworm | Lepidoptera | Pyralidae |
| *Acronicta americana* (Harr.) | American dagger moth | Lepidoptera | Noctuidae |
| *Acronicta dactylina* Grt. | alder dagger moth | Lepidoptera | Noctuidae |
| *Acronicta fragilis* (Gn.) | fragile dagger moth | Lepidoptera | Noctuidae |
| *Acronicta funeralis* G. & R. | paddle caterpillar | Lepidoptera | Noctuidae |
| *Acronicta furcifera* Gn. | forked dagger moth | Lepidoptera | Noctuidae |
| *Acronicta grisea* Wlk. | gray dagger moth | Lepidoptera | Noctuidae |
| *Acronicta hasta* Gn. | cherry dagger moth | Lepidoptera | Noctuidae |
| *Acronicta impressa* Wlk. | willow dagger moth | Lepidoptera | Noctuidae |
| *Acronicta innotata* Gn. | birch dagger moth | Lepidoptera | Noctuidae |
| *Acronicta leporina* (L.) | poplar dagger moth | Lepidoptera | Noctuidae |
| *Acronicta lepusculina* Gn. | cottonwood dagger moth | Lepidoptera | Noctuidae |
| *Acronicta oblinita* (J. E. Smith) | smeared dagger moth | Lepidoptera | Noctuidae |
| *Acronicta tristis* Sm. | sad dagger moth | Lepidoptera | Noctuidae |
| *Acronicta vinnula* (Grt.) | elm dagger moth | Lepidoptera | Noctuidae |
| *Actebia fennica* (Tausch.) | black army cutworm | Lepidoptera | Noctuidae |
| *Actias luna* (L.) | luna moth | Lepidoptera | Saturniidae |
| *Aculops lycopersici* (Tryon) | tomato russet mite | Acari | Eriophyidae |
| *Aculus fockeui* (Nal. & Tr.) | plum rust mite | Acari | Eriophyidae |
| *Aculus schlechtendali* (Nal.) | apple rust mite | Acari | Eriophyidae |
| *Acyrthosiphon caraganae* (Cholodk.) | caragana aphid | Homoptera | Aphididae |
| *Acyrthosiphon pisum* (Harr.) | pea aphid | Homoptera | Aphididae |
| *Adalia bipunctata* (L.) | twospotted lady beetle | Coleoptera | Coccinellidae |
| *Adelges abietis* (L.) | eastern spruce gall adelgid | Homoptera | Adelgidae |
| *Adelges cooleyi* (Gill.) | Cooley spruce gall adelgid | Homoptera | Adelgidae |
| *Adelges lariciatus* (Patch) | spruce gall adelgid | Homoptera | Adelgidae |
| *Adelges laricis* Vallot | pale spruce gall adelgid | Homoptera | Adelgidae |

TABLE 3-continued

INSECTS SUBJECT TO CONTROL BY EMBODIMENTS OF THE INVENTION

| Scientific Name | English Common Name | Order | Family |
|---|---|---|---|
| *Adelges piceae* (Ratz.) | balsam woolly adelgid | Homoptera | Adelgidae |
| *Adelges tsugae* Ann. | hemlock woolly adelgid | Homoptera | Adelgidae |
| *Adelphocoris lineolatus* (Goeze) | alfalfa plant bug | Heteroptera | Miridae |
| *Adelphocoris rapidus* (Say) | rapid plant bug | Heteroptera | Miridae |
| *Adelphocoris superbus* (Uhl.) | superb plant bug | Heteroptera | Miridae |
| *Aedes aegypti* (L.) | yellowfever mosquito | Diptera | Culicidae |
| *Aellopos titan* (Cram.) | whitebanded day sphinx | Lepidoptera | Sphingidae |
| *Aeshna canadensis* Wlk. | Canada darner | Odonata | Aeshnidae |
| *Aeshna umbrosa* Wlk. | shadow darner | Odonata | Aeshnidae |
| *Aglais milberti* (Godt.) | Milbert tortoiseshell | Lepidoptera | Nymphalidae |
| *Agrilus anxius* Gory | bronze birch borer | Coleoptera | Buprestidae |
| *Agrilus aurichalceus* Redt. | rose stem girdler | Coleoptera | Buprestidae |
| *Agrilus bilineatus* (Weber) | twolined chestnut borer | Coleoptera | Buprestidae |
| *Agrilus liragus* B. & B. | bronze poplar borer | Coleoptera | Buprestidae |
| *Agrilus politus* (Say) | willow gall limb borer | Coleoptera | Buprestidae |
| *Agrilus ruficollis* (F.) | rednecked cane borer | Coleoptera | Buprestidae |
| *Agriopodes fallax* (H.-S.) | green marvel | Lepidoptera | Noctuidae |
| *Agriotes limosus* (LeC.) | little brown click beetle | Coleoptera | Elateridae |
| *Agriotes lineatus* (L.) | lined click beetle | Coleoptera | Elateridae |
| *Agriotes mancus* (Say) | wheat wireworm | Coleoptera | Elateridae |
| *Agriotes obscurus* (L.) | dusky wireworm | Coleoptera | Elateridae |
| *Agriotes sparsus* LeC. | western wireworm | Coleoptera | Elateridae |
| *Agriphila vulgivagella* (Clem.) | vagabond crambus | Lepidoptera | Pyralidae |
| *Agrius cingulata* (F.) | pinkspotted hawkmoth | Lepidoptera | Sphingidae |
| *Agromyza aristata* Malloch | elm agromyzid leafminer | Diptera | Agromyzidae |
| *Agromyza frontella* (Rond.) | alfalfa blotch leafminer | Diptera | Agromyzidae |
| *Agromyza melampyga* (Loew) | mockorange leafminer | Diptera | Agromyzidae |
| *Agrotis gladiaria* Morr. | claybacked cutworm | Lepidoptera | Noctuidae |
| *Agrotis ipsilon* (Hufn.) | black cutworm | Lepidoptera | Noctuidae |
| *Agrotis orthogonia* Morr. | pale western cutworm | Lepidoptera | Noctuidae |
| *Ahasverus advena* (Waltl) | foreign grain beetle | Coleoptera | Cucujidae |
| *Alabama argillacea* (Hbn.) | cotton leafworm | Lepidoptera | Noctuidae |
| *Alaus myops* (F.) | smalleyed click beetle | Coleoptera | Elateridae |
| *Alaus oculatus* (L.) | eyed click beetle | Coleoptera | Elateridae |
| *Aleuroglyphus ovatus* (Troup.) | brownlegged grain mite | Acari | Acaridae |
| *Allantus cinctus* (L.) | curled rose sawfly | Hymenoptera | Tenthredinidae |
| *Alniphagus aspericollis* (LeC.) | alder bark beetle | Coleoptera | Scolytidae |
| *Alphitobius diaperinus* (Panz.) | lesser mealworm | Coleoptera | Tenebrionidae |
| *Alphitobius laevigatus* (F.) | black fungus beetle | Coleoptera | Tenebrionidae |
| *Alphitophagus bifasciatus* (Say) | twobanded fungus beetle | Coleoptera | Tenebrionidae |
| *Alsophila pometaria* (Harr.) | fall cankerworm | Lepidoptera | Geometridae |
| *Altica ambiens* LeC. | alder flea beetle | Coleoptera | Chrysomelidae |
| *Altica canadensis* Gent. | prairie flea beetle | Coleoptera | Chrysomelidae |
| *Altica chalybaea* Ill. | grape flea beetle | Coleoptera | Chrysomelidae |
| *Altica prasina* LeC. | poplar flea beetle | Coleoptera | Chrysomelidae |
| *Altica rosae* Woods | rose flea beetle | Coleoptera | Chrysomelidae |
| *Altica sylvia* Malloch | blueberry flea beetle | Coleoptera | Chrysomelidae |
| *Altica ulmi* Woods | elm flea beetle | Coleoptera | Chrysomelidae |
| *Alypia langtoni* Couper | fireweed caterpillar | Lepidoptera | Noctuidae |
| *Alypia octomaculata* (F.) | eightspotted forester | Lepidoptera | Noctuidae |
| *Amblyscirtes vialis* (Edw.) | roadside skipper | Lepidoptera | Hesperiidae |
| *Amphibolips confluenta* (Harr.) | spongy oakapple gall | Hymenoptera | Cynipidae |
| *Amphibolips quercusinanis* (O.S.) | large oakapple gall | Hymenoptera | Cynipidae |
| *Amphicerus bicaudatus* (Say) | apple twig borer | Coleoptera | Bostrichidae |
| *Amphimallon majalis* (Raz.) | European chafer | Coleoptera | Scarabaeidae |
| *Amphion floridensis* B. P. Clark | nessus sphinx | Lepidoptera | Sphingidae |
| *Amphipoea interoceanica* (Sm.) | strawberry cutworm | Lepidoptera | Noctuidae |
| *Amphipyra pyramidoides* Gn. | copper underwing | Lepidoptera | Noctuidae |
| *Amphipyra pyramidoides* Gn. | rearhumped caterpillar | Lepidoptera | Noctuidae |
| *Amplicephalus inimicus* (Say) | painted leafhopper | Homoptera | Cicadellidae |
| *Anabrus simplex* Hald. | Mormon cricket | Orthoptera | Tettigoniidae |

TABLE 3-continued

INSECTS SUBJECT TO CONTROL BY EMBODIMENTS OF THE INVENTION

| Scientific Name | English Common Name | Order | Family |
|---|---|---|---|
| *Anacampsis innocuella* (Zell.) | darkheaded aspen leafroller | Lepidoptera | Gelechiidae |
| *Anacampsis niveopulvella* (Cham.) | paleheaded aspen leafroller | Lepidoptera | Gelechiidae |
| *Anagrapha falcifera* (Kby.) | celery looper | Lepidoptera | Noctuidae |
| *Anaphothrips obscurus* (Mull.) | grass thrips | Tysanoptera | Thripidae |
| *Anarsia lineatella* Zell. | peach twig borer | Lepidoptera | Gelechiidae |
| *Anasa tristis* (DeG.) | squash bug | Heteroptera | Coreidae |
| *Anathix puta* (G. & R.) | poplar catkin moth | Lepidoptera | Noctuidae |
| *Anatis labiculata* (Say) | fifteenspotted lady beetle | Coleoptera | Coccinellidae |
| *Anatis mali* (Say) | eyespotted lady beetle | Coleoptera | Coccinellidae |
| *Ancistronycha bilineata* (Say) | twolined cantharid | Coleoptera | Cantharidae |
| *Ancylis burgessiana* (Zell.) | oak leaffolder | Lepidoptera | Tortricidae |
| *Ancylis comptana* (Fro.) | strawberry leafroller | Lepidoptera | Tortricidae |
| *Ancylis discigerana* (Wlk.) | yellow birch leaffolder | Lepidoptera | Tortricidae |
| *Anelaphus parallelus* (Newm.) | hickory twig pruner | Coleoptera | Cerambycidae |
| *Anelaphus villosus* (F.) | twig pruner | Coleoptera | Cerambycidae |
| *Anisota finlaysoni* Riotte | shorthorned oakworm | Lepidoptera | Saturniidae |
| *Anisota senatoria* (J. E. Smith) | orangestriped oakworm | Lepidoptera | Saturniidae |
| *Anisota stigma* (F.) | spiny oakworm | Lepidoptera | Saturniidae |
| *Anisota virginiensis* (Drury) | pinkstriped oakworm | Lepidoptera | Saturniidae |
| *Anobium punctatum* (DeG.) | furniture beetle | Coleoptera | Anobiidae |
| *Anomoea laticlavia* (Forst.) | claycoloured leaf beetle | Coleoptera | Chrysomelidae |
| *Anoplonyx canadensis* Hgtn. | onelined larch sawfly | Hymenoptera | Tenthredinidae |
| *Anoplonyx luteipes* (Cress.) | threelined larch sawfly | Hymenoptera | Tenthredinidae |
| *Antheraea polyphemus* (Cram.) | polyphemus moth | Lepidoptera | Saturniidae |
| *Anthonomus musculus* Say | cranberry weevil | Coleoptera | Curculionidae |
| *Anthonomus quadrigibbus* (Say) | apple curculio | Coleoptera | Curculionidae |
| *Anthonomus signatus* Say | strawberry bud weevil | Coleoptera | Curculionidae |
| *Anthonomus signatus* Say | strawberry clipper weevil | Coleoptera | Curculionidae |
| *Anthophylax attenuatus* (Hald.) | mottled longhorned beetle | Coleoptera | Cerambycidae |
| *Anthrenus flavipes* LeC. | furniture carpet beetle* | Coleoptera | Dermestidae |
| *Anthrenus museorum* (L.) | museum beetle | Coleoptera | Dermestidae |
| *Anthrenus scrophulariae* (L.) | carpet beetle | Coleoptera | Dermestidae |
| *Anthrenus verbasci* (L.) | varied carpet beetle | Coleoptera | Dermestidae |
| *Antispila nysaefoliella* Clem. | tupelo leafminer | Lepidoptera | Heliozelidae |
| *Apamea amputatrix* (Fitch) | yellowheaded cutworm | Lepidoptera | Noctuidae |
| *Apamea devastator* (Brace) | glassy cutworm | Lepidoptera | Noctuidae |
| *Aphis craccivora* Koch | cowpea aphid | Homoptera | Aphididae |
| *Aphis fabae* Scop. | black bean aphid | Homoptera | Aphididae |
| *Aphis fabae* Scop. | bean aphid | Homoptera | Aphididae |
| *Aphis gossypii* Glov. | melon aphid | Homoptera | Aphididae |
| *Aphis maculatae* Oestl. | spotted poplar aphid | Homoptera | Aphididae |
| *Aphis nasturtii* Kltb. | buckthorn aphid | Homoptera | Aphididae |
| *Aphis pomi* DeG. | apple aphid | Homoptera | Aphididae |
| *Aphis rubicola* Oest. | raspberry aphid | Homoptera | Aphididae |
| *Aphomia gularis* (Zell.) | stored nut moth | Lepidoptera | Pyralidae |
| *Aphrophora cribrata* (Wlk.) | pine spittlebug | Homoptera | Cercopidae |
| *Aphrophora fulva* Doering | western pine spittlebug | Homoptera | Cercopidae |
| *Aphrophora parallela* (Say) | spruce spittlebug | Homoptera | Cercopidae |
| *Aphrophora permutata* Uhl. | Douglas-fir spittlebug | Homoptera | Cercopidae |
| *Aphrophora saratogensis* (Fitch) | Saratoga spittlebug | Homoptera | Cercopidae |
| *Apion longirostre* Oliv. | hollyhock weevil | Coleoptera | Apionidae |
| *Apion nigrum* Hbst. | black locust seed weevil* | Coleoptera | Apionidae |
| *Apion simile* Kby. | birch catkin weevil | Coleoptera | Apionidae |
| *Apis mellifera* L. | honey bee | Hymenoptera | Apidae |
| *Apotomis dextrana* (McD.) | green aspen leafroller | Lepidoptera | Tortricidae |
| *Aradus kormileri* Heiss | pine flat bug | Heteroptera | Aradidae |
| *Araecerus fasciculatus* (DeG.) | coffee bean weevil | Coleoptera | Anthribidae |
| *Araneus trifolium* (Hentz) | shamrock spider | Araneae | Araneidae |
| *Archips argyrospila* (Wlk.) | fruittree leafroller | Lepidoptera | Tortricidae |
| *Archips cerasivorana* (Fitch) | uglynest caterpillar | Lepidoptera | Tortricidae |
| *Archips fervidana* (Clem.) | oak webworm | Lepidoptera | Tortricidae |

TABLE 3-continued

INSECTS SUBJECT TO CONTROL BY EMBODIMENTS OF THE INVENTION

| Scientific Name | English Common Name | Order | Family |
|---|---|---|---|
| *Archips mortuana* Kft. | duskyback leafroller | Lepidoptera | Tortricidae |
| *Archips negundana* (Dyar) | larger boxelder leafroller | Lepidoptera | Tortricidae |
| *Archips packardiana* (Fern.) | spring spruce needle moth | Lepidoptera | Tortricidae |
| *Archips purpurana* (Clem.) | omnivorous leafroller | Lepidoptera | Tortricidae |
| *Archips rosana* (L.) | European leafroller | Lepidoptera | Tortricidae |
| *Archips semiferana* (Wlk.) | oak leafroller | Lepidoptera | Tortricidae |
| *Arctia caja* (L.) | great tiger moth | Lepidoptera | Arctiidae |
| *Argas persicus* (Oken) | fowl tick | Acari | Argasidae |
| *Argyresthia conjugella* Zell. | apple fruit moth | Lepidoptera | Argyresthiidae |
| *Argyresthia laricella* Kft. | larch shoot moth | Lepidoptera | Argyresthiidae |
| *Argyresthia oreasella* Clem. | cherry shoot borer | Lepidoptera | Argyresthiidae |
| *Argyresthia thuiella* (Pack.) | arborvitae leafminer | Lepidoptera | Argyresthiidae |
| *Argyrotaenia citrana* (Fern.) | orange tortrix | Lepidoptera | Tortricidae |
| *Argyrotaenia mariana* (Fern.) | graybanded leafroller | Lepidoptera | Tortricidae |
| *Argyrotaenia occultana* Free. | fall spruce needle moth | Lepidoptera | Tortricidae |
| *Argyrotaenia pinatubana* (Kft.) | pine tube moth | Lepidoptera | Tortricidae |
| *Argyrotaenia quadrifasciana* (Fern.) | fourlined leafroller | Lepidoptera | Tortricidae |
| *Argyrotaenia quercifoliana* (Fitch) | tortricid oakworm | Lepidoptera | Tortricidae |
| *Argyrotaenia tabulana* Free. | jack pine tube moth | Lepidoptera | Tortricidae |
| *Argyrotaenia velutinana* (Wlk.) | redbanded leafroller | Lepidoptera | Tortricidae |
| *Arhopalus foveicollis* (Hald.) | pitted longhorned beetle | Coleoptera | Cerambycidae |
| *Arhopalus productus* (LeC.) | new house borer | Coleoptera | Cerambycidae |
| *Armadillidium vulgare* (Latr.) | pillbug | Isopoda | Armadillidae |
| *Aroga trialbamaculella* (Cham.) | redstriped fireworm | Lepidoptera | Gelechiidae |
| *Arrhenodes minutus* (Drury) | oak timberworm | Coleoptera | Brentidae |
| *Asemum striatum* (L.) | opaque sawyer | Coleoptera | Cerambycidae |
| *Aspidiotus nerii* Bouch, | oleander scale | Homoptera | Diaspididae |
| *Asterodiapsis variolosa* (Ratz.) | golden oak scale | Homoptera | Asterolecaniida |
| *Asynapta hopkinsi* Felt | cone resin midge | Diptera | Cecidomyiidae |
| *Asynonychus cervinus* (Boh.) | Fuller rose beetle | Coleoptera | Curculionidae |
| *Attagenus pellio* (L.) | fur beetle | Coleoptera | Dermestidae |
| *Attagenus unicolor* (Brahm) | black carpet beetle | Coleoptera | Dermestidae |
| *Aulacaspis rosae* (Bouch,) | rose scale | Homoptera | Diaspididae |
| *Aulacorthum solani* (Kltb.) | foxglove aphid | Homoptera | Aphididae |
| *Aulocara elliotti* (Thos.) | bigheaded grasshopper | Orthoptera | Acrididae |
| *Autographa biloba* (Steph.) | bilobed looper | Lepidoptera | Noctuidae |
| *Autographa californica* (Speyer) | alfalfa looper | Lepidoptera | Noctuidae |
| *Automeris io* (F.) | io moth | Lepidoptera | Saturniidae |
| *Bactrocera oleae* (Gmel.) | olive fruit fly | Diptera | Tephritidae |
| *Baliosus nervosus* (Panz.) | basswood leafminer | Coleoptera | Chrysomelidae |
| *Banasa dimiata* (Say) | banasa stink bug | Heteroptera | Pentatomidae |
| *Barbara colfaxiana* (Kft.) | Douglas-fir cone moth | Lepidoptera | Tortricidae |
| *Battus philenor* (L.) | pipevine swallowtail | Lepidoptera | Papilionidae |
| *Bemisia tabaci* (Genn.) | sweetpotato whitefly | Homoptera | Aleyrodidae |
| *Biston betularia cognataria* (Gn.) | pepper-and-salt moth | Lepidoptera | Geometridae |
| *Blastobasis glandulella* (Riley) | acorn moth | Lepidoptera | Blastobasidae |
| *Blatta orientalis* L. | oriental cockroach | Blattodea | Blattellidae |
| *Blattella germanica* (L.) | German cockroach | Blattodea | Blattellidae |
| *Blissus l. leucopterus* (Say) | chinch bug | Heteroptera | Lygaeidae |
| *Blissus leucopterus hirtus* Montd. | hairy chinch bug | Heteroptera | Lygaeidae |
| *Blissus occiduus* Barber | western chinch bug | Heteroptera | Lygaeidae |
| *Boisea rubrolineata* (Barber) | western boxelder bug | Heteroptera | Rhopalidae |
| *Boisea trivittata* (Say) | boxelder bug | Heteroptera | Rhopalidae |
| *Boloria bellona* (F.) | meadow fritillary | Lepidoptera | Nymphalidae |
| *Boloria eunomia* (Esp.) | bog fritillary | Lepidoptera | Nymphalidae |
| *Boloria selene* (D. & S.) | silverbordered fritillary | Lepidoptera | Nymphalidae |
| *Bombyx mori* (L.) | silkworm | Lepidoptera | Bombycidae |
| *Bomolocha deceptalis* (Wlk.) | basswood owlet moth | Lepidoptera | Noctuidae |
| *Bourletiella hortensis* (Fitch) | garden springtail | Collembola | Sminthuridae |
| *Bovicola bovis* (L.) | cattle biting louse | Mallophaga | Trichodectidae |
| *Bovicola caprae* (Gurlt) | goat biting louse | Mallophaga | Trichodectidae |
| *Bovicola equi* (Denny) | horse biting louse | Mallophaga | Trichodectidae |
| *Bovicola ovis* (Schr.) | sheep biting louse | Mallophaga | Trichodectidae |
| *Brachycaudus persicae* (Pass.) | black peach aphid | Homoptera | Aphididae |
| *Brachycoynella asparagi* (Mord.) | asparagus aphid | Homoptera | Aphididae |
| *Brevicoryne brassicae* (L.) | cabbage aphid | Homoptera | Aphididae |

TABLE 3-continued

INSECTS SUBJECT TO CONTROL BY EMBODIMENTS OF THE INVENTION

| Scientific Name | English Common Name | Order | Family |
|---|---|---|---|
| *Brochymena quadripustulata* (F.) | fourhumped stink bug | Heteroptera | Pentatomidae |
| *Bromius obscurus* (L.) | western grape rootworm | Coleoptera | Chrysomelidae |
| *Bruchophagus platypterus* (Wlk.) | clover seed chalcid | Hymenoptera | Eurytomidae |
| *Bruchophagus roddi* (Guss.) | alfalfa seed chalcid | Hymenoptera | Eurytomidae |
| *Bruchus brachialis* Fahr. | vetch bruchid | Coleoptera | Bruchidae |
| *Bruchus pisorum* (L.) | pea weevil | Coleoptera | Bruchidae |
| *Bruchus rufimanus* Boh. | broadbean weevil | Coleoptera | Bruchidae |
| *Bryobia praetiosa* Koch | clover mite | Acari | Tetranychidae |
| *Bryobia rubrioculus* (Scheut.) | brown mite | Acari | Tetranychidae |
| *Bucculatrix ainsliella* Murt. | oak skeletonizer | Lepidoptera | Lyonetiidae |
| *Bucculatrix canadensisella* Cham. | birch skeletonizer | Lepidoptera | Lyonetiidae |
| *Buprestis aurulenta* L. | golden buprestid | Coleoptera | Buprestidae |
| *Buprestis maculativentris* Say | ventrally-spotted buprestid | Coleoptera | Buprestidae |
| *Byturus unicolor* Say | raspberry fruitworm | Coleoptera | Byturidae |
| *Cacopsylla buxi* (L.) | boxwood psyllid | Homoptera | Psyllidae |
| *Cacopsylla mali* (Schmdb.) | apple sucker | Homoptera | Psyllidae |
| *Cacopsylla negundinis* Mally | boxelder psyllid | Homoptera | Psyllidae |
| *Cacopsylla pyricola* Forst. | pear psylla | Homoptera | Psyllidae |
| *Cadra cautella* (Wlk.) | almond moth | Lepidoptera | Pyralidae |
| *Cadra figulilella* (Greg.) | raisin moth | Lepidoptera | Pyralidae |
| *Caenurgina crassiuscula* (Haw.) | clover looper | Lepidoptera | Noctuidae |
| *Caliroa cerasi* (L.) | pear sawfly | Hymenoptera | Tenthredinidae |
| *Caliroa cerasi* (L.) | pearslug | Hymenoptera | Tenthredinidae |
| *Caliroa fasciata* (Nort.) | oakslug | Hymenoptera | Tenthredinidae |
| *Caliroa fasciata* (Nort.) | oak sawfly | Hymenoptera | Tenthredinidae |
| *Callidium antennatum hesperum* Casey | blackhorned pine borer | Coleoptera | Cerambycidae |
| *Calligrapha alni* Schaeff. | russet alder leaf beetle | Coleoptera | Chrysomelidae |
| *Calligrapha philadelphica* (L.) | dogwood leaf beetle | Coleoptera | Chrysomelidae |
| *Calligrapha scalaris* (LeC.) | elm calligrapha | Coleoptera | Chrysomelidae |
| *Callirhytis cornigera* (O.S.) | horned oak gall wasp | Hymenoptera | Cynipidae |
| *Callirhytis quercuspunctata* (Bass.) | gouty oak gall wasp | Hymenoptera | Cynipidae |
| *Callosamia promethea* (Drury) | promethea moth | Lepidoptera | Saturniidae |
| *Calocoris norvegicus* Gmel. | strawberry bug | Heteroptera | Miridae |
| *Calopteryx maculata* (Beauv.) | ebony jeweling | Odonata | Calopterygidae |
| *Caloptilia alnivorella* (Cham.) | alder leafminer | Lepidoptera | Gracillariidae |
| *Caloptilia invariabilis* (Braun) | cherry leafcone caterpillar | Lepidoptera | Gracillariidae |
| *Caloptilia negundella* (Cham.) | boxelder leafroller | Lepidoptera | Gracillariidae |
| *Caloptilia syringella* (F.) | lilac leafminer | Lepidoptera | Gracillariidae |
| *Calosoma calidum* (F.) | fiery hunter | Coleoptera | Carabidae |
| *Calvia quatuordecimguttata* (L.) | fourteenspotted lady beetle | Coleoptera | Coccinellidae |
| *Cameraria aceriella* (Clem.) | maple leafblotch miner | Lepidoptera | Gracillariidae |
| *Cameraria betulivora* (Wlsm.) | birch leafblotch miner | Lepidoptera | Gracillariidae |
| *Cameraria cincinnatiella* (Cham.) | gregarious oak leafminer | Lepidoptera | Gracillariidae |
| *Cameraria hamadryadella* (Clem.) | solitary oak leafminer | Lepidoptera | Gracillariidae |
| *Camnula pellucida* (Scudd.) | clearwinged grasshopper | Orthoptera | Acrididae |
| *Campaea perlata* (Gn.) | fringed looper | Lepidoptera | Geometridae |
| *Camponotus ferrugineus* (F.) | red carpenter ant | Hymenoptera | Formicidae |
| *Camponotus herculeanus* (L.) | boreal carpenter ant | Hymenoptera | Formicidae |
| *Camponotus pennsylvanicus* (DeG.) | black carpenter ant | Hymenoptera | Formicidae |
| *Campylomma verbasci* (Meyer) | mullein bug | Heteroptera | Miridae |
| *Canarsia ulmiarrosorella* (Clem.) | elm leaftier | Lepidoptera | Pyralidae |
| *Caripeta angustiorata* Wlk. | brown pine looper | Lepidoptera | Geometridae |
| *Caripeta divisata* Wlk. | gray spruce looper | Lepidoptera | Geometridae |
| *Carpoglyphus lactis* (L.) | driedfruit mite | Acari | Carpoglyphidae |
| *Carpophilus hemipterus* (L.) | driedfruit beetle | Coleoptera | Nitidulidae |
| *Carterocephalus palaemon* (Pallas) | Arctic skipper | Lepidoptera | Hesperiidae |
| *Cartodere constricta* (Gyll.) | plaster beetle | Coleoptera | Lathridiidae |
| *Carulaspis juniperi* (Bouch,) | juniper scale | Homoptera | Diaspididae |
| *Catastega aceriella* Clem. | maple trumpet skeletonizer | Lepidoptera | Tortricidae |
| *Catocala blandula* Hulst | gray-blue underwing | Lepidoptera | Noctuidae |
| *Catocala briseis* Edw. | briseis underwing | Lepidoptera | Noctuidae |

TABLE 3-continued

INSECTS SUBJECT TO CONTROL BY EMBODIMENTS OF THE INVENTION

| Scientific Name | English Common Name | Order | Family |
|---|---|---|---|
| *Catocala cerogama* Gn. | yellowbanded underwing | Lepidoptera | Noctuidae |
| *Catocala concumbens* Wlk. | pink underwing | Lepidoptera | Noctuidae |
| *Catocala gracilis* Edw. | graceful underwing | Lepidoptera | Noctuidae |
| *Catocala habilis* Grt. | hickory underwing | Lepidoptera | Noctuidae |
| *Catocala ilia* (Cram.) | ilia underwing | Lepidoptera | Noctuidae |
| *Catocala relicta* Wlk. | white underwing | Lepidoptera | Noctuidae |
| *Catocala sordida* Grt. | blueberry underwing | Lepidoptera | Noctuidae |
| *Catocala ultronia* (Hbn.) | plum tree underwing | Lepidoptera | Noctuidae |
| *Catocala unijuga* Wlk. | oncemarried underwing | Lepidoptera | Noctuidae |
| *Caulocampus acericaulis* (MacG.) | maple petiole borer | Hymenoptera | Tenthredinidae |
| *Cavariella aegopodii* (Scop.) | carrot-willow aphid | Homoptera | Aphididae |
| *Cecidomyia pellex* O.S. | ash bulletgall midge | Diptera | Cecidomyiidae |
| *Cecidomyia piniinopis* O.S. | jack pine midge | Diptera | Cecidomyiidae |
| *Cecidomyia resinicola* (O.S.) | jack pine resin midge | Diptera | Cecidomyiidae |
| *Cecidomyia verrucicola* O.S. | linden wart gall midge | Diptera | Cecidomyiidae |
| *Cecidophyopsis ribis* (Westw.) | currant bud mite | Acari | Eriophyidae |
| *Cecidophyopsis ribis* (Westw.) | blackcurrant big bud mite | Acari | Eriophyidae |
| *Celastrina argiolus* (Cram.) | spring azure | Lepidoptera | Lycaenidae |
| *Cephalcia fascipennis* (Cress.) | spruce webspinning sawfly | Hymenoptera | Pamphiliidae |
| *Cephalcia marginata* Middk. | red pine webspinning sawfly | Hymenoptera | Pamphiliidae |
| *Cephaloon lepturoides* Newm. | false leptura beetle | Coleoptera | Cephaloidae |
| *Cephus cinctus* Nort. | wheat stem sawfly | Hymenoptera | Cephidae |
| *Cephus pygmaeus* (L.) | European wheat stem sawfly | Hymenoptera | Cephidae |
| *Cerapteryx graminis* L. | antler moth | Lepidoptera | Noctuidae |
| *Ceratomia amyntor* (Gey.) | elm sphinx | Lepidoptera | Sphingidae |
| *Ceratomia undulosa* (Wlk.) | waved sphinx | Lepidoptera | Sphingidae |
| *Ceratophyllus gallinae* (Schr.) | European chicken flea | Siphonaptera | Ceratophyllidae |
| *Ceratophyllus niger* Fox | western chicken flea | Siphonaptera | Ceratophyllidae |
| *Cercyonis pegala* (F.) | common wood nymph | Lepidoptera | Satyridae |
| *Cerotoma trifurcata* (Forst.) | bean leaf beetle | Coleoptera | Chrysomelidae |
| *Ceutorhynchus assimilis* (Payk.) | cabbage seedpod weevil | Coleoptera | Curculionidae |
| *Ceutorhynchus rapae* Gyll. | cabbage curculio | Coleoptera | Curculionidae |
| *Chaetocnema pulicaria* Melsh. | corn flea beetle | Coleoptera | Chrysomelidae |
| *Chaetophloeus heterodoxus* (Casey) | mountain mahogany bark beetle | Coleoptera | Scolytidae |
| *Chaetosiphon fragaefolii* (Ckll.) | strawberry aphid | Homoptera | Aphididae |
| *Chaitophorus populicola* Thos. | smokywinged poplar aphid | Homoptera | Aphididae |
| *Chalcophora virginiensis* (Drury) | sculptured pine borer | Coleoptera | Buprestidae |
| *Charidotella sexpunctata* bicolor (F.) | golden tortoise beetle | Coleoptera | Chrysomelidae |
| *Charidryas harrisii* (Scudd.) | Harris checkerspot | Lepidoptera | Nymphalidae |
| *Charidryas nycteis* (Dbly.) | silvery checkerspot | Lepidoptera | Nymphalidae |
| *Cheimophila salicella* (Hbn.) | blueberry flagleaf webworm | Lepidoptera | Oecophoridae |
| *Chelopistes meleagridis* (L.) | large turkey louse | Mallophaga | Philopteridae |
| *Chelymorpha cassidea* (F.) | argus tortoise beetle | Coleoptera | Chrysomelidae |
| *Chilocorus stigma* (Say) | twicestabbed lady beetle | Coleoptera | Coccinellidae |
| *Chionaspis americana* Johns. | elm scurfy scale | Homoptera | Diaspididae |
| *Chionaspis corni* Cooley | dogwood scale | Homoptera | Diaspididae |
| *Chionaspis furfura* (Fitch) | scurfy scale | Homoptera | Diaspididae |
| *Chionaspis lintneri* Comst. | Lintner scale | Homoptera | Diaspididae |
| *Chionaspis pinifoliae* (Fitch) | pine needle scale | Homoptera | Diaspididae |
| *Chionaspis salicisnigrae* (Walsh) | willow scurfy scale | Homoptera | Diaspididae |
| *Chionodes formosella* (Murt.) | spring oak leafroller | Lepidoptera | Gelechiidae |
| *Chionodes obscurusella* (Cham.) | boxelder leafworm | Lepidoptera | Gelechiidae |
| *Chlorochlamys chloroleucaria* (Gn.) | blackberry looper | Lepidoptera | Geometridae |
| *Chlorochroa sayi* (Stal) | Say stink bug | Heteroptera | Pentatomidae |
| *Choreutis pariana* (Cl.) | apple-and-thorn skeletonizer | Lepidoptera | Choreutidae |
| *Chorioptes bovis* (Gerl.) | chorioptic mange mite | Acari | Psoroptidae |

TABLE 3-continued

INSECTS SUBJECT TO CONTROL BY EMBODIMENTS OF THE INVENTION

| Scientific Name | English Common Name | Order | Family |
|---|---|---|---|
| *Choristoneura biennis* Free. | two-year-cycle budworm | Lepidoptera | Tortricidae |
| *Choristoneura conflictana* (Wlk.) | large aspen tortrix | Lepidoptera | Tortricidae |
| *Choristoneura fractvittana* (Clem.) | brokenbanded leafroller | Lepidoptera | Tortricidae |
| *Choristoneura fumiferana* (Clem.) | spruce budworm | Lepidoptera | Tortricidae |
| *Choristoneura occidentalis* Free. | western spruce budworm | Lepidoptera | Tortricidae |
| *Choristoneura p. pinus* Free. | jack pine budworm | Lepidoptera | Tortricidae |
| *Choristoneura parallela* (Rob.) | spotted fireworm | Lepidoptera | Tortricidae |
| *Choristoneura rosaceana* (Harr.) | obliquebanded leafroller | Lepidoptera | Tortricidae |
| *Chortippus c. curtipennis* (Harr.) | marsh meadow grasshopper | Orthoptera | Acrididae |
| *Chromatomyia syngenesiae* Hdy. | chrysanthemum leafminer | Diptera | Agromyzidae |
| *Chrysobothris femorata* (Oliv.) | flatheaded appletree borer | Coleoptera | Buprestidae |
| *Chrysochus auratus* (F.) | dogbane beetle | Coleoptera | Chrysomelidae |
| *Chrysomela crotchi* Brown | aspen leaf beetle | Coleoptera | Chrysomelidae |
| *Chrysomela scripta* F. | cottonwood leaf beetle | Coleoptera | Chrysomelidae |
| *Chrysomela walshi* Brown | balsam poplar leaf beetle | Coleoptera | Chrysomelidae |
| *Chrysopa oculata* Say | goldeneyed lacewing | Neuroptera | Chrysopidae |
| *Chrysoperla carnea* (Steph.) | common green lacewing | Neuroptera | Chrysopidae |
| *Chrysoteuchia topiaria* (Zell.) | cranberry girdler | Lepidoptera | Pyralidae |
| *Cimbex americana* Leach | elm sawfly | Hymenoptera | Cimbicidae |
| *Cimex lectularius* L. | bed bug | Heteroptera | Cimicidae |
| *Cimex pilosellus* (Horv.) | bat bug | Heteroptera | Cimicidae |
| *Cinara banksiana* P. & T. | jack pine aphid | Homoptera | Aphididae |
| *Cinara curvipes* (Patch) | balsam fir aphid | Homoptera | Aphididae |
| *Cinara fornacula* Hottes | green spruce aphid | Homoptera | Aphididae |
| *Cinara laricifex* (Fitch) | black larch aphid | Homoptera | Aphididae |
| *Cinara laricis* (Htg.) | larch aphid | Homoptera | Aphididae |
| *Cinara pinea* (Mord.) | pine aphid | Homoptera | Aphididae |
| *Cinara strobi* (Fitch) | white pine aphid | Homoptera | Aphididae |
| *Cingilia catenaria* (Drury) | chainspotted geometer | Lepidoptera | Geometridae |
| *Circulifer tenellus* (Baker) | beet leafhopper | Homoptera | Cicadellidae |
| *Citheronia regalis* (F.) | hickory horned devil | Lepidoptera | Saturniidae |
| *Citheronia regalis* (F.) | regal moth | Lepidoptera | Saturniidae |
| *Clastoptera obtusa* (Say) | alder spittlebug | Homoptera | Cercopidae |
| *Clastoptera proteus* Fitch | dogwood spittlebug | Homoptera | Cercopidae |
| *Clepsis persicana* (Fitch) | whitetriangle leafroller | Lepidoptera | Tortricidae |
| *Clossiana titania grandis* (B. & McD.) | purple lesser fritillary | Lepidoptera | Nymphalidae |
| *Clostera albosigma* Fitch | rustylined leaftier | Lepidoptera | Notodontidae |
| *Clostera apicalis* (Wlk.) | redmarked tentmaker | Lepidoptera | Notodontidae |
| *Clostera inclusa* (Hbn.) | poplar tentmaker | Lepidoptera | Notodontidae |
| *Cnephasia longana* (Haw.) | omnivorous leaftier | Lepidoptera | Tortricidae |
| *Coccinella novemnotata* Hbst. | ninespotted lady beetle | Coleoptera | Coccinellidae |
| *Coccinella septempunctata* L. | sevenspotted lady beetle | Coleoptera | Coccinellidae |
| *Coccinella transversoguttata richardsoni* Brown | transverse lady beetle | Coleoptera | Coccinellidae |
| *Coccinella undecimpunctata* L. | elevenspotted lady beetle | Coleoptera | Coccinellidae |
| *Cochliomyia macellaria* (F.) | secondary screwworm | Diptera | Calliphoridae |
| *Coenonympha inornata* Edw. | inornate ringlet | Lepidoptera | Satyridae |
| *Coleophora laricella* (Hbn.) | larch casebearer | Lepidoptera | Coleophoridae |
| *Coleophora laticornella* Clem. | pecan cigar casebearer | Lepidoptera | Coleophoridae |
| *Coleophora limosipennella* (Dup.) | elm casebearer | Lepidoptera | Coleophoridae |
| *Coleophora malivorella* Riley | pistol casebearer | Lepidoptera | Coleophoridae |
| *Coleophora pruniella* Clem. | cherry casebearer | Lepidoptera | Coleophoridae |
| *Coleophora serratella* (L.) | cigar casebearer | Lepidoptera | Coleophoridae |
| *Coleophora serratella* (L.) | birch casebearer | Lepidoptera | Coleophoridae |
| *Coleotechnites apicitripunctella* (Clem.) | green hemlock needleminer | Lepidoptera | Gelechiidae |

TABLE 3-continued

INSECTS SUBJECT TO CONTROL BY EMBODIMENTS OF THE INVENTION

| Scientific Name | English Common Name | Order | Family |
|---|---|---|---|
| *Coleotechnites canusella* (Free.) | banded jack pine needleminer | Lepidoptera | Gelechiidae |
| *Coleotechnites laricis* (Free.) | orange larch tubemaker | Lepidoptera | Gelechiidae |
| *Coleotechnites macleodi* (Free.) | brown hemlock needleminer | Lepidoptera | Gelechiidae |
| *Coleotechnites milleri* (Bsk.) | lodgepole needleminer | Lepidoptera | Gelechiidae |
| *Coleotechnites piceaella* (Kft.) | orange spruce needleminer | Lepidoptera | Gelechiidae |
| *Coleotechnites resinosae* (Free.) | red pine needleminer | Lepidoptera | Gelechiidae |
| *Coleotechnites thujaella* (Kft.) | brown cedar leafminer | Lepidoptera | Gelechiidae |
| *Colias eurytheme* Bdv. | alfalfa caterpillar | Lepidoptera | Pieridae |
| *Colias interior* Scudd. | pinkedged sulphur | Lepidoptera | Pieridae |
| *Colias philodice* Godt. | clouded sulphur | Lepidoptera | Pieridae |
| *Colomerus vitis* (Pgst.) | grape erineum mite | Acari | Eriophyidae |
| *Colopha ulmicola* (Fitch) | elm cockscombgall aphid | Homoptera | Aphididae |
| *Coloradia pandora* Blake | pandora moth | Lepidoptera | Saturniidae |
| *Conophthorus coniperda* (Schw.) | white pine cone beetle | Coleoptera | Scolytidae |
| *Conophthorus ponderosae* Hopk. | ponderosa pine cone beetle | Coleoptera | Scolytidae |
| *Conophthorus ponderosae* Hopk. | lodgepole cone beetle | Coleoptera | Scolytidae |
| *Conophthorus resinosae* Hopk. | red pine cone beetle | Coleoptera | Scolytidae |
| *Conotrachelus juglandis* LeC. | butternut curculio | Coleoptera | Curculionidae |
| *Conotrachelus nenuphar* (Hbst.) | plum curculio | Coleoptera | Curculionidae |
| *Contarinia baeri* (Prell) | European pineneedle midge | Diptera | Cecidomyiidae |
| *Contarinia bromicola* (M. & A.) | bromegrass seed midge | Diptera | Cecidomyiidae |
| *Contarinia canadensis* Felt | ash midribgall midge | Diptera | Cecidomyiidae |
| *Contarinia johnsoni* Felt | grape blossom midge | Diptera | Cecidomyiidae |
| *Contarinia negundifolia* Felt | boxelder leaf gall midge | Diptera | Cecidomyiidae |
| *Contarinia negundinis* (Gill.) | boxelder budgall midge | Diptera | Cecidomyiidae |
| *Contarinia oregonensis* Foote | Douglas-fir cone gall midge | Diptera | Cecidomyiidae |
| *Contarinia pyrivora* (Riley) | pear midge | Diptera | Cecidomyiidae |
| *Contarinia schulzi* Gagn, | sunflower midge | Diptera | Cecidomyiidae |
| *Contarinia virginianae* (Felt) | chokecherry midge | Diptera | Cecidomyiidae |
| *Contarinia washingtonensis* Johns. | Douglas-fir cone scale midge | Diptera | Cecidomyiidae |
| *Corcyra cephalonica* (Staint.) | rice moth | Lepidoptera | Pyralidae |
| *Corthylus punctatissimus* (Zimm.) | pitted ambrosia beetle | Coleoptera | Scolytidae |
| *Corydalus cornutus* (L.) | dobsonfly | Neuroptera | Corydalidae |
| *Corydalus cornutus* (L.) | hellgrammite | Neuroptera | Corydalidae |
| *Corythucha arcuata* (Say) | oak lace bug | Heteroptera | Tingidae |
| *Corythucha ciliata* (Say) | sycamore lace bug | Heteroptera | Tingidae |
| *Corythucha elegans* Drake | willow lace bug | Heteroptera | Tingidae |
| *Corythucha heidemanni* Drake | alder lace bug | Heteroptera | Tingidae |
| *Corythucha juglandis* (Fitch) | walnut lace bug | Heteroptera | Tingidae |
| *Corythucha pallipes* Parsh. | birch lace bug | Heteroptera | Tingidae |
| *Corythucha ulmi* O. & D. | elm lace bug | Heteroptera | Tingidae |
| *Cotalpa lanigera* (L.) | goldsmith beetle | Coleoptera | Scarabaeidae |
| *Craponius inaequalis* (Say) | grape curculio | Coleoptera | Curculionidae |
| *Creophilus maxillosus* (L.) | hairy rove beetle | Coleoptera | Staphylinidae |
| *Crepidodera nana* (Say) | tiny aspen flea beetle | Coleoptera | Chrysomelidae |
| *Crioceris asparagi* (L.) | asparagus beetle | Coleoptera | Chrysomelidae |
| *Crioceris duodecimpunctata* (L.) | spotted asparagus beetle | Coleoptera | Chrysomelidae |
| *Crocigrapha normani* (Grt.) | climbing cherry cutworm | Lepidoptera | Noctuidae |
| *Croesia curvalana* (Kft.) | blueberry leafier | Lepidoptera | Tortricidae |
| *Croesia semipurpurana* (Kft.) | oak leafshredder | Lepidoptera | Tortricidae |
| *Croesus latitarsus* Nort. | dusky birch sawfly | Hymenoptera | Tenthredinidae |
| *Cryptocala acadiensis* (Bethune) | catocaline dart | Lepidoptera | Noctuidae |
| *Cryptococcus fagisuga* Lind. | beech scale | Homoptera | Eriococcidae |
| *Cryptolestes ferrugineus* (Steph.) | rusty grain beetle | Coleoptera | Cucujidae |
| *Cryptolestes pusillus* (Schonh.) | flat grain beetle | Coleoptera | Cucujidae |
| *Cryptolestes turcicus* (Grouv.) | flourmill beetle | Coleoptera | Cucujidae |
| *Cryptomyzus ribis* (L.) | currant aphid | Homoptera | Aphididae |
| *Cryptophagus varus* W. & C. | sigmoid fungus beetle | Coleoptera | Cryptophagidae |

TABLE 3-continued

INSECTS SUBJECT TO CONTROL BY EMBODIMENTS OF THE INVENTION

| Scientific Name | English Common Name | Order | Family |
|---|---|---|---|
| *Cryptorhynchus lapathi* (L.) | poplar-and-willow borer | Coleoptera | Curculionidae |
| *Ctenicera aeripennis* (Kby.) | Puget Sound wireworm | Coleoptera | Elateridae |
| *Ctenicera destructor* (Brown) | prairie grain wireworm | Coleoptera | Elateridae |
| *Ctenicera propola propola* LeC. | twospotted click beetle | Coleoptera | Elateridae |
| *Ctenicera pruinina* (Horn) | Great Basin wireworm | Coleoptera | Elateridae |
| *Ctenicera r. resplendens* (Esch.) | green click beetle | Coleoptera | Elateridae |
| *Ctenicera triundulata* (Rand.) | threespotted click beetle | Coleoptera | Elateridae |
| *Ctenocephalides canis* (Curt.) | dog flea | Siphonaptera | Pulicidae |
| *Ctenocephalides felis* (Bouch,) | cat flea | Siphonaptera | Pulicidae |
| *Cucullia intermedia* Speyer | goldenrod cutworm | Lepidoptera | Noctuidae |
| *Culex pipiens* L. | northern house mosquito | Diptera | Culicidae |
| *Curculio uniformis* (LeC.) | filbert weevil | Coleoptera | Curculionidae |
| *Cuterebra tenebrosa* Coq. | rodent bot fly | Diptera | Oestridae |
| *Cydia caryana* (Fitch) | hickory shuckworm | Lepidoptera | Tortricidae |
| *Cydia latiferreana* (Wlsm.) | filbertworm | Lepidoptera | Tortricidae |
| *Cydia nigricana* (F.) | pea moth | Lepidoptera | Tortricidae |
| *Cydia piperana* Kft. | ponderosa pine seedworm | Lepidoptera | Tortricidae |
| *Cydia pomonella* (L.) | codling moth | Lepidoptera | Tortricidae |
| *Cydia strobilella* (L.) | spruce seed moth | Lepidoptera | Tortricidae |
| *Cydia toreuta* (Grt.) | eastern pine seedworm | Lepidoptera | Tortricidae |
| *Cynaeus angustus* (LeC.) | larger black flour beetle | Coleoptera | Tenebrionidae |
| *Cytodites nudus* (Vizioli) | airsac mite | Acari | Cytoditidae |
| *Daktulosphaira vitifoliae* (Fitch) | grape phylloxera | Homoptera | Phylloxeridae |
| *Danaus plexippus* (L.) | monarch butterfly | Lepidoptera | Danaidae |
| *Darapsa myron* (Cram.) | Virginiacreeper sphinx | Lepidoptera | Sphingidae |
| *Darapsa versicolor* (Harr.) | hydrangea sphinx | Lepidoptera | Sphingidae |
| *Dasineura balsamicola* (Lint.) | introduced false balsam gall midge | Diptera | Cecidomyiidae |
| *Dasineura communis* Felt | gouty vein midge | Diptera | Cecidomyiidae |
| *Dasineura gleditchiae* O.S. | honeylocust podgall midge | Diptera | Cecidomyiidae |
| *Dasineura leguminicola* (Lint.) | clover seed midge | Diptera | Cecidomyiidae |
| *Dasineura mali* (Keif.) | apple leaf midge | Diptera | Cecidomyiidae |
| *Dasineura rhodophaga* (Coq.) | rose midge | Diptera | Cecidomyiidae |
| *Dasineura swainei* (Felt) | spruce bud midge | Diptera | Cecidomyiidae |
| *Dasychira dorsipennata* (B. & McD.) | hardwood tussock moth | Lepidoptera | Lymantriidae |
| *Dasychira pinicola* (Dyar) | pine tussock moth | Lepidoptera | Lymantriidae |
| *Dasychira plagiata* (Wlk.) | northern pine tussock moth | Lepidoptera | Lymantriidae |
| *Dasylophia thyatiroides* (Wlk.) | beech caterpillar | Lepidoptera | Notodontidae |
| *Datana integerrima* G. & R. | walnut caterpillar | Lepidoptera | Notodontidae |
| *Datana ministra* (Drury) | yellownecked caterpillar | Lepidoptera | Notodontidae |
| *Deidamia inscripta* (Harr.) | lettered sphinx | Lepidoptera | Sphingidae |
| *Delia antiqua* (Meig.) | onion maggot | Diptera | Anthomyiidae |
| *Delia floralis* (Fall.) | turnip maggot | Diptera | Anthomyiidae |
| *Delia platura* (Meig.) | seedcorn maggot | Diptera | Anthomyiidae |
| *Delia radicum* (L.) | cabbage maggot | Diptera | Anthomyiidae |
| *Demodex bovis* Stiles | cattle follicle mite | Acari | Demodicidae |
| *Demodex cati* M, gn. | cat follicle mite | Acari | Demodicidae |
| *Demodex equi* Raill. | horse follicle mite | Acari | Demodicidae |
| *Demodex ovis* Raill. | sheep follicle mite | Acari | Demodicidae |
| *Demodex phylloides* Csokor | hog follicle mite | Acari | Demodicidae |
| *Dendroctonus brevicomis* LeC. | western pine beetle | Coleoptera | Scolytidae |
| *Dendroctonus frontalis* Zimm. | southern pine beetle* | Coleoptera | Scolytidae |
| *Dendroctonus murrayanae* Hopk. | lodgepole pine beetle | Coleoptera | Scolytidae |
| *Dendroctonus ponderosae* Hopk. | mountain pine beetle | Coleoptera | Scolytidae |
| *Dendroctonus pseudotsugae* Hopk. | Douglas-fir beetle | Coleoptera | Scolytidae |
| *Dendroctonus punctatus* LeC. | boreal spruce beetle | Coleoptera | Scolytidae |
| *Dendroctonus rufipennis* (Kby.) | spruce beetle | Coleoptera | Scolytidae |
| *Dendroctonus simplex* LeC. | eastern larch beetle | Coleoptera | Scolytidae |
| *Dendroctonus valens* LeC. | red turpentine beetle | Coleoptera | Scolytidae |

TABLE 3-continued

INSECTS SUBJECT TO CONTROL BY EMBODIMENTS OF THE INVENTION

| Scientific Name | English Common Name | Order | Family |
|---|---|---|---|
| *Depressaria pastinacella* (Dup.) | parsnip webworm | Lepidoptera | Oecophoridae |
| *Dermacentor albipictus* (Pack.) | winter tick | Acari | Ixodidae |
| *Dermacentor andersoni* Stiles | Rocky Mountain wood tick | Acari | Ixodidae |
| *Dermacentor variabilis* (Say) | American dog tick | Acari | Ixodidae |
| *Dermanyssus gallinae* (DeG.) | chicken mite | Acari | Dermanyssidae |
| *Dermatophagoides farinae* Hughes | American house dust mite | Acari | Epidermoptidae |
| *Dermatophagoides pteronyssinus* (Troues.) | European house dust mite | Acari | Epidermoptidae |
| *Dermestes ater* DeG. | black larder beetle | Coleoptera | Dermestidae |
| *Dermestes lardarius* L. | larder beetle | Coleoptera | Dermestidae |
| *Dermestes maculatus* DeG. | hide beetle | Coleoptera | Dermestidae |
| *Desmia funeralis* (Hbn.) | grape leaffolder | Lepidoptera | Pyralidae |
| *Desmocerus palliatus* (Forst.) | elder borer | Coleoptera | Cerambycidae |
| *Diabrotica barberi* S. & L. | northern corn rootworm | Coleoptera | Chrysomelidae |
| *Diabrotica undecimpunctata howardi* Barber | spotted cucumber beetle | Coleoptera | Chrysomelidae |
| *Diabrotica v. virgifera* LeC. | western corn rootworm | Coleoptera | Chrysomelidae |
| *Diapheromera femorata* (Say) | walkingstick | Phasmatodea | Heteronemiidae |
| *Diaspidiotus ancylus* (Putn.) | Putnam scale | Homoptera | Diaspididae |
| *Dicerca divaricata* (Say) | flatheaded hardwood borer | Coleoptera | Buprestidae |
| *Dicerca tenebrica* (Kby.) | flatheaded poplar borer | Coleoptera | Buprestidae |
| *Dicerca tenebrosa* (Kby.) | flatheaded conifer borer | Coleoptera | Buprestidae |
| *Dichelonyx backii* (Kby.) | green rose chafer | Coleoptera | Scarabaeidae |
| *Dichomeris ligulella* Hbn. | palmerworm | Lepidoptera | Gelechiidae |
| *Dichomeris marginella* (F.) | juniper webworm | Lepidoptera | Gelechiidae |
| *Dimorphopteryx melanognathus* Roh. | fringed birch sawfly | Hymenoptera | Tenthredinidae |
| *Dioryctria abietivorella* (Grt.) | fir coneworm | Lepidoptera | Pyralidae |
| *Dioryctria auranticella* (Grt.) | ponderosa pine coneworm | Lepidoptera | Pyralidae |
| *Dioryctria disclusa* Heinr. | webbing coneworm | Lepidoptera | Pyralidae |
| *Dioryctria reniculelloides* Mut. & Mun. | spruce coneworm | Lepidoptera | Pyralidae |
| *Dioryctria resinosella* Mut. | red pine shoot moth | Lepidoptera | Pyralidae |
| *Dioryctria zimmermani* (Grt.) | Zimmerman pine moth | Lepidoptera | Pyralidae |
| *Diplolepis radicum* (O.S.) | rose root gall wasp | Hymenoptera | Cynipidae |
| *Diplolepis rosae* (L.) | mossyrose gall wasp | Hymenoptera | Cynipidae |
| *Diprion similis* (Htg.) | introduced pine sawfly | Hymenoptera | Diprionidae |
| *Diptacus gigantorhynchus* (Nal.) | bigbeaked plum mite | Acari | Diptilomiopidae |
| *Discestra trifolii* (Hufn.) | clover cutworm | Lepidoptera | Noctuidae |
| *Disonycha alternata* (Ill.) | striped willow leaf beetle | Coleoptera | Chrysomelidae |
| *Disonycha triangularis* (Say) | threespotted flea beetle | Coleoptera | Chrysomelidae |
| *Disonycha xanthomelas* (Dalm.) | spinach flea beetle | Coleoptera | Chrysomelidae |
| *Dissosteira carolina* (L.) | Carolina grasshopper | Orthoptera | Acrididae |
| *Diuraphis noxia* (Mordv.) | Russian wheat aphid | Homoptera | Aphididae |
| *Diuraphis tritici* (Gill.) | western wheat aphid | Homoptera | Aphididae |
| *Dolichovespula arenaria* (F.) | aerial yellowjacket | Hymenoptera | Vespidae |
| *Dolichovespula maculata* (L.) | baldfaced hornet | Hymenoptera | Vespidae |
| *Drepana arcuata* Wlk. | masked birch caterpillar | Lepidoptera | Drepanidae |
| *Drepana bilineata* (Pack.) | warty birch caterpillar | Lepidoptera | Drepanidae |
| *Drepanaphis acerifoliae* (Thos.) | painted maple aphid | Homoptera | Aphididae |
| *Dryocampa rubicunda* (F.) | greenstriped mapleworm | Lepidoptera | Saturniidae |
| *Dryocoetes betulae* Hopk. | birch bark beetle | Coleoptera | Scolytidae |
| *Dryocoetes confusus* Swaine | western balsam bark beetle | Coleoptera | Scolytidae |
| *Dysaphis plantaginea* (Pass.) | rosy apple aphid | Homoptera | Aphididae |
| *Dysstroma citrata* (L.) | dark marbled carpet | Lepidoptera | Geometridae |
| *Eacles imperialis pini* Mich. | pine imperial moth | Lepidoptera | Saturniidae |
| *Earomyia abietum* McAlp. | fir seed maggot | Diptera | Lonchaeidae |
| *Ecdytolopha insiticiana* Zell. | locust twig borer | Lepidoptera | Tortricidae |
| *Ectoedemia lindquisti* (Free.) | small birch leafminer | Lepidoptera | Nepticulidae |

TABLE 3-continued

INSECTS SUBJECT TO CONTROL BY EMBODIMENTS OF THE INVENTION

| Scientific Name | English Common Name | Order | Family |
|---|---|---|---|
| *Ectropis crepuscularia* (D. & S.) | saddleback looper | Lepidoptera | Geometridae |
| *Eilema bicolor* (Grt.) | smoky moth | Lepidoptera | Arctiidae |
| *Elaphria versicolor* (Grt.) | fir harlequin | Lepidoptera | Noctuidae |
| *Elasmostethus cruciatus* Say | redcrossed stink bug | Heteroptera | Acanthosomatida |
| *Elatobium abietinum* (Wlk.) | spruce aphid | Homoptera | Aphididae |
| *Empoasca fabae* (Harr.) | potato leafhopper | Homoptera | Cicadellidae |
| *Empoasca maligna* (Walsh) | apple leafhopper | Homoptera | Cicadellidae |
| *Enargia decolor* (Wlk.) | aspen twoleaf tier | Lepidoptera | Noctuidae |
| *Enchenopa binotata* (Say) | twomarked treehopper | Homoptera | Membracidae |
| *Endelomyia aethiops* (F.) | roseslug | Hymenoptera | Tenthredinidae |
| *Endopiza viteana* Clem. | grape berry moth | Lepidoptera | Tortricidae |
| *Endothenia albolineana* (Kft.) | spruce needleminer | Lepidoptera | Tortricidae |
| *Endrosis sarcitrella* (L.) | whiteshouldered house moth | Lepidoptera | Oecophoridae |
| *Ennomos magnaria* Gn. | maple spanworm | Lpidoptera | Geometridae |
| *Ennomos subsignaria* (Hbn.) | elm spanworm | Lepidoptera | Geometridae |
| *Enodia anthedon* Clark | northern pearly eye | Lepidoptera | Satyridae |
| *Entomoscelis americana* Brown | red turnip beetle | Coleoptera | Chrysomelidae |
| *Epargyreus clarus* (Cram.) | silverspotted skipper | Lepidoptera | Hesperiidae |
| *Ephestia elutella* (Hbn.) | tobacco moth | Lepidoptera | Pyralidae |
| *Ephestia kuehniella* Zell. | Mediterranean flour moth | Lepidoptera | Pyralidae |
| *Epicauta fabricii* (LeC.) | ashgray blister beetle | Coleoptera | Meloidae |
| *Epicauta maculata* (Say) | spotted blister beetle | Coleoptera | Meloidae |
| *Epicauta murina* (LeC.) | dark blister beetle | Coleoptera | Meloidae |
| *Epicauta pennsylvanica* (DeG.) | black blister beetle | Coleoptera | Meloidae |
| *Epicauta pestifera* Werner | margined blister beetle* | Coleoptera | Meloidae |
| *Epicauta subglabra* (Fall) | caragana blister beetle | Coleoptera | Meloidae |
| *Epicauta vittata* (F.) | striped blister beetle | Coleoptera | Meloidae |
| *Epilachna varivestis* Muls. | Mexican bean beetle | Coleoptera | Coccinellidae |
| *Epinotia meritana* Heinr. | white fir needleminer | Lepidoptera | Tortricidae |
| *Epinotia nanana* (Treit.) | European spruce needleminer | Lepidoptera | Tortricidae |
| *Epinotia nisella* (Cl.) | yellowheaded aspen leaftier | Lepidoptera | Tortricidae |
| *Epinotia radicana* (Heinr.) | redstriped needleworm | Lepidoptera | Tortricidae |
| *Epinotia solandriana* (L.) | birch-aspen leafroller | Lepidoptera | Tortricidae |
| *Epinotia solicitana* (Wlk.) | birch shootworm | Lepidoptera | Tortricidae |
| *Epinotia timidella* (Clem.) | oak trumpet skeletonizer | Lepidoptera | Tortricidae |
| *Epinotia tsugana* Free. | hemlock needleminer | Lepidoptera | Tortricidae |
| *Epirrita autumnata henshawi* (Swett) | November moth | Lepidoptera | Geometridae |
| *Epitrimerus pyri* (Nal.) | pear rust mite | Acari | Eriophyidae |
| *Epitrix cucumeris* (Harr.) | potato flea beetle | Coleoptera | Chrysomelidae |
| *Epitrix hirtipennis* (Melsh.) | tobacco flea beetle | Coleoptera | Chrysomelidae |
| *Epitrix subcrinita* (LeC.) | western potato flea beetle | Coleoptera | Chrysomelidae |
| *Epitrix tuberis* Gent. | tuber flea beetle | Coleoptera | Chrysomelidae |
| *Erannis tiliaria* (Harr.) | linden looper | Lepidoptera | Geometridae |
| *Erannis tiliaria vancouverensis* Hulst | western winter moth | Lepidoptera | Geometridae |
| *Ergates spiculatus* (LeC.) | ponderous borer | Coleoptera | Cerambycidae |
| *Eriocampa juglandis* (Fitch) | woolly butternut sawfly | Hymenoptera | Tenthredinidae |
| *Eriocampa ovata* (L.) | woolly alder sawfly | Hymenoptera | Tenthredinidae |
| *Eriophyes betulae* (Nal.) | birch witches broom mite | Acari | Eriophyidae |
| *Eriophyes pyri* (Pgst.) | pearleaf blister mite | Acari | Eriophyidae |
| *Eriosoma americanum* (Riley) | woolly elm aphid | Homoptera | Aphididae |
| *Eriosoma crataegi* (Oestl.) | woolly hawthorn aphid | Homoptera | Aphididae |
| *Eriosoma lanigerum* (Hausm.) | woolly apple aphid | Homoptera | Aphididae |
| *Eristalis tenax* (L.) | drone fly | Diptera | Syrphidae |
| *Eristalis tenax* (L.) | rattailed maggot | Diptera | Syrphidae |
| *Erynnis icelus* (Scudd. & Burg.) | dreamy dusky wing | Lepidoptera | Hesperiidae |
| *Erynnis juvenalis* (F.) | Juvenal dusky wing | Lepidoptera | Hesperiidae |
| *Erythroneura comes* (Say) | grape leafhopper | Homoptera | Cicadellidae |
| *Erythroneura tricincta* Fitch | threebanded leafhopper | Homoptera | Cicadellidae |

TABLE 3-continued

INSECTS SUBJECT TO CONTROL BY EMBODIMENTS OF THE INVENTION

| Scientific Name | English Common Name | Order | Family |
|---|---|---|---|
| *Erythroneura vitis* (Harr.) | grapevine leafhopper | Homoptera | Cicadellidae |
| *Erythroneura ziczac* Walsh | Virginiacreeper leafhopper | Homoptera | Cicadellidae |
| *Estigmene acrea* (Drury) | saltmarsh caterpillar | Lepidoptera | Arctiidae |
| *Euceraphis punctipennis* (Zett.) | European birch aphid | Homoptera | Aphididae |
| *Euchaetes egle* (Drury) | milkweed tussock moth | Lepidoptera | Arctiidae |
| *Euclea delphinii* (Bdv.) | spiny slug caterpillar | Lepidoptera | Limacodidae |
| *Eucosma gloriola* Heinr. | eastern pine shoot borer | Lepidoptera | Tortricidae |
| *Eucosma monitorana* Heinr. | red pine cone borer | Lepidoptera | Tortricidae |
| *Eucosma recissoriana* Heinr. | lodgepole pine cone borer | Lepidoptera | Tortricidae |
| *Eucosma siskiyouana* (Kft.) | fir cone borer | Lepidoptera | Tortricidae |
| *Eucosma sonomana* Kft. | western pine shoot borer | Lepidoptera | Tortricidae |
| *Eucosma tocullionana* Heinr. | white pine cone borer | Lepidoptera | Tortricidae |
| *Eudryas grata* (F.) | beautiful wood nymph | Lepidoptera | Noctuidae |
| *Eudryas unio* (Hbn.) | pearly wood nymph | Lepidoptera | Noctuidae |
| *Eulachnus agilis* (Kltb.) | spotted pineneedle aphid | Homoptera | Aphididae |
| *Eulithis diversilineata* (Hbn.) | grapevine looper | Lepidoptera | Geometridae |
| *Eumerus strigatus* (Fall.) | onion bulb fly | Diptera | Syrphidae |
| *Eumerus tuberculatus* Rond. | lesser bulb fly | Diptera | Syrphidae |
| *Eumorpha achemon* (Drury) | achemon sphinx | Lepidoptera | Sphingidae |
| *Eumorpha pandorus* (Hbn.) | pandora sphinx | Lepidoptera | Sphingidae |
| *Eupareophora parca* (Cress.) | spiny ash sawfly | Hymenoptera | Tenthredinidae |
| *Euparthenos nubilis* (Hbn.) | locust underwing | Lepidoptera | Noctuidae |
| *Euphoria inda* (L.) | bumble flower beetle | Coleoptera | Scarabaeidae |
| *Euphranta canadensis* (Loew) | currant fruit fly | Diptera | Tephritidae |
| *Euphydryas phaeton* (Drury) | Baltimore | Lepidoptera | Nymphalidae |
| *Euphyes vestris* (Bdv.) | dun skipper | Lepidoptera | Hesperiidae |
| *Eupithecia filmata* Pears. | early brown looper | Lepidoptera | Geometridae |
| *Eupithecia luteata* Pack. | fir needle inchworm | Lepidoptera | Geometridae |
| *Eupithecia mutata* Pears. | spruce cone looper | Lepidoptera | Geometridae |
| *Eupithecia palpata* Pack. | small pine looper | Lepidoptera | Geometridae |
| *Eupithecia spermaphaga* (Dyar) | fir cone looper | Lepidoptera | Geometridae |
| *Eupithecia transcanadata* MacK. | small conifer looper | Lepidoptera | Geometridae |
| *Euproctis chrysorrhoea* (L.) | browntail moth | Lepidoptera | Lymantriidae |
| *Eupsilia tristigmata* (Grt.) | brown fruitworm | Lepidoptera | Noctuidae |
| *Euptoieta claudia* (Cram.) | variegated fritillary | Lepidoptera | Nymphalidae |
| *Eurema lisa* Bdv. & LeC. | little sulphur | Lepidoptera | Pieridae |
| *Eurema nicippe* (Cram.) | sleepy orange | Lepidoptera | Pieridae |
| *Euschistus tristigmus* (Say) | dusky stink bug | Heteroptera | Pentatomidae |
| *Euschistus variolarius* (P. de B.) | onespotted stink bug | Heteroptera | Pentatomidae |
| *Eutrapela clemataria* (J. E. Smith) | purplishbrown looper | Lepidoptera | Geometridae |
| *Eutrombidium trigonum* (Herm.) | red grasshopper mite | Acari | Trombidiidae |
| *Euura atra* (Jur.) | smaller willow shoot sawfly | Hymenoptera | Tenthredinidae |
| *Euxoa auxiliaris* (Grt.) | army cutworm | Lepidoptera | Noctuidae |
| *Euxoa detersa* (Wlk.) | sand cutworm | Lepidoptera | Noctuidae |
| *Euxoa messoria* (Harr.) | darksided cutworm | Lepidoptera | Noctuidae |
| *Euxoa ochrogaster* (Gn.) | redbacked cutworm | Lepidoptera | Noctuidae |
| *Euxoa scandens* (Riley) | white cutworm | Lepidoptera | Noctuidae |
| *Euxoa tessellata* (Harr.) | striped cutworm | Lepidoptera | Noctuidae |
| *Euxoa tristicula* (Morr.) | early cutworm | Lepidoptera | Noctuidae |
| *Euzophera semifuneralis* (Wlk.) | American plum borer | Lepidoptera | Pyralidae |
| *Everes amyntula* (Bdv.) | western tailed blue | Lepidoptera | Lycaenidae |
| *Everes comyntas* (Godt.) | eastern tailed blue | Lepidoptera | Lycaenidae |
| *Evergestis pallidata* (Hufn.) | purplebacked cabbageworm | Lepidoptera | Pyralidae |
| *Evergestis rimosalis* (Gn.) | cross-striped cabbageworm | Lepidoptera | Pyralidae |
| *Evora hemidesma* (Zell.) | spirea leaftier | Lepidoptera | Tortricidae |
| *Exoteleia dodecella* (L.) | pine bud moth | Lepidoptera | Gelechiidae |
| *Exoteleia nepheos* Free. | pine candle moth | Lepidoptera | Gelechiidae |
| *Fannia canicularis* (L.) | little house fly | Diptera | Muscidae |
| *Fannia scalaris* (F.) | latrine fly | Diptera | Muscidae |
| *Faronta diffusa* (Wlk.) | wheat head armyworm | Lepidoptera | Noctuidae |
| *Felicola subrostratus* (Burm.) | cat louse | Mallophaga | Trichodectidae |
| *Feltia jaculifera* (Gn.) | dingy cutworm | Lepidoptera | Noctuidae |
| *Feniseca tarquinius* (F.) | harvester | Lepidoptera | Lycaenidae |

TABLE 3-continued

INSECTS SUBJECT TO CONTROL BY EMBODIMENTS OF THE INVENTION

| Scientific Name | English Common Name | Order | Family |
|---|---|---|---|
| *Fenusa dohrnii* (Tisch.) | European alder leafminer | Hymenoptera | Tenthredinidae |
| *Fenusa pusilla* (Lep.) | birch leafminer | Hymenoptera | Tenthredinidae |
| *Fidia viticida* Walsh | grape rootworm | Coleoptera | Chrysomelidae |
| *Fishia discors* (Grt.) | garden cutworm | Lepidoptera | Noctuidae |
| *Forficula auricularia* L. | European earwig | Dermaptera | Forficulidae |
| *Formica exsectoides* Forel | Allegheny mound ant | Hymenoptera | Formicidae |
| *Formica fusca* L. | silky ant | Hymenoptera | Formicidae |
| *Formica obscuripes* Forel | western thatching ant | Hymenoptera | Formicidae |
| *Frankliniella occidentalis* (Perg.) | western flower thrips | Thysanoptera | Thripidae |
| *Frankliniella tritici* (Fitch) | flower thrips | Thysanoptera | Thripidae |
| *Frankliniella vaccinii* Morg. | blueberry thrips | Thysanoptera | Thripidae |
| *Galeruca browni* Blake | peppergrass beetle | Coleoptera | Chrysomelidae |
| *Galerucella nymphaeae* (L.) | waterlily leaf beetle | Coleoptera | Chrysomelidae |
| *Galleria mellonella* (L.) | greater wax moth | Lepidoptera | Pyralidae |
| *Galleria mellonella* (L.) | waxworm | Lepidoptera | Pyralidae |
| *Gargaphia tiliae* (Walsh) | basswood lace bug | Heteroptera | Tingidae |
| *Gasterophilus haemorrhoidalis* (L.) | nose bot fly | Diptera | Oestridae |
| *Gasterophilus intestinalis* (DeG.) | horse bot fly | Diptera | Oestridae |
| *Gasterophilus nasalis* (L.) | throat bot fly | Diptera | Oestridae |
| *Gilpinia frutetorum* (F.) | nursery pine sawfly | Hymenoptera | Diprionidae |
| *Gilpinia hercyniae* (Htg.) | European spruce sawfly | Hymenoptera | Diprionidae |
| *Givira lotta* B.& McD. | pine carpenterworm | Lepidoptera | Cossidae |
| *Glaucopsyche lygdamus* (Dbly.) | silvery blue | Lepidoptera | Lycaenidae |
| *Glischrochilus quadrisignatus* (Say) | fourspotted sap beetle | Coleoptera | Nitidulidae |
| *Glycobius speciosus* (Say) | sugar maple borer | Coleoptera | Cerambycidae |
| *Glyphipteryx linneella* (Cl.) | linden bark borer | Lepidoptera | Glyphipterigidae |
| *Glyptoscelis pubescens* (F.) | hairy leaf beetle | Coleoptera | Chrysomelidae |
| *Gnatocerus cornutus* (F.) | broadhorned flour beetle | Coleoptera | Tenebrionidae |
| *Goes tesselatus* (Hald.) | oak sapling borer* | Coleoptera | Cerambycidae |
| *Gonioctena americana* (Schaeff.) | American aspen beetle | Coleoptera | Chrysomelidae |
| *Goniodes gigas* (Tasch.) | large chicken louse | Mallophaga | Philopteridae |
| *Gossyparia spuria* (Mod.) | European elm scale | Homoptera | Eriococcidae |
| *Grammia virguncula* (Kby.) | little virgin tiger moth | Lepidoptera | Arctiidae |
| *Grapholita interstinctana* (Clem.) | clover head caterpillar | Lepidoptera | Tortricidae |
| *Grapholita molesta* (Bsk.) | oriental fruit moth | Lepidoptera | Tortricidae |
| *Grapholita packardi* Zell. | cherry fruitworm | Lepidoptera | Tortricidae |
| *Grapholita prunivora* (Walsh) | lesser appleworm | Lepidoptera | Tortricidae |
| *Gretchena delicatana* Heinr. | ironwood fruitworm | Lepidoptera | Tortricidae |
| *Grylloprociphilus imbricator* (Fitch) | beech blight aphid | Homoptera | Aphididae |
| *Gryllus pennsylvanicus* Burm. | fall field cricket | Grylloptera | Gryllidae |
| *Gryllus veletis* (Alex. & Big.) | spring field cricket | Grylloptera | Gryllidae |
| *Gypsonoma haimbachiana* (Kft.) | cottonwood twig borer | Lepidoptera | Tortricidae |
| *Haemaphysalis chordeilis* (Pack.) | bird tick | Acari | Ixodidae |
| *Haemaphysalis leporispalustris* (Pack.) | rabbit tick | Acari | Ixodidae |
| *Haematobia irritans* (L.) | horn fly | Diptera | Muscidae |
| *Haematopinus asini* (L.) | horse sucking louse | Anoplura | Haematopinidae |
| *Haematopinus eurysternus* (Nitz.) | shortnosed cattle louse | Anoplura | Haematopinidae |
| *Haematopinus suis* (L.) | hog louse | Anoplura | Haematopinidae |
| *Haemodipsus ventricosus* (Denny) | rabbit louse | Anoplura | Hoplopleuridae |
| *Halysidota harrisii* Walsh | sycamore tussock moth | Lepidoptera | Arctiidae |
| *Halysidota tessellaris* (J. E. Smith) | pale tussock moth | Lepidoptera | Arctiidae |
| *Hamamelistes spinosus* Shimer | witch hazel gall aphid | Homoptera | Aphididae |
| *Haploa confusa* (Lyman) | Lyman haploa | Lepidoptera | Arctiidae |
| *Haploa lecontei* (G.-M.) | Leconte haploa | Lepidoptera | Arctiidae |
| *Haplothrips leucanthemi* Schr. | clover thrips | Thysanoptera | Phlaeothripidae |
| *Harkenclenus titus* (F.) | coral hairstreak | Lepidoptera | Lycaenidae |
| *Harrisimemna trisignata* (Wlk.) | Harris threespot | Lepidoptera | Zygaenidae |
| *Hedya nubiferana* (Haw.) | green budworm | Lepidoptera | Tortricidae |
| *Helicoverpa zea* (Boddie) | tomato fruitworm | Lepidoptera | Noctuidae |
| *Helicoverpa zea* (Boddie) | corn earworm | Lepidoptera | Noctuidae |
| *Heliothis ononis* (D. & S.) | flax bollworm | Lepidoptera | Noctuidae |

TABLE 3-continued

INSECTS SUBJECT TO CONTROL BY EMBODIMENTS OF THE INVENTION

| Scientific Name | English Common Name | Order | Family |
|---|---|---|---|
| *Heliothis virescens* (F.) | tobacco budworm | Lepidoptera | Noctuidae |
| *Heliothrips haemorrhoidalis* (Bouch,) | greenhouse thrips | Thysanoptera | Thripidae |
| *Hemaris diffinis* (Bdv.) | snowberry clearwing | Lepidoptera | Sphingidae |
| *Hemaris thysbe* (F.) | hummingbird moth | Lepidoptera | Sphingidae |
| *Hemichroa crocea* (Geoff.) | striped alder sawfly | Hymenoptera | Tenthredinidae |
| *Henricus fuscodorsanus* (Kft.) | cone cochylid | Lepidoptera | Cochylidae |
| *Hepialus gracilis* Grt. | graceful ghost moth | Lepidoptera | Hepialidae |
| *Hercinothrips femoralis* (Reut.) | banded greenhouse thrips | Thysanoptera | Thripidae |
| *Herculia thymetusalis* (Wlk.) | spruce needleworm | Lepidoptera | Pyralidae |
| *Hesperia comma borealis* Linds. | Labrador skipper | Lepidoptera | Hesperiidae |
| *Hesperia comma laurentina* (Lyman) | Laurentian skipper | Lepidoptera | Hesperiidae |
| *Heterarthrus nemoratus* (Fall.) | late birch leaf edgeminer | Hymenoptera | Tenthredinidae |
| *Heterocampa guttivitta* (Wlk.) | saddled prominent | Lepidoptera | Notodontidae |
| *Hippodamia convergens* G.-M. | convergent lady beetle | Coleoptera | Coccinellidae |
| *Hippodamia tredecimpunctata tibialis* (Say) | thirteenspotted lady beetle | Coleoptera | Coccinellidae |
| *Hofmannophila pseudospretella* (Staint.) | brown house moth | Lepidoptera | Oecophoridae |
| *Homadaula anisocentra* Meyr. | mimosa webworm | Lepidoptera | Plutellidae |
| *Homoeosoma electellum* (Hulst) | sunflower moth | Lepidoptera | Pyralidae |
| *Homoglaea hircina* Morr. | goat sallow | Lepidoptera | Noctuidae |
| *Homohadena badistriga* (Grt.) | honeysuckle budworm | Lepidoptera | Noctuidae |
| *Hoplocampa halcyon* (Nort.) | shadbush sawfly | Hymenoptera | Tenthredinidae |
| *Hoplocampa testudinea* (Klug) | European apple sawfly | Hymenoptera | Tenthredinidae |
| *Hyalophora cecropia* (L.) | cecropia moth | Lepidoptera | Saturniidae |
| *Hyalophora columbia* (S. I. Smith) | Columbian silk moth | Lepidoptera | Saturniidae |
| *Hyalophora columbia* (S. I. Smith) | larch silkworm | Lepidoptera | Saturniidae |
| *Hyalopterus pruni* (Geoff.) | mealy plum aphid | Homoptera | Aphididae |
| *Hydraecia immanis* Gn. | hop vine borer | Lepidoptera | Noctuidae |
| *Hydraecia micacea* (Esp.) | potato stem borer | Lepidoptera | Noctuidae |
| *Hydria prunivorata* (Fgn.) | cherry scallopshell moth | Lepidoptera | Geometridae |
| *Hydriomena divisaria* (Wlk.) | transversebanded looper | Lepidoptera | Geometridae |
| *Hylastinus obscurus* (Marsh.) | clover root borer | Coleoptera | Scolytidae |
| *Hyles gallii* (Rott.) | bedstraw hawkmoth | Lepidoptera | Sphingidae |
| *Hyles lineata* (F.) | whitelined sphinx | Lepidoptera | Sphingidae |
| *Hylesinus aculeatus* Say | eastern ash bark beetle | Coleoptera | Scolytidae |
| *Hylesinus californicus* (Swaine) | western ash bark beetle | Coleoptera | Scolytidae |
| *Hyllolycaena hyllus* (Cram.) | bronze copper | Lepidoptera | Lycaenidae |
| *Hylobius congener* D.T., S. & M. | seedling debarking weevil | Coleoptera | Curculionidae |
| *Hylobius pales* (Hbst.) | pales weevil | Coleoptera | Curculionidae |
| *Hylobius piceus* (DeG.) | large spruce weevil* | Coleoptera | Curculionidae |
| *Hylobius pinicola* (Couper) | Couper collar weevil | Coleoptera | Curculionidae |
| *Hylobius radicis* Buch. | pine root collar weevil | Coleoptera | Curculionidae |
| *Hylobius warreni* Wood | Warren root collar weevil | Coleoptera | Curculionidae |
| *Hylotrupes bajulus* (L.) | old house borer | Coleoptera | Cerambycidae |
| *Hylurgopinus rufipes* (Eichh.) | native elm bark beetle | Coleoptera | Scolytidae |
| *Hypagyrtis unipunctata* (Haw.) | onespotted variant | Lepidoptera | Geometridae |
| *Hypena scabra* (F.) | green cloverworm | Lepidoptera | Noctuidae |
| *Hypera meles* (F.) | clover head weevil | Coleoptera | Curculionidae |
| *Hypera nigrirostris* (F.) | lesser clover leaf weevil | Coleoptera | Curculionidae |
| *Hypera postica* (Gyll.) | alfalfa weevil | Coleoptera | Curculionidae |
| *Hypera punctata* (F.) | clover leaf weevil | Coleoptera | Curculionidae |
| *Hyphantria cunea* (Drury) | fall webworm | Lepidoptera | Arctiidae |
| *Hypnoidus abbreviatus* (Say) | abbreviated wireworm | Coleoptera | Elateridae |
| *Hypoderma bovis* (L.) | northern cattle grub | Diptera | Oestridae |
| *Hypoderma lineatum* (DeVill.) | common cattle grub | Diptera | Oestridae |
| *Hypoderma tarandi* (L.) | caribou warble fly | Diptera | Oestridae |
| *Hypogastrura nivicola* (Fitch) | snow flea | Collembola | Hypogastruridae |

TABLE 3-continued

INSECTS SUBJECT TO CONTROL BY EMBODIMENTS OF THE INVENTION

| Scientific Name | English Common Name | Order | Family |
| --- | --- | --- | --- |
| Hypoprepia fucosa Hbn. | painted lichen moth | Lepidoptera | Arctiidae |
| Hypoprepia miniata (Kby.) | scarletwinged lichen moth | Lepidoptera | Arctiidae |
| Hyppa xylinoides (Gn.) | cranberry cutworm | Lepidoptera | Noctuidae |
| Incisalia augustinus (Westw.) | brown elfin | Lepidoptera | Lycaenidae |
| Incisalia henrici (G. & R.) | Henry elfin | Lepidoptera | Lycaenidae |
| Incisalia irus (Godt.) | frosted elfin | Lepidoptera | Lycaenidae |
| Incisalia lanoraieensis Shep. | bog elfin | Lepidoptera | Lycaenidae |
| Incisalia niphon clarki Free. | pine elfin | Lepidoptera | Lycaenidae |
| Incisalia polia C. & W. | hoary elfin | Lepidoptera | Lycaenidae |
| Ipimorpha pleonectusa Grt. | blackcheeked aspen caterpillar | Lepidoptera | Noctuidae |
| Ips borealis Swaine | northern engraver | Coleoptera | Scolytidae |
| Ips calligraphus (Germ.) | coarsewriting engraver | Coleoptera | Scolytidae |
| Ips grandicollis (Eichh.) | southern pine engraver | Coleoptera | Scolytidae |
| Ips perturbatus (Eichh.) | northern spruce engraver | Coleoptera | Scolytidae |
| Ips pini (Say) | pine engraver | Coleoptera | Scolytidae |
| Isochnus rufipes (LeC.) | willow flea weevil | Coleoptera | Curculionidae |
| Itame loricaria (Evers.) | false bruce spanworm | Lepidoptera | Geometridae |
| Itame pustularia (Gn.) | lesser maple spanworm | Lepidoptera | Geometridae |
| Itame ribearia (Fitch) | currant spanworm | Lepidoptera | Geometridae |
| Ithycerus noveboracensis (Forst.) | New York weevil | Coleoptera | Ithyceridae |
| Ixodes pacificus Cooley & Kohls | western blacklegged tick | Acari | Ixodidae |
| Janus abbreviatus (Say) | willow shoot sawfly | Hymenoptera | Cephidae |
| Janus integer (Nort.) | currant stem girdler | Hymenoptera | Cephidae |
| Junonia coenia (Hbn.) | buckeye | Lepidoptera | Nymphalidae |
| Kaliofenusa ulmi (Sund.) | elm leafminer | Hymenoptera | Tenthredinidae |
| Kaltenbachiella ulmifusa (W. & R.) | elm pouchgall aphid | Homoptera | Aphididae |
| Kaltenbachiola canadensis (Felt) | spruce cone gall midge | Diptera | Cecidomyiidae |
| Kaltenbachiola rachiphaga (Tripp) | spruce cone axis midge | Diptera | Cecidomyiidae |
| Keiferia lycopersicella (Wlsm.) | tomato pinworm | Lepidoptera | Gelechiidae |
| Kleidocerys resedae geminatus Say | birch catkin bug | Heteroptera | Lygaeidae |
| Labidomera clivicollis (Kby.) | milkweed leaf beetle | Coleoptera | Chrysomelidae |
| Labops hesperius Uhl. | black grass bug | Heteroptera | Miridae |
| Lacinipolia meditata (Grt.) | pinkbacked cutworm | Lepidoptera | Noctuidae |
| Lacinipolia renigera (Steph.) | bristly cutworm | Lepidoptera | Noctuidae |
| Lambdina f. fiscellaria (Gn.) | hemlock looper | Lepidoptera | Geometridae |
| Lambdina fiscellaria lugubrosa (Hulst) | western hemlock looper | Lepidoptera | Geometridae |
| Lambdina fiscellaria somniaria (Hulst) | western oak looper | Lepidoptera | Geometridae |
| Lampronia rubiella (Bjerk.) | raspberry bud moth | Lepidoptera | Incurvariidae |
| Laothoe juglandis (J. E. Smith) | walnut sphinx | Lepidoptera | Sphingidae |
| Lapara bombycoides Wlk. | pine tree sphinx | Lepidoptera | Sphingidae |
| Lasioderma serricorne (F.) | cigarette beetle | Coleoptera | Anobiidae |
| Latheticus oryzae Waterh. | longheaded flour beetle | Coleoptera | Tenebrionidae |
| Lathridius minutus (L.) | squarenosed fungus beetle | Coleoptera | Lathridiidae |
| Latrodectus variolus Walck. | northern widow spider | Araneae | Theridiidae |
| Lema t. trilinea White | threelined potato beetle | Coleoptera | Chrysomelidae |
| Lepidosaphes ulmi (L.) | oystershell scale | Homoptera | Diaspididae |
| Lepisma saccharina L. | silverfish | Thysanura | Lepismatidae |
| Leptinotarsa decemlineata (Say) | Colorado potato beetle | Coleoptera | Chrysomelidae |
| Leptoglossus occidentalis Heid. | western conifer-seed bug | Heteroptera | Coreidae |
| Leptopterna dolabrata (L.) | meadow plant bug | Heteroptera | Miridae |
| Lepyrus nordenskioeldi canadensis Casey | poplar-willow leaf weevil | Coleoptera | Curculionidae |
| Lethocerus americanus (Leidy) | giant water bug | Heteroptera | Belostomatidae |
| Leucoma salicis (L.) | satin moth | Lepidoptera | Lymantriidae |
| Ligyrus gibbosus (DeG.) | carrot beetle | Coleoptera | Scarabaeidae |
| Lilioceris lilii (Scop.) | lily leaf beetle | Coleoptera | Chrysomelidae |

TABLE 3-continued

INSECTS SUBJECT TO CONTROL BY EMBODIMENTS OF THE INVENTION

| Scientific Name | English Common Name | Order | Family |
|---|---|---|---|
| *Limenitis a. arthemis* (Drury) | white admiral | Lepidoptera | Nymphalidae |
| *Limenitis archippus* (Cram.) | viceroy | Lepidoptera | Nymphalidae |
| *Limenitis arthemis astyanax* (F.) | redspotted purple | Lepidoptera | Nymphalidae |
| *Limonius agonus* (Say) | eastern field wireworm | Coleoptera | Elateridae |
| *Limonius californicus* (Man.) | sugarbeet wireworm | Coleoptera | Elateridae |
| *Limonius canus* LeC. | Pacific Coast wireworm | Coleoptera | Elateridae |
| *Limonius infuscatus* Mots. | western field wireworm | Coleoptera | Elateridae |
| *Limothrips denticornis* Hal. | barley thrips | Thysanoptera | Thripidae |
| *Linognathus ovillus* (Nm.) | sheep sucking louse | Anoplura | Linognathidae |
| *Linognathus pedalis* (Osb.) | sheep foot louse | Anoplura | Linognathidae |
| *Linognathus setosus* (Olf.) | dog sucking louse | Anoplura | Linognathidae |
| *Linognathus stenopsis* (Burm.) | goat sucking louse | Anoplura | Linognathidae |
| *Linognathus vituli* (L.) | longnosed cattle louse | Anoplura | Linognathidae |
| *Linsleya sphaericollis* (Say) | ash blister beetle | Coleoptera | Meloidae |
| *Lipaphis erysimi* (Kltb.) | turnip aphid | Homoptera | Aphididae |
| *Lipeurus caponis* (L.) | wing louse | Mallophaga | Philopteridae |
| *Liriomyza sativae* Blanch. | vegetable leafminer | Diptera | Agromyzidae |
| *Listronotus oregonensis* (LeC.) | carrot weevil | Coleoptera | Curculionidae |
| *Lithophane antennata* (Wlk.) | green fruitworm | Lepidoptera | Noctuidae |
| *Lixus concavus* Say | rhubarb curcuilo | Coleoptera | Curculionidae |
| *Lobophora nivigerata* Wlk. | twolined aspen looper | Lepidoptera | Geometridae |
| *Lochmaeus bilineata* (Pack.) | elm prominent | Lepidoptera | Notodontidae |
| *Lochmaeus manteo* Dbly. | variable oakleaf caterpillar | Lepidoptera | Notodontidae |
| *Lomographa semiclarata* (Wlk.) | wild cherry looper | Lepidoptera | Geometridae |
| *Lophocampa caryae* Harr. | hickory tussock moth | Lepidoptera | Arctiidae |
| *Lophocampa maculata* Harr. | spotted tussock moth | Lepidoptera | Arctiidae |
| *Loxostege cerealis* (Zell.) | alfalfa webworm | Lepidoptera | Pyralidae |
| *Loxostege sticticalis* (L.) | beet webworm | Lepidoptera | Pyralidae |
| *Lucilia sericata* (Meig.) | sheep blow fly | Diptera | Calliphoridae |
| *Lycaeides idas* (L.) | northern blue | Lepidoptera | Lycaenidae |
| *Lycaena dorcas* (Kby.) | dorcas copper | Lepidoptera | Lycaenidae |
| *Lycaena epixanthe* (Bdv. & LeC.) | bog copper | Lepidoptera | Lycaenidae |
| *Lycaena phlaeas americana* Harr. | American copper | Lepidoptera | Lycaenidae |
| *Lycia ursaria* (Wlk.) | stout spanworm | Lepidoptera | Geometridae |
| *Lyctus linearis* (Goeze) | cosmopolitan powderpost beetle | Coleoptera | Lyctidae |
| *Lyctus planicollis* LeC. | southern lyctus beetle | Coleoptera | Lyctidae |
| *Lygidea mendax* Reut. | apple red bug | Heteroptera | Miridae |
| *Lygocoris caryae* (Knight) | hickory plant bug | Heteroptera | Miridae |
| *Lygocoris communis* (Knight) | green apple bug | Heteroptera | Miridae |
| *Lygocoris communis* (Knight) | pear plant bug | Heteroptera | Miridae |
| *Lygocoris quercalbae* (Knight) | oak plant bug | Heteroptera | Miridae |
| *Lygus elisus* Van D. | lucerne plant bug | Heteroptera | Miridae |
| *Lygus elisus* Van D. | pale legume bug | Heteroptera | Miridae |
| *Lygus hesperus* Knight | western tarnished plant bug | Heteroptera | Miridae |
| *Lygus lineolaris* (P. de B.) | tarnished plant bug | Heteroptera | Miridae |
| *Lymantria dispar* (L.) | gypsy moth | Lepidoptera | Lymantriidae |
| *Lytta nuttalli* Say | Nuttall blister beetle | Coleoptera | Meloidae |
| *Macrodactylus subspinosus* (F.) | rose chafer | Coleoptera | Scarabaeidae |
| *Macronoctua onusta* Grt. | iris borer | Lepidoptera | Noctuidae |
| *Macropsis trimaculata* (Fitch) | plum leafhopper | Homoptera | Cicadellidae |
| *Macrosiphoniella sanborni* (Gill.) | chrysanthemum aphid | Homoptera | Aphididae |
| *Macrosiphum euphorbiae* (Thos.) | potato aphid | Homoptera | Aphididae |
| *Macrosiphum rosae* (L.) | rose aphid | Homoptera | Aphididae |
| *Macrosteles quadrilineatus* Fbs. | aster leafhopper | Homoptera | Cicadellidae |
| *Magdalis armicollis* (Say) | red elm bark weevil | Coleoptera | Curculionidae |
| *Magdalis barbita* (Say) | black elm bark weevil | Coleoptera | Curculionidae |
| *Magicicada septendecim* (L.) | periodical cicada | Homoptera | Cicadidae |
| *Malacosoma americanum* (F.) | eastern tent caterpillar | Lepidoptera | Lasiocampidae |
| *Malacosoma californicum lutescens* (N. & D.) | prairie tent caterpillar | Lepidoptera | Lasiocampidae |
| *Malacosoma californicum pluviale* (Dyar) | northern tent caterpillar | Lepidoptera | Lasiocampidae |
| *Malacosoma disstria* Hbn. | forest tent caterpillar | Lepidoptera | Lasiocampidae |
| *Mamestra configurata* Wlk. | bertha armyworm | Lepidoptera | Noctuidae |
| *Manduca quinquemaculata* (Haw.) | tomato hornworm | Lepidoptera | Sphingidae |
| *Manduca sexta* (L.) | tobacco hornworm | Lepidoptera | Sphingidae |
| *Mantis religiosa* L. | praying mantis | Mantodea | Mantidae |
| *Mantis religiosa* L. | European mantid | Mantodea | Mantidae |

TABLE 3-continued

INSECTS SUBJECT TO CONTROL BY EMBODIMENTS OF THE INVENTION

| Scientific Name | English Common Name | Order | Family |
|---|---|---|---|
| *Marmara elotella* (Bsk.) | apple barkminer | Lepidoptera | Gracillariidae |
| *Marmara fasciella* (Cham.) | white pine barkminer | Lepidoptera | Gracillariidae |
| *Marmara pomonella* Bsk. | apple fruitminer | Lepidoptera | Gracillariidae |
| *Matsucoccus macrocicatrices* Rich. | white pine fungus scale | Homoptera | Margarodidae |
| *Matsucoccus resinosae* B. & God. | red pine scale | Homoptera | Margarodidae |
| *Mayetiola carpophaga* (Tripp) | spruce seed midge | Diptera | Cecidomyiidae |
| *Mayetiola destructor* (Say) | Hessian fly | Diptera | Cecidomyiidae |
| *Mayetiola piceae* (Felt) | spruce gall midge | Diptera | Cecidomyiidae |
| *Mayetiola thujae* (Hed.) | western red cedar cone midge | Diptera | Cecidomyiidae |
| *Mecas confusa* C. & L. | poplar gall borer* | Coleoptera | Cerambycidae |
| *Megachile rotundata* (F.) | alfalfa leafcutting bee | Hymenoptera | Megachilidae |
| *Megacyllene robiniae* (Forst.) | locust borer | Coleoptera | Cerambycidae |
| *Megastigmus atedius* Wlk. | spruce seed chalcid | Hymenoptera | Torymidae |
| *Megastigmus laricis* Marc. | larch seed chalcid | Hymenoptera | Torymidae |
| *Megastigmus pinus* Parf. | fir seed chalcid | Hymenoptera | Torymidae |
| *Megastigmus specularis* Walley | balsam fir seed chalcid | Hymenoptera | Torymidae |
| *Megastigmus spermotrophus* Wachtl | Douglas-fir seed chalcid | Hymenoptera | Torymidae |
| *Megisto cymela* (Cram.) | little wood satyr | Lepidoptera | Satyridae |
| *Melanchra picta* (Harr.) | zebra caterpillar | Lepidoptera | Noctuidae |
| *Melanolophia canadaria* (Gn.) | variable redmarked looper | Lepidoptera | Geometridae |
| *Melanolophia imitata* (Wlk.) | greenstriped forest looper | Lepidoptera | Geometridae |
| *Melanophila acuminata* (DeG.) | black fire beetle | Coleoptera | Buprestidae |
| *Melanoplus bivittatus* (Say) | twostriped grasshopper | Orthoptera | Acrididae |
| *Melanoplus borealis* (Fieb.) | northern grasshopper | Orthoptera | Acrididae |
| *Melanoplus femurrubrum* (DeG.) | redlegged grasshopper | Orthoptera | Acrididae |
| *Melanoplus packardii* Scudd. | Packard grasshopper | Orthoptera | Acrididae |
| *Melanoplus sanguinipes* (F.) | migratory grasshopper | Orthoptera | Acrididae |
| *Melanoplus spretus* (Walsh) | Rocky Mountain grasshopper | Orthoptera | Acrididae |
| *Melittia cucurbitae* (Harr.) | squash vine borer | Lepidoptera | Sesiidae |
| *Meloe americanus* Leach | buttercup oil beetle | Coleoptera | Meloidae |
| *Melophagus ovinus* (L.) | sheep ked | Diptera | Hippoboscidae |
| *Menacanthus stramineus* (Nitz.) | chicken body louse | Mallophaga | Menoponidae |
| *Menopon gallinae* (L.) | shaft louse | Mallophaga | Menoponidae |
| *Merhynchites bicolor* (F.) | rose curculio | Coleoptera | Rhynchitidae |
| *Merodon equestris* (F.) | narcissus bulb fly | Diptera | Syrphidae |
| *Meromyza americana* Fitch | wheat stem maggot | Diptera | Chloropidae |
| *Meroptera pravella* (Grt.) | lesser aspen webworm | Lepidoptera | Pyralidae |
| *Mesolecanium nigrofasciatum* (Perg.) | terrapin scale | Homoptera | Coccidae |
| *Messa nana* (Klug) | early birch leaf edgeminer | Hymenoptera | Tenthredinidae |
| *Messa populifoliella* (Towns.) | poplar leafmining sawfly | Hymenoptera | Tenthredinidae |
| *Metopolophium dirhodum* (Wlk.) | rose-grass aphid | Homoptera | Aphididae |
| *Micrurapteryx salicifoliella* (Cham.) | willow leafminer | Coleoptera | Cerambycidae |
| *Mindarus abietinus* Koch | balsam twig aphid | Homoptera | Aphididae |
| *Monochamus marmorator* Kby. | balsam fir sawyer | Coleoptera | Cerambycidae |
| *Monochamus mutator* LeC. | spotted pine sawyer | Coleoptera | Cerambycidae |
| *Monochamus notatus* (Drury) | northeastern sawyer | Coleoptera | Cerambycidae |
| *Monochamus s. scutellatus* (Say) | whitespotted sawyer | Coleoptera | Cerambycidae |
| *Monochamus scutellatus oregonensis* (LeC.) | Oregon fir sawyer | Coleoptera | Cerambycidae |
| *Monochroa fragariae* (Bsk.) | strawberry crownminer | Lepidoptera | Gelechiidae |
| *Monoctenus fulvus* (Nort.) | cedar sawfly | Hymenoptera | Diprionidae |
| *Monoctenus suffusus* (Cress.) | arborvitae sawfly | Hymenoptera | Diprionidae |
| *Monomorium minimum* (Buckl.) | little black ant | Hymenoptera | Formicidae |
| *Monomorium pharaonis* (L.) | pharaoh ant | Hymenoptera | Formicidae |
| *Mononychus vulpeculus* (F.) | iris weevil | Coleoptera | Curculionidae |
| *Monophadnoides geniculatus* (Htg.) | raspberry sawfly | Hymenoptera | Tenthredinidae |
| *Mordwilkoja vagabunda* (Walsh) | poplar vagabond aphid | Homoptera | Aphididae |

TABLE 3-continued

INSECTS SUBJECT TO CONTROL BY EMBODIMENTS OF THE INVENTION

| Scientific Name | English Common Name | Order | Family |
|---|---|---|---|
| *Mulsantina picta* (Rand.) | pine lady beetle | Coleoptera | Coccinellidae |
| *Murgantia histrionica* (Hahn) | harlequin bug | Heteroptera | Pentatomidae |
| *Musca autumnalis* DeG. | face fly | Diptera | Muscidae |
| *Neodiprion pratti banksianae* Roh. | jack pine sawfly | Hymenoptera | Diprionidae |
| *Neodiprion rugifrons* Midd. | redheaded jack pine sawfly | Hymenoptera | Diprionidae |
| *Neodiprion sertifer* (Geoff.) | European pine sawfly | Hymenoptera | Diprionidae |
| *Neodiprion swainei* Midd. | Swaine jack pine sawfly | Hymenoptera | Diprionidae |
| *Neodiprion tsugae* Midd. | hemlock sawfly | Hymenoptera | Diprionidae |
| *Neohydatothrips tiliae* (Hood) | basswood thrips | Thysanoptera | Thripidae |
| *Neophasia menapia* (C. & R.F.) | pine white | Lepidoptera | Pieridae |
| *Nephelodes minians* Gn. | bronzed cutworm | Lepidoptera | Noctuidae |
| *Nephopterix subcaesiella* (Clem.) | locust leafroller | Lepidoptera | Pyralidae |
| *Nephopterix subfuscella* (Rag.) | striped sumac leafroller | Lepidoptera | Pyralidae |
| *Nepytia canosaria* (Wlk.) | false hemlock looper | Lepidoptera | Geometridae |
| *Nepytia freemani* Mun. | western false hemlock looper | Lepidoptera | Geometridae |
| *Nepytia phantasmaria* (Stkr.) | phantom hemlock looper | Lepidoptera | Geometridae |
| *Neurotoma inconspicua* (Nort.) | plum webspinning sawfly | Hymenoptera | Pamphiliidae |
| *Niptus hololeucus* (Fald.) | golden spider beetle | Coleoptera | Ptinidae |
| *Nites betulella* (Bsk.) | blackdotted birch leaftier | Lepidoptera | Oecophoridae |
| *Nites grotella* (Rob.) | hazel leaftier | Lepidoptera | Oecophoridae |
| *Nodonota puncticollis* (Say) | rose leaf beetle | Coleoptera | Chrysomelidae |
| *Nomia melanderi* Ckll. | alkali bee | Hymenoptera | Halictidae |
| *Nomius pygmaeus* (Dej.) | stink beetle | Coleoptera | Carabidae |
| *Nomophila nearctica* Mun. | celery stalkworm | Lepidoptera | Pyralidae |
| *Nosopsyllus fasciatus* (Bosc) | northern rat flea | Siphonaptera | Ceratophyllidae |
| *Nymphalis antiopa* (L.) | mourningcloak butterfly | Lepidoptera | Nymphalidae |
| *Nymphalis antiopa* (L.) | spiny elm caterpillar | Lepidoptera | Nymphalidae |
| *Nymphalis californica* (Bdv.) | California tortoiseshell | Lepidoptera | Nymphalidae |
| *Nymphalis vau-album* (D. & S.) | Compton tortoise-shell | Lepidoptera | Nymphalidae |
| *Nysius niger* Baker | northern false chinch bug | Heteroptera | Lygaeidae |
| *Oberea bimaculata* (Oliv.) | raspberry cane borer | Coleoptera | Cerambycidae |
| *Oberea schaumii* LeC. | poplar branch borer | Coleoptera | Cerambycidae |
| *Obolodiplosis robiniae* (Hald.) | locust gall midge | Diptera | Cecidomyiidae |
| *Obrussa ochrefasciella* (Cham.) | hard maple budminer | Lepidoptera | Nepticulidae |
| *Odontopus calceatus* (Say) | tuliptree leafminer | Coleoptera | Curculionidae |
| *Odontota dorsalis* (Thunb.) | locust leafminer | Coleoptera | Chrysomelidae |
| *Oecanthus fultoni* T. J. Wlk. | snowy tree cricket | Grylloptera | Gryllidae |
| *Oecanthus nigricornis* Wlk. | blackhorned tree cricket | Grylloptera | Gryllidae |
| *Oecanthus quadripunctatus* Beut. | fourspotted tree cricket | Grylloptera | Gryllidae |
| *Oeciacus vicarius* Horv. | swallow bug | Heteroptera | Cimicidae |
| *Oeneis chryxus* (Dbly. & Hew.) | chryxus arctic | Lepidoptera | Satyridae |
| *Oeneis jutta* (Hbn.) | jutta arctic | Lepidoptera | Satyridae |
| *Oeneis macounii* (Edw.) | Macoun arctic | Lepidoptera | Satyridae |
| *Oeneis polixenes* (F.) | polixenes arctic | Lepidoptera | Satyridae |
| *Oeneis taygete* Gey. | whiteveined arctic | Lepidoptera | Satyridae |
| *Oenensis melissa* (F.) | melissa arctic | Lepidoptera | Satyridae |
| *Oestrus ovis* L. | sheep bot fly | Diptera | Oestridae |
| *Olethreutes permundana* (Clem.) | raspberry leafroller | Lepidoptera | Tortricidae |
| *Oligocentria lignicolor* (Wlk.) | lacecapped caterpillar | Lepidoptera | Notodontidae |
| *Oligonychus pratensis* (Banks) | Banks grass mite | Acari | Tetranychidae |
| *Oligonychus ununguis* (Jac.) | spruce spider mite | Acari | Tetranychidae |
| *Omanodus floralis* (L.) | narrownecked grain beetle | Coleoptera | Anthicidae |
| *Omias saccatus* (LeC.) | sagebrush weevil | Coleoptera | Curculionidae |
| *Oncideres cingulata* (Say) | twig girdler | Coleoptera | Cerambycidae |
| *Oncopeltus fasciatus* (Dall.) | large milkweed bug | Heteroptera | Lygaeidae |
| *Operophtera bruceata* (Hulst) | Bruce spanworm | Lepidoptera | Geometridae |
| *Operophtera brumata* (L.) | winter moth | Lepidoptera | Geometridae |
| *Orgyia antiqua* (L.) | rusty tussock moth | Lepidoptera | Lymantriidae |
| *Orgyia leucostigma* (J. E. Smith) | whitemarked tussock moth | Lepidoptera | Lymantriidae |

TABLE 3-continued

INSECTS SUBJECT TO CONTROL BY EMBODIMENTS OF THE INVENTION

| Scientific Name | English Common Name | Order | Family |
|---|---|---|---|
| *Orgyia pseudotsugata* (McD.) | Douglas-fir tussock moth | Lepidoptera | Lymantriidae |
| *Ornithonyssus bacoti* (Hirst) | tropical rat mite | Acari | Macronyssidae |
| *Ornithonyssus sylviarum* (C. & F.) | northern fowl mite | Acari | Macronyssidae |
| *Ortholepis pasadamia* (Dyar) | striped birch pyralid | Lepidoptera | Pyralidae |
| *Orthosia hibisci* (Gn.) | speckled green fruitworm | Lepidoptera | Noctuidae |
| *Orthosia revicta* (Morr.) | rusty whitesided caterpillar | Lepidoptera | Noctuidae |
| *Oryzaephilus mercator* (Fauvel) | merchant grain beetle | Coleoptera | Cucujidae |
| *Oryzaephilus surinamensis* (L.) | sawtoothed grain beetle | Coleoptera | Cucujidae |
| *Oscinella frit* (L.) | frit fly | Diptera | Chloropidae |
| *Ostrinia nubilalis* (Hbn.) | European corn borer | Lepidoptera | Pyralidae |
| *Ostrinia obumbratalis* (Led.) | smartweed borer | Lepidoptera | Pyralidae |
| *Otiorhynchus ligustici* (L.) | alfalfa snout beetle | Coleoptera | Curculionidae |
| *Otiorhynchus ovatus* (L.) | strawberry root weevil | Coleoptera | Curculionidae |
| *Otiorhynchus rugosostriatus* (Goeze) | rough strawberry weevil | Coleoptera | Curculionidae |
| *Otiorhynchus sulcatus* (F.) | black vine weevil | Coleoptera | Curculionidae |
| *Otobius megnini* (Duges) | ear tick | Acari | Argasidae |
| *Otodectes cynotis* (Her.) | ear mite | Acari | Psoroptidae |
| *Oulema melanopus* (L.) | cereal leaf beetle | Coleoptera | Chrysomelidae |
| *Pachypsylla celtidismamma* (Fletcher) | hackberry nipplegall maker | Homoptera | Psyllidae |
| *Pachyrhinus ferrugineus* (Casey) | rusty pineneedle weevil | Coleoptera | Curculionidae |
| *Pachysphinx modesta* (Harr.) | big poplar sphinx | Lepidoptera | Sphingidae |
| *Paleacrita vernata* (Peck) | spring cankerworm | Lepidoptera | Geometridae |
| *Palorus ratzeburgii* (Wissm.) | smalleyed flour beetle | Coleoptera | Tenebrionidae |
| *Palorus subdepressus* (Woll.) | depressed flour beetle | Coleoptera | Tenebrionidae |
| *Palpita magniferalis* (Wlk.) | ash leafroller | Lepidoptera | Pyralidae |
| *Palthis angulalis* (Hbn.) | spruce harlequin | Lepidoptera | Noctuidae |
| *Pamphilius ochreipes* (Cress.) | viburnum webspinning sawfly | Hymenoptera | Pamphiliidae |
| *Pandemis canadana* Kft. | green aspen leaftier | Lepidoptera | Tortricidae |
| *Pandemis limitata* (Rob.) | threelined leafroller | Lepidoptera | Tortricidae |
| *Panonychus ulmi* (Koch) | European red mite | Acari | Tetranychidae |
| *Panthea acronyctoides* (Wlk.) | tufted spruce caterpillar | Lepidoptera | Noctuidae |
| *Panthea furcilla* (Pack.) | tufted white pine caterpillar | Lepidoptera | Noctuidae |
| *Paonias excaecatus* (J. E. Smith) | blindeyed sphinx | Lepidoptera | Sphingidae |
| *Paonias myops* (J. E. Smith) | smalleyed sphinx | Lepidoptera | Sphingidae |
| *Papaipema cataphracta* (Grt.) | burdock borer | Lepidoptera | Noctuidae |
| *Papaipema nebris* (Gn.) | stalk borer | Lepidoptera | Noctuidae |
| *Papilio brevicauda* Saund. | shorttailed swallowtail | Lepidoptera | Papilionidae |
| *Papilio canadensis* (R. & J.) | Canadian tiger swallowtail | Lepidoptera | Papilionidae |
| *Papilio cresphontes* Cram. | giant swallowtail | Lepidoptera | Papilionidae |
| *Papilio cresphontes* Cram. | orangedog | Lepidoptera | Papilionidae |
| *Papilio glaucus* L. | tiger swallowtail | Lepidoptera | Papilionidae |
| *Papilio polyxenes asterias* Stoll | parsleyworm | Lepidoptera | Papilionidae |
| *Papilio polyxenes asterias* Stoll | celeryworm | Lepidoptera | Papilionidae |
| *Papilio polyxenes asterias* Stoll | black swallowtail | Lepidoptera | Papilionidae |
| *Papilio troilus* L. | spicebush swallowtail | Lepidoptera | Papilionidae |
| *Paraclemensia acerifoliella* (Fitch) | maple leafcutter | Lepidoptera | Incurvariidae |
| *Paradiplosis tumifex* Gagn, | balsam gall midge | Diptera | Cecidomyiidae |
| *Paraleucoptera albella* (Cham.) | cottonwood leafminer | Lepidoptera | Lyonetiidae |
| *Parandra brunnea brunnea* (F.) | pole borer | Coleoptera | Cerambycidae |
| *Paraphytomyza populicola* (Wlk.) | Lombardy leafminer | Diptera | Agromyzidae |
| *Paraprociphilus tessellatus* (Fitch) | woolly alder aphid | Homoptera | Aphididae |
| *Paratrioza cockerelli* (Sulc) | tomato psyllid | Homoptera | Psyllidae |
| *Paratrioza cockerelli* (Sulc) | potato psyllid | Homoptera | Psyllidae |
| *Parcoblatta pennsylvanica* (DeG.) | Pennsylvania wood cockroach | Blattodea | Blattellidae |
| *Parectopa robiniella* Clem. | locust digitate leafminer | Lepidoptera | Gracillariidae |
| *Paria fragariae* Wilcox | strawberry rootworm | Coleoptera | Chrysomelidae |
| *Parornix geminatella* Pack. | unspotted tentiform leafminer | Lepidoptera | Gracillariidae |

TABLE 3-continued

INSECTS SUBJECT TO CONTROL BY EMBODIMENTS OF THE INVENTION

| Scientific Name | English Common Name | Order | Family |
|---|---|---|---|
| *Parthenolecanium corni* (Bouch.) | European fruit lecanium | Homoptera | Coccidae |
| *Parthenolecanium persicae* (F.) | European peach scale | Homoptera | Coccidae |
| *Parthenolecanium quercifex* (Fitch) | oak lecanium | Homoptera | Coccidae |
| *Pediculus humanus capitis* DeG. | head louse | Anoplura | Pediculidae |
| *Pediculus humanus humanus* L. | body louse | Anoplura | Pediculidae |
| *Pegomya hyoscyami* (Panz.) | spinach leafminer | Diptera | Anthomyiidae |
| *Pegomya rubivora* (Coq.) | raspberry cane maggot | Diptera | Anthomyiidae |
| *Pegomya* spp. | beet leafminer | Diptera | Anthomyiidae |
| *Pemphigus bursarius* (L.) | lettuce aphid | Homoptera | Aphididae |
| *Pemphigus populitransversus* Riley | poplar petiolegall aphid | Homoptera | Aphididae |
| *Pemphigus populivenae* Fitch | sugarbeet root aphid | Homoptera | Aphididae |
| *Pennisetia marginata* (Harr.) | raspberry crown borer | Lepidoptera | Sesiidae |
| *Peranabrus scabricollis* (Thos.) | coulee cricket | Grylloptera | Tettigoniidae |
| *Peridroma saucia* (Hbn.) | variegated cutworm | Lepidoptera | Noctuidae |
| *Perillus bioculatus* (F.) | twospotted stink bug | Heteroptera | Pentatomidae |
| *Periphyllus lyropictus* (Kess.) | Norway maple aphid | Homoptera | Aphididae |
| *Periphyllus negundinis* (Thos.) | boxelder aphid | Homoptera | Aphididae |
| *Periplaneta americana* (L.) | American cockroach | Blattodea | Blattidae |
| *Periplaneta australasiae* (F.) | Australian cockroach | Blattodea | Blattidae |
| *Periplaneta brunnea* Burm. | brown cockroach | Blattodea | Blattidae |
| *Petrobia latens* (Mull.) | brown wheat mite | Acari | Tetranychidae |
| *Petrova albicapitana* (Bsk.) | northern pitch twig moth | Lepidoptera | Tortricidae |
| *Petrova comstockiana* (Fern.) | pitch twig moth | Lepidoptera | Tortricidae |
| *Phenacoccus aceris* (Sign.) | apple mealybug | Homoptera | Pseudococcidae |
| *Phenacoccus gossypii* T. & C. | Mexican mealybug | Homoptera | Pseudococcidae |
| *Pheosia rimosa* Pack. | false hornworm | Lepidoptera | Notodontidae |
| *Phigalia titea* (Cram.) | spiny looper | Lepidoptera | Geometridae |
| *Philaenus spumarius* (L.) | meadow spittlebug | Homoptera | Cercopidae |
| *Phloeosinus canadensis* Swaine | northern cedar bark beetle | Coleoptera | Scolytidae |
| *Phloeosinus punctatus* LeC. | western cedar bark beetle | Coleoptera | Scolytidae |
| *Phloeotribus liminaris* (Harr.) | peach bark beetle | Coleoptera | Scolytidae |
| *Phobetron pithecium* (J. E. Smith) | hag moth | Lepidoptera | Limacodidae |
| *Pholisora catullus* (F.) | common sooty wing | Lepidoptera | Hesperiidae |
| *Phormia regina* (Meig.) | black blow fly | Diptera | Calliphoridae |
| *Phorodon humuli* (Schr.) | hop aphid | Homoptera | Aphididae |
| *Phragmatobia assimilans* Wlk. | dusky red tiger moth | Lepidoptera | Arctiidae |
| *Phragmatobia fuliginosa rubricosa* (Harr.) | ruby tiger moth | Lepidoptera | Arctiidae |
| *Phratora p. purpurea* Brown | aspen skeletonizer | Coleoptera | Chrysomelidae |
| *Phthorimaea operculella* (Zell.) | potato tuberworm | Lepidoptera | Gelechiidae |
| *Phyciodes batesii* (Reak.) | tawny crescent | Lepidoptera | Nymphalidae |
| *Phyciodes selenis* (Kby.) | northern pearl crescent | Lepidoptera | Nymphalidae |
| *Phyllobius intrusus* Kono | arborvitae weevil | Coleoptera | Curculionidae |
| *Phyllobius oblongus* (L.) | European snout beetle | Coleoptera | Curculionidae |
| *Phyllocnistis populiella* Cham. | aspen serpentine leafminer | Lepidoptera | Lyonetiidae |
| *Phyllocolpa bozemani* (Cooley) | poplar leaffolding sawfly | Hymenoptera | Tenthredinidae |
| *Phyllocolpa popuella* (Ross) | poplar edgefolding sawfly | Hymenoptera | Tenthredinidae |
| *Phyllodesma americana* (Harr.) | lappet moth | Lepidoptera | Lasiocampidae |
| *Phyllonorycter apparella* (H.-S.) | aspen leafblotch miner | Lepidoptera | Gracillariidae |
| *Phyllonorycter blancardella* (F.) | spotted tentiform leafminer | Lepidoptera | Gracillariidae |
| *Phyllonorycter crataegella* (Clem.) | apple blotch leafminer | Lepidoptera | Gracillariidae |
| *Phyllonorycter lucetiella* (Clem.) | basswood squareblotch miner | Lepidoptera | Gracillariidae |
| *Phyllonorycter lucidicostella* (Clem.) | lesser maple leafblotch miner | Lepidoptera | Gracillariidae |
| *Phyllonorycter nipigon* (Free.) | balsam poplar leafblotch miner | Lepidoptera | Gracillariidae |
| *Phyllonorycter populiella* (Cham.) | poplar leafminer | Lepidoptera | Gracillariidae |
| *Phyllonorycter propinquinella* (Braun) | cherry blotchminer | Lepidoptera | Gracillariidae |

TABLE 3-continued

INSECTS SUBJECT TO CONTROL BY EMBODIMENTS OF THE INVENTION

| Scientific Name | English Common Name | Order | Family |
|---|---|---|---|
| Phyllonorycter salicifoliella (Cham.) | willow leafblotch miner | Lepidoptera | Gracillariidae |
| Phyllonorycter tiliacella (Cham.) | basswood roundblotch miner | Lepidoptera | Gracillariidae |
| Phyllonorycter tremuloidiella (Braun) | aspen blotchminer | Lepidoptera | Gracillariidae |
| Phyllophaga fusca (Fro.) | northern June beetle | Coleoptera | Scarabaeidae |
| Phyllophaga futilis (LeC.) | lesser June beetle | Coleoptera | Scarabaeidae |
| Phyllophaga rugosa (Melsh.) | rugose June beetle | Coleoptera | Scarabaeidae |
| Phyllotreta albionica (LeC.) | cabbage flea beetle | Coleoptera | Chrysomelidae |
| Phyllotreta armoraciae (Koch) | horseradish flea beetle | Coleoptera | Chrysomelidae |
| Phyllotreta cruciferae (Goeze) | crucifer flea beetle | Coleoptera | Chrysomelidae |
| Phyllotreta pusilla Horn | western black flea beetle | Coleoptera | Chrysomelidae |
| Phyllotreta robusta LeC. | garden flea beetle | Coleoptera | Chrysomelidae |
| Phyllotreta striolata (F.) | striped flea beetle | Coleoptera | Chrysomelidae |
| Physokermes piceae (Schr.) | spruce bud scale | Homoptera | Coccidae |
| Phytobia amelanchieris (Greene) | amelanchier twig borer | Diptera | Agromyzidae |
| Phytobia betulivora Spencer | birch cambium miner | Diptera | Agromyzidae |
| Phytobia setosa (Loew) | red maple cambium borer | Diptera | Agromyzidae |
| Phytomyza ilicis Curt. | holly leafminer | Diptera | Agromyzidae |
| Phytonemus pallidus (Banks) | cyclamen mite | Acari | Tarsonemidae |
| Pieris napi (L.) | mustard white | Lepidoptera | Pieridae |
| Pieris rapae (L.) | cabbage butterfly | Lepidoptera | Pieridae |
| Pieris rapae (L.) | imported cabbageworm | Lepidoptera | Pieridae |
| Pieris virginiensis (Edw.) | West Virginia white | Lepidoptera | Pieridae |
| Pikonema alaskensis (Roh.) | yellowheaded spruce sawfly | Hymenoptera | Tenthredinidae |
| Pikonema dimmockii (Cress.) | greenheaded spruce sawfly | Hymenoptera | Tenthredinidae |
| Pineus floccus (Patch) | red spruce adelgid | Homoptera | Adelgidae |
| Pineus pinifoliae (Fitch) | pine leaf adelgid | Homoptera | Adelgidae |
| Pineus similis (Gill.) | ragged spruce gall adelgid | Homoptera | Adelgidae |
| Pineus strobi (Htg.) | pine bark adelgid | Homoptera | Adelgidae |
| Piophila casei (L.) | cheese skipper | Diptera | Piophilidae |
| Pissodes nemorensis Germ. | northern pine weevil | Coleoptera | Curculionidae |
| Pissodes rotundatus LeC. | small spruce weevil | Coleoptera | Curculionidae |
| Pissodes striatulus (F.) | balsam bark weevil | Coleoptera | Curculionidae |
| Pissodes strobi (Peck) | white pine weevil | Coleoptera | Curculionidae |
| Pissodes terminalis Hopping | lodgepole terminal weevil | Coleoptera | Curculionidae |
| Pityokteines sparsus (LeC.) | balsam fir bark beetle | Coleoptera | Scolytidae |
| Plagiodera versicolora (Laich.) | imported willow leaf beetle | Coleoptera | Chrysomelidae |
| Plagiognathus obscurus Uhl. | obscure plant bug | Heteroptera | Miridae |
| Planococcus citri (Risso) | citrus mealybug | Homoptera | Pseudococcidae |
| Platycotis vittata (F.) | oak treehopper | Homoptera | Membracidae |
| Plebejus saepiolus (Bdv.) | greenish blue | Lepidoptera | Lycaenidae |
| Pleroneura brunneicornis Roh. | balsam shootboring sawfly | Hymenoptera | Xyelidae |
| Plodia interpunctella (Hbn.) | Indianmeal moth | Lepidoptera | Pyralidae |
| Plutella xylostella (L.) | diamondback moth | Lepidoptera | Plutellidae |
| Pnyxia scabiei (Hopk.) | potato scab gnat | Diptera | Sciaridae |
| Poanes hobomok (Harr.) | Hobomok skipper | Lepidoptera | Hesperiidae |
| Poanes viator (Edw.) | broadwinged skipper | Lepidoptera | Hesperiidae |
| Pococera aplastella (Hulst) | aspen webworm | Lepidoptera | Pyralidae |
| Pococera asperatella (Clem.) | maple webworm | Lepidoptera | Pyralidae |
| Pococera expandens (Wlk.) | striped oak webworm | Lepidoptera | Pyralidae |
| Pococera militella (Zell.) | sycamore webworm | Lepidoptera | Pyralidae |
| Pococera robustella (Zell.) | pine webworm | Lepidoptera | Pyralidae |
| Podapion gallicola Riley | pine gall weevil | Coleoptera | Apionidae |
| Podisus maculiventris (Say) | spined soldier bug | Heteroptera | Pentatomidae |
| Podosesia syringae (Harr.) | lilac borer | Lepidoptera | Sesiidae |
| Podosesia syringae (Harr.) | ash borer | Lepidoptera | Sesiidae |
| Poecilocapsus lineatus (F.) | fourlined plant bug | Heteroptera | Miridae |
| Pogonomyrmex occidentalis (Cress.) | western harvester ant | Hymenoptera | Formicidae |
| Polites mystic (Edw.) | long dash | Lepidoptera | Hesperiidae |
| Polites peckius (Kby.) | Peck skipper | Lepidoptera | Hesperiidae |

TABLE 3-continued

INSECTS SUBJECT TO CONTROL BY EMBODIMENTS OF THE INVENTION

| Scientific Name | English Common Name | Order | Family |
|---|---|---|---|
| *Polites themistocles* (Latr.) | tawnyedged skipper | Lepidoptera | Hesperiidae |
| *Pollenia rudis* (F.) | cluster fly | Diptera | Calliphoridae |
| *Polychrysia moneta* (F.) | delphinium cutworm | Lepidoptera | Noctuidae |
| *Polydrusus impressifrons* (Gyll.) | pale green weevil | Coleoptera | Curculionidae |
| *Polygonia comma* (Harr.) | hop merchant | Lepidoptera | Nymphalidae |
| *Polygonia faunus* (Edw.) | green comma | Lepidoptera | Nymphalidae |
| *Polygonia gracilis* (G. & R.) | hoary comma | Lepidoptera | Nymphalidae |
| *Polygonia interrogationis* (F.) | question mark | Lepidoptera | Nymphalidae |
| *Polygonia progne* (Cram.) | gray comma | Lepidoptera | Nymphalidae |
| *Polygonia satyrus* (Edw.) | satyr anglewing | Lepidoptera | Nymphalidae |
| *Polygraphus rufipennis* (Kby.) | foureyed spruce bark beetle | Coleoptera | Scolytidae |
| *Polyphylla decemlineata* (Say) | tenlined June beetle | Coleoptera | Scarabaeidae |
| *Pontania proxima* (Lep.) | willow redgall sawfly | Hymenoptera | Tenthredinidae |
| *Pontania s-pomum* (Walsh) | willow applegall sawfly | Hymenoptera | Tenthredinidae |
| *Pontia occidentalis* (Reak.) | checkered white cabbageworm | Lepidoptera | Pieridae |
| *Pontia occidentalis* (Reak.) | western checkered white | Lepidoptera | Pieridae |
| *Pontia protodice* (Bdv. & LeC.) | checkered white | Lepidoptera | Pieridae |
| *Popillia japonica* Newm. | Japanese beetle | Coleoptera | Scarabaeidae |
| *Prionoxystus macmurtrei* (Guer.) | little carpenterworm | Lepidoptera | Cossidae |
| *Prionoxystus robiniae* (Peck) | carpenterworm | Lepidoptera | Cossidae |
| *Prionus laticollis* (Drury) | broadnecked root borer | Coleoptera | Cerambycidae |
| *Pristiphora erichsonii* (Htg.) | larch sawfly | Hymenoptera | Tenthredinidae |
| *Pristiphora geniculata* (Htg.) | mountain-ash sawfly | Hymenoptera | Tenthredinidae |
| *Pristiphora lena* Kinc. | little spruce sawfly | Hymenoptera | Tenthredinidae |
| *Probole amicaria* (H.-S.) | redcheeked looper | Lepidoptera | Geometridae |
| *Prochoerodes transversata* (Drury) | large maple spanworm | Lepidoptera | Geometridae |
| *Prodiplosis morrisi* Gagn, | leafcurl midge | Diptera | Cecidomyiidae |
| *Profenusa canadensis* (Marl.) | hawthorn leafmining sawfly | Hymenoptera | Tenthredinidae |
| *Profenusa lucifex* (Ross) | oak leafmining sawfly | Hymenoptera | Tenthredinidae |
| *Profenusa thomsoni* (Konow) | ambermarked birch leafminer | Hymenoptera | Tenthredinidae |
| *Proserpinus flavofasciata* (Wlk.) | yellowbanded day sphinx | Lepidoptera | Sphingidae |
| *Proteoteras aesculana* Riley | maple twig borer | Lepidoptera | Tortricidae |
| *Proteoteras moffatiana* Fern. | maple shoot borer | Lepidoptera | Tortricidae |
| *Proteoteras willingana* (Kft.) | boxelder twig borer | Lepidoptera | Tortricidae |
| *Protoboarmia porcelaria indictaria* (Wlk.) | dashlined looper | Lepidoptera | Geometridae |
| *Protophormia terraenovae* (Rob.-Desv.) | northern blow fly | Diptera | Calliphoridae |
| *Pseudaletia unipuncta* (Haw.) | armyworm | Lepidoptera | Noctuidae |
| *Pseudexentera cressoniana* (Clem.) | oak olethreutid leafroller | Lepidoptera | Tortricidae |
| *Pseudexentera mali* Free. | pale apple leafroller | Lepidoptera | Tortricidae |
| *Pseudococcus comstocki* (Kuw.) | Comstock mealybug | Homoptera | Pseudococcidae |
| *Pseudococcus longispinus* (Targ.) | longtailed mealybug | Homoptera | Pseudococcidae |
| *Pseudococcus maritimus* (Ehrh.) | grape mealybug | Homoptera | Pseudococcidae |
| *Pseudopityophthorus minutissimus* (Zimm.) | oak bark beetle | Coleoptera | Scolytidae |
| *Pseudopityophthorus pubipennis* (LeC.) | western oak bark beetle | Coleoptera | Scolytidae |
| *Pseudosciaphila duplex* (Wlsm.) | poplar leafroller | Lepidoptera | Tortricidae |
| *Psila rosae* (F.) | carrot rust fly | Diptera | Psilidae |
| *Psilocorsis cryptolechiella* (Cham.) | twoleaf tier | Lepidoptera | Oecophoridae |
| *Psilocorsis quercicella* Clem. | oak leaftier | Lepidoptera | Oecophoridae |
| *Psilocorsis reflexella* Clem. | flat leaftier | Lepidoptera | Oecophoridae |
| *Psinidia f. fenestralis* (Aud.-Serv.) | longhorned grasshopper | Orthoptera | Acrididae |
| *Psoroptes equi* (Rasp.) | scab mite | Acari | Psoroptidae |
| *Psoroptes ovis* (Her.) | sheep scab mite | Acari | Psoroptidae |
| *Psorosina hammondi* (Riley) | appleleaf skeletonizer | Lepidoptera | Pyralidae |
| *Psylla striata* Patch | birch psyllid | Homoptera | Psyllidae |
| *Psylliodes punctulata* Melsh. | hop flea beetle | Coleoptera | Chrysomelidae |
| *Pterocomma smithiae* (Monell) | black willow aphid | Homoptera | Aphididae |
| *Pthirus pubis* (L.) | crab louse | Anoplura | Pediculidae |
| *Ptinus clavipes* Panz. | brown spider beetle | Coleoptera | Ptinidae |

TABLE 3-continued

INSECTS SUBJECT TO CONTROL BY EMBODIMENTS OF THE INVENTION

| Scientific Name | English Common Name | Order | Family |
|---|---|---|---|
| *Ptinus fur* (L.) | whitemarked spider beetle | Coleoptera | Ptinidae |
| *Ptinus ocellus* Brown | Australian spider beetle | Coleoptera | Ptinidae |
| *Ptinus raptor* Sturm | eastern spider beetle | Coleoptera | Ptinidae |
| *Ptinus villiger* (Reitter) | hairy spider beetle | Coleoptera | Ptinidae |
| *Ptycholoma peritana* (Clem.) | garden tortrix | Lepidoptera | Tortricidae |
| *Pulex irritans* (L.) | human flea | Siphonaptera | Pulicidae |
| *Pulvinaria amygdali* Ckll. | cottony peach scale | Homoptera | Coccidae |
| *Pulvinaria innumerabilis* (Rathv.) | cottony maple scale | Homoptera | Coccidae |
| *Puto cupressi* (Colm.) | fir mealybug | Homoptera | Pseudococcidae |
| *Puto sandini* Wash. | spruce mealybug | Homoptera | Pseudococcidae |
| *Pyemotes tritici* (L.-F. & M.) | straw itch mite | Acari | Pyemotidae |
| *Pyralis farinalis* L. | meal moth | Lepidoptera | Pyralidae |
| *Pyrgus centaureae* (Rambur) | grizzled skipper | Lepidoptera | Hesperiidae |
| *Pyrrharctia isabella* (J. E. Smith) | banded woollybear | Lepidoptera | Arctiidae |
| *Pyrrhia umbra* (Hufn.) | rose budworm | Lepidoptera | Noctuidae |
| *Quadraspidiotus juglandsregiae* (Comst.) | walnut scale | Homoptera | Diaspididae |
| *Quadraspidiotus ostreaeformis* (Curt.) | European fruit scale | Homoptera | Diaspididae |
| *Quadraspidiotus perniciosus* (Comst.) | San Jose scale | Homoptera | Diaspididae |
| *Rabdophaga rigidae* (O.S.) | willow beakedgall midge | Diptera | Cecidomyiidae |
| *Rabdophaga salicisbatatas* (O.S.) | willow potatogall midge | Diptera | Cecidomyiidae |
| *Rabdophaga salicisbrassicoides* (Pack.) | willow cabbagegall midge | Diptera | Cecidomyiidae |
| *Rabdophaga strobiloides* (O.S.) | willow pinecone gall midge | Diptera | Cecidomyiidae |
| *Raphia frater* Grt. | yellowmarked caterpillar | Lepidoptera | Noctuidae |
| *Recurvaria nanella* (D. & S.) | lesser bud moth | Lepidoptera | Gelechiidae |
| *Reduvius personatus* (L.) | masked hunter | Heteroptera | Reduviidae |
| *Reticulitermes flavipes* (Koll.) | eastern subterranean termite | Isoptera | Rhinotermitidae |
| *Reticulitermes hesperus* Banks | western subterranean termite | Isoptera | Rhinotermitidae |
| *Rhabdopterus picipes* (Oliv.) | cranberry rootworm | Coleoptera | Chrysomelidae |
| *Rhagoletis cingulata* (Loew) | cherry fruit fly | Diptera | Tephritidae |
| *Rhagoletis cingulata* (Loew) | cherry maggot | Diptera | Tephritidae |
| *Rhagoletis completa* Cress. | husk maggot | Diptera | Tephritidae |
| *Rhagoletis completa* Cress. | walnut husk fly | Diptera | Tephritidae |
| *Rhagoletis fausta* (O.S.) | black cherry fruit fly | Diptera | Tephritidae |
| *Rhagoletis indifferens* Curran | western cherry fruit fly | Diptera | Tephritidae |
| *Rhagoletis mendax* Curran | blueberry maggot | Diptera | Tephritidae |
| *Rhagoletis pomonella* (Walsh) | apple maggot | Diptera | Tephritidae |
| *Rhaxonycha carolina* (F.) | Carolina cantharid | Coleoptera | Cantharidae |
| *Rheumaptera hastata* (L.) | spearmarked black moth | Lepidoptera | Geometridae |
| *Rhipicephalus sanguineus* (Latr.) | brown dog tick | Acari | Ixodidae |
| *Rhizoglyphus echinopus* (F. & R.) | bulb mite | Acari | Acaridae |
| *Rhopalomyia chrysanthemi* (Ahlb.) | chrysanthemum gall midge | Diptera | Cecidomyiidae |
| *Rhopalosiphum fitchii* (Sand.) | apple grain aphid | Homoptera | Aphididae |
| *Rhopalosiphum maidis* (Fitch) | corn leaf aphid | Homoptera | Aphididae |
| *Rhopalosiphum padi* (L.) | oat-birdcherry aphid | Homoptera | Aphididae |
| *Rhopobota naevana* (Hbn.) | blackheaded fireworm | Lepidoptera | Tortricidae |
| *Rhyacionia buoliana* (D. & S.) | European pine shoot moth | Lepidoptera | Tortricidae |
| *Rhyacionia busckana* Heinr. | red pine shoot borer | Lepidoptera | Tortricidae |
| *Rhyacionia frustrana* (Comst.) | Nantucket pine tip moth | Lepidoptera | Tortricidae |
| *Rhyacionia granti* Miller | jack pine shoot borer | Lepidoptera | Tortricidae |
| *Rhyacionia rigidana* (Fern.) | pitch pine tip moth | Lepidoptera | Tortricidae |
| *Rhyacionia sonia* Miller | yellow jack pine shoot borer | Lepidoptera | Tortricidae |
| *Rhynchaenus pallicornis* (Say) | apple flea weevil | Coleoptera | Curculionidae |
| *Rhynchaenus testaceus* (Mull.) | birch and alder flea weevil | Coleoptera | Curculionidae |
| *Rhyzopertha dominica* (F.) | lesser grain borer | Coleoptera | Bostrichidae |
| *Ribautiana tenerrima* (H.-S.) | bramble leafhopper | Homoptera | Cicadellidae |

TABLE 3-continued

INSECTS SUBJECT TO CONTROL BY EMBODIMENTS OF THE INVENTION

| Scientific Name | English Common Name | Order | Family |
| --- | --- | --- | --- |
| *Saissetia coffeae* (Wlk.) | hemispherical scale | Homoptera | Coccidae |
| *Saperda calcarata* Say | poplar borer | Coleoptera | Cerambycidae |
| *Saperda candida* F. | Saskatoon borer | Coleoptera | Cerambycidae |
| *Saperda candida* F. | roundheaded appletree borer | Coleoptera | Cerambycidae |
| *Saperda tridentata* Oliv. | elm borer | Coleoptera | Cerambycidae |
| *Saperda vestita* Say | linden borer | Coleoptera | Cerambycidae |
| *Sarcophaga aldrichi* Park. | large flesh fly | Diptera | Sarcophagidae |
| *Sarcoptes scabiei* (DeG.) | itch mite | Acari | Sarcoptidae |
| *Satyrium acadicum* (Edw.) | Acadian hairstreak | Lepidoptera | Lycaenidae |
| *Satyrium calanus* (Hbn.) | banded hairstreak | Lepidoptera | Lycaenidae |
| *Satyrium caryaevorum* (McD.) | hickory hairstreak | Lepidoptera | Lycaenidae |
| *Satyrium edwardsii* (G. & R.) | Edwards hairstreak | Lepidoptera | Lycaenidae |
| *Satyrium liparops* (LeC.) | striped hairstreak | Lepidoptera | Lycaenidae |
| *Satyrodes eurydice* (Johan.) | eyed brown | Lepidoptera | Satyridae |
| *Schinia florida* (Gn.) | primrose moth | Lepidoptera | Noctuidae |
| *Schizaphis graminum* (Rond.) | greenbug | Homoptera | Aphididae |
| *Schizolachnus piniradiatae* (Dav.) | woolly pineneedle aphid | Homoptera | Aphididae |
| *Schizura concinna* (J. E. Smith) | redhumped caterpillar | Lepidoptera | Notodontidae |
| *Schizura ipomoeae* Dbly. | oak-maple humped caterpillar | Lepidoptera | Notodontidae |
| *Schizura unicorns* (J. E. Smith) | unicorn caterpillar | Lepidoptera | Notodontidae |
| *Sciopithes obscurus* Horn | obscure root weevil | Coleoptera | Curculionidae |
| *Scoliopteryx libatrix* (L.) | herald moth | Lepidoptera | Noctuidae |
| *Scolytus mali* (Bech.) | larger shothole borer | Coleoptera | Scolytidae |
| *Scolytus multistriatus* (Marsh.) | European elm bark beetle | Coleoptera | Scolytidae |
| *Scolytus quadrispinosus* Say | hickory bark beetle | Coleoptera | Scolytidae |
| *Scolytus rugulosus* (Mull.) | shothole borer | Coleoptera | Scolytidae |
| *Scolytus tsugae* (Swaine) | hemlock engraver | Coleoptera | Scolytidae |
| *Scolytus unispinosus* LeC. | Douglas-fir engraver | Coleoptera | Scolytidae |
| *Scolytus ventralis* LeC. | fir engraver | Coleoptera | Scolytidae |
| *Scudderia furcata* B. von W. | forktailed bush katydid | Grylloptera | Tettigoniidae |
| *Scutigerella immaculata* (Newp.) | garden symphylan | Symphyla | Scutigerellidae |
| *Semanotus ligneus* (F.) | cedartree borer | Coleoptera | Cerambycidae |
| *Semanotus litigiosus* (Casey) | firtree borer | Coleoptera | Cerambycidae |
| *Semiothisa granitata* (Gn.) | green spruce looper | Lepidoptera | Geometridae |
| *Semiothisa ocellinata* (Gn.) | locust looper | Lepidoptera | Geometridae |
| *Semiothisa sexmaculata* (Pack.) | green larch looper | Lepidoptera | Geometridae |
| *Semiothisa signaria dispuncta* (Wlk.) | spruce-fir looper | Lepidoptera | Geometridae |
| *Sesia tibialis* (Harr.) | cottonwood crown borer | Lepidoptera | Sesiidae |
| *Setoptus jonesi* (Keif.) | red pine needle mite | Acari | Phytoptidae |
| *Sicya macularia* (Harr.) | twopronged looper | Lepidoptera | Geometridae |
| *Simulium arcticum* Malloch | northern black fly | Diptera | Simuliidae |
| *Simulium venustum* Say | whitestockinged black fly | Diptera | Simuliidae |
| *Simulium vittatum* Zett. | striped black fly | Diptera | Simuliidae |
| *Sinea diadema* (F.) | spined assassin bug | Heteroptera | Reduviidae |
| *Sirex cyaneus* F. | blue horntail | Hymenoptera | Siricidae |
| *Sirex juvencus juvencus* (L.) | European blue horntail | Hymenoptera | Siricidae |
| *Sitobion avenae* (F.) | English grain aphid | Homoptera | Aphididae |
| *Sitodiplosis mosellana* (Gehin) | wheat midge | Diptera | Cecidomyiidae |
| *Sitona cylindricollis* (Fahr.) | sweetclover weevil | Coleoptera | Curculionidae |
| *Sitona hispidulus* (F.) | clover root curculio | Coleoptera | Curculionidae |
| *Sitona lineatus* (L.) | pea leaf weevil | Coleoptera | Curculionidae |
| *Sitophilus granarius* (L.) | granary weevil | Coleoptera | Curculionidae |
| *Sitophilus oryzae* (L.) | rice weevil | Coleoptera | Curculionidae |
| *Sitotroga cerealella* (Oliv.) | Angoumois grain moth | Lepidoptera | Gelechiidae |
| *Smerinthus cerisyi* Kby. | willow sphinx | Lepidoptera | Sphingidae |
| *Smerinthus jamaicensis* (Drury) | twinspot sphinx | Lepidoptera | Sphingidae |
| *Solenopsis molesta* (Say) | thief ant | Hymenoptera | Formicidae |
| *Solenoptes capillatus* End. | little blue cattle louse | Anoplura | Linognathidae |
| *Spaelotis clandestina* (Harr.) | w-marked cutworm | Lepidoptera | Noctuidae |
| *Spaelotis havilae* (Grt.) | western w-marked cutworm | Lepidoptera | Noctuidae |
| *Sparganothis acerivorana* MacK. | maple leafroller | Lepidoptera | Tortricidae |
| *Sparganothis directana* (Wlk.) | chokecherry leafroller | Lepidoptera | Tortricidae |

TABLE 3-continued

INSECTS SUBJECT TO CONTROL BY EMBODIMENTS OF THE INVENTION

| Scientific Name | English Common Name | Order | Family |
|---|---|---|---|
| *Sparganothis pettitana* (Rob.) | maple-basswood leafroller | Lepidoptera | Tortricidae |
| *Speyeria aphrodite* (F.) | aphrodite fritillary | Lepidoptera | Nymphalidae |
| *Speyeria atlantis* (Edw.) | Atlantis fritillary | Lepidoptera | Nymphalidae |
| *Speyeria cybele* (F.) | great spangled fritillary | Lepidoptera | Nymphalidae |
| *Sphaerolecanium prunastri* (Fonsc.) | globose scale | Homoptera | Coccidae |
| *Spharagemon collare* (Scudd.) | mottled sand grasshopper | Orthoptera | Acrididae |
| *Sphinx canadensis* Bdv. | northern ash sphinx | Lepidoptera | Sphingidae |
| *Sphinx chersis* (Hbn.) | great ash sphinx | Lepidoptera | Sphingidae |
| *Sphinx drupiferarum* J. E. Smith | wild cherry sphinx | Lepidoptera | Sphingidae |
| *Sphinx drupiferarum* J. E. Smith | plum sphinx | Lepidoptera | Sphingidae |
| *Sphinx eremitus* (Hbn.) | hermit sphinx | Lepidoptera | Sphingidae |
| *Sphinx gordius* Cram. | apple sphinx | Lepidoptera | Sphingidae |
| *Sphinx kalmiae* J. E. Smith | laurel sphinx | Lepidoptera | Sphingidae |
| *Sphinx luscitiosa* Clem. | poplar-and-willow sphinx | Lepidoptera | Sphingidae |
| *Sphinx vashti* Stkr. | snowberry sphinx | Lepidoptera | Sphingidae |
| *Spilonota ocellana* (D. & S.) | eyespotted bud moth | Lepidoptera | Tortricidae |
| *Spilosoma virginica* (F.) | yellow woollybear | Lepidoptera | Arctiidae |
| *Spodoptera exigua* (Hbn.) | beet armyworm | Lepidoptera | Noctuidae |
| *Spodoptera frugiperda* (J. E. Smith) | fall armyworm | Lepidoptera | Noctuidae |
| *Spodoptera ornithogalli* (Gn.) | yellowstriped armyworm | Lepidoptera | Noctuidae |
| *Spodoptera praefica* (Grt.) | western yellowstriped armyworm | Lepidoptera | Noctuidae |
| *Stegobium paniceum* (L.) | drugstore beetle | Coleoptera | Anobiidae |
| *Stenolophus lecontei* (Chaud.) | seedcorn beetle | Coleoptera | Carabidae |
| *Steremnius carinatus* (Boh.) | conifer seedling weevil | Coleoptera | Curculionidae |
| *Stethophyma lineatum* (Scudd.) | striped sedge grasshopper | Orthoptera | Acrididae |
| *Sthenopis argenteomaculatus* (Harr.) | alder root borer | Lepidoptera | Hepialidae |
| *Stictocephala bisonia* K. & Y. | buffalo treehopper | Homoptera | Membracidae |
| *Stictoleptura canadensis* Oliv. | redshouldered pine borer | Coleoptera | Cerambycidae |
| *Stilbosis ostryaeella* (Cham.) | ironwood leafminer | Lepidoptera | Cosmopterigidae |
| *Stomoxys calcitrans* (L.) | stable fly | Diptera | Muscidae |
| *Strauzia longipennis* (Wied.) | sunflower maggot | Diptera | Tephritidae |
| *Strobilomyia appalachensis* Michelsen | black spruce cone maggot | Diptera | Anthomyiidae |
| *Strobilomyia laricis* Michelsen | larch cone maggot | Diptera | Anthomyiidae |
| *Strobilomyia neanthracina* Michelsen | white spruce cone maggot | Diptera | Anthomyiidae |
| *Strobilomyia varia* (Huckett) | tamarack cone maggot | Diptera | Anthomyiidae |
| *Strymon melinus* Hbn. | gray hairstreak | Lepidoptera | Lycaenidae |
| *Supella longipalpa* (F.) | brownbanded cockroach | Blattodea | Blattellidae |
| *Symmerista albifrons* (J. E. Smith) | orangehumped oakworm | Lepidoptera | Notodontidae |
| *Symmerista canicosta* Franc. | redhumped oakworm | Lepidoptera | Notodontidae |
| *Symmerista leucitys* Franc. | orangehumped mapleworm | Lepidoptera | Notodontidae |
| *Symydobius americanus* Baker | dark birch aphid | Homoptera | Aphididae |
| *Synanthedon acerni* (Clem.) | maple callus borer | Lepidoptera | Sesiidae |
| *Synanthedon albicornis* (Hy.Edw.) | willow stem borer | Lepidoptera | Sesiidae |
| *Synanthedon bibionipennis* (Bdv.) | strawberry crown moth | Lepidoptera | Sesiidae |
| *Synanthedon decipiens* (Hy.Edw.) | oak gall borer | Lepidoptera | Sesiidae |
| *Synanthedon exitiosa* (Say) | peachtree borer | Lepidoptera | Sesiidae |
| *Synanthedon pictipes* (G. & R.) | lesser peachtree borer | Lepidoptera | Sesiidae |
| *Synanthedon pini* (Kell.) | pitch mass borer | Lepidoptera | Sesiidae |
| *Synanthedon pyri* (Harr.) | apple bark borer | Lepidoptera | Sesiidae |
| *Synanthedon scitula* (Harr.) | dogwood borer | Lepidoptera | Sesiidae |
| *Synanthedon sequoiae* (Hy.Edw.) | sequoia pitch moth | Lepidoptera | Sesiidae |
| *Synanthedon tipuliformis* (Cl.) | currant borer | Lepidoptera | Sesiidae |
| *Syneta ferruginea* (Germ.) | rusty leaf beetle | Coleoptera | Chrysomelidae |
| *Syngrapha alias* (Ottol.) | spruce climbing cutworm | Lepidoptera | Noctuidae |

TABLE 3-continued

INSECTS SUBJECT TO CONTROL BY EMBODIMENTS OF THE INVENTION

| Scientific Name | English Common Name | Order | Family |
|---|---|---|---|
| *Syngrapha rectangula* (Kby.) | angulated cutworm | Lepidoptera | Noctuidae |
| *Syngrapha selecta* (Wlk.) | spruce false looper | Lepidoptera | Noctuidae |
| *Systena blanda* (Melsh.) | palestriped flea beetle | Coleoptera | Chrysomelidae |
| *Systena frontalis* (F.) | redheaded flea beetle | Coleoptera | Chrysomelidae |
| *Tabanus lineola* F. | striped horse fly | Diptera | Tabanidae |
| *Tachycines asynamorus* Adel. | greenhouse stone cricket | Grylloptera | Gryllacrididae |
| *Taeniothrips inconsequens* (Uzel) | pear thrips | Thysanoptera | Thripidae |
| *Tapinoma sessile* (Say) | odorous house ant | Hymenoptera | Formicidae |
| *Tarsonemus granarius* Lindquist | glossy grain mite | Acari | Tarsonemidae |
| *Telamona tremulata* Ball | aspen treehopper | Homoptera | Membracidae |
| *Tenebrio molitor* L. | yellow mealworm | Coleoptera | Tenebrionidae |
| *Tenebrio obscurus* F. | dark mealworm | Coleoptera | Tenebrionidae |
| *Tenebroides mauritanicus* (L.) | cadelle | Coleoptera | Trogositidae |
| *Tenodera aridifolia sinensis* Sauss. | Chinese mantid | Mantodea | Mantidae |
| *Tetanops myopaeformis* (Roder) | sugarbeet root maggot | Diptera | Otitidae |
| *Tethida cordigera* (Beauv.) | blackheaded ash sawfly | Hymenoptera | Tenthredinidae |
| *Tetramesa hordei* (Harr.) | barley jointworm | Hymenoptera | Eurytomidae |
| *Tetramesa secale* (Fitch) | rye jointworm | Hymenoptera | Eurytomidae |
| *Tetramesa tritici* (Fitch) | wheat jointworm | Hymenoptera | Eurytomidae |
| *Tetranychus canadensis* (McG.) | fourspotted spider mite | Acari | Tetranychidae |
| *Tetranychus mcdanieli* McG. | McDaniel spider mite | Acari | Tetranychidae |
| *Tetranychus urticae* Koch | twospotted spider mite | Acari | Tetranychidae |
| *Tetraopes tetrophthalmus* (Forst.) | red milkweed beetle | Coleoptera | Cerambycidae |
| *Tetropium cinnamopterum* Kby. | eastern larch borer | Coleoptera | Cerambycidae |
| *Tetropium parvulum* Casey | northern spruce borer | Coleoptera | Cerambycidae |
| *Tetropium velutinum* LeC. | western larch borer | Coleoptera | Cerambycidae |
| *Tetyra bipunctata* (H.-S.) | shieldbacked pine seed bug | Heteroptera | Pentatomidae |
| *Thecodiplosis piniresinosae* Kearby | red pine needle midge | Diptera | Cecidomyiidae |
| *Therioaphis riehmi* (Borner) | sweetclover aphid | Homoptera | Aphididae |
| *Thermobia domestica* (Pack.) | firebrat | Thysanura | Lepismatidae |
| *Thorybes pylades* (Scudd.) | northern cloudy wing | Lepidoptera | Hesperiidae |
| *Thrips nigropilosus* Uzel | chrysanthemum thrips | Thysanoptera | Thripidae |
| *Thrips simplex* (Mor.) | gladiolus thrips | Thysanoptera | Thripidae |
| *Thrips tabaci* Lind. | onion thrips | Thysanoptera | Thripidae |
| *Thylodrias contractus* Mots. | odd beetle | Coleoptera | Dermestidae |
| *Thymelicus lineola* (Ochs.) | European skipper | Lepidoptera | Hesperiidae |
| *Thyridopteryx ephemeraeformis* (Haw.) | bagworm | Lepidoptera | Psychidae |
| *Tibicen pruinosa* (Say) | dogday cicada | Homoptera | Cicadidae |
| *Tinea pellionella* L. | casemaking clothes moth | Lepidoptera | Tineidae |
| *Tineola bisselliella* (Hum.) | webbing clothes moth | Lepidoptera | Tineidae |
| *Tipula paludosa* Meig. | European crane fly | Diptera | Tipulidae |
| *Tischeria malifoliella* Clem. | appleleaf trumpet miner | Lepidoptera | Tischeriidae |
| *Tischeria quercitella* Clem. | oak blotchminer | Lepidoptera | Tischeriidae |
| *Tolype laricis* (Fitch) | larch lappet moth | Lepidoptera | Lasiocampidae |
| *Tolype velleda* (Stoll) | velleda lappet moth | Lepidoptera | Lasiocampidae |
| *Tomostethus multicinctus* (Roh.) | brownheaded ash sawfly | Hymenoptera | Tenthredinidae |
| *Torymus varians* (Wlk.) | apple seed chalcid | Hymenoptera | Torymidae |
| *Toumeyella liriodendri* (Gmel.) | tuliptree scale | Homoptera | Coccidae |
| *Toumeyella parvicornis* (Ckll.) | pine tortoise scale | Homoptera | Coccidae |
| *Trachykele blondeli* Marseul | western cedar borer | Coleoptera | Buprestidae |
| *Tremex columba* (L.) | pigeon tremex | Hymenoptera | Siricidae |
| *Trialeurodes vaporariorum* (Westw.) | greenhouse whitefly | Homoptera | Aleyrodidae |
| *Tribolium audax* Halst. | American black flour beetle | Coleoptera | Tenebrionidae |
| *Tribolium castaneum* (Hbst.) | red flour beetle | Coleoptera | Tenebrionidae |
| *Tribolium confusum* Duv. | confused flour beetle | Coleoptera | Tenebrionidae |
| *Tribolium destructor* Uytt. | large flour beetle | Coleoptera | Tenebrionidae |
| *Tribolium madens* (Charp.) | European black flour beetle | Coleoptera | Tenebrionidae |
| *Trichiocampus simplicicornis* (Nort.) | hairy willow sawfly | Hymenoptera | Tenthredinidae |
| *Trichiocampus viminalis* (Fall.) | hairy poplar sawfly | Hymenoptera | Tenthredinidae |
| *Trichiosoma triangulum* Kby. | giant birch sawfly | Hymenoptera | Cimbicidae |

TABLE 3-continued

INSECTS SUBJECT TO CONTROL BY EMBODIMENTS OF THE INVENTION

| Scientific Name | English Common Name | Order | Family |
|---|---|---|---|
| *Trichobaris trinotata* (Say) | potato stalk borer | Coleoptera | Curculionidae |
| *Trichodectes canis* (DeG.) | dog biting louse | Mallophaga | Trichodectidae |
| *Trichogramma minutum* Riley | minute egg parasite | Hymenoptera | Trichogrammatid |
| *Tricholochmaea d. decora* (Say) | gray willow leaf beetle | Coleoptera | Chrysomelidae |
| *Tricholochmaea decora carbo* (LeC.) | Pacific willow leaf beetle | Coleoptera | Chrysomelidae |
| *Tricholochmaea vaccinii* (Fall) | blueberry leaf beetle | Coleoptera | Chrysomelidae |
| *Trichophaga tapetzella* (L.) | carpet moth | Lepidoptera | Tineidae |
| *Trichoplusia ni* (Hbn.) | cabbage looper | Lepidoptera | Noctuidae |
| *Trichordestra legitima* (Grt.) | striped garden caterpillar | Lepidoptera | Noctuidae |
| *Trigonogenius globulus* Sol. | globular spider beetle | Coleoptera | Ptinidae |
| *Trisetacus ehmanni* Keif. | pine needle mite | Acari | Phytoptidae |
| *Trisetacus grosmanni* Keif. | spruce bud mite | Acari | Phytoptidae |
| *Trisetacus grosmanni* Keif. | fir bud mite | Acari | Phytoptidae |
| *Trogium pulsatorium* (L.) | larger pale booklouse | Psocoptera | Trogiidae |
| *Trogium pulsatorium* (L.) | deathwatch | Psocoptera | Trogiidae |
| *Trogoderma granarium* Everts | khapra beetle | Coleoptera | Dermestidae |
| *Trogoderma inclusum* LeC. | larger cabinet beetle | Coleoptera | Dermestidae |
| *Trogoderma variabile* Ballion | warehouse beetle | Coleoptera | Dermestidae |
| *Tropidosteptes amoenus* Reut. | ash plant bug | Heteroptera | Miridae |
| *Trypodendron betulae* Swaine | birch ambrosia beetle | Coleoptera | Scolytidae |
| *Trypodendron lineatum* (Oliv.) | striped ambrosia beetle | Coleoptera | Scolytidae |
| *Trypodendron retusum* (LeC.) | poplar ambrosia beetle | Coleoptera | Scolytidae |
| *Tuberolachnus salignus* (Gmel.) | giant willow aphid | Homoptera | Aphididae |
| *Tychius picirostris* (F.) | clover seed weevil | Coleoptera | Curculionidae |
| *Tychius stephensi* Schonh. | red clover seed weevil | Coleoptera | Curculionidae |
| *Typhaea stercorea* (L.) | hairy fungus beetle | Coleoptera | Mycetophagidae |
| *Typhlocyba froggatti* Baker | yellow apple leafhopper | Homoptera | Cicadellidae |
| *Typhlocyba pomaria* McA. | white apple leafhopper | Homoptera | Cicadellidae |
| *Tyria jacobaeae* (L.) | cinnabar moth | Lepidoptera | Arctiidae |
| *Tyrolichus casei* Oud. | cheese mite | Acari | Acaridae |
| *Tyrophagus putrescentiae* (Schr.) | mold mite | Acari | Acaridae |
| *Udea rubigalis* (Gn.) | celery leaftier | Lepidoptera | Pyralidae |
| *Udea rubigalis* (Gn.) | greenhouse leaftier | Lepidoptera | Pyralidae |
| *Unaspis euonymi* (Comst.) | euonymus scale | Homoptera | Diaspididae |
| *Upis ceramboides* (L.) | roughened darkling beetle | Coleoptera | Tenebrionidae |
| *Urocerus albicornis* (F.) | black horntail | Hymenoptera | Siricidae |
| *Urocerus cressoni* Nort. | black and red horntail | Hymenoptera | Siricidae |
| *Urocerus gigas flavicornis* (F.) | banded horntail | Hymenoptera | Siricidae |
| *Utetheisa bella* (L.) | bella moth | Lepidoptera | Arctiidae |
| *Vanessa atalanta* (L.) | red admiral | Lepidoptera | Nymphalidae |
| *Vanessa cardui* (L.) | painted lady | Lepidoptera | Nymphalidae |
| *Vanessa virginiensis* (Drury) | American painted lady | Lepidoptera | Nymphalidae |
| *Vasates quadripedes* Shimer | maple bladdergall mite | Acari | Eriophyidae |
| *Vespa crabro germana* Christ | European hornet | Hymenoptera | Vespidae |
| *Vespa crabro germana* Christ | giant hornet | Hymenoptera | Vespidae |
| *Vespula germanica* (F.) | German yellowjacket | Hymenoptera | Vespidae |
| *Vespula maculifrons* (Buys.) | eastern yellowjacket | Hymenoptera | Vespidae |
| *Vespula pensylvanica* (Sauss.) | western yellowjacket | Hymenoptera | Vespidae |
| *Wohlfahrtia vigil* (Wlk.) | myiasis fly | Diptera | Sarcophagidae |
| *Wyeomyia smithii* (Coq.) | pitcherplant mosquito | Diptera | Culicidae |
| *Xanthia togata* (Esp.) | pinkbarred sallow | Lepidoptera | Noctuidae |
| *Xanthogaleruca luteola* (Mull.) | elm leaf beetle | Coleoptera | Chrysomelidae |
| *Xanthonia decemnotata* (Say) | tenspotted leaf beetle | Coleoptera | Chrysomelidae |
| *Xanthoteras quercusforticorne* (Walsh) | oak figgall wasp | Hymenoptera | Cynipidae |
| *Xanthotype sospeta* (Drury) | crocus geometer | Lepidoptera | Geometridae |
| *Xenopsylla cheopis* (Roths.) | oriental rat flea | Siphonaptera | Pulicidae |
| *Xestia perquiritata* (Morr.) | gray spruce cutworm | Lepidoptera | Noctuidae |
| *Xestia* spp. | spotted cutworm | Lepidoptera | Noctuidae |
| *Xestobium rufovillosum* (DeG.) | deathwatch beetle* | Coleoptera | Anobiidae |
| *Xestobium rufovillosum* (DeG.) | knock beetle* | Coleoptera | Anobiidae |
| *Xyela minor* Nort. | pine flower sawfly | Hymenoptera | Xyelidae |
| *Xylotrechus aceris* Fisher | gallmaking maple borer | Coleoptera | Cerambycidae |

TABLE 3-continued

INSECTS SUBJECT TO CONTROL BY EMBODIMENTS OF THE INVENTION

| Scientific Name | English Common Name | Order | Family |
|---|---|---|---|
| Xylotrechus colonus (F.) | rustic borer | Coleoptera | Cerambycidae |
| Xylotrechus obliteratus LeC. | poplar butt borer* | Coleoptera | Cerambycidae |
| Xylotrechus undulatus (Say) | spruce zebra beetle | Coleoptera | Cerambycidae |
| Yponomeuta cognatella Hbn. | euonymus webworm | Lepidoptera | Yponomeutidae |
| Yponomeuta malinella Zell. | apple ermine moth | Lepidoptera | Yponomeutidae |
| Ypsolopha dentella (F.) | European honeysuckle leafroller | Lepidoptera | Plutellidae |
| Zale helata (Sm.) | white pine false looper | Lepidoptera | Noctuidae |
| Zale lunifera (Hbn.) | pine false looper | Lepidoptera | Noctuidae |
| Zale metatoides McD. | jack pine false looper | Lepidoptera | Noctuidae |
| Zale minerea (Gn.) | large false looper | Lepidoptera | Noctuidae |
| Zale undularis (Drury) | locust false looper | Lepidoptera | Noctuidae |
| Zaraea inflata Nort. | honeysuckle sawfly | Hymenoptera | Cimbicidae |
| Zeiraphera canadensis Mut. & Free. | spruce bud moth | Lepidoptera | Tortricidae |
| Zeiraphera fortunana (Kft.) | yellow spruce budworm | Lepidoptera | Tortricidae |
| Zeiraphera improbana (Wlk.) | larch needleworm | Lepidoptera | Tortricidae |
| Zeiraphera unfortunana Powell | purplestriped shootworm | Lepidoptera | Tortricidae |
| Zelleria haimbachi Bsk. | pine needle sheathminer | Lepidoptera | Yponomeutidae |
| Zeugophora scutellaris Suffr. | cottonwood leafmining beetle | Coleoptera | Chrysomelidae |
| Zeuzera pyrina (L.) | leopard moth | Lepidoptera | Cossidae |
| Zonosemata electa (Say) | pepper maggot | Diptera | Tephritidae |
| Zootermopsis angusticollis (Hagen) | Pacific dampwood termite | Isoptera | Termopsidae |
| Zophodia grossulariella (Hbn.) | gooseberry fruitworm | Lepidoptera | Pyralidae |
| Zygogramma exclamationis (F.) | sunflower beetle | Coleoptera | Chrysomelidae |

For purposes of simplicity, the term "insect" shall be used throughout this application; however, it should be understood that the term "insect" refers, not only to insects, but also to arachnids, larvae, and like invertebrates. Also for purposes of this application, the term "insect control" shall refer to having a repellant effect, a pesticidal effect, or both.

"Target pest" refers to the organism that is the subject of the insect control effort.

"Repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition.

"Pesticidal effect" is an effect wherein treatment with a composition causes at least about 1% of the insects to die. In this regard, an $LC_1$ to $LC_{100}$ (lethal concentration) or an $LD_1$ to $LD_{100}$ (lethal dose) of a composition will cause a pesticidal effect. In some embodiments, the pesticidal effect is an effect wherein treatment with a composition causes at least about 5% of the exposed insects to die. In some embodiments, the pesticidal effect is an effect wherein treatment with a composition causes at least about 10% of the exposed insects to die. In some embodiments, the pesticidal effect is an effect wherein treatment with a composition causes at least about 25% of the insects to die. In some embodiments the pesticidal effect is an effect wherein treatment with a composition causes at least about 50% of the exposed insects to die. In some embodiments the pesticidal effect is an effect wherein treatment with a composition causes at least about 75% of the exposed insects to die. In some embodiments the pesticidal effect is an effect wherein treatment with a composition causes at least about 90% of the exposed insects to die.

"Disablement" is an effect wherein insects are mobility-impaired such that their mobility is reduced as compared to insects that have not been exposed to the composition. In some embodiments, disablement is an effect wherein at least about 75% of insects are mobility-impaired such that their mobility is reduced as compared to insects that have not been exposed to the composition. In some embodiments, disablement is an effect wherein at least about 90% of insects are mobility-impaired such that their mobility is reduced as compared to insects that have not been exposed to the composition. In some embodiments, disablement can be caused by a disabling effect at the cellular or whole-organism level.

Embodiments of the invention can be used to control parasites. As used herein, the term "parasite" includes parasites, such as but not limited to, protozoa, including intestinal protozoa, tissue protozoa, and blood protozoa. Examples of intestinal protozoa include, but are not limited to: *Entamoeba hystolytica, Giardia lamblia, Cryptosporidium muris,* and *Cryptosporidium parvum.* Examples of tissue protozoa include, but are not limited to: *Trypanosomatida gambiense, Trypanosomatida rhodesiense, Trypanosomatida crusi, Leishmania mexicana, Leishmania braziliensis, Leishmania tropica, Leishmania donovani, Toxoplasma gondii,* and *Trichomonas vaginalis.* Examples of blood protozoa include, but are not limited to *Plasmodium vivax, Plasmodium ovale, Plasmodium malariae,* and *Plasmodium falciparum. Histomonas meleagridis* is yet another example of a protozoan parasite.

As used herein, the term "parasite" further includes, but is not limited to: helminthes or parasitic worms, including nematodes (round worms) and platyhelminthes (flat worms). Examples of nematodes include, but are not limited to: animal and plant nematodes of the adenophorea class, such as the intestinal nematode *Trichuris trichiura* (whipworm) and the plant nematode *Trichodorus obtusus* (stubby-root nematode); intestinal nematodes of the secementea class, such as *Ascaris lumbricoides, Enterobius vermicularis* (pinworm), *Ancylostoma duodenale* (hookworm), *Necator americanus* (hookworm), and *Strongyloides stercoralis*; and tissue nematodes of the secementea class, such as *Wuchereria bancrofti* (Filaria bancrofti) and *Dracunculus medinensis* (Guinea worm). Examples of plathyeminthes include, but are not limited to: Trematodes (flukes), including blood flukes, such as *Schistosoma mansoni* (intestinal Schistosomiasis), *Schistosoma haematobium*, and *Schistosoma japonicum*; liver flukes, such as *Fasciola hepatica*, and *Fasciola gigantica*; intestinal flukes, such as *Heterophyes heterophyes*; and lung flukes such as *Paragonimus westermani*. Examples of platheminthes further include, but are not limited to: Cestodes (tapeworms), including *Taenia solium, Taenia saginata, Hymenolepis nana*, and *Echinococcus granulosus*.

Furthermore, the term "parasite" further includes, but is not limited to those organisms and classes of organisms listed in the following table:

TABLE 4

PARASITES SUBJECT TO CONTROL BY EMBODIMENTS OF THE INVENTION

| Parasite (Genus) | (Species) | Context |
|---|---|---|
| Protozoa (sub-groups: rhizopods, flagellates, ciliate, sporozoans) | | |
| *Entamoeba* | coli | Example of gut rhizopod that can switch from commensal to parasite depending on circumstances. Several species are found in humans. *E. histolytica* is the pathogen responsible for amoebiasis (which includes amoebic dysentery and amoebic liver abscesses). |
| | dispar | |
| | histolytica | |
| | gingivalis | |
| *Balantidium* | coli | Example of parasitic ciliate and zoonosis |
| *Giardia* | intenstinalis | Example of water-borne flagellate and zoonosis |
| | lamblia | |
| *Trichomonas* | vaginalis | Example of gut flagellate in birds. Venereally transmitted flagellate causing abortion & infertility |
| *Histomonas* | meleagridis | Example of a parasite transmitted by another parasite - *Heterakis* |
| *Trypanosoma* | avium | Example of a venerally transmitted flagellate |
| | brucei | |
| | cruzi | |
| | equiperdum | |
| | evansi | |
| | vivax | |
| *Eimeria* | acervulina | A picomplexan parasite responsible for the poultry disease coccidiosis. Used to illustrate the basic characteristics of the coccidian direct lifecycle. Ovine, bovine & rabbit coccidiosis mentioned but not by species. |
| | brunetti | |
| | jemezi | |
| | maxima | |
| | nextrix | |
| | tenella | |
| | stiedae | |
| | meleagridis | |
| *Isospora* | belli | Mentioned as the dog/cat/pig equivalent of *Eimeria* |
| | felis | |
| | canis | |
| *Cyclospora* | cayetanensis | Traveler's Diarrhea. |
| *Cryptosporidium* | parvum | Of the Phylum Apicomplexa and causes a diarrheal illness called cryptosporidiosis. Example of an important water borne zoonosis. |
| | hominis | |
| | canis | |
| | felis | |
| | hominis | |
| | meleagridis | |
| | muris | |
| *Sarcocystis* | cruzi | Used to illustrate the basic characteristics of the coccidian indirect lifecycle. Can happen when undercooked meat is ingested. Symptoms include diarrhea, which may be mild and transient or severe and life threatening. |
| | hominis | |
| | muris | |
| *Toxoplasma* | gondii | The definitive host is the cat, but the parasite can be carried by the vast majority of warm-blooded animals, including humans. The causative agent of toxoplasmosis. |
| *Neospora* | caninum | Important pathogen in cattle and dogs. Highly transmissible with some herds having up to 90% prevalence. Causes abortions. |
| *Babesia* | major | Example of tick-borne protozoa, responsible for causing Texas Fever. |
| | microti | |
| | divergens | |
| | duncani | |
| | gibsoni | |

TABLE 4-continued

PARASITES SUBJECT TO CONTROL BY EMBODIMENTS OF THE INVENTION

| | | |
|---|---|---|
| *Plasmodium* | *falciparum* | Example of an endemic insect borne protozoan. |
| | *vivax* | Causative agent of malaria. |
| | *ovale* | |
| | *malariae* | |
| | *knowlesi* | |
| | *gigliolii* | |
| *Leishmania* | *aethiopica* | Example of insect borne protozoan that lives inside |
| | *donovani* | host macrophages |
| | *major* | |
| | *mexicana* | |
| | *tropica* | |
| | *braziliensis* | |
| | Trematodes | |
| *Fasciola* | *hepatica* | Also known as the common liver fluke it is a |
| | *magna* | parasitic flatworm of phylum Platyhelminthes that |
| | *gigantica* | infects liver of a various mammals, including man. |
| | *jacksoni* | The disease caused by the fluke is called fascioliasis (also known as fasciolosis). *F. hepatica* is worldwide distributed and causes great economic losses in sheep and cattle. |
| *Dicrocoelium* | *dendriticum* | The Lancet liver fluke is a parasite fluke that tends to live in cattle or other grazing mammals. |
| *Schistosoma* | *mansoni* | Commonly known as blood-flukes and bilharzia, |
| | *japonicum* | cause the most significant infection of humans by |
| | *mekongi* | flatworms. Considered by the World Health |
| | *intercalatum* | Organization as second in importance only to |
| | *haematobium* | malaria. |
| | Cestodes | |
| *Taenia* | *crassiceps* | Example of tapeworms with humans as natural |
| | *pisiformis* | definite hosts but with implications for zoonoses and |
| | *saginata* | meat inspection |
| | *solium* | |
| *Dipylidium* | *caninum* | Also called the cucumber tapeworm or the double-pore tapeworm, it infects organisms afflicted with fleas, including canids, felids, and pet-owners, especially children. |
| *Echinococcus* | *granulosus* | Includes six species of cyclophyllid tapeworms. |
| | *multilocularis* | Infection with *Echinococcus* results in hydatid |
| | *shiquicus* | disease, also known as echinococcosis. |
| | Nematodes | |
| *Aphelenchoides* | *fragariae* | Foliar nematodes are plant parasitic roundworms |
| | *ritzemabosi* | which are a widespread problem for the ornamental |
| | *besseyi.* | and nursery industries. |
| *Heterodera* | | Soybean cyst nematode. |
| *Globodera* | *solanacearum* | Potato cyst nematode. |
| | *virginiae* | |
| | *tabacum* | |
| *Nacobbus* | *dorsalis* | False Root-knot. |
| *Pratylenchus* | *brachurus* | Brown root rot. |
| | *penetrans* | |
| *Ditylenchus* | *dipsaci* | Plant pathogenic nematode which infects the bud and stem. |
| *Xiphinema* | *americanum* | American dagger nematode; plant pathogen. |
| *Longidorus* | *sylphus* | Attacks mint. |
| *Paratrichodorus* | *minor* | Christie's stubby root nematode. |
| *Dioctophyma* | *renale* | Giant kidney worm; common parasital worm found in carnivorous animals. |
| *Meloidogyne* | *hapla* | Root-knot nematodes infect plant roots and are |
| | *incognita* | one of the three most economically damaging |
| | *javanica* | genera of nematodes on horticultural and field crops. |
| *Trichostrongylus* | *tenius* | Used as a basic nematode lifecycle |
| *Ostertagia* | | Highlights impact of larval development in |
| or *Teladorsagia* | | abomasum wall, differences between type I & II, example of seasonally-induced hypobiosis |
| *Nematodirus* | | Example of nematode developing in the gut lumen, example of nematode with critical hatching conditions |
| *Haemonchus* | | Example of blood-feeding nematode |
| *Cooperia* | | Distinctive coiled nematode of ruminants |
| *Trichuris* | | Distinctive whip-like nematode of ruminants |
| *Ascaris* | | Example of hepato-trachael migratory nematode |
| *Parascaris* | | Important equine nematode |
| *Oxyuris* | | Distinctive pin-worm of equines |

TABLE 4-continued

PARASITES SUBJECT TO CONTROL BY EMBODIMENTS OF THE INVENTION

| | | |
|---|---|---|
| *Toxascaris* | | Example of non-migratory ascarid of dogs & cats referred forward to the migratory *Toxocara* sp |
| *Toxocara* | | Example of complex migratory nematode with hypobiotic larval stages, complex biochemical interactions between host & parasite, congenital infections, vertical transmission, zoonosis, reproductive-related hypobiosis, Comparison with *T. catti*, refs back to non-migratory *Toxascaris* |
| *Trichinella* | | Example of hypobiotic larvae, no external stages, zoonosis |
| *Oesophagostomum* | | Example of strongyle of ruminants with extensive cuticular ornamentation and nodule formation on gut wall |
| *Chabertia* | | Example of strongyle of ruminants with large buccal capsule as adaptation to tissue feeding |
| *Cyathostomes* or *Trichonemes* | | Horse colic. |
| *Strongylus* | *vulgaris* | Blood worm; common horse parasite. |
| *Bunostomum* | | Example of hookworm of ruminants |
| *Uncinaria* | | Example of canine/feline "northern" hookworm |
| *Ancylostoma* | | Example of potential emerging hookworm related to climate change/behaviour |
| *Dictyocaulus* | | Basic lungworm direct lifecycle, vaccination using irradiated larvae |
| *Metastrongylus* | | Lungworm with indirect lifecycle, used to reinforce concepts of transport, paratenic & intermediate host using earthworm as example |
| *Parafilaria* | | Example of filarial worm, example of insect-borne parasite that does not involve a blood-feeding vector |
| *Dirofialria* | | Example of filarial worm transmitted by blood-feeding vector, distribution limited by that of vector, potential impact of climate change on distribution |
| | Fungi | |
| *Cercospora* | *zeae-maydis* | Etiological agent of grey leaf spot in cereal plants. |
| *Ustilago* | *maydis* | Etiological agent of corn smut disease of maize. |
| *Magnaporthe* | *grisea* | Most significant disease affecting rice cultivation; rice blast. |
| *Bipolaris* | *oryzae* | Brown spot can infect both seedlings and mature plants. |

| Parasite | Context |
|---|---|
| Acarina - Mites and Ticks | |
| Psoroptic mites - *Psoroptes ovis*, *Chorioptes* | Sheep scab aetiology and control. Topology of infestation in relation to skin histology. |
| Sarcoptic mites - *Sarcoptes*, *Knemidocoptes* | Causation of mange, hypersensitivity and pruritus. Topology of infestation in relation to skin histology. |
| Demodectic mites - *Demodex*, *Trombicula*, *Cheyletiella* | Causation of demodecosis. Topology of infestation in relation to histology of skin. Aesthetic and zoonotic problems with *Cheyletiella*. |
| Dermanyssid mites - *Dermanyssus*, *Ornithonyssus* | Nature of infestation as micro-predator. Importance to poultry industry. Control by hygiene and pesticides. |
| *Ixodes ricinus* | Vector of agents of babesiosis, tick borne fever, louping ill and Lyme disease. |
| Lice and Fleas | |
| *Linognathus* and *Haematopinus* sp. | Example of sessile ectoparasites with incomplete metamorphosis causing stress and hide damage. Example of blood feeding anopluran lice. |
| *Trichodectes* and *Felicola* | Lice problems in small companion animals caused by chewing lice. Role as intermediate host of *Dipylidium* tapeworm. |
| *Lipeurus*, *Cuclotogaster*, *Menopon* | Two families of chewing lice on birds. All bird lice are chewing lice causing irritation and production losses. |
| *Ctenocephalides felis* and *C. canis* | Cat/Dog flea; one of the most abundant and widespead fleas in the world. |

TABLE 4-continued

PARASITES SUBJECT TO CONTROL BY EMBODIMENTS OF THE INVENTION

| | |
|---|---|
| *Ceratophyllus* and *Echidnophaga* | Parasitizes mainly rodents and birds. |

Flies

| | |
|---|---|
| Muscid flies | Importance of flies with sponging mouthparts a nuisance leading to production losses in dairy cattle and as mechanical vectors of pathogens such as *Moraxella* bacteria. |
| *Haematobia* and *Stomoxys* | Horn fly; *H. irritans* is a bloodsucking fly dangerous to livestock. |
| Tabanid flies | Examples of biting stress caused by flies with complex slashing and sponging blood feeding mouthparts. Example of life cycle of flies with complete metamorphosis. |
| *Melophagus ovinus* | Louse flies or keds; obligate parasite of mammals and birds - can serve as the vector of pigeon malaria. |
| *Culicoides* midges | Example of how flies act as vectors. |
| Mosquitoes | Vectors of viral, protozoal and nematode pathogens. |
| *Phlebotomus* sand flies | Vector of *Leishmania* protozoa. |
| *Lucilia cuprina* blowfly | Example of facultative myiasis - blowfly strike. |
| *Hypoderma bovis* | Example of obligate myiasis - warble fly. Example of low reproduction/high survival system. |
| *Gasterophilus* and *Oestrus* bots | Illustration of these forms of myiasis. |

Embodiments of the invention can be used to prevent or treat the following parasite hosts:

TABLE 5

PARASITE HOSTS

Fungal Diseases afflicting Canola (*Brassica rapa*)

| | |
|---|---|
| Alternaria black spot = | *Alternaria brassicae, Alternaria brassicicola* |
| Dark pod spot (UK) | *Alternaria japonica* = Alternaria raphani |
| Anthracnose | *Colletotrichum gloeosporioides, Glomerella cingulata* [teleomorph] |
| | *Colletotrichum higginsianum* |
| Black leg = stem canker (UK) | *Leptosphaeria maculans* |
| | *Phoma lingam* [anamorph] |
| Black mold rot | *Rhizopus stolonifer* |
| Black root | *Aphanomyces raphani* |
| Brown girdling root rot | *Rhizoctonia solani* |
| | *Thanatephorus cucumeris* [teleomorph] |
| *Cercospora* leaf spot | *Cercospora brassicicola* |
| Clubroot | *Plasmodiophora brassicae* |
| Downy mildew | *Peronospora parasitica* |
| *Fusarium* wilt | *Fusarium oxysporum* f.sp. *conglutinans* |
| Gray mold | *Botrytis cinerea* |
| | *Botryotinia fuckeliana* [teleomorph] |
| Head rot | *Rhizoctonia solani* |
| | *Thanatephorus cucumeris* [teleomorph] |
| Leaf spot | *Alternaria alternata* |
| | *Ascochyta* spp. |
| Light leaf spot | *Pyrenopeziza brassicae* |
| | *Cylindrosporium concentricum* [anamorph] |
| Pod rot | *Alternaria alternata* |
| | *Cladosporium* spp. |
| Powdery mildew | *Erysiphe polygoni* |
| | *Erysiphe cruciferarum* |
| Ring spot | *Mycosphaerella brassicicola* |
| | *Asteromella brassicae* [anamorph] |
| Root rot | *Alternaria alternata* |
| | *Fusarium* spp. |
| | *Macrophomina phaseolina* |
| | *Phymatotrichopsis omnivora* |
| | *Phytophthora megasperma* |
| | *Pythium debaryanum* |
| | *Pythium irregulare* |
| | *Rhizoctonia solani* |
| | *Thanatephorus cucumeris* [teleomorph] |
| | *Sclerotium rolfsii* |
| | *Athelia rolfsii* [teleomorph] |

TABLE 5-continued

| PARASITE HOSTS | |
|---|---|
| *Sclerotinia* stem rot | *Sclerotinia sclerotiorum* |
| Seed rot, damping-off | *Alternaria* spp. |
| | *Fusarium* spp. |
| | *Gliocladium roseum* |
| | *Nectria ochroleuca* [teleomorph] |
| | *Pythium* spp. |
| | *Rhizoctonia solani* |
| | *Thanatephorus cucumeris* [teleomorph] |
| | *Rhizopus stolonifer* |
| | *Sclerotium rolfsii* |
| Root gall smut | *Urocystis brassicae* |
| Southern blight (leaf, root and seed rot) | *Sclerotium rolfsii* |
| *Verticillium* wilt | *Verticillium longisporum* |
| White blight | *Rhizoctonia solani* |
| | *Thanatephorus cucumeris* [teleomorph] |
| White leaf spot = grey stem (Canada) | *Pseudocercosporella capsellae* = *Cercosporella brassicae* |
| | *Mycosphaerella capsellae* [teleomorph] |
| White rust = staghead | *Albugo candida* = |
| | *Albugo cruciferarum* |
| | (*Peronospora* sp. commonly present in staghead phase) |
| Yellows | *Fusarium oxysporum* |

Cat (*Felis catus*)
Apicomplexa:

*Besnoitia* sp. (*oocysts*)
*Isospora felis*
*Isospora rivolta*
*Sarcocystis gigantea* (*sporocysts*)
*Sarcocystis hirsuta* (*sporocysts*)
*Sarcocystis medusijormis* (*sporocysts*)
*Sarcocystis muris* (*sporocysts*)
*Sarcocystis* sp. (*sporocysts*)
*Toxoplasma gondii* (*cysts*)
*Toxoplasma gondii* (*oocysts*
Sarcomastigophora:

*Giardia intestinalis*
Dog (*Canis familiaris*)
Apicomplexa:

*Hammondia heydorni* (*oocysts*)
*Isospora canis*
*Isospora ohicensis*
*Neospora caninum*
*Sarcocystis arieticanis* (*sporocysts*)
*Sarcocystis capracanis* (*sporocysts*)
*Sarcocystis cruzi* (*sporocysts*)
*Sarcocystis tenella* (*sporocysts*)
*Sarcocystis* sp. (*sporocy sts*)
*Toxoplasma gondii* (*cysts*)
Sarcomastigophora:

*Giardia intestinalis*
Goat (*Capra hircus*)
Apicomplexa:

*Cvptosporidiurn* sp.
*Eimeria alijevi*
*Eimeria apsheronica*
*Eimeria arloingi*
*Eimeria capralis*
*Eimeria caprina*
*Eimeria caprovina*
*Eimeria charlestoni*
*Eimeria christenseni*
*Eimeria hirci*
*Eimeria jolchejevi*
*Eimeria masseyensis*
*Eimeria ninakohlyakimovae*
*Eimeria punctata*
*Eimeria tunisiensis*
*Sarcocystis capracanis* (*cysts*)
*Toxoplasma gondii* (*cysts*)

TABLE 5-continued

| PARASITE HOSTS | |
|---|---|
| | Sarcomastigophora: |
| | *Giardia* sp. |
| | Horse (*Equus caballus*) |
| | Apicomplexa: |
| | *Eimeria leuckarti* |
| | *Klossiella equi* |
| | *Sarcocystis* sp. (*cysts*) |
| | Man (*Homo sapiens*) |
| | Apicomplexa: |
| | *Cryptosporidium* sp. |
| | *Isospora hominis** |
| | *Plasmodium* sp.* |
| | *Toxoplasma gondii* (*cysts*) |
| | Sarcomastigophora: |
| | *Chilomastix mesnili* |
| | *Dientamoeba fragilis* |
| | *Endolimax nana* |
| | *Entamoeba coli* |
| | *Entamoeba hartmanni* |
| | *Entamoeba histolytica* |
| | *Giardia intestinalis* |
| | *Iodamoeba buetschlii* |
| | *Leishmania donovani** |
| | *Trichomonas hominis* |
| | *Trichomonas vaginalis* |
| Fungal diseases afflicting Maize (*Zea mays*) | |
| Anthracnose leaf blight | *Colletotrichum graminicola* |
| Anthracnose stalk rot | *Glomerella graminicola* |
| | *Glomerella tucumanensis* |
| | *Glomerella falcatum* |
| Aspergillus ear and kernel rot | *Aspergillus flavus* |
| Banded leaf and sheath spot | *Rhizoctonia solani* = *Rhizoctonia microsclerotia* |
| | *Thanatephorus cucumeris* |
| Black bundle disease | *Acremonium strictum* = *Cephalosporium acremonium* |
| Black kernel rot | *Lasiodiplodia theobromae* = *Botryodiplodia theobromae* |
| Borde blanco | *Marasmiellus* sp. |
| Brown spot | *Physoderma maydis* |
| Black spot | |
| Stalk rot | |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata* |
| | *C. eragrostidis* = *C. maculans* |
| | *Cochliobolus eragrostidis* |
| | *Curvularia inaequalis* |
| | *C. intermedia* |
| | *Cochliobolus intermedius* |
| | *Curvularia lunata* |
| | *Cochliobolus lunatus* |
| | *Curvularia pallescens Cochliobolus pallescens* |
| | *Curvularia senegalensis* |
| | *C. tuberculata* |
| | *Cochliobolus tuberculatus* |
| *Didymella* leaf spot | *Didymella exitalis* |
| *Diplodia* ear rot and stalk rot | *Diplodia frumenti* |
| | *Botryosphaeria festucae* |
| *Diplodia* ear rot | *Diplodia maydis* |
| Stalk rot | |
| Seed rot | |
| Seedling blight | |
| *Diplodia* leaf spot or leaf streak | *Stenocarpella macrospora* = *Diplodia macrospora* |
| Downy mildews afflicting Maize (*Zea mays*) | |
| Brown stripe downy mildew | *Sclerophthora rayssiae* |
| Crazy top downy mildew | *Sclerophthora macrospora* = *Sclerospora macrospora* |

TABLE 5-continued

| PARASITE HOSTS | |
|---|---|
| Green ear downy mildew | *Sclerospora graminicola* |
| *Graminicola* downy mildew | |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| Spontaneum downy mildew | *Peronosclerospora spontanea* = *Sclerospora spontanea* |
| Sugarcane downy mildew | *Peronosclerospora sacchari* = *Sclerospora sacchari* |
| Dry ear rot | *Nigrospora oryzae* |
| Cob, kernel and stalk rot | *Khuskia oryzae* |
| Ear rots, minor | *Alternaria alternata* = *A. tenuis* |
| | *Aspergillus glaucus* |
| | *A. niger* |
| | *Aspergillus* spp. |
| | *Botrytis cinerea* |
| | *Botryotinia fuckeliana* |
| | *Cunninghamella* sp. |
| | *Curvularia pallescens* |
| | *Doratomyces stemonitis* = *Cephalotrichum stemonitis* |
| | *Fusarium culmorum* |
| | *Gonatobotrys simplex* |
| | *Pithomyces maydicus* |
| | *Rhizopus microsporus* |
| | *R. stolonifer* = *R. nigricans* |
| | *Scopulariopsis brumptii* |
| Ergot | *Claviceps gigantea* |
| Horse's tooth | *Sphacelia* sp. |
| Eyespot | *Aureobasidium zeae* = *Kabatiella zeae* |
| *Fusarium* ear and stalk rot | *Fusarium subglutinans* = *F. moniliforme* |
| *Fusarium* kernel, root and stalk rot, seed rot and seedling blight | *Fusarium moniliforme* |
| | *Gibberella fujikuroi* |
| *Fusarium* stalk rot | *Fusarium avenaceum* |
| Seedling root rot | *Gibberella avenacea* |
| *Gibberella* ear and stalk rot | *Gibberella zeae* |
| | *Fusarium graminearum* |
| Gray ear rot | *Botryosphaeria zeae* = *Physalospora zeae* |
| | *Macrophoma zeae* |
| Gray leaf spot | *Cercospora sorghi* = *C. sorghi* |
| *Cercospora* leaf spot | *C. zeae-maydis* |
| *Helminthosporium* root rot | *Exserohilum pedicellatum* = *Helminthosporium pedicellatum* |
| | *Setosphaeria pedicellata* |
| *Hormodendrum* ear rot | *Cladosporium cladosporioides* = *Hormodendrum cladosporioides* |
| *Cladosporium* rot | |
| | *C. herbarum* |
| | *Mycosphaerella tassiana* |
| *Hyalothyridium* leaf spot | *Hyalothyridium maydis* |
| Late wilt | *Cephalosporium maydis* |
| Leaf spots, minor | *Alternaria alternata* |
| | [[[*Ascochyta maydis*]] |
| | *A. tritici* |
| | *A. zeicola* |
| | *Bipolaris victoriae* = *Helminthosporium victoriae* |
| | *Cochliobolus victoriae* |
| | *C. sativus* |
| | *Bipolaris sorokiniana* = *H. sorokinianum* = *H. sativum* |
| | *Epicoccum nigrum* |
| | *Exserohilum prolatum* = *Drechslera prolata* |
| | *Setosphaeria prolata* |
| | *Graphium penicillioides* |
| | *Leptosphaeria maydis* |
| | *Leptothyrium zeae* |
| | *Ophiosphaerella herpotricha* |
| | *Scolecosporiella* sp. |
| | *Paraphaeosphaeria michotii* |
| | *Phoma* sp. |
| | *Septoria zeae* |
| | *S. zeicola* |
| | *S. zeina* |

TABLE 5-continued

| PARASITE | HOSTS |
|---|---|
| Northern corn leaf blight | *Setosphaeria turcica* |
| White blast | *Exserohilum turcicum = Helminthosporium turcicum* |
| Crown stalk rot | |
| Stripe | |
| Northern corn leaf spot | *Cochliobolus carbonum* |
| *Helminthosporium* ear rot (race 1) | *Bipolaris zeicola = Helminthosporium carbonum* |
| *Penicillium* ear rot | *Penicillium* spp. |
| Blue eye | *P. chrysogenum* |
| Blue mold | *P. expansum* |
| | *P. oxalicum* |
| *Phaeocytostroma* stalk rot and root rot | *Phaeocytostroma ambiguum = Phaeocytosporella zeae* |
| *Phaeosphaeria* leaf spot | *Phaeosphaeria maydis = Sphaerulina maydis* |
| *Physalospora* ear rot | *Botryosphaeria festucae = Physalospora zeicola* |
| *Botryosphaeria* ear rot | *Diplodia frumenti* |
| Purple leaf sheath | Hemiparasitic bacteria and fungi |
| *Pyrenochaeta* stalk rot and root rot | *Phoma terrestris = Pyrenochaeta terrestris* |
| *Pythium* root rot | *Pythium* spp. |
| | *P. arrhenomanes* |
| | *P. graminicola* |
| *Pythium* stalk rot | *Pythium aphanidermatum = P. butleri* |
| Red kernel disease | *Epicoccum nigrum* |
| Ear mold, leaf and seed rot | |
| *Rhizoctonia* ear rot | *Rhizoctonia zeae* |
| Sclerotial rot | *Waitea circinata* |
| *Rhizoctonia* root rot and stalk rot | *Rhizoctonia solani* |
| | *R. zeae* |
| Root rots, minor | *Alternaria alternata* |
| | *Cercospora sorghi* |
| | *Dictochaeta fertilis* |
| | *Fusarium acuminatum Gibberella acuminata* |
| | *F. equiseti* |
| | *G. intricans* |
| | *F. oxysporum* |
| | *F. pallidoroseum* |
| | *F. poae* |
| | *F. roseum* |
| | *G. cyanogena* |
| | *F. sulphureum* |
| | *Microdochium bolleyi* |
| | *Mucor* sp. |
| | *Periconia circinata* |
| | *Phytophthora cactorum* |
| | *P. drechsleri* |
| | *P. nicotianae* |
| | *Rhizopus arrhizus* |
| Rostratum leaf spot | *Setosphaeria rostrata = Helminthosporium rostratum* |
| *Helminthosporium* leaf disease, ear and stalk rot | |
| Rust, common corn | *Puccinia sorghi* |
| Rust, southern corn | *Puccinia polysora* |
| Rust, tropical corn | *Physopella pallescens* |
| | *P. zeae = Angiopsora zeae* |
| Sclerotium ear rot | *Sclerotium rolfsii* |
| Southern blight | *Athelia rolfsii* |
| Seed rot-seedling blight | *Bipolaris sorokiniana* |
| | *B. zeicola = Helminthosporium carbonum* |
| | *Diplodia maydis* |
| | *Exserohilum pedicillatum* |
| | *Exserohilum turcicum = Helminthosporium turcicum* |
| | *Fusarium avenaceum* |
| | |F. culmorum* |
| | *F. moniliforme* |
| | *Gibberella zeae* |
| | *F. graminearum* |
| | *Macrophomina phaseolina* |
| | *Penicillium* spp. |
| | *Phomopsis* spp. |
| | *Pythium* spp. |
| | *Rhizoctonia solani* |
| | [[*Rhizoctonia zeae*|*R. zeae*]] |
| | *Sclerotium rolfsii* |
| | *Spicaria* spp. |

TABLE 5-continued

| PARASITE HOSTS | |
|---|---|
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus* |
| | *M. ruber* |
| Smut, common | *Ustilago zeae = U. maydis* |
| Smut, false | *Ustilaginoidea virens* |
| Smut, head | *Sphacelotheca reiliana = Sporisorium holci-sorghi* |
| Southern corn leaf blight and stalk rot | *Cochliobolus heterostrophus* |
| | *Bipolaris maydis = Helminthosporium maydis* |
| Southern leaf spot | *Stenocarpella macrospora = Diplodia macrospora* |
| Stalk rots, minor | *Cercospora sorghi* |
| | *Fusarium episphaeria* |
| | *F. merismoides* |
| | *F. oxysporum* |
| | *F. poae* |
| | *F. roseum* |
| | *F. solani* |
| | *Nectria haematococca* |
| | *F. tricinctum* |
| | *Mariannaea elegans* |
| | *Mucor* spp. |
| | *Rhopographus zeae* |
| | *Spicaria* spp. |
| Storage rots | *Aspergillus* spp. |
| | *Penicillium* spp. and other fungi |
| Tar spot | *Phyllachora maydis* |
| *Trichoderma* ear rot and root rot | *Trichoderma viride = T. lignorum* |
| | *Hypocrea* sp. |
| White ear rot, root and stalk rot | *Stenocarpella maydis = Diplodia zeae* |
| Yellow leaf blight | *Ascochyta ischaemi* |
| | *Phyllosticta maydis* |
| | *Mycosphaerella zeae-maydis* |
| Zonate leaf spot | *Gloeocercospora sorghi* |
| Nematodes afflicting Maize (*Zea mays*) | |
| Awl | *Dolichodorus* spp., *D. heterocephalus* |
| Bulb and stem | *Ditylenchus dipsaci* |
| Burrowing | *Radopholus similis* |
| Cyst | *Heterodera avenae* |
| | *H. zeae* |
| | *Punctodera chalcoensis* |
| Dagger | *Xiphinema* spp. |
| | *X. americanum X. mediterraneum* |
| False root-knot | *Nacobbus dorsalis* |
| Lance, Columbia | *Hoplolaimus columbus* |
| Lance | *Hoplolaimus* spp. |
| | *H. galeatus* |
| Lesion | *Pratylenchus* spp., *P. brachyurus, P. crenatus, P. hexincisus, P. neglectus P. penetrans, P. scribneri, P. thornei, P. zeae* |
| Needle | *Longidorus* spp. |
| | *L. breviannulatus* |
| Ring | *Criconemella* spp. |
| | *C. ornata* |
| Root-knot | *Meloidogyne* spp. |
| | *M. chitwoodi* |
| | *M. incognita* |
| | *M. javanica* |
| Spiral | *Helicotylenchus* spp. |
| Sting | *Belonolaimus* spp. |
| | *B. longicaudatus* |
| Stubby-root | *Paratrichodorus* spp. |
| | *P. christiei* |
| | *P. minor* |

TABLE 5-continued

| PARASITE HOSTS |
|---|

| | *Quinisulcius acutus* |
| | *Trichodorus* spp. |
| Stunt | *Tylenchorhynchus dubius* |

Mouse (*Mus musculus*)
Apicomplexa:

*Hepatozoon musculi*
*Sarcocystis muris* (cysts)
Sarcomastigophora:

*Giardia intestinalis*
*Giardia muris*
Ox
(*Bos tarus*)
Apicomplexa:

*Ctyptosporidium* sp.
*Eimeria alabamensis*
*Eimeria auburnensis*
*Eimeria bovis*
*Eimeria brasiliensis*
*Eimeria bukidnonensis*
*Eimeria canadensis*
*Eimeria cylindrica*
*Eimeria ellipsoidalis*
*Eimeria subspherica*
*Eimeria wyomingensis*
*Eimeria zurnii*
*Isospora* sp.
*Neospora caninum*
*Sarcocystis cruzi* (cysts)
*Sarcocystis hirsuta* (cysts)
*Theileria orientalis*
Sarcomastigophora:

*Tritrichomonas foetus*
Ciliophora:

*Balantidium coli*
Pig (*Sus scrofa*)
Apicomplexa:

*Ctyptosporidium* sp.
*Eimeria cerdonis*
*Eimeria debliecki*
*Eimeria neodebliecki*
*Eimeria porci*
*Eimeria scabra*
*Eimeria suis*
*Isospora suis*
*Sarcocystis* sp. (cysts)
*Toxoplasma gondii* (cysts)
Ciliophora:

*Balantidium coli*
Poultry (*Gallus gallus*)
Endoparasites:
Protozoa:

*Histomonas meleagridis*
*Hexamita meleagridis*
*Eimeria* spp.
Helminths:

*Ascaridia galli*
*Ascaridia dissimilis*
*Ascardidia columbae*
*Capillaria contorta*
*Capillaria obsingata*
*Capillaria caudinflata*
*Heterakis gallinarum*
*Heterakis isolonche*
*Syngamus trachea*
Ectoparasites:
Mites:

*Cnemidocoptes mutans*
*Cnemidocoptes gallinae*

TABLE 5-continued

| PARASITE HOSTS | |
|---|---|
| *Dermanyssus gallinae* | |
| *Lamiosioptes cysticola* | |
| *Ornithonyssus slyvarium* | |
| Fleas: | |
| *Ceratophyllus gallinae* | |
| *Echindnophaga gallinacea* | |
| Lice: | |
| *Menacanthus stramineus* | |
| Rabbit (*Otyctolagus cuniculus*) | |
| Apicomplexa: | |
| *Eimeria jlavescens* | |
| *Eimeria irresidua* | |
| *Eimeria media* | |
| *Eimeria petforans* | |
| *Eimeria pyriformis* | |
| *Eimeria stiedae* | |
| *Hepatozoon cuniculi* | |
| *Sarcocystis* sp. (*cysts*) | |
| *Toxoplasma gondii* (*cysts*) | |
| Rice (*Oryza sativa*) | |

| Fungal diseases afflicting Rice | |
|---|---|
| Aggregate sheath spot | *Ceratobasidium oryzae-sativae* |
| | *Rhizoctonia oryzae-sativae* |
| Black kernel | *Curvularia lunata* |
| | *Cochliobolus lunatus* |
| Blast (leaf, neck [rotten neck], nodal and collar) | *Pyricularia grisea* = |
| | *Pyricularia oryzae* |
| | *Magnaporthe grisea* |
| Brown spot | *Cochliobolus miyabeanus* |
| | *Bipolaris oryzae* |
| Crown sheath rot | *Gaeumannomyces graminis* |
| Downy mildew | *Sclerophthora macrospora* |
| Eyespot | *Drechslera gigantea* |
| False smut | *Ustilaginoidea virens* |
| Kernel smut | *Tilletia barclayana* = |
| | *Neovossia horrida* |
| Leaf smut | *Entyloma oryzae* |
| Leaf scald | *Microdochium oryzae* = |
| | *Rhynchosporium oryzae* |
| Narrow brown leaf spot | *Cercospora janseana* = |
| | *Cercospora oryzae* |
| | *Sphaerulina oryzina* |
| Pecky rice (kernel spotting) | Damage by many fungi including |
| | *Cochliobolus miyabeanus* |
| | *Curvularia* spp. |
| | *Fusarium* spp. |
| | *Microdochium oryzae* |
| | *Sarocladium oryzae* |
| | and other fungi. |
| Root rots | *Fusarium* spp. |
| | *Pythium* spp. |
| | *Pythium dissotocum* |
| | *Pythium spinosum* |
| Seedling blight | *Cochliobolus miyabeanus* |
| | *Curvularia* spp. |
| | *Fusarium* spp. |
| | *Rhizoctonia solani* |
| | *Sclerotium rolfsii* |
| | *Athelia rolfsii* |
| Sheath blight | *Thanatephorus cucumeris* |
| | *Rhizoctonia solani* |
| Sheath rot | *Sarocladium oryzae* = |
| | *Acrocylindrium oryzae* |
| Sheath spot | *Rhizoctonia oryzae* |
| Stackburn (Alternaria leaf spot) | *Alternaria padwickii* |
| Stem rot | *Magnaporthe salvinii* |
| | *Sclerotium oryzae* |
| Water-mold (seed-rot and seedling disease) | *Achlya conspicua* |
| | *Achlya klebsiana* |
| | *Fusarium* spp. |
| | *Pythium* spp. |
| | *Pythium dissotocum* |
| | *Pythium spinosum* |

TABLE 5-continued

PARASITE HOSTS

Nematodes, parasitic

| | |
|---|---|
| Crimp nematode, summer | *Aphelenchoides besseyi* |
| Root-knot | *Meloidogyne* spp. |
| Root nematode, rice | *Hirschmanniella oryzae* |
| Stem nematode, rice | *Ditylenchus angustus* |

| | |
|---|---|
| | Sheep (*Ovis aries*) Apicomplexa: |
| | *Ctyptosporidium* sp. |
| | *Eimeria ahsata* |
| | *Eimeria crandallis* |
| | *Eimeria faurei* |
| | *Eimeria granulosa* |
| | *Eimeria intricata* |
| | *Eimeria ovinoidalis* |
| | *Eimeria ovis* |
| | *Eimeria pallida* |
| | *Eimeria pama* |
| | *Eimeria punctata* |
| | *Eimeria weybridgensis* |
| | *Sarcocystis arieticanis* (cysts) |
| | *Sarcocystis gigantea* (cysts) |
| | *Sarcocystis medusiformis* (cysts) |
| | *Sarcocystis tenella* (cysts) |
| | *Toxoplasma gondii* (cysts) |
| | Soybean (*Glycine max*) |

Fungal diseases afflicting Soybeans

| | |
|---|---|
| *Alternaria* leaf spot | *Alternaria* spp. |
| Anthracnose | *Colletotrichum truncatum* |
| | *Colletotrichum dematium f. truncatum* |
| | *Glomerella glycines* |
| | *Colletotrichum destructivum* |
| Black leaf blight | *Arkoola nigra* |
| Black root rot | *Thielaviopsis basicola* |
| | *Chalara elegans* [synanamorph] |
| Brown spot | *Septoria glycines* |
| | *Mycosphaerella usoenskajae* |
| Brown stem rot | *Phialophora gregata* = |
| | *Cephalosporium gregatum* |
| Charcoal rot | *Macrophomina phaseolina* |
| *Choanephora* leaf blight | *Choanephora infundibulifera* |
| | *Choanephora trispora* |
| Damping-off | *Rhizoctonia solani* |
| | *Thanatephorus cucumeris* |
| | *Pythium aphanidermatum* |
| | *Pythium debaryanum* |
| | *Pythium irregulare* |
| | *Pythium myriotylum* |
| | *Pythium ultimum* |
| Downy mildew | *Peronospora manshurica* |
| *Drechslera* blight | *Drechslera glycines* |
| *Frogeye* leaf spot | *Cercospora sojina* |
| *Fusarium* root rot | *Fusarium* spp. |
| *Leptosphaerulina* leaf spot | *Leptosphaerulina trifolii* |
| *Mycoleptodiscus* root rot | *Mycoleptodiscus terrestris* |
| *Neocosmospora* stem rot | *Neocosmospora vasinfecta* |
| | *Acremonium* spp. |
| *Phomopsis* seed decay | *Phomopsis* spp. |
| *Phytophthora* root and stem rot | *Phytophthora sojae* |
| *Phyllosticta* leaf spot | *Phyllosticta sojaecola* |
| *Phymatotrichum* root rot = cotton root rot | *Phymatotrichopsis omnivora* = |
| | *Phymatotrichum omnivorum* |
| Pod and stem blight | *Diaporthe phaseolorum* |
| | *Phomopsis sojae* |
| Powdery mildew | *Microsphaera diffusa* |
| Purple seed stain | *Cercospora kikuchii* |
| *Pyrenochaeta* leaf spot | *Pyrenochaeta glycines* |
| Pythium rot | *Pythium aphanidermatum* |
| | *Pythium debaryanum* |

TABLE 5-continued

PARASITE HOSTS

| | |
|---|---|
| | *Pythium irregulare* |
| | *Pythium myriotylum* |
| | *Pythium ultimum* |
| Red crown rot | *Cylindrocladium crotalariae* |
| | *Calonectria crotalariae* |
| Red leaf blotch = *Dactuliophora* leaf spot | *Dactuliochaeta glycines* = |
| | *Pyrenochaeta glycines* |
| | *Dactuliophora glycines* [synanamorph] |
| *Rhizoctonia* aerial blight | *Rhizoctonia solani* |
| | *Thanatephorus cucumeris* |
| *Rhizoctonia* root and stem rot | *Rhizoctonia solani* |
| Rust | *Phakopsora pachyrhizi* |
| Scab | *Spaceloma glycines* |
| *Sclerotinia* stem rot | *Sclerotinia sclerotiorum* |
| Southern blight (damping-off and stem rot) = | *Sclerotium rolfsii* |
| *Sclerotium* blight | *Athelia rolfsii* |
| Stem canker | *Diaporthe phaseolorum* |
| | *Diaporthe phaseolorum* var. *caulivora* |
| | *Phomopsis phaseoli* |
| *Stemphylium* leaf blight | *Stemphylium botryosum* |
| | *Pleospora tarda* |
| Sudden death syndrome | *Fusarium solani* f.sp. *glycines* |
| Target spot | *Corynespora cassiicola* |
| Yeast spot | *Nematospora coryli* |
| | Nematodes, parasitic |
| Lance | *Hoplolaimus columbus* |
| nematode | *Hoplolaimus galeatus* |
| | *Hoplolaimus magnistylus* |
| Lesion | *Pratylenchus* spp. |
| nematode | |
| Pin nematode | *Paratylenchus projectus* |
| | *Paratylenchus tenuicaudatus* |
| Reniform | *Rotylenchulus reniformis* |
| nematode | |
| Ring | *Criconemella ornata* |
| nematode | |
| Root-knot | *Meloidogyne arenaria* |
| nematode | *Meloidogyne hapla* |
| | *Meloidogyne incognita* |
| | *Meloidogyne javanica* |
| Sheath | *Hemicycliophora* spp. |
| nematode | |
| Soybean cyst | *Heterodera glycines* |
| nematode | |
| Spiral | *Helicotylenchus* spp. |
| nematode | |
| Sting | *Belonolainus gracilis* |
| nematode | *Belonolainus longicaudatus* |
| Stubby root | *Paratrichodorus minor* |
| nematode | |
| Stunt | *Quinisulcius acutus* |
| nematode | *Tylenchorhynchus* spp. |
| | Tobacco (*Nicotiana tabacum*) |
| | Fungal diseases afflicting Tobacco |
| Anthracnose | *Colletotrichum destructivum* |
| | *Glomerella glycines* |
| Barn spot | *Cercospora nicotianae* |
| Barn rot | Several fungi and bacteria |
| Black root rot | *Thielaviopsis basicola* |
| Black shank | *Phytophthora nicotianae* |
| Blue mold | *Peronospora tabacina* = |
| (downy mildew) | *Peronospora hyoscyami* f.sp. *tabacina* |
| Brown spot | *Alternaria alternata* |
| Charcoal rot | *Macrophomina phaseolina* |
| Collar rot | *Sclerotinia sclerotiorum* |
| Damping-off, | *Pythium* spp. |
| *Pythium* | *Pythium aphanidermatum* |
| | *Pythium ultimum* |
| Frogeye leaf spot | *Cercospora nicotianae* |
| *Fusarium* wilt | *Fusarium oxysporum* |
| Gray mold | *Botrytis cinerea* |
| | *Botryotinia fuckeliana* |
| *Mycosphaerella* | *Mycosphaerella nicotianae* |
| leaf spot | |
| *Olpidium* | *Olpidium brassicae* |
| seedling blight | |

TABLE 5-continued

| PARASITE HOSTS | |
|---|---|
| *Phyllosticta* leaf spot | *Phyllosticta nicotiana* |
| Powdery mildew | *Erysiphe cichoracearum* |
| Ragged leaf spot | *Phoma exigua* var. *exigua* = *Ascochyta phaseolorum* |
| Scab | *Hymenula affinis* = *Fusarium affine* |
| Sore shin and damping-off | *Rhizoctonia solani* *Thanatephorus cucumeris* |
| Southern stem rot | *Sclerotium rolfsii* |
| Southern blight | *Athelia rolfsii* |
| Stem rot of tranplants | *Pythium* spp. |
| Target spot | *Rhizoctonia solani* |
| *Verticillium* wilt | *Verticillium albo-atrum* *Verticillium dahliae* |
| | Nematodes, parasitic |
| Bulb and stem (stem break) | *Ditylenchus dipsaci* |
| Cyst | *Globodera solanacearum* = *Globodera virginiae* *Globodera tabacum* |
| Dagger, American | *Xiphinema americanum* |
| Foliar | *Aphelenchoides ritzemabosi* |
| Lesion | *Pratylenchus brachyurus* *Pratylenchus penetrans* *Pratylenchus* spp. |
| Reniform | *Rotylenchulus reniformis* |
| Root-knot | *Meloidogyne arenaria*, *Meloidogyne hapla*, *Meloidogyne incognita*, *Meloidogyne javanica* |
| Spiral | *Helicotylenchus* spp. |
| Stubby-root | *Paratrichodorus* spp. *Trichodorus* spp. |
| Stunt | *Merlinius* spp. *Tylenchorhynchus* spp. |
| | Wheat (*Triticum spp.*) |
| | Fungal diseases afflicting Wheat |
| *Alternaria* leaf blight | *Alternaria triticina* |
| Anthracnose | *Colletotrichum graminicola* *Glomerella graminicola* |
| *Ascochyta* leaf spot | *Ascochyta tritici* |
| *Aureobasidium* decay | *Microdochium bolleyi* = *Aureobasidium bolleyi* |
| Black head molds = sooty molds | *Alternaria* spp. *Cladosporium* spp. *Epicoccum* spp. *Sporobolomyces* spp. *Stemphylium* spp. and other genera |
| *Cephalosporium* stripe | *Hymenula cerealis* = *Cephalosporium gramineum* |
| Common bunt = stinking smut | *Tilletia tritici* = *Tilletia caries* *Tilletia laevis* = *Tilletia foetida* |
| Common root rot | *Cochliobolus sativus* *Bipolaris sorokiniana* = *Helminthosporium sativum* |
| Cottony snow mold | *Coprinus psychromorbidus* |
| Crown rot = foot rot, seedling blight, dryland root rot | *Fusarium* spp. *Fusarium pseudograminearum* *Gibberella zeae* *Fusarium graminearum* Group II *Gibberella avenacea* *Fusarium avenaceum* *Fusarium culmorum* |
| *Dilophospora* leaf spot = twist | *Dilophospora alopecuri* |
| Downy mildew = crazy top | *Sclerophthora macrospora* |
| Dwarf bunt | *Tilletia controversa* |
| Ergot | *Claviceps purpurea* *Sphacelia segetum* |
| Eyespot = foot rot, strawbreaker | *Tapesia yallundae* *Ramulispora herpotrichoides* = *Pseudocercosporella herpotrichoides* W-pathotype *T. acuformis* |

TABLE 5-continued

| PARASITE HOSTS | |
|---|---|
| | *Ramulispora acuformis* = |
| | *Pseudocercosporella herpotrichoides* var. |
| | *acuformis* R-pathoytpe |
| False eyespot | *Gibellina cerealis* |
| Flag smut | *Urocystis agropyri* |
| Foot rot = dryland foot rot | *Fusarium* spp. |
| Halo spot | *Pseudoseptoria donacis* = |
| | *Selenophoma donacis* |
| Karnal bunt = partial bunt | *Tilletia indica* = |
| | *Neovossia indica* |
| Leaf rust = brown rust | *Puccinia triticina* = |
| | *Puccinia recondita* f.sp. *tritici* |
| | *Puccinia tritici-duri* |
| *Leptosphaeria* leaf spot | *Phaeosphaeria herpotrichoides* = |
| | *Leptosphaeria herpotrichoides* |
| | *Stagonospora* sp. |
| Loose smut | *Ustilago tritici* = |
| | *Ustilago segetum* var. *tritici* |
| | *Ustilago segetum* var. *nuda* |
| | *Ustilago segetum* var. *avenae* |
| *Microscopica* leaf spot | *Phaeosphaeria microscopica* = |
| | *Leptosphaeria microscopica* |
| *Phoma* spot | *Phoma* spp. |
| | *Phoma glomerata* |
| | *Phoma sorghina* = |
| | *Phoma insidiosa* |
| Pink snow mold = *Fusarium* patch | *Microdochium nivale* = |
| | *Fusarium nivale* |
| | *Monographella nivalis* |
| *Platyspora* leaf spot | *Clathrospora pentamera* = |
| | *Platyspora pentamera* |
| Powdery mildew | *Erysiphe graminis* f.sp. *tritici* |
| | *Blumeria graminis* = |
| | *Erysiphe graminis* |
| | *Oidium monilioides* |
| *Pythium* root rot | *Pythium aphanidermatum* |
| | *Pythium arrhenomanes* |
| | *Pythium graminicola* |
| | *Pythium myriotylum* |
| | *Pythium volutum* |
| *Rhizoctonia* root rot | *Rhizoctonia solani* |
| | *Thanatephorus cucumeris* |
| Ring spot = Wirrega blotch | *Pyrenophora seminiperda* = |
| | *Drechslera campanulata* |
| | *Drechslera wirreganensis* |
| Scab = head blight | *Fusarium* spp. |
| | *Gibberella zeae* |
| | *Fusarium graminearum* Group II |
| | *Gibberella avenacea* |
| | *Fusarium avenaceum* |
| | *Fusarium culmorum* |
| | *Microdochium nivale* = |
| | *Fusarium nivale* |
| | *Monographella nivalis* |
| *Sclerotinia* snow mold = snow scald | *Myriosclerotinia borealis* = |
| | *Sclerotinia borealis* |
| *Sclerotium* wilt (see Southern blight) | *Sclerotium rolfsii* |
| | *Athelia rolfsii* |
| *Septoria* blotch | *Septoria tritici* |
| | *Mycosphaerella graminicola* |
| Sharp eyespot | *Rhizoctonia cerealis* |
| | *Ceratobasidium cereale* |
| Snow rot | *Pythium* spp. |
| | *Pythium aristosporum* |
| | *Pythium iwayamae* |
| | *Pythium okanoganense* |
| Southern blight = *Sclerotium base* rot | *Sclerotium rolfsii* |
| | *Athelia rolfsii* |
| Speckled snow mold = gray snow mold or | *Typhula idahoensis* |
| *Typhula* blight | *Typhula incarnata* |
| | *Typhula ishikariensis* |
| | *Typhula ishikariensis* var. *canadensis* |
| Spot blotch | *Cochliobolus sativus* |
| | *Bipolaris sorokiniana* = |
| | *Helminthosporium sativum* |
| *Stagonospora* blotch | *Phaeosphaeria avenaria* f.sp. *triticae* |
| | *Stagonospora avenae* f.sp. *triticae* = |
| | *Septoria avenae* f.sp. *triticea* |

TABLE 5-continued

PARASITE HOSTS

| | |
|---|---|
| | *Phaeosphaeria nodorum* |
| | *Stagonospora nodorum* = *Septoria nodorum* |
| Stem rust = black rust | *Puccinia graminis* = |
| | *Puccinia graminis* f.sp. *tritici* |
| Storage molds | *Aspergillus* spp. |
| | *Penicillium* spp. |
| | and others |
| Stripe rust = yellow rust | *Puccinia striiformis* |
| | *Uredo glumarum* |
| Take-all | *Gaeumannomyces graminis* var. *tritici* |
| | *Gaeumannomyces graminis* var. *avenae* |
| Tan spot = yellow leaf spot, red smudge | *Pyrenophora tritici-repentis* |
| | *Drechslera tritici-repentis* |
| Tar spot | *Phyllachora graminis* |
| | *Linochora graminis* |
| Wheat Blast | *Magnaporthe grisea* |
| Zoosporic root rot | *Lagena radicicola* |
| | *Ligniera pilorum* |
| | *Olpidium brassicae* |
| | *Rhizophydium graminis* |

Embodiments of the invention can be used to treat crops in order to limit or prevent insect infestation. The types of crops that can be treated can include, for example, any of the following, or the like:

TABLE 6

CROPS SUITABLE FOR TREATMENT WITH COMPOSITIONS AND METHODS OF THE INVENTION

| Crop name | Botanical name |
|---|---|
| Abaca (Manila hemp) | *Musa textilis* |
| Alfalfa for fodder | *Medicago sativa* |
| Alfalfa for seed | *Medicago sativa* |
| Almond | *Prunus dulcis* |
| Anise seeds | *Pimpinella animus* |
| Apple | *Malus sylvestris* |
| Apricot | *Prunus armeniaca* |
| *Areca* (betel nut) | *Areca catechu* |
| Arracha | *Arracacia xanthorrhiza* |
| Arrowroot | *Maranta arundinacea* |
| Artichoke | *Cynara scolymus* |
| Asparagus | *Asparagus officinalis* |
| Avocado | *Persea americana* |
| Bajra (Pearl millet) | *Pennisetum americanum* |
| Bambara groundnut | *Vigna subterranea* |
| Banana | *Musa paradisiaca* |
| Barley | *Hordeum vulgare* |
| Beans, dry, edible, for grains | *Phaseolus vulgaris* |
| Beans, harvested green | *Phaseolus* and *Vigna* spp. |
| Beet, fodder (mangel) | *Beta vulgaris* |
| Beet, red | *Beta vulgaris* |
| Beet, sugar | *Beta vulgaris* |
| Beet, sugar for fodder | *Beta vulgaris* |
| Beet, sugar for seeds | *Beta vulgaris* |
| Bergamot | *Citrus bergamia* |
| Betel nut | *Areca catechu* |
| Black pepper | *Piper nigrum* |
| Black wattle | *Acacia mearnsii* |
| Blackberries of various species | *Rubus* spp. |
| Blueberry | *Vaccinium* spp. |
| Brazil nut | *Bertholletia excelsa* |
| Breadfruit | *Artocarpus altilis* |
| Broad bean, dry | *Vicia faba* |
| Broad bean, harvested green | *Vicia faba* |
| Broccoli | *Brassica oleracea* var. *botrytis* |
| Broom millet | *Sorghum bicolor* |
| Broom sorghum | *Sorghum bicolor* |
| Brussels sprouts | *Brassica oleracea* var. *gemmifera* |
| Buckwheat | *Fagopyrum esculentum* |
| Cabbage (red, white, Savoy) | *Brassica oleracea* var. *capitata* |
| Cabbage, Chinese | *Brassica chinensis* |

TABLE 6-continued

CROPS SUITABLE FOR TREATMENT WITH COMPOSITIONS AND METHODS OF THE INVENTION

| Crop name | Botanical name |
|---|---|
| Cabbage, for fodder | *Brassica* spp. |
| Cacao (cocoa) | *Theobroma cacao* |
| Cantaloupe | *Cucumis melo* |
| Caraway seeds | *Carum carvi* |
| Cardamom | *Elettaria cardamomum* |
| Cardoon | *Cynara cardunculus* |
| Carob | *Ceratonia siliqua* |
| Carrot, edible | *Daucus carota* ssp. *sativa* |
| Carrot, for fodder | *Daucus carota* ssp. *sativa* |
| Cashew nuts | *Anacardium occidentale* |
| Cassava (manioc) | *Manihot esculenta* |
| Castor bean | *Ricinus communis* |
| Cauliflower | *Brassica oleracea* var. *botrytis* |
| Celeriac | *Apium graveolens* var. *rapaceum* |
| Celery | *Apium graveolens* |
| Chayote | *Sechium edule* |
| Cherry (all varieties) | *Prunus* spp. |
| Chestnut | *Castanea sativa* |
| Chickpea (gram pea) | *Cicer arietinum* |
| Chicory | *Cichorium intybus* |
| Chicory for greens | *Cichorium intybus* |
| Chili, dry (all varieties) | *Capsicum* spp. (*annuum*) |
| Chili, fresh (all varieties) | *Capsicum* spp. (*annuum*) |
| Cinnamon | *Cinnamomum verum* |
| Citron | *Citrus medica* |
| Citronella | *Cymbopogon citrates*/*Cymbopogon nar* |
| Clementine | *Citrus reticulata* |
| Clove | *Eugenia aromatica* (*Syzygium aromaticu* |
| Clover for fodder (all varieties) | *Trifolium* spp. |
| Clover for seed (all varieties) | *Trifolium* spp. |
| Cocoa (cacao) | *Theobroma cacao* |
| Coconut | *Cocos nucifera* |
| Cocoyam | *Colocasia esculenta* |
| Coffee | *Coffea* spp. |
| Cola nut (all varieties) | *Cola acuminata* |
| Colza (rapeseed) | *Brassica napus* |
| Corn (maize), for cereals | *Zea mays* |
| Corn (maize), for silage | *Zea mays* |
| Corn (sweet), for vegetable | *Zea mays* |
| Corn for salad | *Valerianella locusta* |
| Cotton (all varieties) | *Gossypium* spp. |
| Cottonseed (all varieties) | *Gossypium* spp. |
| Cowpea, for grain | *Vigna unguiculata* |
| Cowpea, harvested green | *Vigna unguiculata* |
| Cranberry | *Vaccinium* spp. |
| Cress | *Lepidium sativum* |

TABLE 6-continued

CROPS SUITABLE FOR TREATMENT WITH COMPOSITIONS AND METHODS OF THE INVENTION

| Crop name | Botanical name |
|---|---|
| Cucumber | *Cucumis sativus* |
| Currants (all varieties) | *Ribes* spp. |
| Custard apple | *Annona reticulate* |
| Dasheen | *Colocasia esculenta* |
| Dates | *Phoenix dactylifera* |
| Drumstick tree | *Moringa oleifera* |
| Durra (sorghum) | *Sorghum bicolour* |
| Durum wheat | *Triticum durum* |
| Earth pea | *Vigna subterranea* |
| Edo (eddoe) | *Xanthosoma* spp.; *Colocasia* spp. |
| Eggplant | *Solanum melongena* |
| Endive | *Cichorium endivia* |
| Fennel | *Foeniculum vulgare* |
| Fenugreek | *Trigonella foenum-graecum* |
| Fig | *Ficus carica* |
| Filbert (Hazelnut) | *Corylus avellana* |
| Fique | *Furcraea macrophylla* |
| Flax for fibre | *Linum usitatissimum* |
| Flax for oil seed (linseed) | *Linum usitatissimum* |
| Formio (New Zealand flax) | *Phormium tenax* |
| Garlic, dry | *Alium sativum* |
| Garlic, green | *Alium sativum* |
| Geranium | *Pelargonium* spp.; *Geranium* spp. |
| Ginger | *Zingiber officinale* |
| Gooseberry (all varieties) | *Ribes* spp. |
| Gourd | *Lagenaria* spp; *Cucurbita* spp. |
| Gram pea (chickpea) | *Cicer arietinum* |
| Grape | *Vitis vinifera* |
| Grapefruit | *Citrus paradisi* |
| Grapes for raisins | *Vitis vinifera* |
| Grapes for table use | *Vitis vinifera* |
| Grapes for wine | *Vitis vinifera* |
| Grass esparto | *Lygeum spartum* |
| Grass, orchard | *Dactylis glomerata* |
| Grass, Sudan | *Sorghum bicolor* var. *sudanense* |
| Groundnut (peanut) | *Arachis hypogaea* |
| Guava | *Psidium guajava* |
| Guinea corn (*sorghum*) | *Sorghum bicolor* |
| Hazelnut (filbert) | *Corylus avellana* |
| Hemp fibre | *Cannabis sativa* ssp. *indica* |
| Hemp, Manila (abaca) | *Musa textilis* |
| Hemp, sun | *Crotalaria juncea* |
| Hempseed | *Cannabis sativa* (marijuana) |
| Henequen | *Agave fourcroydes* |
| Henna | *Lawsonia inermis* |
| Hop | *Humulus lupulus* |
| Horse bean | *Vicia faba* |
| Horseradish | *Armoracia rusticana* |
| Hybrid maize | *Zea mays* |
| Indigo | *Indigofera tinctoria* |
| Jasmine | *Jasminum* spp. |
| Jerusalem artichoke | *Helianthus tuberosus* |
| Jowar (*sorghum*) | *Sorghum bicolor* |
| Jute | *Corchorus* spp. (over 30 sp.) |
| Kale | *Brassica oleracea* var. *acephala* |
| Kapok | *Ceiba pentandra* |
| Kenaf | *Hibiscus cannabinus* |
| Kohlrabi | *Brassica oleracea* var. *gongylodes* |
| Lavender | *Lavandula* spp. (over 15 sp.) |
| Leek | *Alium ampeloprasum*; *Alium porrum* |
| Lemon | *Citrus limon* |
| Lemon grass | *Cymbopogon citratus* |
| Lentil | *Lens culinaris* |
| Lespedeza (all varieties) | *Lespedeza* spp. |
| Lettuce | *Lactuca sativa* var. *capitata* |
| Lime, sour | *Citrus aurantifolia* |
| Lime, sweet | *Citrus limetta* |
| Linseed (flax for oil seed) | *Linum usitatissimum* |
| Liquorice | *Glycyrrhiza glabra* |
| Litchi | *Litchi chinensis* |
| Loquat | *Eriobotrya japonica* |
| Lupine (all varieties) | *Lupinus* spp. |
| *Macadamia* (Queensland nut) | *Macadamia* spp. *ternifolia* |
| Mace | *Myristica fragrans* |
| Maguey | *Agave atrovirens* |
| Maize (corn) | *Zea mays* |
| Maize (corn) for silage | *Zea mays* |
| Maize (hybrid) | *Zea mays* |
| Maize, ordinary | *Zea mays* |
| Mandarin | *Citrus reticulata* |
| Mangel (fodder beet) | *Beta vulgaris* |
| Mango | *Mangifera indica* |
| Manioc (cassava) | *Manihot esculenta* |
| Maslin (mixed cereals) | Mixture of *Triticum* spp.; *Secale cereale* |
| Medlar | *Mespilus germanica* |
| Melon (except watermelon) | *Cucumis melo* |
| Millet broom | *Sorghum bicolor* |
| Millet, bajra | *Pennisetum americanum* |
| Millet, bulrush | *Pennisetum americanum* |
| Millet, finger | *Eleusine coracana* |
| Millet, foxtail | *Setaria italica* |
| Millet, Japanese | *Echinochloa esculenta* |
| Millet, pearl (bajra, bulrush) | *Pennisetum americanum* |
| Millet, proso | *Panicum miliaceum* |
| Mint (all varieties) | *Mentha* spp. |
| Mulberry for fruit (all varieties) | *Morus* spp. |
| Mulberry for silkworms | *Morus alba* |
| Mushrooms | *Agaricus* spp.; *Pleurotus* spp.; *Volvariela* |
| Mustard | *Brassica nigra*; *Sinapis alba* |
| Nectarine | *Prunus persica* var. *nectarina* |
| New Zealand flax (formio) | *Phormium tenax* |
| Niger seed | *Guizotia abyssinica* |
| Nutmeg | *Myristica fragrans* |
| Oats, for fodder | *Avena* spp. (about 30 sp.) |
| Oats, for grain | *Avena* spp. (about 30 sp.) |
| Oil palm | *Elaeis guineensis* |
| Okra | *Abelmoschus esculentus* |
| Olive | *Olea europaea* |
| Onion seed | *Alium cepa* |
| Onion, dry | *Alium cepa* |
| Onion, green | *Alium cepa* |
| Opium | *Papaver somniferum* |
| Orange | *Citrus sinensis* |
| Orange, bitter | *Citrus aurantium* |
| Ornamental plants | Various |
| Palm palmyra | *Borassus flabellifer* |
| Palm, kernel oil | *Elaeis guineensis* |
| Palm, oil | *Elaeis guineensis* |
| Palm, sago | *Metroxylon sagu* |
| Papaya (pawpaw) | *Carica papaya* |
| Parsnip | *Pastinaca sativa* |
| Pea, edible dry, for grain | *Pisum sativum* |
| Pea, harvested green | *Pisum sativum* |
| Peach | *Prunus persica* |
| Peanut (groundnut) | *Arachis hypogaea* |
| Pear | *Pyrus communis* |
| Pecan nut | *Carya ilinoensis* |
| Pepper, black | *Piper nigrum* |
| Pepper, dry | *Capsicum* spp. (over 30 sp.) |
| Persimmon | *Diospyros kaki*; *Diospyros virginiana* |
| Pigeon pea | *Cajanus cajan* |
| Pineapple | *Ananas comosus* |
| Pistachio nut | *Pistacia vera* |
| Plantain | *Musa sapientum* |
| Plum | *Prunus domestica* |
| Pomegranate | *Punica granatum* |
| Pomelo | *Citrus grandis* |
| Poppy seed | *Papaver somniferum* |
| Potato | *Solanum tuberosum* |
| Potato, sweet | *Ipomoea batatas* |
| Prune | *Prunus domestica* |
| Pumpkin, edible | *Cucurbita* spp. (over 25 sp.) |
| Pumpkin, for fodder | *Cucurbita* spp. (over 25 sp.) |
| Pyrethum | *Chrysanthemum cinerariaefolium* |
| Quebracho | *Aspidosperma* spp. (more than 3 sp.) |
| Queensland nut | See *Macadamia* |
| Quince | *Cydonia oblonga* |
| Quinine | *Cinchona* spp. (more than 6 sp.) |

TABLE 6-continued

CROPS SUITABLE FOR TREATMENT WITH COMPOSITIONS AND METHODS OF THE INVENTION

| Crop name | Botanical name |
| --- | --- |
| Quinoa | *Chenopodium quinoa* |
| Radish | *Raphanus sativus* (inc. *Cochlearia armoracia*) |
| Ramie | *Boehmeria nivea* |
| Rapeseed (colza) | *Brassica napus* |
| Raspberry (all varieties) | *Rubus* spp. (over 360 sp.) |
| Red beet | *Beta vulgaris* |
| Redtop | *Agrostis* spp. |
| Rhea | *Boehmeria nivea* |
| Rhubarb | *Rheum* spp. |
| Rice | *Oryza sativa*; *Oryza glaberrima* |
| Rose | *Rose* spp. |
| Rubber | *Hevea brasiliensis* |
| Rutabaga (swede) | *Brassica napus* var. napobrassica |
| Rye | *Secale cereale* |
| Ryegrass seed | *Lolium* spp. (about 20 sp.) |
| Safflower | *Carthamus tinctorius* |
| Sainfoin | *Onobrychis vicifolia* |
| Salsify | *Tragopogon porrifolius* |
| Sapodilla | *Achras sapota* |
| Satsuma (mandarin/tangerine) | *Citrus reticulata* |
| *Scorzonera* - black salsify | *Scorzonera hispanica* |
| Sesame | *Sesamum indicum* |
| Shea butter (nut) | *Vitelaria paradoxa* |
| Sisal | *Agave sisalana* |
| *Sorghum* | *Sorghum bicolor* |
| *Sorghum*, broom | *Sorghum bicolor* |
| *Sorghum*, durra | *Sorghum bicolor* |
| *Sorghum*, Guinea corn | *Sorghum bicolor* |
| *Sorghum*, jowar | *Sorghum bicolor* |
| *Sorghum*, sweet | *Sorghum bicolor* |
| Soybean | *Glycine max* |
| Soybean hay | *Glycine max* |
| Spelt wheat | *Triticum spelta* |
| Spinach | *Spinacia oleracea* |
| Squash | *Cucurbita* spp. (over 25 sp.) |
| Strawberry | *Fragaria* spp. (over 30 sp.) |
| Sugar beet | *Beta vulgaris* |
| Sugar beet for fodder | *Beta vulgaris* |
| Sugar beet for seed | *Beta vulgaris* |
| Sugarcane for fodder | *Saccharum officinarum* |
| Sugarcane for sugar or alcohol | *Saccharum officinarum* |
| Sugarcane for thatching | *Saccharum officinarum* |
| Sunflower for fodder | *Helianthus annuus* |
| Sunflower for oil seed | *Helianthus annuus* |
| Sunhemp | *Crotalaria juncea* |
| Swede | *Brassica napus* var. napobrassica |
| Swede for fodder | *Brassica napus* var. napobrassica |
| Sweet corn | *Zea mays* |
| Sweet lime | *Citrus limetta* |
| Sweet pepper | *Capsicum annuum* |
| Sweet potato | *Lopmoea batatas* |
| Sweet *sorghum* | *Sorghum bicolor* |
| Tangerine | *Citrus reticulata* |
| Tannia | *Xanthosoma sagittifolium* |
| Tapioca (cassava) | *Manihot esculenta* |
| Taro | *Colocasia esculenta* |
| Tea | *Camelia sinensis* |
| Tef | *Eragrostis abyssinica* |
| Timothy | *Phleum pratense* |
| Tobacco | *Nicotiana tabacum* |
| Tomato | *Lycopersicon esculentum* |
| Trefoil | *Lotus* spp. (about 100 sp.) |
| Triticale for fodder | Hybrid of *Triticum aestivum* and *Secale cereale* |
| Tung tree | *Aleurites* spp.; *Fordii* |
| Turnip, edible | *Brassica rapa* |
| Turnip, for fodder | *Brassica rapa* |
| *Urena* (Congo jute) | *Urena lobata* |
| Vanilla | *Vanilla planifolia* |
| Vetch for grain | *Vicia sativa* |
| Walnut | *Juglans* spp. (over 20 sp.), ep. regia |
| Watermelon | *Citrulus lanatus* |
| Wheat | *Triticum aestivum* |
| Yam | *Dioscorea* spp. (over 120 sp.) |
| Yerba mate | *Ilex paraguariensis* |

In certain embodiments of the invention, an area can be treated with a composition of the present invention, for example, by using a spray formulation, such as an aerosol or a pump spray, or a burning formulation, such as a candle or a piece of incense containing the composition, or the like. In certain embodiments of the invention, an area can be treated, for example, via aerial delivery, by truck-mounted equipment, or the like. Of course, various treatment methods can be used without departing from the spirit and scope of the present invention. For example, compositions can be comprised in household products, for example, hard surface cleaners, and the like.

An exemplary dispenser of a system of the present invention can deliver an pest control composition to the atmosphere in a continuous manner over a period of time. The exemplary dispenser can include a reservoir for holding a pest control composition, and a wick for drawing the composition from the reservoir and releasing the insect control composition into the atmosphere. The reservoir can be constructed from a material that is impermeable to the pest control composition, for example, appropriate glass, ceramic, or polymeric materials can be used. The reservoir can include an aperture, which can be sealed or unsealed, as desired. When the exemplary system of the present invention is not in use, the aperture can be sealed to prevent the release of the pest control composition into the atmosphere. It may be desirable, for example, to seal the aperture when the exemplary system is being stored or transported. When the system is in use, the aperture is unsealed, such that the wick can draw the pest control composition from the reservoir, and release the control composition through the aperture into the atmosphere.

In certain embodiments of the invention, the rate of release of the composition can be controlled, for example, by making adjustments to the wick of the dispenser. For example, the surface area of the wick that is exposed to the atmosphere can be altered. Generally, the greater the exposed surface area, the greater the rate of release of the pest control composition. In this regard, in certain embodiments, the dispenser can include multiple wicks and the reservoir can include multiple apertures through which the insect control composition can be released into the atmosphere. As another example, the wick can be constructed from a particular material that draws the pest control composition from the reservoir and releases it into the environment at a desired rate, such as, for example, a wick made of wood, a wick made of a synthetic fiber, or the like.

Another exemplary dispenser of a system of the present invention can deliver an insect control composition to a desired area. The dispenser can include a sealed pouch that can be constructed from a material that is impermeable to the insect control composition, for example, a metallic foil, a polymeric material, or the like. The pouch can define a volume for holding the insect control composition. The composition can be provided in a material disposed within the volume of the pouch, for example, a sponge, a cloth saturated with the material, or the like. When it becomes desirable to place the exemplary system into use, the pouch can be unsealed, exposing the composition for release into the atmosphere or for application to a desired area.

In certain embodiments the insect control composition is provided in a saturated cloth within the pouch, which can be used to apply the control composition a desired area. For example, a desired area can be an animal, such as a human, a domestic animal, surfaces within a dwelling, an outdoor living area, or the like.

In certain embodiments, the dispenser can further include a hook, allowing the pouch and exposed control composition to be hung in a desired location, such as in a closet or a pantry.

In certain embodiments, a method of the present invention can deliver insect an control composition to a desired area. In certain embodiments, a dispenser used with the method can be constructed from a substantially planar, integral piece of material, having a first side that is coated with control composition, and a second side that is not coated with control composition. The integral piece of material can be folded and sealed such that the side coated with the control composition is contained within the volume defined by the sealed pouch. When the pouch is unsealed, the side that is coated with control composition is exposed. The substantially planar piece of material can be placed in a desired location to deliver control composition to the atmosphere, or to crawling insects that walk across the material.

Another exemplary dispenser of a system of the present invention can deliver an insect control composition to a desired area. The control composition can be incorporated into an appropriate material. In certain embodiments, the composition-containing material can be a material that is capable of controlling the release rate of the control composition, i.e., controlled-release material, allowing the control composition to be released into the atmosphere at a desired rate that can be adjusted by providing controlled-release material having appropriate specifications. The controlled-release material can be constructed from an appropriate polymer. In other embodiments the composition-containing material does not allow the control composition to be released into the atmosphere, but rather retains the control composition. An optional casing that is impermeable to the insect control composition can be provided to hold the composition-containing material until the system is ready for use. When the system is ready for use, the casing can be peeled away, exposing the composition-containing material. The composition-containing material can be placed in a desired location to deliver control composition to crawling insects that walk across the material, or to deliver the control composition to the atmosphere when a controlled-release material is used, e.g., control flying insects.

In certain embodiments, the composition-containing material can have a substantially planar design, appropriate for positioning adjacent a mattress for controlling bed bugs, e.g., *Cimex lectularius*. A substantially planar design can also be used, for example, as or with a picnic table cloth. In certain embodiments, the composition-containing material can be used as ground cover for a garden bed or adjacent crop plants to control weeds. In certain embodiments, the composition-containing material can take the shape of a bag, and could be used for trash collection, while controlling insect commonly attracted to household garbage or other trash.

Another exemplary dispenser of a system of the present invention can be a substantially dry sheet containing the control composition, which control composition can be applied to a desired location upon exposing the cloth to water or an aqueous liquid, e.g., perspiration. In certain embodiments, the dry sheet containing the control composition can dissolve into a cream or gel when exposed to water or an aqueous liquid, which can then be applied to a desired area. For example, a desired area can be an animal, such as a human, a domestic animal, or another animal.

The present invention is further illustrated by the following examples.

EXAMPLES

Various exemplary compositions containing plant essential oils have been prepared and tested for efficacy against different targets including insects, spiders, and fungi. The following examples provide details of certain exemplary compositions. As disclosed herein, it is within the scope of the present invention to vary the concentrations of components of each composition within useful ranges. Accordingly, these specific compositions are merely representative of certain embodiments of the invention.

Example 1

Synergy for Blend 24

Five microliters of the oil or oil blend listed in the table below were applied to the sternum of a male German Cockroach, and the time to death was recorded (time keeping was stopped at one hour). Sample size N=60 for Blend 24 and N=40 for each of the oil components. Components were diluted with acetone.

| | Time to Kill | | | | |
|---|---|---|---|---|---|
| Response in Tested Insects | Blend 24 | 83% D-Limonene | 4% Lilac Flower Oil | 3% Thyme Oil | 10% Lime Oil |
| Percent of Tested Insects >1 hr Time to Death | 2.5% | 25% | 100% | 100% | 95% |

Figure 4:
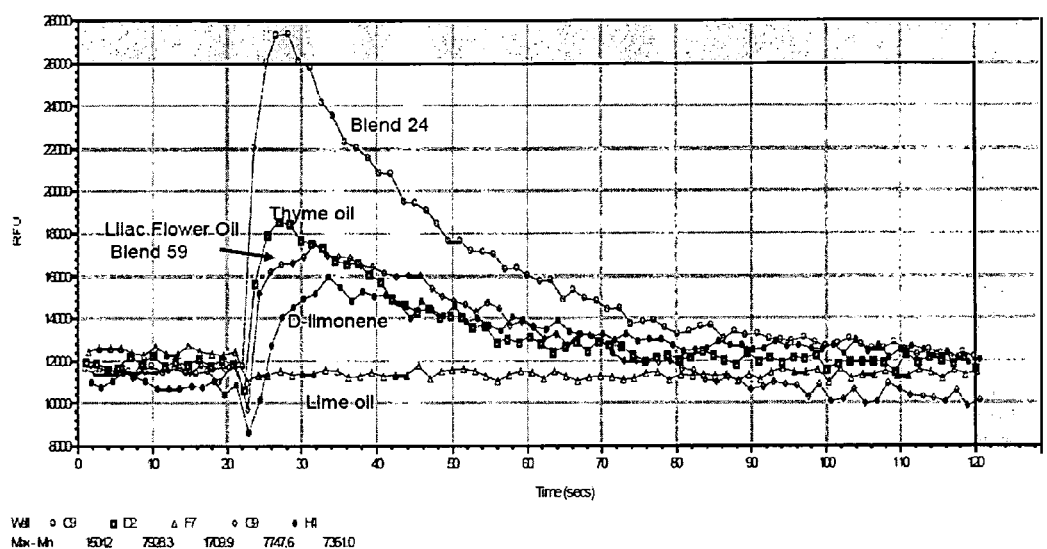
FIG. 4 shows the synergistic increase in $Ca^{2+}$ release triggered by olfactory receptor activation in Drosophila S2 cells treated with Blend 24.

FIG. 4 depicts the synergistic $Ca^{2+}$ response observed in *Drosophila melanogaster* S2 cells expressing dro-TyrR when the cells are assayed after treatment with Blend 24 or each of its components. All ingredients tested at 1 mg/ml.

Example 2

Synergy for Blend 41

Five microliters of the oil or oil blend listed in the table below were applied to the sternum of a male German Cockroach, and the time to death was recorded (time keeping was stopped at one hour). Sample size N=60 for Blend 41 and each of the oil components. Components were diluted with acetone.

| | Time to Kill | | | |
|---|---|---|---|---|
| Response in Tested Insects | Blend 41 | 22% Thyme Oil | 38% Wintergreen Oil | 40% Isopropyl myristate |
| Percent of Tested Insects > 1 hr Time to Death | 2.5% | 25% | 100% | 100% |

Figure 5:
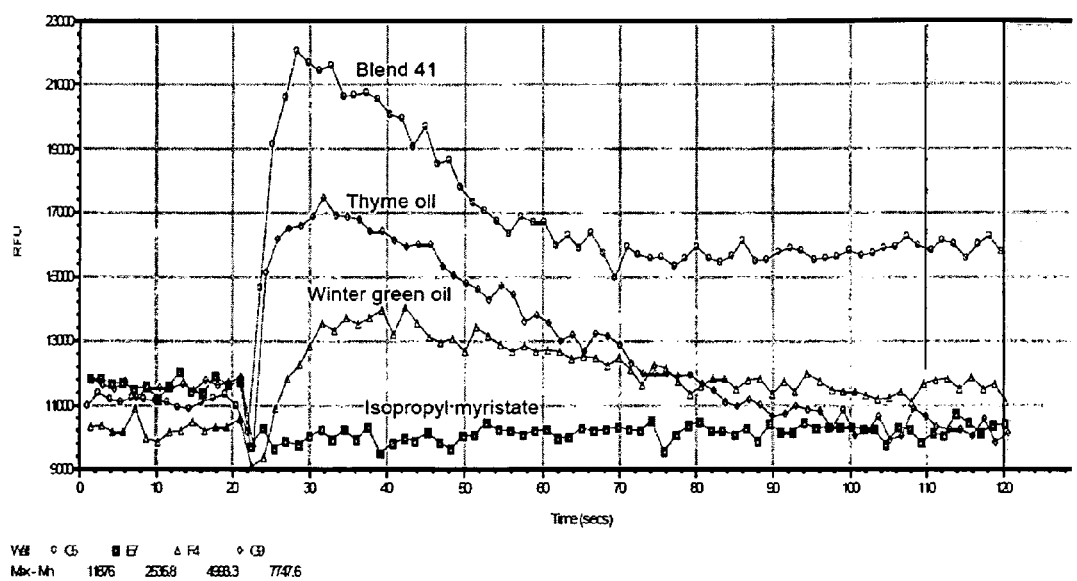
FIG. 5 shows the synergistic increase in $Ca^{2+}$ release triggered by olfactory receptor activation in Drosophila S2 cells treated with Blend 41.

FIG. 5 depicts the synergistic $Ca^{2+}$ response observed in *Drosophila melanogaster* S2 cells expressing dro-TyrR when the cells are assayed after treatment with Blend 41 or each of its components. All ingredients were tested at 1 mg/ml.

The compositions were tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. For testing purposes, one (1) gallon of the formulation was applied per 1000 $ft^2$ of surface area and allowed to dry for two (2) hours. Insects were then introduced to the surface area. Data corresponding to one such test is provided in the table below. The table shows results for Blend 41 applied to a stainless steel surface.

| Essentail Oil | Application Rate (grams/square cm glass surface area) | German Cockroach Mortality After 5 Min. Exposure to Treated Glass Surface |
|---|---|---|
| Thyme Oil White | 6.3 mg/cm² | 0% mortality |
| Wintergreen Oil | 6.3 mg/cm² | 0% mortality |
| Isopropyl Myristate | 6.3 mg/cm² | 0% mortality |
| Blend 41 22% Thyme Oil White 38% Wintergreen Oil 40% Isopropyl Myristate | 6.3 mg/cm² | 100% mortality |

Example 3

Synergy for Blend 31

Five microliters of the oil or oil blend listed in the table below were applied to the sternum of a male German Cockroach, and the time to death was recorded (time keeping was stopped at one hour). Sample size N=40 for Blend 41 and each of the oil components. Components were diluted with acetone. (No mortality was observed in acetone controls.)

| | | Time to Kill | |
|---|---|---|---|
| Response in Tested Insects | Blend 31 | Lilac Flower Oil | D-Limonene | Thyme Oil White |
| Percent of Tested Insects > 1 hr Time to Death | 0% | 70% | 22.5% | 47.5% |

Figure 6:
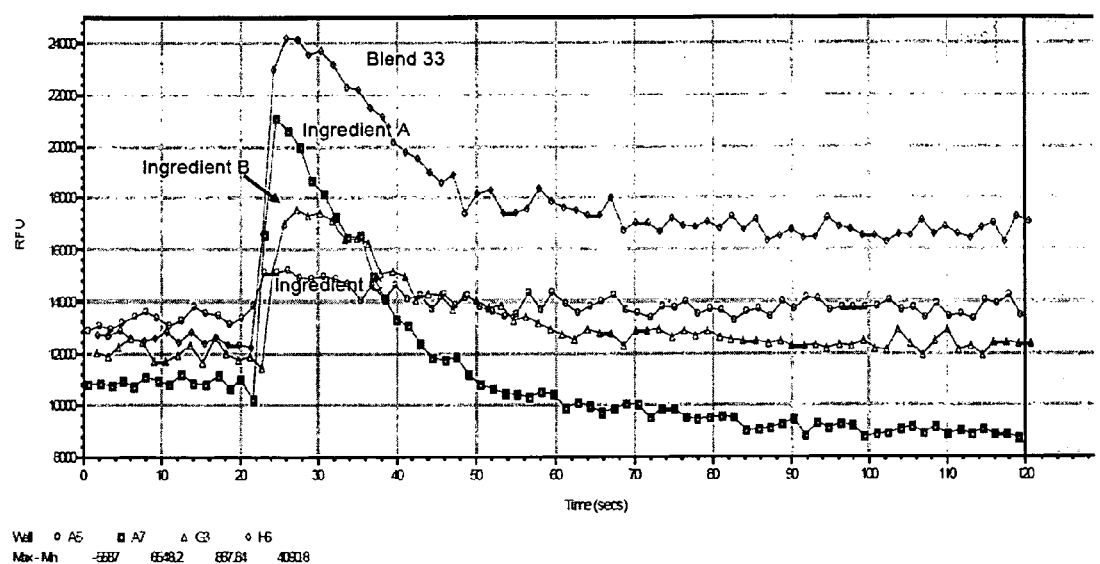
FIG. 6 shows the synergistic increase in $Ca^{2+}$ release triggered by olfactory receptor activation in Drosophila S2 cells treated with Blend 33.

FIG. 6 depicts the synergistic $Ca^{2+}$ response observed in *Drosophila melanogaster* S2 cells expressing dro-TyrR when the cells are assayed after treatment with Blend 31 (HL1) or each of its components. All ingredients were tested at 1 mg/ml.

Example 4

Synergy for Armor Blend 19

Figure 7:
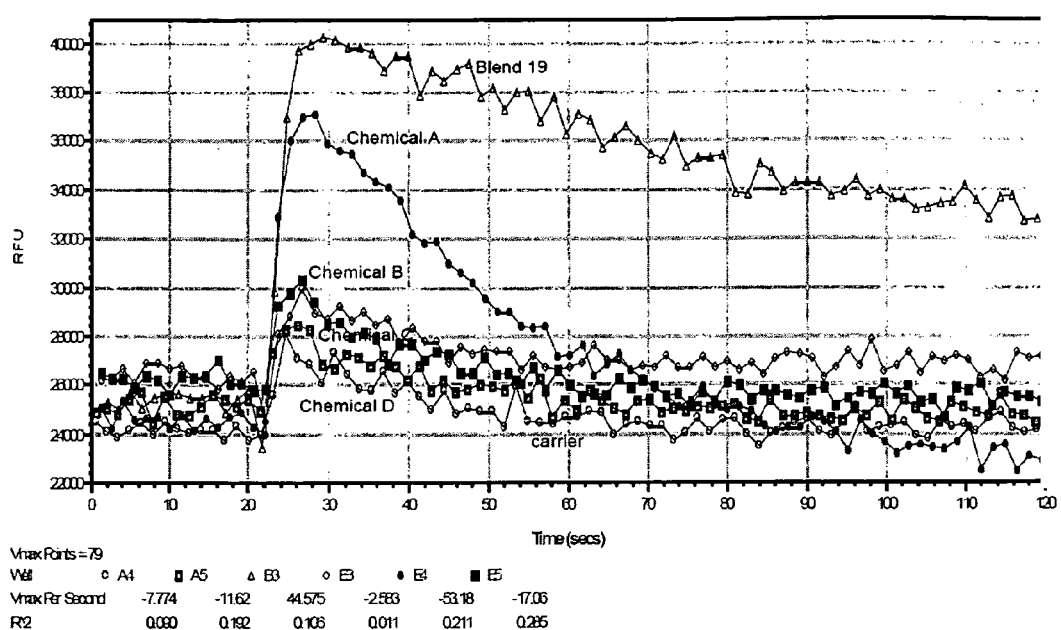
FIG. 7 shows the synergistic increase in $Ca^{2+}$ release triggered by olfactory receptor activation in Drosophila S2 cells treated with Blend 19.
Figure 8:
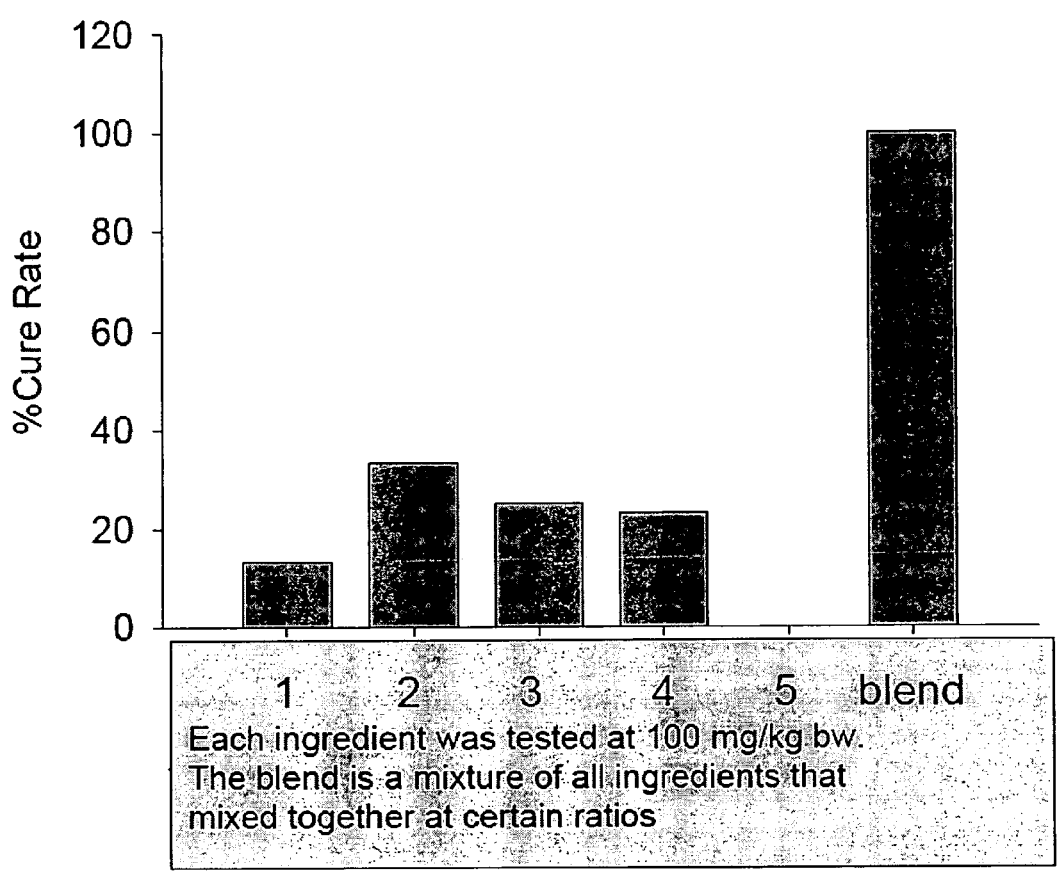
FIG. 8 shows the synergistic effect of an exemplary oil blend, relative to its individual components, on the cure rate of Hymenolepis nana infections in beetles.

FIG. 7 depicts the synergistic $Ca^{2+}$ response observed in *Drosophila melanogaster* S2 cells expressing dro-TyrR when the cells are assayed after treatment with Blend 19 (Armor Blend) or each of its components. All ingredients were tested at 0.5 mg/ml.

Table 4-A shows the synergy of Blend 19 against *Ascaris suum* in culture media. LT100 was determined from the dose response ranging between 1-100 μg/ml. Ten hours was the selected length of time for the synergy study because it was the length of time that produced 100% kill (LT100) of treated *Ascaris* with 10 μg/ml. 10 worms were used per test.

| Test agent | % as presented in the blend (Blend 19) | Tested concentration | % kill in 10 hrs after exposure |
|---|---|---|---|
| Control (surfactant#7) | 0.12% | N/A | 0.0% |
| Blend 19 | 100% | 10 μg/ml | 100% |
| Chemical D | 7% | 0.7 μg/ml | 10% |
| Chemical A | 35% | 3.5 μg/ml | 40% |
| Chemical C | 4% | 0.4 μg/ml | 0.0% |
| Chemical B | 30% | 3.0 μg/ml | 20% |
| Carrier | 24% | 2.4 μg/ml | 10% |

Example 5

Essential Oil Blend Efficacy Against Various Insect Pests

Various insects were exposed to the essential oil blends indicated in the table below using the technique described in Example 2. For each blend, the table lists the insects whose observed mortality rates in the exposure test were above 80%.

Essential Oil Blend Efficacy Against Various Insect Pests

Essential Oil Blend Susceptible Insects (Insects with >80% Mortality in a Standard Efficacy Test)

41 American Cockroaches, German Cockroaches, Bed Bugs, Stable Fly, Adult house fly, Paper Wasp, White Fly Adult, Darkling Beetle Larvae, Western Flower *Thrip* nymphs, Phorid Flies Larvae, Slug, Snail, Ticks, Fleas (cat), Black Widow Spider, Brown Recluse Spider, Dust Mites, Northern Fowl Mites, Spring Tails, House Crickets 18 Flour Beetle, Indian Meal Moth Adult and larvae, Fruit flies, House Spiders, Phorid Flies Larvae 24 Stable Fly, Adult house Fly, Paper Wasp, Indian Meal Moth Adult and larvae, Mold Mite, Scorpion, White Fly Adult, Darkling Beetle Larvae, Darkling Beetle, Western Flower *Thrips* nymphs, *Aedes Aegypti* larvae, all life stages of *Culex quinquefaciatus, Anopheles gambia* larvae 7 German Cockroaches, White Fly Adult and Larvae, Darkling Beetle Adult and Larvae, Aphids, *Thrips*, Two Spotted Spider Mite, Dermestid Beetle, Cabbage looper moth, Diamond Back Moth, Tobacco Horn Worm, Prairie Grain Wire Worm, Argentine Ants, Mold mite, All life stages of *Aedes Aegypti*, All life stages of *Culex quinquefaciatus*, all life stages of *Anopheles gambia*, Slug, Snail

Example 6

Preparation of Blend 50

Composition are prepared having the ingredients and ratios as specified in the following table:

Blend 50 Compositions

| Oil | % (by weight) |
| --- | --- |
| d-limonene | 70 |
| Black Seed Oil | 4.5 |
| | (=15 * 0.3) |
| Lilac Flower Oil (IFF) | 15 |
| | (=50 * 0.3) |
| Thyme Oil | 10.5 |
| | (=35 * 0.3) |

Blend 50 is prepared as follows: Step 1—mix 50% LFO (supplied by IFF; LFO is free of diethyl phthalate) with 35% thyme oil and 15% black seed oil (BSO). This initial mix is then combined in Step 2, in a 30:70 ratio, with d-limonene, such that the final mixture is 70% d-limonene and 30% of the LFO/thyme oil/BSO mixture from Step 1. The values in parantheses indicate the calculation of the final concentration of the specified ingredient upon the dilution of the initial mix from Step 1 into d-limonene at Step 2.

The compositions are tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Testing showed high efficacy and synergy.

Example 7

Preparation of Blend 66

A blend of oils, denoted as Blend 41, is prepared and set aside. The composition of this blend in weight percent format is provided below:

Blend 41 from Oils

| CAS | Description | wt/wt |
| --- | --- | --- |
| 8007-46-3 | Thyme Oil White | 20.6% |
| 68917-75-9 | Wintergreen Oil | 45.1% |
| 110-27-0 | Isopropyl myristate | 34.3% |

Using proportions in the table below, a solution is prepared of Polyglycerol-4-oleate, Lecithin and water. Then Blend 41 is added slowly above surface to this solution with mild mixing at the interface to create a concentrate denoted as Blend 65.

Composition of Blend 65 Concentrate

Blend 65 from Blend 41

| CAS | Description | wt/wt |
| --- | --- | --- |
| 9007-48-1 | Polyglycerol-4-oleate | 0.90% |
| 8002-43-5 | Lecithin | 0.20% |
| 7732-18-5 | Water | 9.8% |
| | Blend 41 | 89.1% |

The Blend 65 concentrate is diluted with a mixture of potassium sorbate and xanthan gum in water in the following ratios to create the finished product Blend 66 according to proportions in the table below:

Composition of Blend 66 Product

Blend 66 from Blend 65

| CAS | Description | wt/wt |
| --- | --- | --- |
| 590-00-1 or 24634-61-5 | Potassium Sorbate | 1.00% |
| 11138-66-2 | Xanthan Gum | 0.28% |
| 7732-18-5 | Water | 81.82% |
| | Blend 65 | 16.90% |

The exploded and summarized formula for Blend 66, a finished product ready for spraying, is as follows in the following table.

F4002

| CAS | Description | wt/wt |
| --- | --- | --- |
| 8007-46-3 | Thyme Oil White | 3.09% |
| 68917-75-9 | Wintergreen Oil | 6.77% |
| 110-27-0 | Isopropyl myristate | 5.15% |
| 590-00-1 or 24634-61-5 | Potassium Sorbate | 0.11% |
| 9007-48-1 | Polyglycerol-4-oleate | 0.15% |
| 11138-66-2 | Xanthan Gum | 0.28% |
| 8002-43-5 | Lecithin or Soya Lecithin | 0.034% |
| 7732-18-5 | Water | 84.41% |

Example 8

Composition of Blend 78 (Methyl Salicylate Version of Blend 66)

This product is identical to Blend 66 except that the Wintergreen Oil is replaced with Methyl Salicylate.

A blend of oils, denoted as Blend 47, is prepared and set aside. The composition of this blend in weight percent format is provided in the table below. This product can be manufactured in the following way:

Composition of Blend 47

Blend 47 from Oils

| CAS | Description | wt/wt |
| --- | --- | --- |
| 8007-46-3 | Thyme Oil White | 20.6% |
| 119-36-8 | Methyl Salicylate | 45.1% |
| 110-27-0 | Isopropyl myristate | 34.3% |

Using the proportions in the table below, a solution is prepared of Polyglycerol-4-oleate, Lecithin and water. Then Blend 47 is added slowly above surface to this solution with mild mixing at the interface to create a concentrate denoted as Blend 77.

Composition of Blend 77 Concentrate

Blend 77 from Blend 47

| CAS | Description | wt/wt |
| --- | --- | --- |
| 9007-48-1 | Polyglycerol-4-oleate | 0.90% |
| 8002-43-5 | Lecithin | 0.20% |
| 7732-18-5 | Water | 9.8% |
|  | Blend 47 | 89.1% |

The Blend 77 concentrate is diluted with a mixture of potassium sorbate and xanthan gum in water in the following ratios to create the finished product Blend 78 according to proportions in the following table.

Composition of Blend 78 RTU Product

Blend 78 from Blend 77

| CAS | Description | wt/wt |
| --- | --- | --- |
| 590-00-1 or 24634-61-5 | Potassium Sorbate | 1.00% |
| 11138-66-2 | Xanthan Gum | 0.28% |
| 7732-18-5 | Water | 81.82% |
|  | Blend 77 | 16.90% |

The exploded and summarized formula for Blend 78, a finished product ready for spraying, is as follows in the following table.

Total Composition of Blend 78 RTU Spray Product after Explosion and Summarization.

Blend 78 Exploded & Summarized PCT

| CAS | Description | wt/wt |
|---|---|---|
| 8007-46-3 | Thyme Oil White | 3.09% |
| 119-36-8 | Methyl Salicyate | 6.77% |
| 110-27-0 | Isopropyl myristate | 5.15% |
| 590-00-1 or 24634-61-5 | Potasium Sorbate | 0.11% |
| 9007-48-1 | Polyglycerol-4-oleate | 0.15% |
| 11138-66-2 | Xanthan Gum | 0.275 |
| 8002-43-18-5 | Lecithin or Soya Lecithin | 0.034% |
| 7732-18-5 | Water | 84.41% |

Example 9

Composition Blend 75 (High Residual Version of Blend 66 Made with Blend 18)

This product can be manufactured in the following way: A blend of oils, denoted as Blend 18, is prepared and set aside. The composition of this blend in weight percent format is provided in the following table.

Composition of Oil Blend 18

Blend 18 from Oils

| CAS | Description | wt/wt |
|---|---|---|
| 8007-46-3 | Thyme Oil White | 39.2% |
| 68917-75-9 | Wintergreen Oil | 24.8% |
| 110-27-0 | Isopropyl myristate | 35.9% |

Using the proportions in the table below, a solution is prepared of Polyglycerol-4-oleate, Lecithin and water. Then Blend 18 is added slowly above surface to this solution with mild mixing at the interface to create a concentrate denoted as Blend 69.

Composition of Blend 69 Concentrate

Blend 69 from Blend 18

| CAS | Description | wt/wt |
|---|---|---|
| 9007-48-1 | Polyglycerol-4-oleate | 0.90% |
| 8002-43-5 | Lecithin | 0.20% |
| 7732-18.5 | Water | 9.8% |
| | Blend 18 | 89.1% |

The Blend 69 concentrate is diluted with a mixture of potassium sorbate and xanthan gum in water in the following ratios to create the finished product Blend 75 according to proportions in the following table.

Composition of Blend 75 RTU Product

Blend 75 from Blend 69

| CAS | Description | wt/wt |
|---|---|---|
| 590-00-1 or 24634-61-5 | Potassium Sorbate | 1.00% |
| 11138-66-2 | Xanthan Gum | 0.28% |
| 7732-18-5 | Water | 81.8% |
| | Blend 69 | 16.9% |

The exploded and summarized formula for Blend 75, a finished product that has high residual ready for spraying, is as follows in the table below. This product uses Blend 18, a mix which shows high residual efficacy.

Total Composition of Blend 75 RTU Spray Product after Explosion and Summarization.

Blend 75 Exploded & Summarized PCT

| CAS | Description | wt/wt |
|---|---|---|
| 8007-46-3 | Thyme Oil White | 5.89% |
| 68917-75-9 | Wintergreen Oil | 3.72% |
| 110-27-0 | Isopropyl myristate | 5.39% |
| 590-00-1 or 24634-61-5 | Potasium Sorbate | 0.11% |
| 9007-48-1 | Polyglycerol-4-oleate | 0.15% |
| 11138-66-2 | Xanthan Gum | 0.275% |
| 8002-43-18-5 | Lecithin or Soya Lecithin | 0.034% |
| 7732-18-5 | Water | 84.4% |

Example 10

Composition of Blend 64 (Blend 41 in 1% SLS & 10% Water)

A stock solution of 10% Sodium Lauryl Sulfate in water, denoted as S-1002, is prepared according to weight percentages in the table below or the solution can be purchased.

Preparation of 10% Sodium Lauryl Sulfate in Water

S-1002 10% SLS Solution

| CAS | Description | wt/wt |
|---|---|---|
| 151-21-3 | Sodium Lauryl Sulfate | 90% |
| 7732-18-5 | Water | 10% |

The S-1002 solution is then added to Blend 41 according to weight percentages in the table below to create Blend 64, Blend 41 in 1% SLS.

Preparation of Blend 64 (Blend 41 with 1% SLS & 10% Water)

Blend 64 (Blend 41 with 1% SLS & 10% water)

| | Description | wt/wt |
|---|---|---|
| Blend 41 | (preparation in Example 7) | 90% |
| S-1002 | Stock 10% SLS Solution | 10% |

Example 11

Composition of Blend 7

In some embodiments, a blend of LFO, D-Limonene, Thyme Oil White, and Blend 61 is preferred. Various embodiments are directed to variations on the blend. A preferred embodiment is:

| CAS # | Ingredient | Weight % |
|---|---|---|
| | LFO | 12.94% |
| 5989-27-5 | D-Limonene | 8.72%% |
| 8007-46-3 | Thyme Oil White | 9.58% |
| | Blend 61 | 68.76% |

In some embodiments, the LFO of Blend 7 can be replaced by its major components.

Example 12

Composition of Blend 9

The formulation for manufacture of Blend 9, the insect repellent product containing a volumetric ratio of 4 parts LFO to 1 part BSO is provided below.

Composition of Blend 9

Blend 9 PCT

| CAS | Description | wt/wt |
|---|---|---|
| | LFO | 80.09% |
| 977017 | BSO | 19.91% |

Example 13

Composition of Blend 10

In some embodiments, a blend of Lilac Flower Oil and Black Seed Oil is preferred. Various embodiments are directed to variations on the blend. For example, in some embodiments, a ratio of approximately 1:1 is desirable. Where such a ratio is based upon volume measurements, the weight/weight ratio can be somewhat more or less than exactly 1:1, including a ratio of 2:1. In some embodiments, XL 101 1:1 can include the following ingredients:
Blend 10:

| CAS # | Ingredient | Weight % |
|---|---|---|
| | LFO | 50.13% |
| 977017-84-7 | BSO | 49.87% |

In other embodiments, LFO is replaced by a combination of other oils found in LFO, such that a 1:1 formulation includes the following ingredients:
Blend 16:

| CAS # | Ingredient | Weight % |
|---|---|---|
| 977017-84-7 | BSO | 52.28% |
| 78-70-6 | Linalool Coeur | 9.63% |
| 78-69-3 | Tetrahydrolinalool | 11.57% |
| 121-33-5 | Vanillin | 1.12% |
| 110-27-0 | Isopropyl myristate | 14.26% |
| 120-57-0 | Piperonal (aldehyde) | 4.75% |
| 106-24-1 | Geraniol Fine FCC | 6.38% |

In still other embodiments, a ratio of 4:1 is desirable. Some embodiments of blends having this characteristic, with either LFO or LFO ingredient oils, include the ingredients found in the following three tables:

Blend 9:

| CAS # | Ingredient | Weight % |
|---|---|---|
|  | LFO | 80.09% |
| 977017-84-7 | BSO | 19.91% |

Blend 3 with Lilac Flower Oil substituted with Lilac Flower Oil components:

| CAS # | Ingredient | Weight % |
|---|---|---|
| 977017-84-7 | BSO | 21.50% |
| 78-70-6 | Linalool Coeur | 15.90% |
| 78-69-3 | Tetrahydrolinalool | 19.00% |
| 121-33-5 | Vanillin | 1.80% |
| 110-27-0 | Isopropyl myristate | 23.50% |
| 120-57-0 | Piperonal (aldehyde) | 7.80% |
| 106-24-1 | Geraniol Fine FCC | 10.50% |

Blend 42:

| CAS # | Ingredient | Weight % |
|---|---|---|
| 977017-84-7 | BSO | 21.5% |
| 78-70-6 | Linalool Coeur | 15.8% |
| 78-69-3 | Tetrahydrolinalool | 19.0% |
| 121-33-5 | Vanillin | 1.9% |
| 110-27-0 | Isopropyl myristate | 23.4% |
| 120-57-0 | Piperonal (aldehyde) | 7.8% |
| 106-24-1 | Geraniol Fine FCC | 10.5% |

Example 14

Blend 18

In some embodiments, a blend of Thyme Oil White, Wintergreen Oil, and Isopropyl myristate is preferred. Various embodiments are directed to variations on the blend. In some embodiments, Blend 18 can include the following ingredients:

Blend 18:

| CAS # | Ingredient | Weight % |
|---|---|---|
| 8007-46-3 | Thyme Oil White | 39.24% |
| 68917-75-9 | Wintergreen Oil | 24.82% |
| 110-27-0 | Isopropyl myristate | 35.94% |

In other embodiments, Blend 18 is diluted to an 89% concentration through the addition of Polyglycerol-4-oleate, Lecithin, and water to form Blend 69:

Blend 69:

| CAS # | Ingredient | Weight % |
|---|---|---|
| 9007-48-1 | Polyglycerol-4-oleate | 0.90% |
| 8002-43-5 | Lecithin | 0.20% |
| 7732-18-5 | water | 9.8% |
|  | Blend 18 | 89.10% |

Example 15

Blend 41

In some embodiments, a blend of Thyme Oil White, Wintergreen Oil, and Isopropyl myristate is preferred. Various embodiments are directed to variations on the blend. In some embodiments, Blend 41 can include the following ingredients:

Blend 41:

| CAS # | Ingredient | Weight % |
|---|---|---|
| 8007-46-3 | Thyme Oil White | 20.6% |
| 68917-75-9 | Wintergreen Oil | 45.1% |
| 110-27-0 | Isopropyl myristate | 34.3% |

In other embodiments, synthetic Methyl salicylate is substituted for the Wintergreen Oil, resulting in Blend 47:

Blend 47:

| CAS # | Ingredient | Weight % |
|---|---|---|
| 8007-46-3 | Thyme Oil White | 20.6% |
|  | Methyl salicylate synthetic | 45.1% |
| 110-27-0 | Isopropyl myristate | 34.3% |

Example 16

Composition of Blend 7

In some embodiments, a blend of LFO, D-Limonene, Thyme Oil White, and Blend 61 is preferred. Various embodiments are directed to variations on the blend. A preferred embodiment is:

| CAS # | Ingredient | Weight % |
|---|---|---|
|  | LFO | 12.94% |
| 5989-27-5 | D-Limonene | 8.72%% |
| 8007-46-3 | Thyme Oil White | 9.58% |
|  | Blend 61 | 68.76% |

In some embodiments, the LFO of Blend 7 can be replaced by its major components, as indicated for Blend 3 in Example 13.

Example 17

Coefficient of Synergy

A blend is prepared and tested against a target organism. Likewise, each individual ingredient is also tested against the target organism. Both knockdown (KD) and kill are measured. The blends act more quickly than any individual ingredient. The ratio of time for the effect is the coefficient of synergy. For the "constant total AI amount" test, each individual ingredient was used in the same amount, as the total amount of all active ingredients within the blend. For the "constant ingredient amount" test, each ingredient was used in the same amount as that ingredient was present in the blend.

Thus, for example, if 15 mg/sq cm of the blend were applied to a test dish in each case, then for "constant total AI" 15 mg/sq cm of each individual active was also used, singly, in the comparison tests. In contrast, if chemical A was present as 10% of the blend, then in the constant ingredient amount test, chemical A was present at 1.5 mg/sq cm, 10% of the total amount of the blend administered.

Example 18

Blend 41 Plus Deltamethrin

Figure 9:
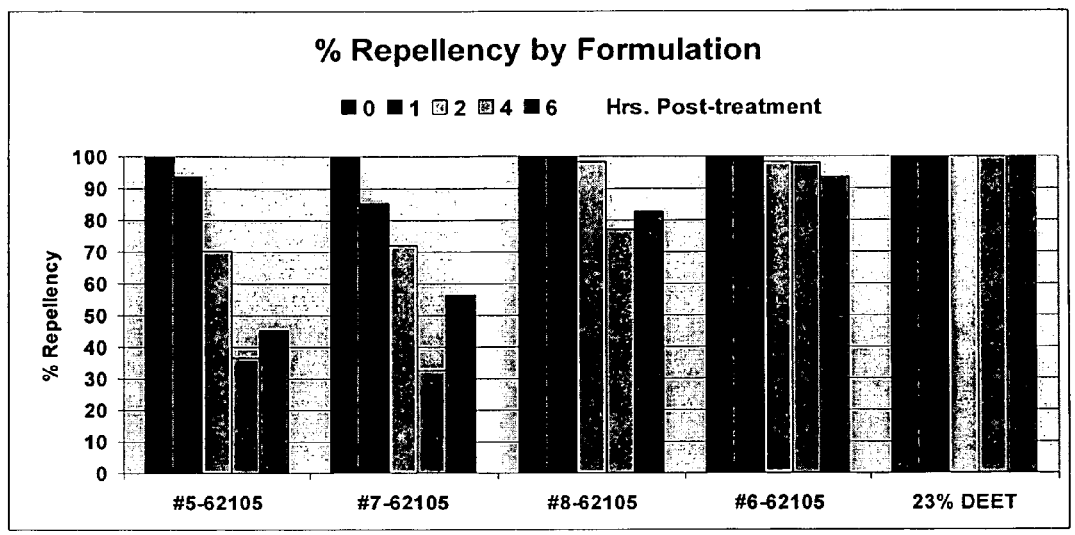
FIG. 9 is a bar graph of repellancy data for exemplary oil blends tested in comparison to 23% DEET.

A blend can is prepared and combined with a synthetic pyrethroid such as delatmetrhin. For example, Blend 41 was combined with deltamethrin (DM) and the efficacy of Blend 41 and DM individually were compared to the efficacy of Blend 41 and DM combined. FIG. 9 the synergistic increase in $Ca^{2+}$ release triggered by olfactory receptor activation in *Drosophila* S2 cells treated with Blend 41 with deltamethrin.

To test efficacy of the composition, a small amount of each test chemical is introduced to a separate jar. About 3 to 5 American cockroaches are introduced to each jar at different time intervals. Mortality and/or immobilization (knockdown, KD) data is recorded and compared. Such data is recorded as seconds (s) following introduction of the insect to the treated jar. The resulting data is contained in the following table.

Table 18-A shows the comparative results for Blend 41 alone, Deltamethrin alone (DM), and Blend 41+DM. The data is the average of 3 replicates, 5 roaches in each replicate.

TABLE 18-A

| Chemicals | Bioactivity | |
|---|---|---|
| | KD | 100% Kill |
| Blend 41 | 10 sec | 45 sec |
| DM | 140 sec | 12 min |
| Blend 41 + DM | 5 sec | 17 sec |

Example 19

Stabilized Compositions

A solution of 5% thyme crystals (TC) is prepared in acetone and about 2 ml of the solution is applied to the bottom of a glass jar. About 2 ml of six compositions (R1-R6), set forth in Table 19-A, are each applied to the bottom of a separate jar. Thyme Crystals (5%, by weight) are combined with the six compositions (R1-R6) to produce six formulations. About 2 ml of each formulation is applied to a separate jar.

TABLE 19-A

| Composition | Ingredients (% expressed by weight) |
|---|---|
| R1 | 30% Thyme Oil; 40% Lilac Flower Oil; 30% d-limonene |
| R2 | 30% methyl salicylate; 30% lilac flower oil; 40% phenethyl propionate |
| R3 | 70% phenethyl propionate, 30% methyl salicylate |
| R4 | 50% lilac flower oil; 50% black seed oil |
| R5 | 25% methyl salicylate; 25% benzyl alcohol; 25% lilac flower oil; 25% phenethyl propionate |
| R6 | 10% R1 in isopar M |

Three American cockroaches are introduced to each jar about 1 hour after application of the thyme crystals, the compositions, or the formulations. Mortality is recorded about 24 hours after exposure. All jars are kept under room temperature and reused at subsequent time points to evaluate residual activity. Three American cockroaches are introduced to each jar at about 7 days, 14 days, 18 days and 21 days after application of the thyme crystals, the compositions, or the formulations to the jars. Mortality is recorded about 24 hours after each exposure. The residual activity, expressed based on mortality, is set forth in Table 19-B.

TABLE 19-B

| | Mortality (# perished/total #) Time elapsed after jar treatment | | | | |
|---|---|---|---|---|---|
| Treatment | 1 hr | 7 days | 14 days | 18 days | 21 days |
| R1 | 3/3 | 2/3 | 0/3 | | |
| R2 | 3/3 | 2/3 | 0/3 | | |
| R3 | 3/3 | 1/3 | 0/3 | | |
| R4 | 3/3 | 2/3 | 0/3 | | |
| R5 | 3/3 | 2/3 | 0/3 | | |
| R6 | 3/3 | 0/3 | 0/3 | | |
| Thyme crystals (TC) | 3/3 | 0/3 | 0/3 | | |
| R1 + TC | 3/3 | 3/3 | 2/3 | 1/3 | 0/3 |
| R2 + TC | 3/3 | 3/3 | 2/3 | 1/3 | 0/3 |
| R3 + TC | 3/3 | 3/3 | 1/3 | 0/3 | 0/3 |
| R4 + TC | 3/3 | 3/3 | 2/3 | 2/3 | 0/3 |
| R5 + TC | 3/3 | 3/3 | 2/3 | 0/3 | 1/3 |
| R6 + TC | 3/3 | 2/3 | 0/3 | 0/3 | 0/3 |

The thyme crystal stabilizer alone does not have residual activity when tested about 48 hours after application. The compositions alone exhibit residual insect control for about 2 to 18 hours, the insect control decreases after about 7 days, and is no longer present 14 days after application. The formulations exhibit increased residual insect control for about 2 or more weeks. Only formulation R6 did not demonstrate residual toxicity after 7 days. Formulation R6 consists of 10% of formulation R1, diluted in isopar M. The lower concentration of the "active" ingredient in Formulation R6, coupled with the shortened residual activity when compared to Formulation R1, indicate that a sufficient amount of "active" ingredient must be available to coat the surfaces of the stabilizer in order to increase residual activity.

Example 20

Stabilized Compositions

In studies where treatment jars are reused at various time intervals, as described in Example 19, the materials in the jars are lost after each exposure due to contact with and transfer to the insect body, rather than via loss due to volatility of the material. As such, additional studies are conducted wherein a separate jar is prepared for each time period.

A solution of 5% thyme crystal (TC) is prepared in acetone and about 2 ml of the solution is applied to the bottom of five separate glass jars, one for each time point at which mortality is assessed. About 2 ml of six compositions (R1-R6), set forth above in Table 19-A, are each applied to the bottom of five separate jars. Thyme Crystals (5%, by weight) are combined with the six compositions (R1-R6) to produce six formulations. About 2 ml of each formulation is applied to five separate jars.

Three American cockroaches are introduced to a first set of jars about 1 hour after application of the thyme crystals, the compositions, or the formulations. Mortality is recorded about 24 hours after exposure. Three American cockroaches are introduced to the other sets of jars at about 7 days, 14 days, 18 days and 21 days after application of the thyme crystals, the compositions, or the formulations to the jars. Mortality is recorded about 24 hours after each exposure.

The thyme crystal stabilizer alone does not have residual activity when tested about 48 hours after application. The compositions alone are no longer present 14 days after application. The formulations exhibit increased residual insect control for about 2 to 5 or more weeks, with the exception of formulation R6.

Example 20

Water-Based Compositions

Various test insect-control compositions are used to prepare water-based formulations. The following compositions are used:

| Composition | Ingredients (% expressed by weight) |
|---|---|
| WB1 | 30% Thyme Oil; 40% Lilac Flower Oil; 30% d-limonene |
| WB2 | 30% methyl salicylate; 30% lilac flower oil; 40% phenethyl propionate |
| WB3 | 50% lilac flower oil; 50% black seed oil |
| WB4 | 25% methyl salicylate; 50% benzyl alcohol; 25% lilac flower oil |

The water-based formulations are prepared by mixing the composition with water containing about 10% (by weight) surfactant to give about 25% (by weight) concentration of the composition. The mixture is then mixed with solvent to yield a final concentration of about 12.5% (by weight) composition. Formulations without solvent and having the same final concentration of compositions were prepared for comparative testing purposes.

One to two ml of each water-based formulation is applied to the bottom of separate jars and each solvent-free formulation is applied to the bottom of separate jars. About 3 to 5 American cockroaches or about 5-20 carpenter ants are introduced to each jar at different time intervals. Mortality and/or immobilization (knockdown, KD) data is recorded and compared. Such data is recorded as seconds (s) following introduction of the insect to the treated jar. The resulting data is contained in the following table.

| | Without Solvent | | With Solvent | | | |
|---|---|---|---|---|---|---|
| | | | Am. cockroach | | Carpenter ants | |
| Treatment | Am. cockroach | Carpenter ants | KD | Kill | KD | kill |
| WB1 | No knockdown; slow killing agents. | No knockdown; slow killing agents. | 10 s | 49 s | 20 s | 30 s |
| WB2 | | | 5-10 s | 30 s | 15 s | 35 s |
| WB3 | | | 25 s | 35 s | 30 s | 90 s |
| WB4 | | | 10 s | 20 s | 20 s | 55 s |

Example 21

Water-Based Compositions

Various test insect-control compositions are used to prepare water-based formulations having residual efficacy. The following compositions are used:

| Composition | Ingredients (% expressed by weight) |
|---|---|
| WB1 | 30% Thyme Oil; 40% Lilac Flower Oil; 30% d-limonene |
| WB2 | 30% methyl salicylate; 30% lilac flower oil; 40% phenethyl propionate |
| WB3 | 50% lilac flower oil; 50% black seed oil |
| WB4 | 25% methyl salicylate; 50% benzyl alcohol; 25% lilac flower oil |

The water-based formulations are prepared by mixing the composition with water containing about 10% surfactant to give about 25% concentration of the composition. The mixture is then mixed with solvent. Thyme crystals are provided as a stabilizer and mixed until no more crystals are dissolved, i.e., saturated solution. In another experiment, about 1-5% crystals are used. Each water-based formulation is applied to the bottom of multiple separate jars, a jar being prepared for each test time point. American cockroaches are introduced to each jar at certain test time points and mortality is recorded about 24 hours later. The resulting data is contained in the following table.

| | Mortality Time elapsed after jar treatment | | | |
|---|---|---|---|---|
| Treatment | 1st wk | 2nd wk | 3rd wk | 4th wk |
| WB1 | 3/3 | 3/3 | 3/3 | 3/3 |
| WB2 | 3/3 | 3/3 | 3/3 | 3/3 |
| WB3 | 3/3 | 3/3 | 3/3 | 3/3 |
| WB4 | 3/3 | 3/3 | 3/3 | 3/3 |

Example 22

Mortality Testing

The effect of compositions on the mortality of insects is tested. Multiple plexiglass chambers are used, at least one as a treatment container that is sprayed (aerosol spray) evenly on all surfaces with the composition being tested, and the other as a non-treated control. Southern house mosquitoes, *Culex quinquefasciatus*, are obtained as test organisms. Multiple laboratory cultured, sucrose-fed female mosquitoes aged about 2-5 days are released into the glass chambers prior to the spraying of aerosol. The discharge rate (gm/second) of each can of aerosol to be tested is predetermined. Based on the dosage required, an estimated time of spray of aerosol is discharged into the glass chamber.

Knockdown of mosquitoes are observed at indicated intervals up to about 20 minutes. After about 20 minutes, all mosquitoes are collected and placed in cylindrical polyethylene containers with 10% sucrose pad. Mortality is observed 24 hours post-treatment. The mortality value is based on a combination of dead and moriband mosquitoes over the total number of mosquitoes initially released. The data from an exemplary study is shown in Table 22-A (Treatment) and Table B (Control), which study tests a composition comprising the following: lilac flower oil (City Chemical, Kentucky; containing no diethyl phthalate (DEP)) and black seed oil at a ratio of 2:1. As shown, the % mortality of the mosquitoes treated with the composition is 100%, compared to >2% in the non-treated control.

TABLE 22-A

| | | | Treatment | | | | |
|---|---|---|---|---|---|---|---|
| | | | | Mosquitoes | | | |
| Day | Time | Activity | #Added | Total Added | #Dead/ Removed | Total Dead | Total Alive |
| 1 | −10 min | Composition sprayed on chamber surfaces | 0 | 0 | 0 | 0 | 0 |
| 1 | 0 hr | Mosquitoes released into chamber | 20 | 20 | 0 | 0 | 20 |
| 1 | 0.5 hr | Dead mosquitoes counted, removed & mosquitoes added | 20 | 40 | 5 | 5 | 35 |
| 1 | 3 hr | Dead mosquitoes counted, removed & mosquitoes added | 20 | 60 | 35 | 40 | 20 |
| 1 | 8 hr | Sugar water provided | 0 | 60 | 20 | 60 | 0 |
| 2 | 24 hr | Dead mosquitoes counted | 0 | 60 | 0 | 60 | 0 |

TABLE 22-B

| | | | Control | | | | |
|---|---|---|---|---|---|---|---|
| | | | | Mosquitoes | | | |
| Day | Time | Activity | #Added | Total Added | #Dead/ Removed | Total Dead | Total Alive |
| 1 | −10 min | Non-treated | 0 | 0 | 0 | 0 | 0 |
| 1 | 0 hr | Mosquitoes released into chamber | 20 | 20 | 0 | 0 | 20 |
| 1 | 0.5 hr | Dead mosquitoes counted, removed & mosquitoes added | 20 | 40 | 0 | 0 | 40 |
| 1 | 3 hr | Dead mosquitoes counted, removed & mosquitoes added | 20 | 60 | 0 | 0 | 60 |
| 1 | 8 hr | Sugar water provided | 0 | 60 | 1 | 1 | 59 |
| 2 | 24 hr | Dead mosquitoes counted | 0 | 60 | 0 | 1 | 59 |

In another study, a composition was tested comprising the following: lilac flower oil (Alpine Chemicals, New Jersey; containing diethyl phthalate (DEP)) and black seed oil at a ratio of 2:1. The presence or absence of DEP in the lilac flower oil had no effect on the insect control activity of the composition. Because DEP may be toxic, it is generally desirable to use lilac flower oil that does not contain DEP.

The repellency of exemplary compositions of the present invention are compared to DEET and a non-treated control. Southern house mosquitoes, *Culex quinquefasciatus*, are obtained as test organisms. Multiple human evaluators test each treatment in a replicated experiment. Experimentation is conducted in a laboratory using multiple-chambered, plexiglass modules, each chamber stocked with about 2-10 day-old colony-reared female mosquitoes. The modules are equipped with sliding doors to expose the mosquitoes to the legs of three volunteers. Treatments are applied at about 28.6 µl to 12 cm$^2$ rectangular sections of skin located directly beneath the chamber openings. Each volunteer conducts 2-minute biting counts for each treatment at five time intervals: 0, 1, 2, 4 & 6 hrs post-treatment. Each treatment and time interval combination is replicated multiple times and the entire experiment is repeated multiple times on separate days. New mosquitoes are stocked into the chamber for each time interval and day of testing. Ambient temperature and humidity data is recorded with a HOBO datalogger.

Data from this study is statistically analyzed and combined as appropriate so that the mean response (% repellency) for each product is based on about 30 observations per time exposure interval. Results are charted with error variance as average biting count per exposure interval and as % repellency compared to control means using the formula: Control−Treatment/Control×100.

The exemplary compositions tested are described in Table 22-C. The repellency data is set forth in Table 22-D and Table 22-E and is illustrated in a bar-graph shown in FIG. 9. As shown, the % repellency of the compositions is high and rivals or approaches that of DEET at various time points.

TABLE 22-C

| | |
|---|---|
| #5-62105 | Lilac flower oil and black seed oil mixed together as 2:1, respectively. Lilac flower oil was purchased from City Chemical (KY). The lilac flower oil does not contain diethyl phthalate (DEP). |
| #6-62105 | Lilac flower oil and black seed oil mixed together as 2:1, respectively. Lilac flower oil was purchased from IFF (New Jersey). The lilac flower oil does not contain diethyl phthalate (DEP). |
| #7-62105 | Lilac flower oil and black seed oil mixed together as 1:1, respectively. Lilac flower oil was purchased from alpine chemicals (New Jersey). The lilac flower oil contains diethyl phthalate (DEP). |
| #8-62105 | Lilac flower oil and black seed oil mixed together as 2:1, respectively. Lilac flower oil was purchased from alpine chemicals (New Jersey). The lilac flower oil contains diethyl phthalate (DEP). |

TABLE 22-D

| | # Biting Counts | | | | | |
|---|---|---|---|---|---|---|
| Treatment | 0 | 1 Hour | 2 Hours | 4 Hours | 6 Hours | Grand Total |
| Control | 40 | 48 | 57 | 52 | 64 | 261 |
| #5-62105 | 0 | 3 | 17 | 33 | 35 | 88 |
| #7-62105 | 0 | 7 | 16 | 35 | 28 | 86 |

TABLE 22-D-continued

| | # Biting Counts | | | | | |
|---|---|---|---|---|---|---|
| Treatment | 0 | 1 Hour | 2 Hours | 4 Hours | 6 Hours | Grand Total |
| #8-62105 | 0 | 0 | 1 | 12 | 11 | 24 |
| #6-62105 | 0 | 0 | 1 | 1 | 4 | 6 |
| 23% DEET | 0 | 0 | 0 | 0 | 0 | 0 |
| Grand Total | 40 | 58 | 92 | 133 | 142 | 465 |

TABLE 22-E

| | % REPELLENCY | | | | |
|---|---|---|---|---|---|
| | 0 | 1 Hour | 2 Hours | 4 Hours | 6 Hours |
| #5-62105 | 100.0 | 93.8 | 70.2 | 36.5 | 45.3 |
| #7-62105 | 100.0 | 85.4 | 71.9 | 32.7 | 56.3 |
| #8-62105 | 100.0 | 100.0 | 98.2 | 76.9 | 82.8 |
| #6-62105 | 100.0 | 100.0 | 98.2 | 98.1 | 93.8 |
| 23% DEET | 100.0 | 100.0 | 100.0 | 100.0 | 100.0 |

Figure 10:
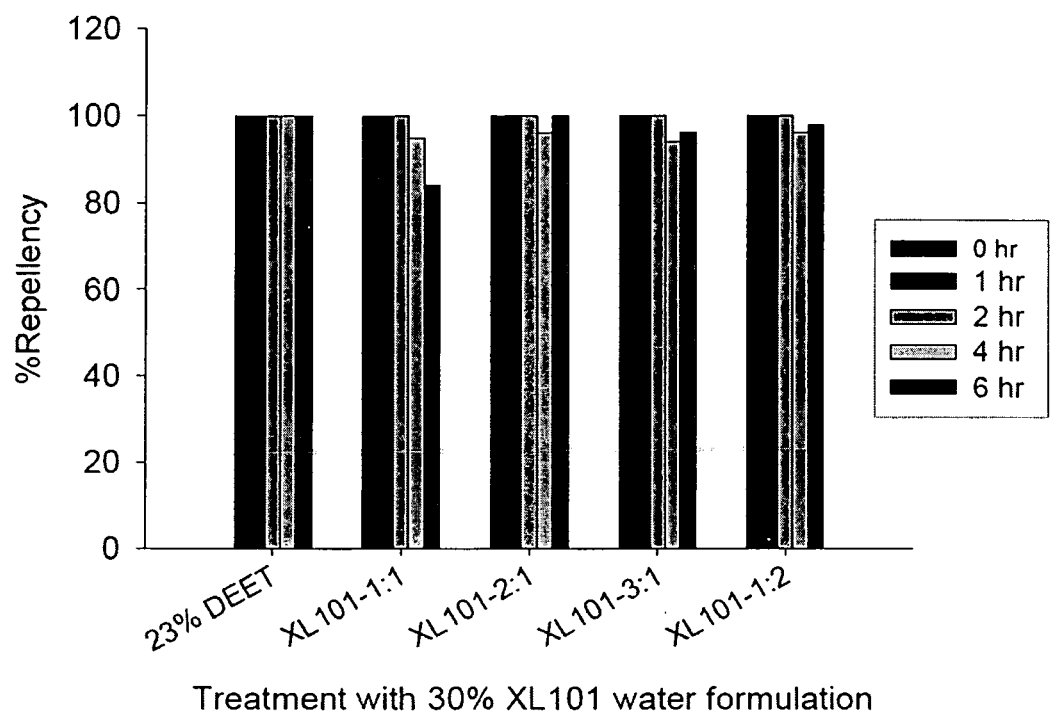
FIG. 10 is a bar graph of repellancy data for water-based formulations of an exemplary composition tested in comparison to 23% DEET.

In another study the repellency of an exemplary composition comprising about 66.6% (wt) lilac flower oil and about 33.3% (wt) black seed oil ("XL101") is tested. The XL101 composition is combined with water in various ratios (1:1; 2:1; 3:1; 1:2) and compared with DEET. The repellency data is set forth in a bar-graph shown in FIG. 10. As shown, the % repellency of the composition is high and rivals or approaches that of DEET at various time points.

Example 23

Formulations with Residual Activity

A composition of 20% BSO, 40% geranium oil, 20% piperonal, and 20% linalool was prepared by mixing by hand in a glass beaker. 10% (by weight) of this mixture was added to diatomaceous earth, then mixed thoroughly. The insect repellency properties of the formulation were tested as described.

A 36 cm×36 cm glass container was used for each test. The walls of the container were painted with Fluon to prevent insects from traveling along the side walls of the container. The container was divided into two equal halves, with one half left blank as a control surface. The other half of the container was treated with the formulation described above at an amount of 150 gm dust per m$^2$. All of the treated test containers were kept uncovered and exposed to sunlight for time intervals of 24 hours or 10 days. Five insects per replicate were used, with one replicate used for each treatment. Controls were performed with untreated glass containers. One insect at a time was placed on the untreated side of the glass container, as far as possible from the treated side. After one minute, the time that the insect spent on each half of the container was measured up to 300 seconds. The percent repellency (% R) for each replicate was calculated as follows:

$$\% R = \frac{\text{\# min/sec on control surface} - \text{\# min/sec on treated surface}}{\text{\# total min/sec duration of test}}$$

if R>0 then repellant
if R<0 then attractant

| Test Formulation (expressed as time exposed to sunlight) | Average time spent on treated surface in seconds | Average time spent on untreated surface in seconds | % R |
|---|---|---|---|
| 0 hour | 20 | 280 | 86.7 |
| 24 hours | 25 | 275 | 83.3 |
| 240 hours | 50 | 250 | 66.6 |

Example 24

Formulations with Residual Activity

A composition of 20% BSO, 40% geranium oil, 20% piperonal, and 20% linalool was prepared by mixing in a glass beaker. 10% (by weight) of this mixture was added to diatomaceous earth. The insect repellency properties of the formulation were tested as follows: The insecticidal properties of the formulation were tested as described.

2.5 g portions of the formulation were exposed to sunlight for time intervals of 0, 24, and 240 hours. All samples (but for the 0 time point portions) were exposed to sunlight between 8 am and 2 pm. During the test period, the ambient temperature was between 70-85 F. For each replicate, 5 insects were weighed then held in a 1 quart glass jar, and sprinkled directly with 2.5 grams of the formulation using a 3-screen flour sieve. This treatment had a duration of approximately 4 seconds. The insects were immediately transferred out of the test jar. The weight of the 5 insects was determined post-treatment, and insects were transferred to a clean jar with a screened cap for post-treatment observation period. Post-treatment observations were recorded up to 24 hours. Controls were kept under the same conditions.

| | Insect weight in grams | | Formulation weight in grams | |
|---|---|---|---|---|
| Test Insect | Pre-treatment* | Post-treatment | Weight/replicate* | Weight/insect* |
| German cockroach | 0.35 + 0.06 | 0.41 + 0.05 | 0.06 | 0.012 |
| Carpenter ant | 0.09 + 0.02 | 0.093 + 0.03 | 0.003 | 0.0006 |

Each treatment replicated two times to give a total of 10 insects per test.
*Pre-dust and Post dust each represents the average insects weight of five replicates ± standard deviation.

| Results | | | |
|---|---|---|---|
| Insect | | Number of test insects | Mortality |
| 0 hr aged dust: | | | |
| German cockroach | R1 | 5 | 5/5 in 45 minutes |
| | R2 | 5 | 5/5 in 60 minutes |
| Carpenter ant | R1 | 5 | 3/5 in 180 minutes |
| | R2 | 5 | 2/5 in 200 minutes |
| 24 hr aged dust: | | | |
| German cockroach | R1 | 5 | 5/5 in 75 minutes |
| | R2 | 5 | 5/5 in 60 minutes |
| Carpenter ant | R1 | 5 | 4/5 in 360 minutes |
| | R2 | 5 | 5/5 in 360 minutes |
| 10 days aged dust: | | | |
| German cockroach | R1 | 5 | 5/5 in 6 hours |
| | R2 | 5 | 5/5 in 6 hours |
| Carpenter ant | R1 | 5 | 5/5 in 24 hours |
| | R2 | 5 | 5/5 in 24 hours |

Example 24

Other Blends in Combination with Deltamethrin

Like the testing described in Example 18, other insect control blends were combined with delatamethrin and responses to the combinations compared to response obtained with the blend alone or deltamethrin alone.

Table 24-A shows results in response to treatment of the German cockroach with Blend 13 in combination with deltamethrin (DM), and compared to the efficacy of deltamethrin alone and Blend 13 alone.

TABLE 24-A

| | Bioactivity | |
|---|---|---|
| Chemicals | KD | 100% Kill |
| DM | 120 sec | 15 min |
| Blend 13 | 20 sec | 5 min |
| Blend 13 + DM | 5 sec | 55 sec |

Figure 11:
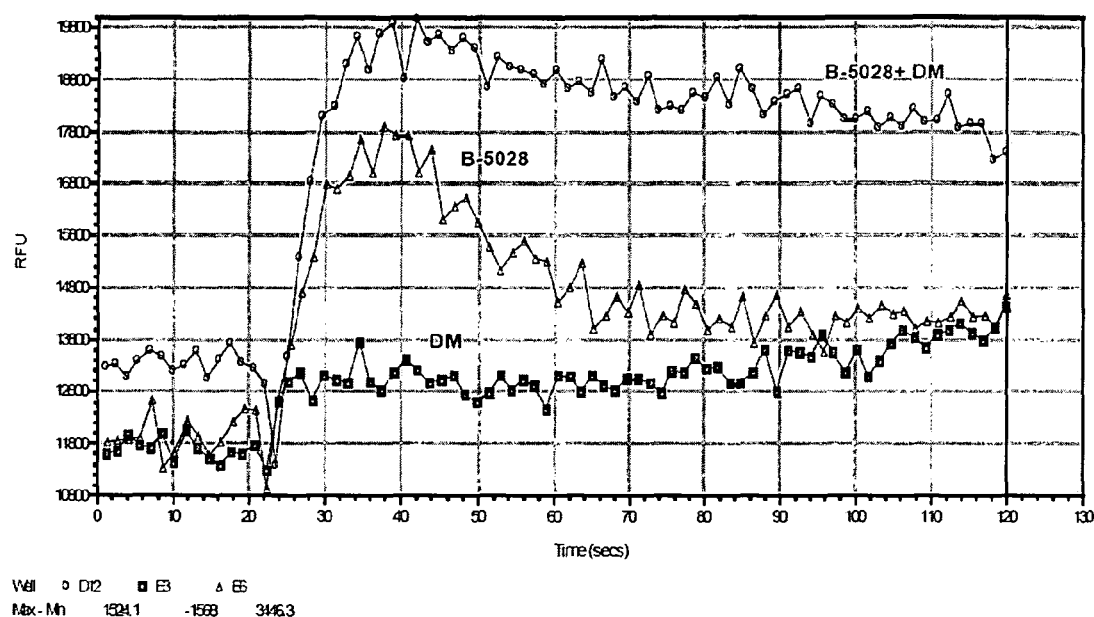
FIG. 11 shows the synergistic increase in $Ca^{2+}$ release triggered by olfactory receptor activation in Drosophila S2 cells treated with Blend 41, Deltametrin (DM), and a combination of Blend 41 with DM.
Figure 12:
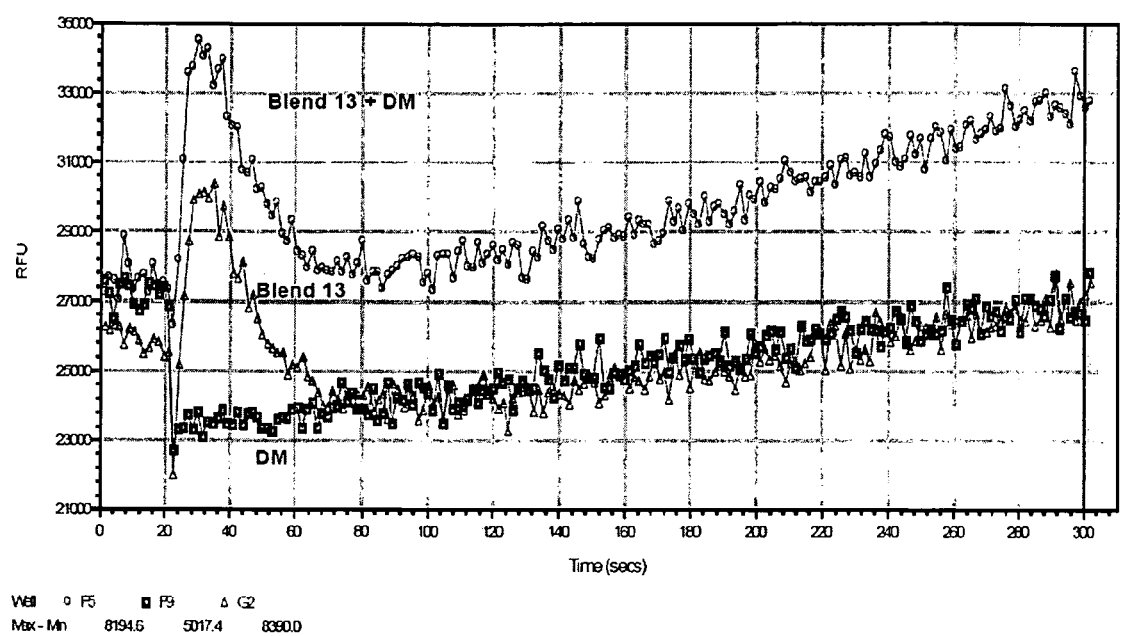
FIG. 12 shows the synergistic increase in $Ca^{2+}$ release triggered by olfactory receptor activation in Drosophila S2 cells treated with Blend 13 with Deltamethrin.

FIG. 11 shows the synergistic increase in $Ca^{2+}$ release triggered by olfactory receptor activation in *Drosophila* S2 cells treated with Blend 41, Deltametrin (DM), and a combination of Blend 41 with DM. FIG. 12 shows the synergistic increase in $Ca^{2+}$ release triggered by olfactory receptor activation in *Drosophila* S2 cells treated with Blend 13 with Deltamethrin.

Example 25

Blend 33 in Combination with Clothianidin

Insect control blends were combined with clothianidin and responses to the combinations compared to response obtained with the blend alone or clothianidin alone.

Figure 13:
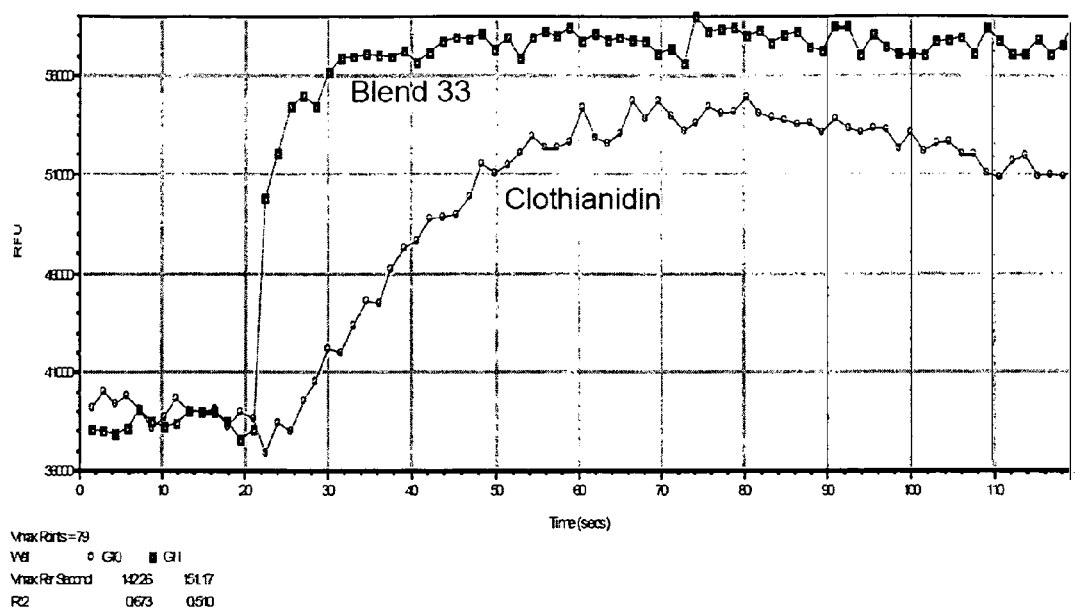
FIG. 13 shows the increase in $Ca^{2+}$ release triggered by olfactory receptor activation in Drosophila S2 cells treated with Blend 33 alone and with Clothianidin alone.
Figure 14:
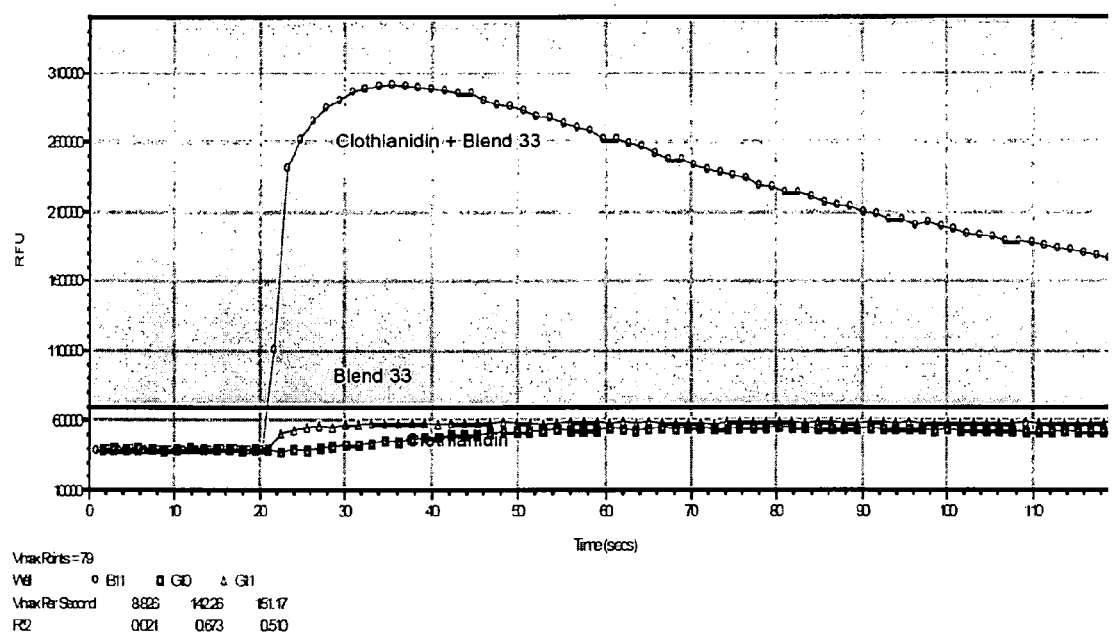
FIG. 14 shows the synergistic increase in $Ca^{2+}$ release triggered by olfactory receptor activation in Drosophila S2 cells treated with Blend 33 in combination with Clothianidin.
Figure 15:
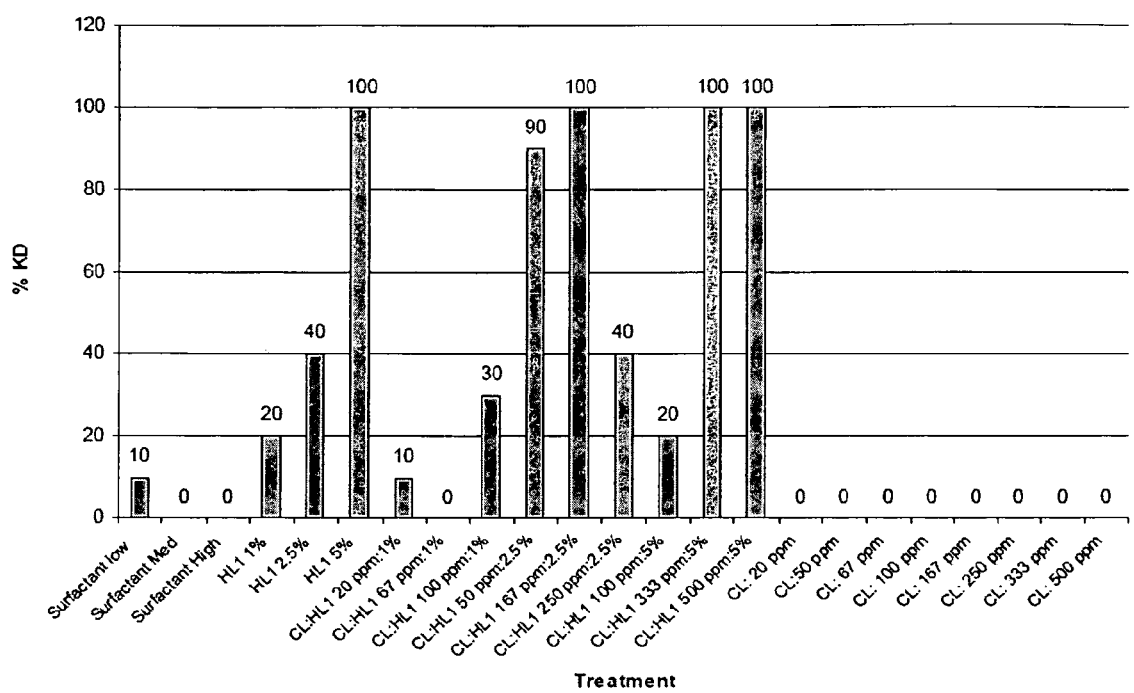
FIG. 15 is a bar graph showing percent knockdown in response to treatment of Aedes aegypti with various compositions of including Blend 33 alone, Clothianidin alone, and various combinations of Blend 33 and Clothianidin.
Figure 16:
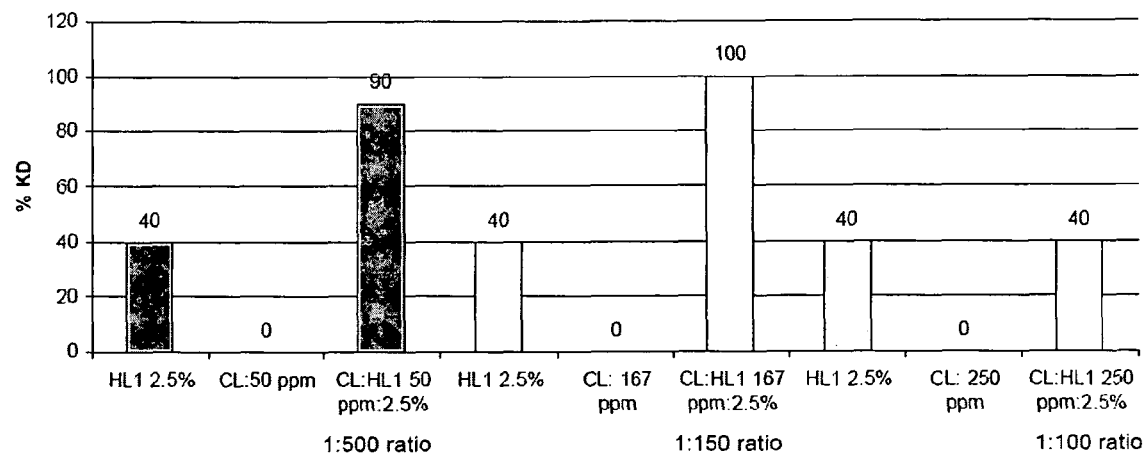
FIG. 16 is a bar graph showing percent knockdown in response to treatment of Aedes aegypti with selected middle range doses of Blend 33 in combination with Clothianidin, compared with results in response to Blend 33 alone and Clothianidin alone.
Figure 17:
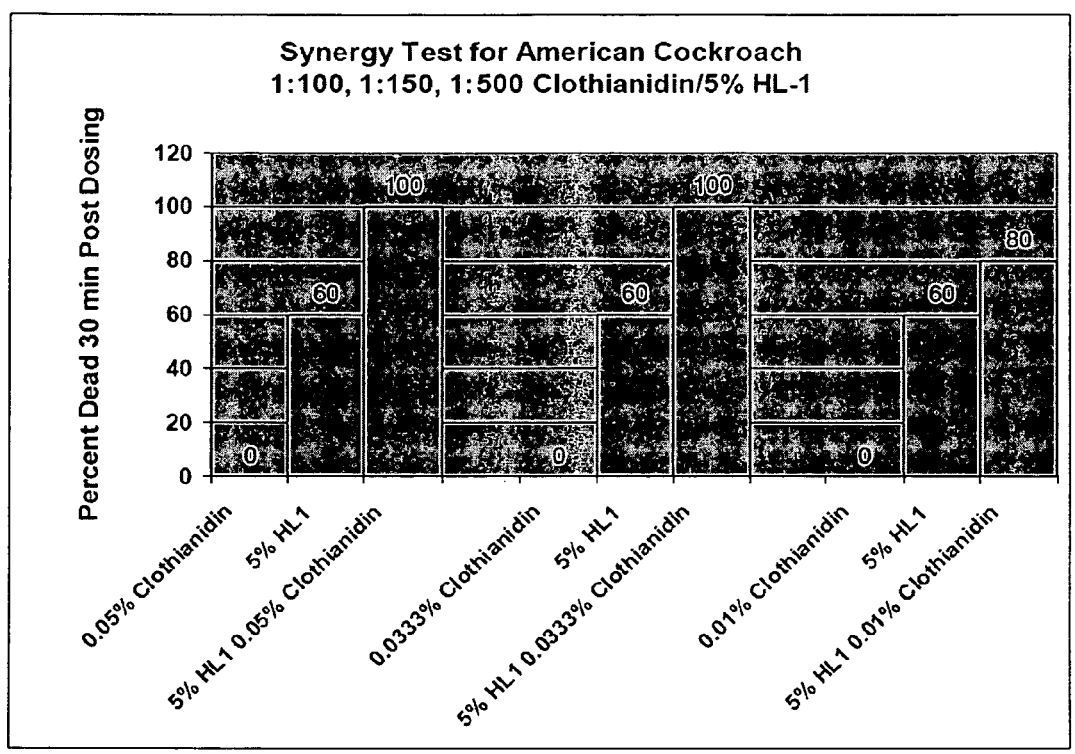
FIG. 17 is a bar graph showing synergy results in response to treatment of American cockroach with various amounts of Clothianidin in combination with 5% Blend 33.

FIG. 13 shows the increase in $Ca^{2+}$ release triggered by olfactory receptor activation in *Drosophila* S2 cells treated with Blend 33 alone and with clothianidin alone. FIG. 14 shows the synergistic increase in $Ca^{2+}$ release triggered by olfactory receptor activation in *Drosophila* S2 cells treated with Blend 33 in combination with clothianidin. FIG. 15 is a bar graph showing percent knockdown in response to treatment of *Aedes aegypti* with various compositions of including Blend 33 alone, clothianidin alone, and various combinations of Blend 33 and clothianidin. FIG. 16 is a bar graph showing percent knockdown in response to treatment of *Aedes aegypti* with selected middle range doses of Blend 33 in combination with clothianidin, compared with results in response to Blend 33 alone and clothianidin alone. FIG. 17 is a bar graph showing synergy results in response to treatment of American cockroach with various amounts of clothianidin in combination with 5% Blend 33.

Example 26

Other Blends in Combination with Imidacloprid

Insect control blends were combined with clothianidin and responses to the combinations compared to response obtained with the blend alone or imidacloprid alone.

For example, Table 25-A shows the cAMP response generated in cells treated with a combination of Blend 41 and imidacloprid.

TABLE 25-A

| Treatment | cAMP (nM) |
|---|---|
| FK | 65 |
| Control | 8.9 |
| Blend 41 | 6.5 |
| 100 PPM Imidacloprid | 9.1 |
| 333 PPM Imidacloprid | 9.4 |
| 500 PPM Imidacloprid | 8.8 |
| 1:100 PPM Imidacloprid/Blend 41 | 3.1 |
| 1:150 PPM Imidacloprid/Blend 41 | 5.3 |
| 1:500 PPM Imidacloprid/Blend 41 | 4.8 |

Figure 18:
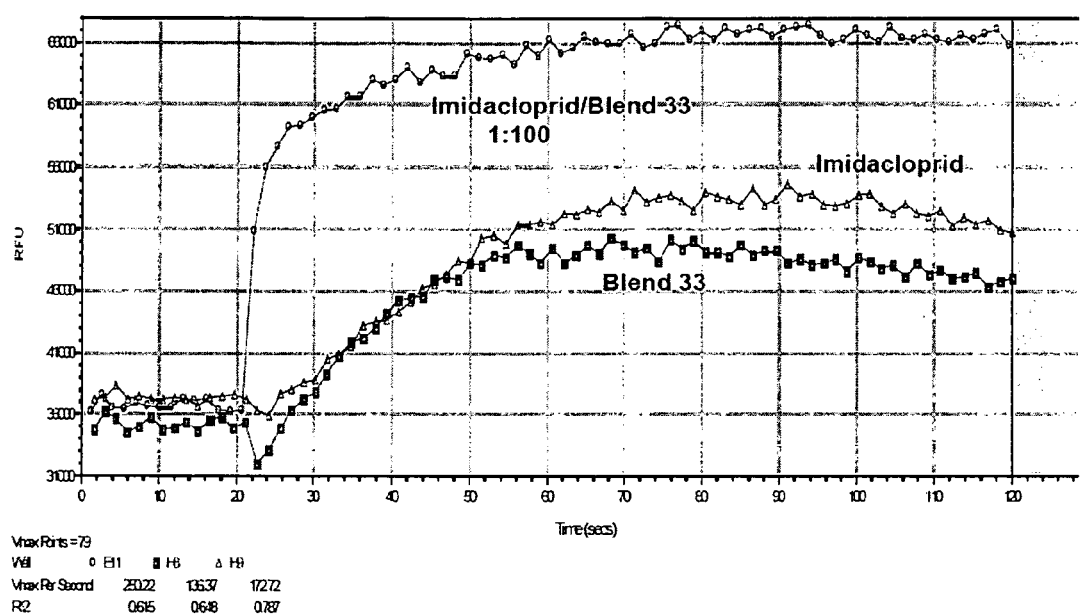
FIG. 18 shows the synergistic increase in $Ca^{2+}$ release triggered by olfactory receptor activation in Drosophila S2 cells treated with a combination of Blend 33 and Imidacloprid.
Figure 19:
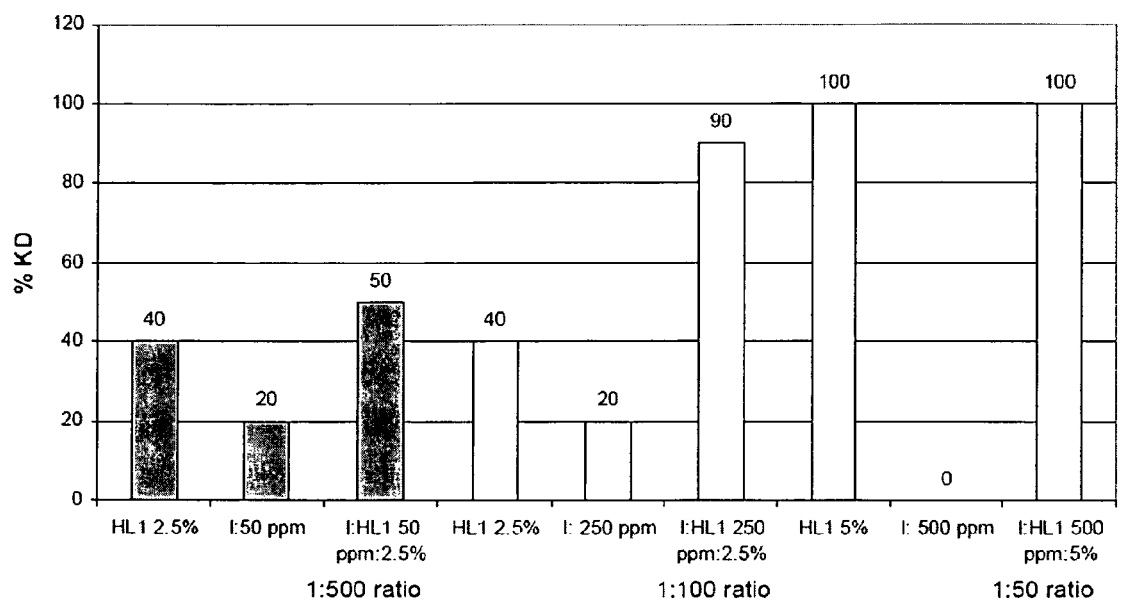
FIG. 19 is a bar graph showing percent knockdown in response to treatment of Aedes aegypti with selected doses of Blend 33 in combination with Imidacloprid (I), compared with results in response to Blend 33 alone and Imidacloprid.
Figure 20:
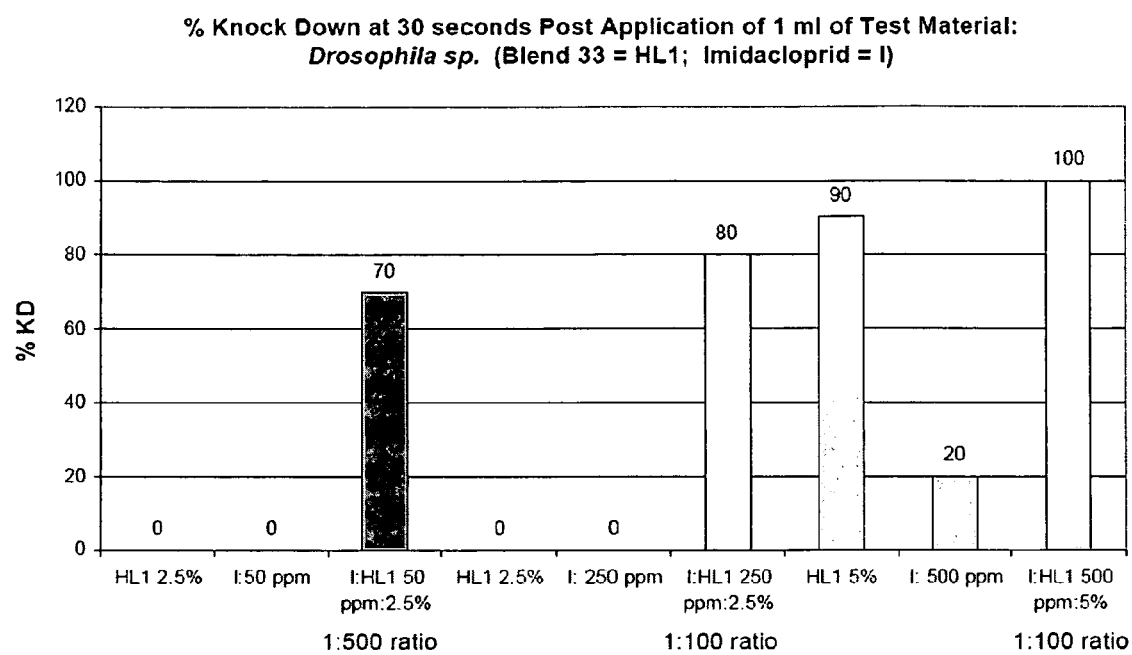
FIG. 20 is a bar graph showing percent knockdown in response to treatment of Drosophila sp. with selected doses of Blend 33 in combination with Imidacloprid (I), compared with results in response to Blend 33 alone and Imidacloprid.
Figure 21:
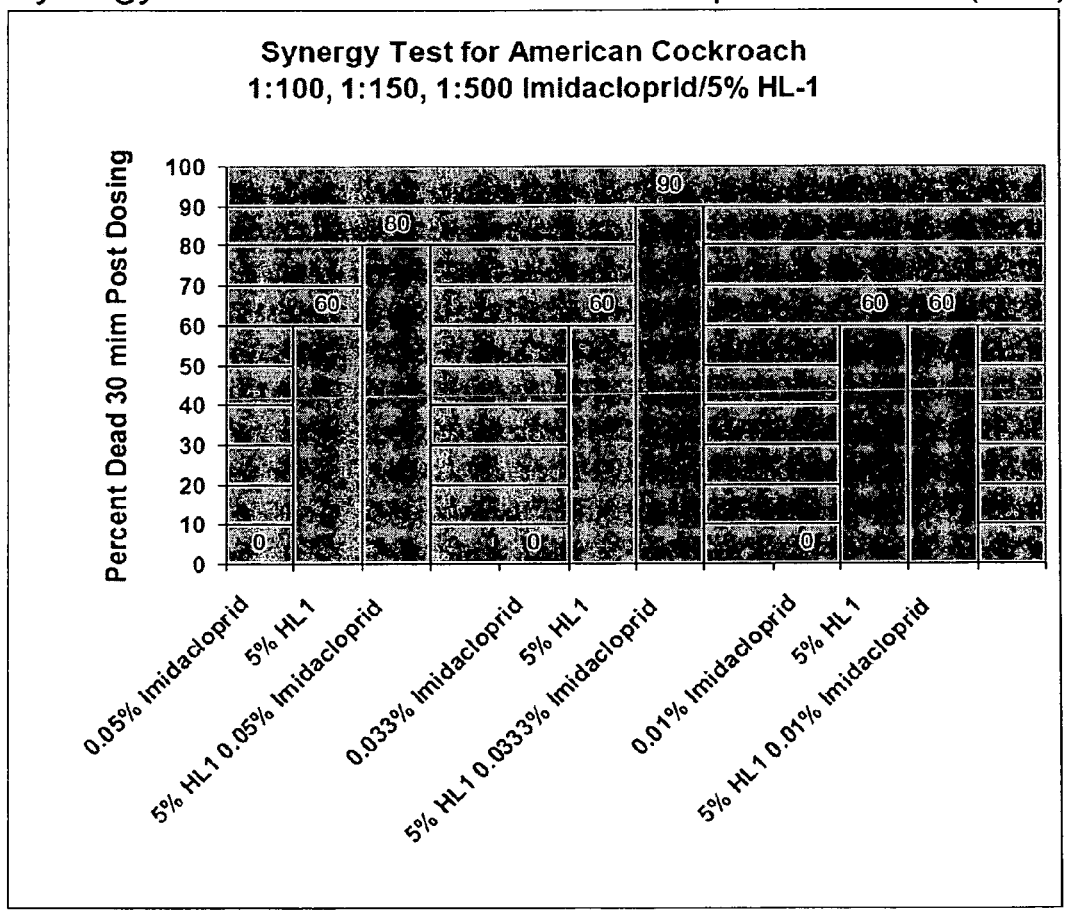
FIG. 21 is a bar graph showing synergy results in response to treatment of American cockroach with various amounts of Imidacloprid in combination with 5% Blend 33.

FIG. 18 shows the synergistic increase in $Ca^{2+}$ release triggered by olfactory receptor activation in *Drosophila* S2 cells treated with a combination of Blend 33 and imidacloprid. FIG. 19 is a bar graph showing percent knockdown in response to treatment of *Aedes aegypti* with selected doses of Blend 33 in combination with Imidacloprid (I), compared with results in response to Blend 33 alone and Imidacloprid. FIG. 20 is a bar graph showing percent knockdown in response to treatment of *Drosophila* sp. with selected doses of Blend 33 in combination with Imidacloprid (I), compared with results in response to Blend 33 alone and Imidacloprid. FIG. 21 is a bar graph showing synergy results in response to treatment of American cockroach with various amounts of Imidacloprid in combination with 5% Blend 33.

Figure 22:
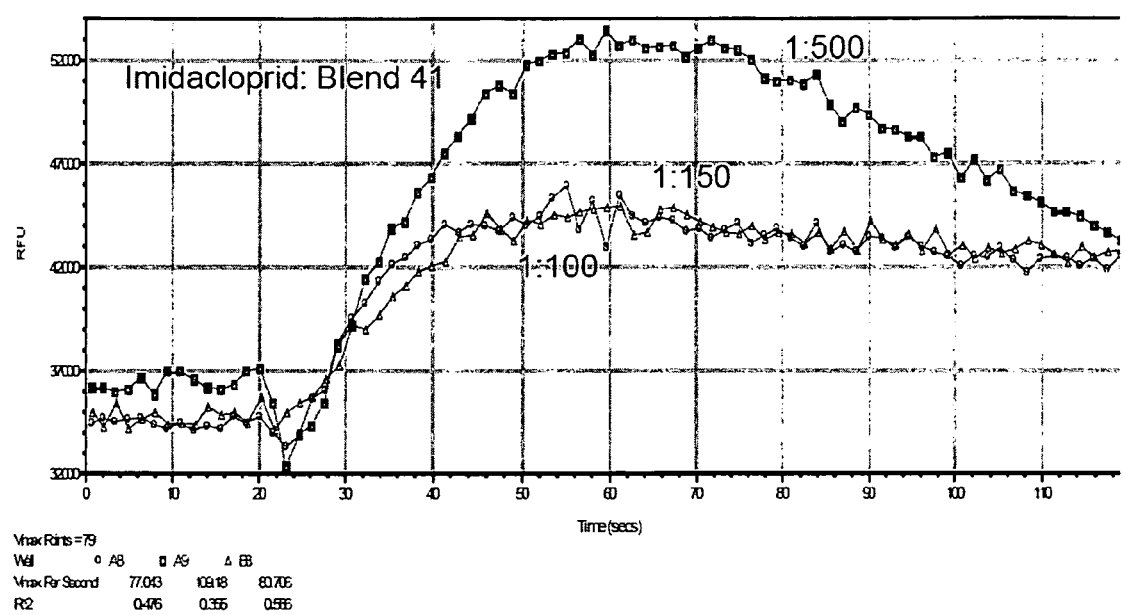
FIG. 22 shows the synergistic increase in $Ca^{2+}$ release triggered by olfactory receptor activation in Drosophila S2 cells treated with Blend 41 in combination in varying ratios with Imidacloprid.
Figure 23:
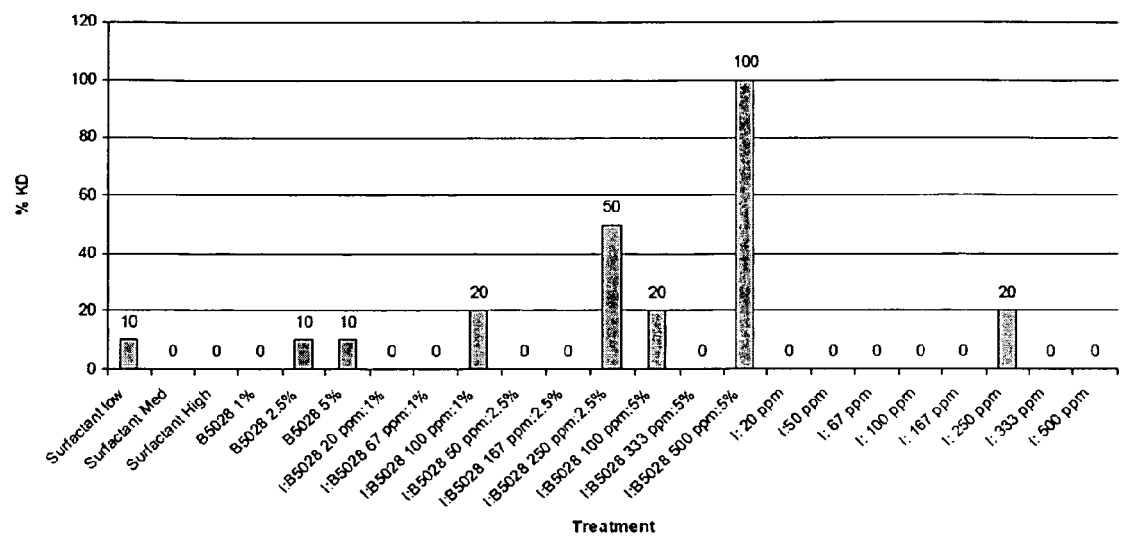
FIG. 23 is a bar graph showing percent knockdown in response to treatment of Aedes aegypti with various compositions of including Blend 41 alone, Imidacloprid alone, and combinations of Blend 41 and Imidacloprid.
Figure 24:
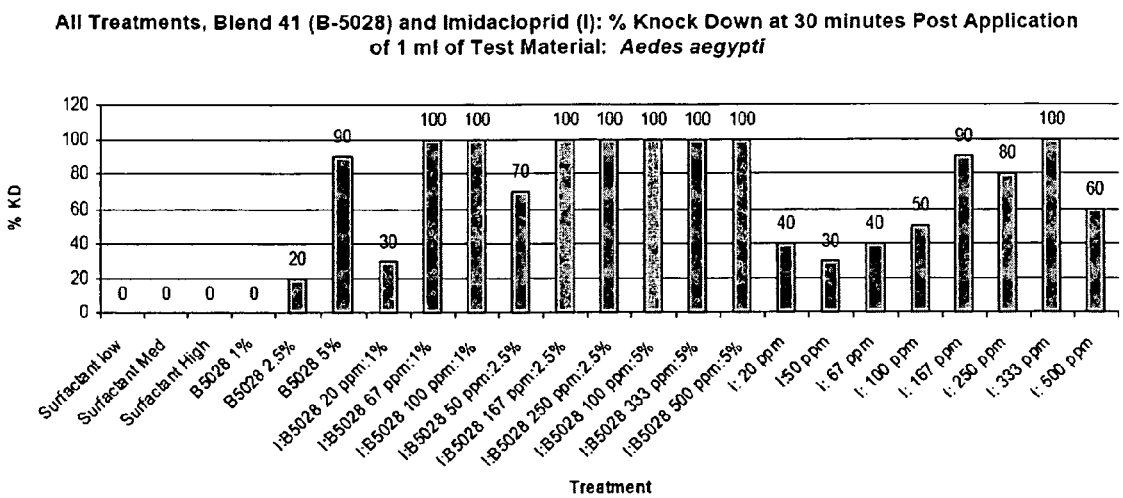
FIG. 24 is a bar graph showing percent knockdown in response to treatment of Aedes aegypti with various compositions of including Blend 41 alone, Imidacloprid alone, and combinations of Blend 41 and Imidacloprid.
Figure 25:
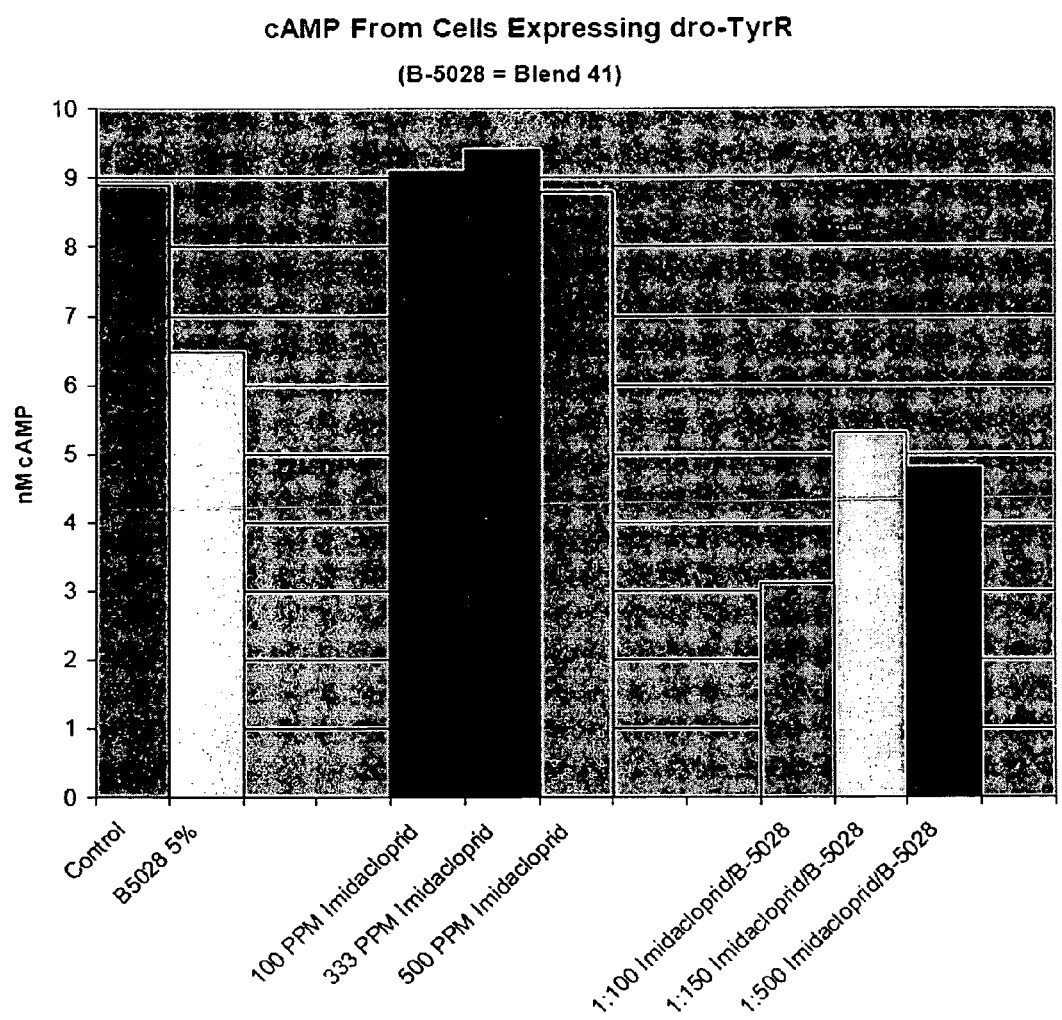
FIG. 25 is a bar graph showing cAMP signal produced in response to treatment of Drosophila S2 cells treated with various compositions of including Blend 41 alone, Imidacloprid alone, and combinations of Blend 41 and Imidacloprid.

FIG. 22 shows the synergistic increase in $Ca^{2+}$ release triggered by olfactory receptor activation in *Drosophila* S2 cells treated with Blend 41 in combination in varying ratios with Imidacloprid. FIG. 23 is a bar graph showing percent knockdown in response to treatment of *Aedes aegypti* with various compositions of including Blend 41 alone, Imidacloprid alone, and combinations of Blend 41 and Imidacloprid. FIG. 24 is a bar graph showing percent knockdown in response to treatment of *Aedes aegypti* with various compositions of including Blend 41 alone, Imidacloprid alone, and combinations of Blend 41 and Imidacloprid. FIG. 25 is a bar graph showing cAMP signal produced in response to treatment of *Drosophila* S2 cells treated with various compositions of including Blend 41 alone, Imidacloprid alone, and combinations of Blend 41 and Imidacloprid.

Figure 26:
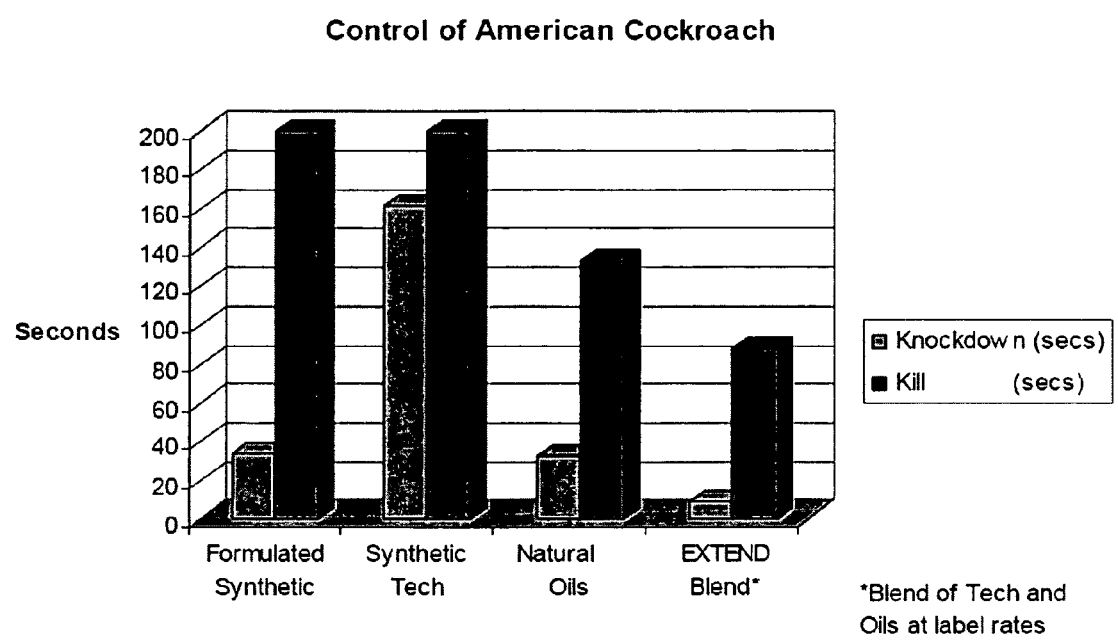
FIG. 26 is a bar graph showing percent Knockdown and Kill rate in response to treatment of American cockroach with formulated synthetics, natural oils alone, and [EXTEND Blend] including natural oils and synthetics.

FIG. 26 is a bar graph showing percent Knockdown and Kill rate in response to treatment of American cockroach with formulated synthetics, natural oils alone, and Blend 13 including natural oils and synthetics.

Figure 27:
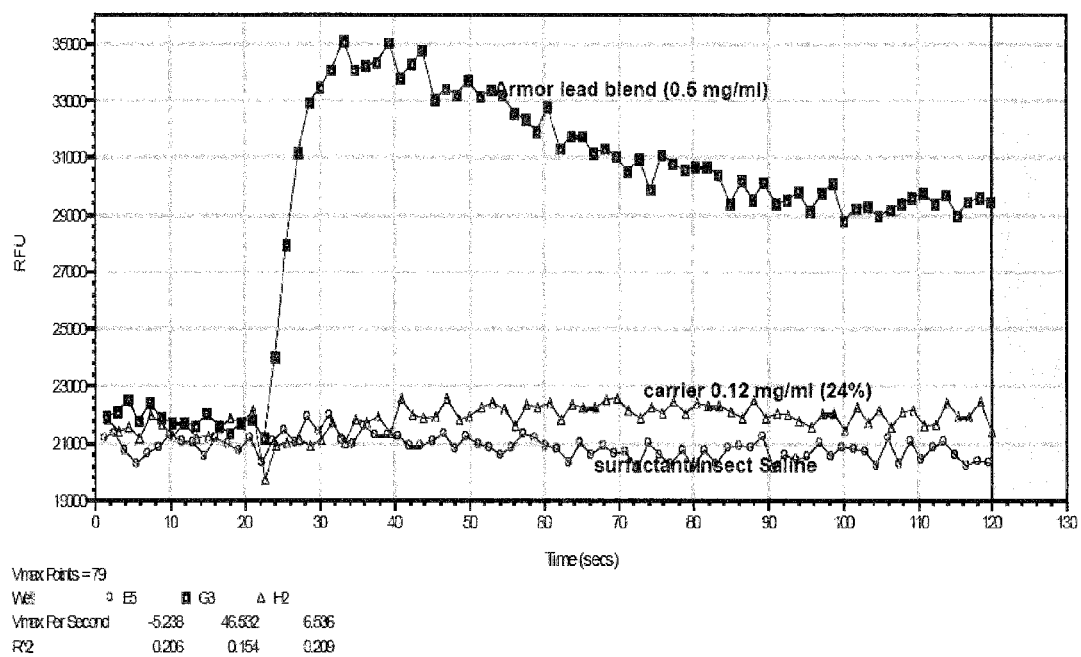
FIG. 27 shows the synergistic increase in $Ca^{2+}$ release triggered by olfactory receptor activation in Drosophila S2 cells treated with Blend 54 in comparison to carrier alone and surfactant alone.
Figure 28:
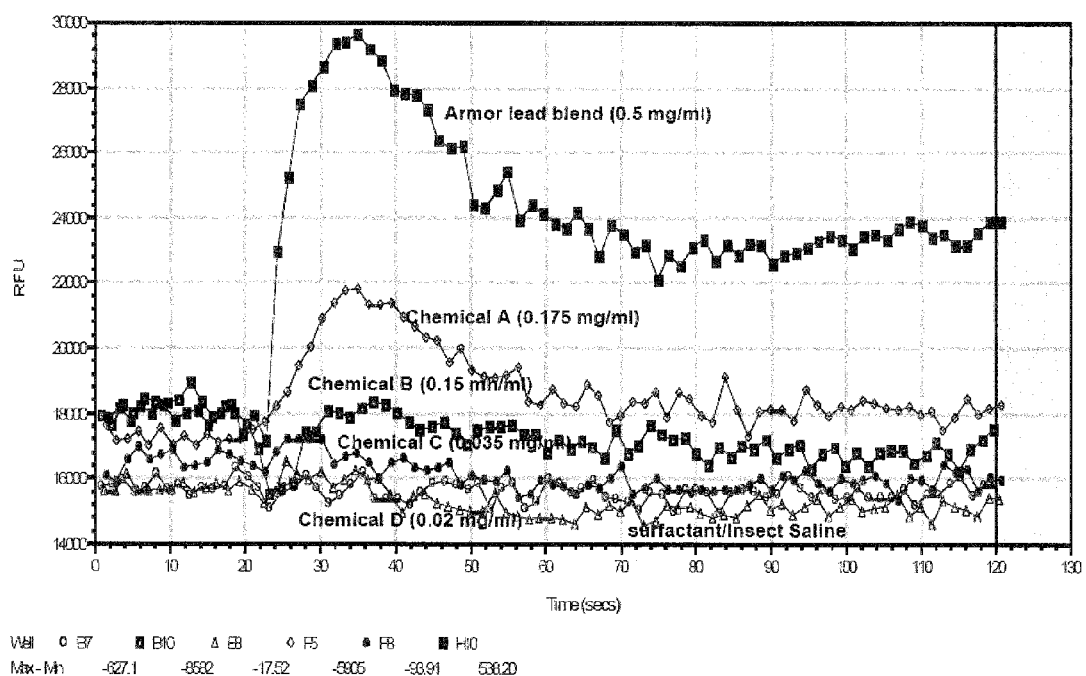
FIG. 28 shows the synergistic increase in $Ca^{2+}$ release triggered by olfactory receptor activation in Drosophila S2 cells treated with Blend 54 and its individual ingredients at concentrations contained in Blend 54.
Figure 29:
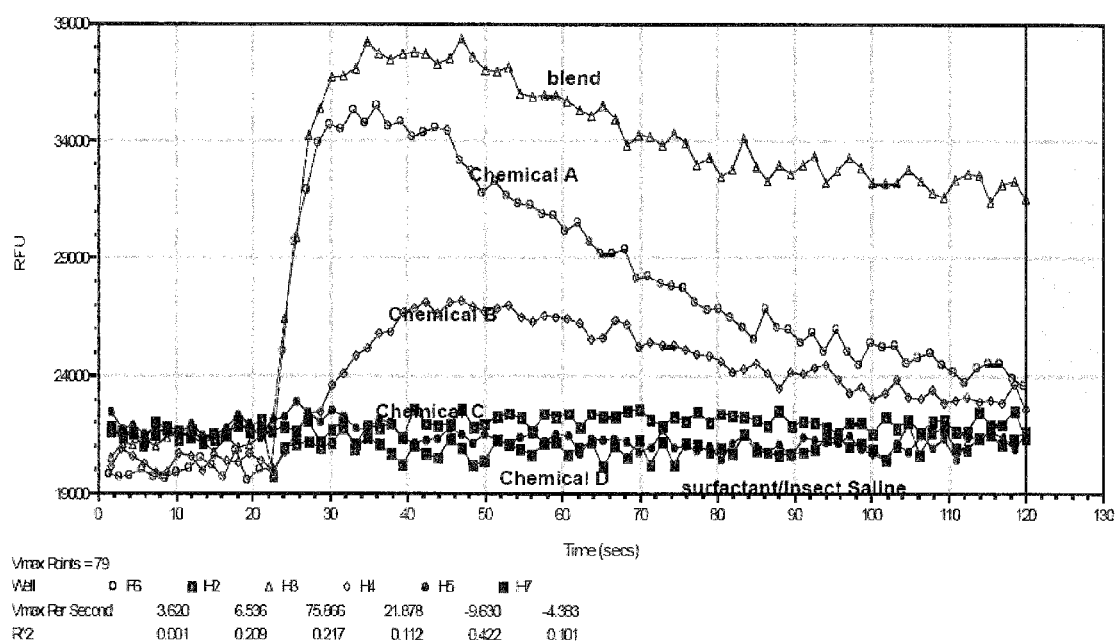
FIG. 29 shows the synergistic increase in $Ca^{2+}$ release triggered by olfactory receptor activation in Drosophila S2 cells treated with Blend 54 and its individual ingredients at concentrations contained in Blend 54.

FIG. 27 shows the synergistic increase in $Ca^{2+}$ release triggered by olfactory receptor activation in *Drosophila* S2 cells treated with Blend 54 in comparison to carrier alone and surfactant alone. FIG. 28 shows the synergistic increase in $Ca^{2+}$ release triggered by olfactory receptor activation in *Drosophila* S2 cells treated with Blend 54 and its individual ingredients at concentrations contained in Blend 54. FIG. 29 shows the synergistic increase in $Ca^{2+}$ release triggered by olfactory receptor activation in *Drosophila* S2 cells treated with Blend 54 and its individual ingredients at concentrations contained in Blend 54.

Unless otherwise indicated, all numbers expressing quantities of ingredients, properties such as reaction conditions, and so forth used in this document are to be understood as being modified in all instances by the term "about." Accordingly, unless indicated to the contrary, the numerical parameters set forth in this document are approximations that may vary depending upon the desired properties sought to be determined by the present invention.

It will be obvious to those skilled in the art that further modifications may be made to the embodiments described herein without departing from the spirit and scope of the present invention.

What is claimed is:

1. A pest-control composition comprising a synergistic combination of the ingredients geraniol, thyme oil white, linalool, tetrahydrolinalool, and piperonal, wherein the concentration of geraniol is between 0.42% and 12.60%, the concentration of thyme oil white is between 3.01% and 90.30%, the concentration of linalool is between 0.57% and 17.10%, the concentration of tetrahydrolinalool is between 0.79% and 23.70%, and the concentration of piperonal is between 0.81% and 24.30%, and wherein the combination has a synergistic pest control activity that exceeds additive effects of the ingredients.

2. The pest-control composition of claim 1, wherein the concentration of geraniol is 4.68%, the concentration of thyme oil white is 50.76%, the concentration of linalool is 6.42%, the concentration of tetrahydrolinalool is 8.82%; and the concentration of piperonal is 10.65%.

3. The pest-control composition of claim 1, wherein the ingredients interact with at least one receptor selected from a tyramine receptor, an olfactory receptor Or43a, and an olfactory receptor Or83b, and the interaction with the receptor results in a disruption of an intracellular level of at least one of cAMP and calcium.

4. The pest control composition of claim 3, wherein at least two of the ingredients interact with different receptors.

5. The pest control composition of claim 1, wherein the synergistic pest control activity comprises a residual pest control period associated with the composition that is longer than the residual pest control period associated with any single selected ingredient.

6. The pest control composition of claim 1, additionally comprising vanillin.

7. The pest control composition of claim 1, additionally comprising triethyl citrate.

8. The pest control composition of claim 1, wherein the composition has a coefficient of synergy of at least 1.5.

9. The pest control composition of claim 1, additionally comprising isopropyl myristate.

* * * * *